United States Patent
Gomtsyan et al.

(10) Patent No.: US 8,604,053 B2
(45) Date of Patent: *Dec. 10, 2013

(54) TRPV1 ANTAGONISTS

(75) Inventors: Arthur R. Gomtsyan, Vernon Hills, IL (US); Eric A. Voight, Pleasant Prairie, WI (US); Erol K. Bayburt, Gurnee, IL (US); Jun Chen, Lake Bluff, IL (US); Jerome F. Daanen, Racine, WI (US); Stanley DiDomenico, Richmond, IL (US); Michael E. Kort, Lake Bluff, IL (US); Philip R. Kym, Libertyville, IL (US); Heath A. McDonald, Plainfield, IL (US); Richard J. Perner, Gurnee, IL (US); Robert G. Schmidt, Antioch, IL (US)

(73) Assignee: AbbVie Inc., North Chicago, IL (US)

( * ) Notice: Subject to any disclaimer, the term of this patent is extended or adjusted under 35 U.S.C. 154(b) by 586 days.

This patent is subject to a terminal disclaimer.

(21) Appl. No.: 12/579,821

(22) Filed: Oct. 15, 2009

(65) Prior Publication Data

US 2010/0137360 A1 Jun. 3, 2010

Related U.S. Application Data

(60) Provisional application No. 61/220,075, filed on Jun. 24, 2009, provisional application No. 61/106,369, filed on Oct. 17, 2008.

(51) Int. Cl.
*C07D 405/12* (2006.01)
*A61K 31/4709* (2006.01)

(52) U.S. Cl.
USPC .......................... 514/310; 546/143

(58) Field of Classification Search
None
See application file for complete search history.

(56) References Cited

U.S. PATENT DOCUMENTS

| | | | |
|---|---|---|---|
| 7,015,233 B2 | 3/2006 | Gomtsyan et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 2005/0131449 A1 | 6/2005 | Salahieh et al. |
| 2006/0128689 A1 | 6/2006 | Gomtsyan et al. |
| 2008/0153871 A1 | 6/2008 | Bayburt et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131449 A1 | 5/2009 | Yanni et al. |
| 2009/0131485 A1 | 5/2009 | Liu et al. |
| 2009/0137457 A1 | 5/2009 | Harbeson |

FOREIGN PATENT DOCUMENTS

| | | |
|---|---|---|
| WO | WO9507271 A1 | 3/1995 |
| WO | WO9710223 A1 | 3/1997 |
| WO | WO2004046133 A1 | 6/2004 |
| WO | WO2005099353 A2 | 10/2005 |
| WO | WO2006008754 A1 | 1/2006 |
| WO | WO2007042906 A1 | 4/2007 |
| WO | WO2007050732 A1 | 5/2007 |
| WO | WO2007121299 A2 | 10/2007 |
| WO | WO2008040360 A2 | 4/2008 |
| WO | WO2008040361 A2 | 4/2008 |
| WO | WO2008059339 A2 | 5/2008 |
| WO | WO2008079683 A2 | 7/2008 |
| WO | WO2008110863 A1 | 9/2008 |

OTHER PUBLICATIONS

Wu et al., Toxicology, 236, pp. 1-6, 2007.*
West, Anthony R., Solid State Chemistry and its Applications, Wiley, New York, 1988, pp. 358 & 365.*
Apostolidis A., et al., "Capsaicin receptor TRPV1 in urothelium of neurogenic human bladders and effect of intravesical resiniferatoxin," Urology, 2005, 65 (2), 400-405.
Barone F. C. et al., "brain cooling during transient focal ischemia provides complete neuroprotection", Neurosci. Biobehay. Rev., 1997, pp. 31-44, vol. 2 (1).
Bernard S. A. et al., "Mild Therapeutic Hypothermia to Improve the Neurologic Outcome After Cardiac Arrest", N. Engl. J. Med. , 2002, p. 549, vol. 346.

(Continued)

*Primary Examiner* — Zinna Northington Davis

(57) ABSTRACT

Disclosed herein are compounds of formula (I) or pharmaceutically acceptable salts, solvates, prodrugs, salts of prodrugs, or combinations thereof,

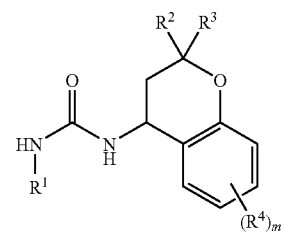

wherein $R^1$, $R^2$, $R^3$, $R^4$, and m are defined in the specification. Compositions comprising such compounds and methods for treating conditions and disorders using such compounds and compositions are also disclosed.

32 Claims, 1 Drawing Sheet

(56) References Cited

OTHER PUBLICATIONS

Bernard S. A. et al., "Treatment of Comatose Survivors of Out-of-Hospital Cardiac Arrest with Induced Hypothermia," N. Engl. J. Med., 2002, pp. 557-563, vol. 346.
Beylot M., et al., "In vivo studies of intrahepatic metabolic pathways," Diabetes Metabolism, 1997, 23 (3), 251-257.
Blagojevic N., et al., "Role of heavy water in Boron Neutron Capture Therapy," in Topics in Dosimetry & Treatment Planning for Neutron Capture Therapy, Advanced Medical Publishing, Madison, WI, 1994, 125-134.
Blake et al., "Studies with deuterated drugs," J. Pharm. Sci., 1975, 64 (3), 367-391.
Brickner S. J., et al., "Synthesis and antibacterial activity of U-100592 and U-100766, two oxazolidinone antibacterial agents for the potential treatment of multidrug-resistant gram-positive bacterial infections," J Med Chem., 1996, 39 (3), 673-679.
Burgard A., et al., "Asymmetric synthesis of 4-amino-3,4-dihydro-2,2-dimethyl-2H-1-benzopyrans," Tetrahedron, 1999, 55, 7555-7562.
Butte N. F., et al., "Measurement of milk intake: tracer-to-infant deuterium dilution method," Br. J. Nutr., 1991, 65, 3-14.
Caterina M. J., et al., "Impaired Nociception and Pain Sensation in Mice Lacking the Capsaicin Receptor," Science, 2000, 288, 306-313.
Caterina M. J., et al., "The Capsaicin Receptor: A Heat-Activated Ion Channel in the Pain Pathway," Nature, 1997, 389, 816-824.
Caterina M. J., et al., "The Vanilloid Receptor: A Molecular Gateway to the Pain Pathway," Annu Rev Neurosci., 2001, 24, 487-517.
Coimbra C. et al., "Moderate hypothermia mitigates neuronal damage in the rat brain when initiated several hours following transient cerebral ischemia.," Acta Neuropathol. (Berl), 1994, pp. 325-331, vol. 87.
Colbourne F. et al. , "Prolonged but delayed postischemic hypothermia: a long-term outcome study in the rat middle cerebral artery occlusion model.," J. Cereb. Blood Flow Metab., 2000, pp. 1702-1708, vol. 20 (12).
Corey E. J., et al., "An Efficient and Catalytically Enantioselective Route to (S )-(−)-Phenyloxirane," J. Org. Chem., 1988, 53 (12), 2861-2863.
Coward W. A., et al., "New Method for Measuring Milk Intakes in Breast-Fed Babies," Lancet, 1979, 13-14.
Czajka D. M., "Effect of deuterium oxide on the reproductive potential of mice," Ann NY Acad Sci, 1960, vol. 84, pp. 770-779.
Czajka D.M., et al., "Physiological effects of deuterium on dogs," Am. J. Physiol., 1961, 201 (2), 357-362.
Davis J.B., et al., "Vanilloid receptor-1 is essential for inflammatory thermal hyperalgesia," Nature, 2000, 405, 183-187.
Eaton P.E., et al., "Phosphorus Pentoxide-Methanesulfonic Acid. A Convenient Alternative to Polyphosphoric Acid," J. Org. Chem., 1973, 38 (23), 4071-4073.
Fernihough J., et al., "Regulation of calcitonin gene-related peptide and TRPV1 in a rat model of osteoarthritis," Neurosci Lett., 2005, 388, 75-80.
Foster, A.B., et al., "Deuterium Isotope Effects in the Metabolism of Drugs and Xenobiotics: Implications for Drug Design," Advances in Drug Research, 1985, 14, Academic Press, London, 2-36.
Garrett C. E., et al., "The enantioselective reduction of 2'-fluoroacetophenone utilizing a simplified CBS-reduction procedure," Tetrahedron Asymmetry, 2002, 13, 1347-1349.
Gavva N. R. et al. , "The vanilloid receptor TRPV1 is tonically activated in vivo and involved in body temperature regulation," J Neurosci., 2007, pp. 3366-3374, vol. 27 (13).
Gavva N. R. et al., "Pharmacological blockade of the vanilloid receptor TRPV1 elicits marked hyperthermia in humans," Pain, 2008, pp. 202-210, vol. 136 (1-2).
Gavva N. R. et al., "Repeated administration of vanilloid receptor TRPV1 antagonists attenuates hyperthermia elicited by TRPV1 blockade," J Pharmacol Exp Ther., 2007, pp. 128-137, vol. 323 (1).

Geppetti P., et al., "The transient receptor potential vanilloid 1: role in airway inflmmation and disease," Eur J Pharmacol., 2006, 533 (1-3), 207-214.
Gololobov Y. G., et al., "Sixty years of staudinger reaction," Tetrahedron, 1981, 37, 437-472.
Gonzalez V.,"A New Treatment for Ocular Pain Associated to Dry Eye Syndrome Based on RNAi Technology: In Viva Results", Association for Research in Vision and Ophthalmology Meeting, 2009, Abstract.
Greene T.W., et al., "Protection for the Amino group," Protective Groups in Organic Synthesis, 1999, Edition 3, John Wiley & Sons, 494-653.
Grennan D.M., et al., "Rheumatoid arthritis," Textbook of Pain, 1994, 397-407.
Hayes P., et al., "Cloning and Functional Expression of a Human Orthologue of Rat Vanilloid Receptor-1," Pain, 2000, 88, 205-215.
Higuchi T., et al., "Pro-Drugs as Novel Drug Delivery Systems (ACS Symposium Series, 14)," American Chemical Society, 1975, Table of Contents.
Honore P., et al., "A-425619 [1-lsoquinolin-5-yl-3-(4-trifluoromethyl-benzyl)urea], a Novel Transient Receptor Potential Type V1 Receptor Antagonist, Relieves Pathophysiological Pain Associated with Inflammation and Tissue Injury in Rats," J Pharmacol Exp Thera, 2005, 314 (1), 410-421.
Houge and Mersfelder, "Pathophysiology and First-Line Treatment of Osteoarthritis," Ann. Pharmacother., 2002, 36 (4), 679-686.
Iida T. et al., "Attenuated fever response in mice lacking TRPV1," Neurosci Lett., 2005, pp. 28-33, vol. 378 (1).
International search report for PCT application No. PCT/US2009/060732, dated Feb. 18, 2010, 2 pages.
IUPAC Commission on Nomenclature of Organic Chemistry: Rules for the Nomenclature of Organic Chemistry Section E: Stereochemistry, Pure Appl Chem, 1976, 45, 11-30.
Jancso-Gabor A. et al., "Irreversible impairment of thermoregulation induced by capsaicin and similar pungent substances in rats and guinea-pigs," J Physiol., 1970, pp. 495-507, vol. 206 (3).
Jia Y., et al., "Anandamide induces cough in conscious guinea-pigs through VR1 receptors," Br J Pharmacol, 2002, 137 (6), 831-836.
Kato et al., "Synthesis of Deuterated Mosapride Citrate," J. Labelled Comp. Radiopharmaceut, 1995, 36 (10), 927-932.
Kawai N. et al., "Effects of delayed intraischemic and postischemic hypothermia on a focal model of transient cerebral ischemia in rats," Stroke, 2000, pp. 1982-1989, vol. 31 (8).
Kawanami Y., et al., "Practical enantioselective reduction of ketones using oxazaborolidine catalyst generated in situ from chiral lactam alcohol and borane", Tetrahedron, 2003, 59, 8411-8414.
Kushner et al., "Pharmacological uses and perspectives of heavy water and deuterated compounds," Can J Physiol Pharmacol, 1999, vol. 77, pp. 79-88.
Lehto S. G. et al., "Antihyperalgesic effects of (R,E)-N-(2-hydroxy-2,3-dihydro-1H-inden-4-yl)-3-(2-(piperidin-1-yl)-4-(trifluorornethyl)phenyl)-acrylamide (AMG8562), a novel transient receptor potential vanilloid type 1 modulator that does not cause hyperthermia in rats," J. Pharmacol, 2008, vol. 326, pp. 218.
Lizondo J., et al., "Linezolid: Oxazolidinone antibacterial," Drugs of the Future, 1996, 21 (11), 1116-1123.
MacLennan A. H., et al., "Neonatal body water turnover: a putative index of perinatal morbidity," Am J Obstet Gynecol., 1981, 139 (8), 948-952.
Maier C. M. et al., "Delayed induction and long-term effects of mild hypothermia in a focal model of transient cerebral ischemia: neurological outcome and infarct size," J Neurosurg, 2001, pp. 90-96, vol. 94 (1).
Maier C. M. et al., "Optimal depth and duration of mild hypothermia in a focal model of transient cerebral ischemia: effects on neurologic outcome, infarct size, apoptosis, and inflammation," 1998, pp. 2171-2180, vol. 29 (10).
Mallesham B., et al., "Highly efficient CuI-catalyzed coupling of aryl bromides with oxazolidinones using Buchwald's protocol: a short route to linezolid and toloxatone," Org. Lett., 2003, 5 (7), 963-965.

(56) References Cited

OTHER PUBLICATIONS

Marsch R., et al., "Reduced anxiety, conditioned fear, and hippocampal long-term potentiation in transient receptor potential vanilloid type 1 receptor-deficient mice," J. Neurosci., 2007, 27 (4), 832-839.
McCarthy., C., et al., "Osteoarthritis," Textbook of Pain, 1994, 387-396.
Millan, "The induction of pain: an intergrative review," Progress in Neurobiology, 1999, 57, 1-164.
Murata Y., et al., "Peripheral and central distribution of TRPV1, substance P and CGRP of rat corneal neurons," Brain Res., 2006, 1085 (1), 87-94.
Nolano M., et al., "Topical Capsaicin in Humans: Parallel Loss of Epidermal Nerve Fibers and Pain Sensation," Pain, 1999, 81, 135-145.
Onesti S. T. et al., "Transient hypothermia reduces focal ischemic brain injury in the rat," Neurosurgery, 1991, pp. 369-373, vol. 29 (3).
Ooboshi H. et al., "Hypothermia inhibits ischemia-induced efflux of amino acids and neuronal damage in the hippocampus of aged rats," Brain Res, 2000, pp. 23-30, vol. 884 (1-2).
Pons G. et al., "Stable isotopes labeling of drugs in pediatric clinical pharmacology", Pediatrics, 1999, 104 (3 Pt 2), 633-639.
Prescott et al., "Lipid Vesicles as Carriers for Introducing Biologically Active Materials into Cells," Methods in Cell Biology, 1976, Academic Press, 33-71.
Rathelot P., et al, "synthesis of novel functionized 5-nitroisoquinolines and evaluation of in vitro antimalarial activity," Eur. J. Med. Chem., 1995, 30, 503-508.
Roche E.B., et al., "Bioreversable Carries in Drug design Theory and Application", Pergamon Press, 1987, Table of Contents.
Rodewald L. E., et al., "Deuterium oxide as a tracer for measurement of compliance in pediatric clinical drug trials," J Pediatr, 1989, 885-891, 114 (5).
Sappington R. M. et al., "TRPV1: contribution to retinal ganglion cell apoptosis and increased intracellular Ca2+ with exposure to hydrostatic pressure," Invest Ophthalmol Vis Sci., 2009, pp. 717-728, vol. 50 (2).
Schwarcz H. P., "Use of stable isotopes to determine compliance," Control. Clin. Trials, 1984, 5 (4 Suppl), 573-575.
Steiner A. A. et al., "Nonthermal activation of transient receptor potential vanilloid-1 channels in abdominal viscera tonically inhibits autonomic cold-defense effectors.," J. Neurosci, 2007, pp. 7459-7468, vol. 27.
Suri A., et al., "The emerging role of TRPV1 in diabetes and obesity," Trends in Pharmacology ciences, 2008, 29 (1), 29-36.
Swanson D. M. et al., "Identification and biological evaluation of 4-(3-trifluoromethylpyridin-2-yl)piperazine-1-carboxylic acid (5-trifluoromethylpyridin-2-yl)amide, a high affinity TRPV1 (VR1) vanilloid receptor antagonist.," J. Med. Chem, 2005, pp. 1857.
Szallasi A. et al., "The vanilloid receptor TRPV1: 10 years from channel cloning to antagonist proof-of-concept," Nature Reviews | Drug Discovery, 2007, 6, 357-372.
Tamayo N. et al., "Design and synthesis of peripherally restricted transient receptor potential vanilloid 1 (TRPV1) antagonists.," J. Med. Chem, 2008, pp. 2744-2757, vol. 51.
Tanuwidjaja J., et al., "One-pot asymmetric synthesis of either diastereomer of tert-butanesulfinyl-protected amines from ketones," J. Org. Chem., 2007, 72, 626-629.
Thomson J. F., "Physiological effects of D20 in mammals," Ann. New York Acad. Sci., 1960, 84, 736-744.
Tzavara E.T., et al., "Endocannabinoids activate transient receptor potential vanilloid 1 receptors to reduce hyperdoaminergia-related hyperactivity: therapeutic implications," Biol Psychiatry, 2006, 59 (6), 508-515.
Watanabe N., et al., "Immunohistochemical localization of vanilloid receptor subtype 1 (TRPV1) in the guinea pig respiratory system," Pulm Pharmacol Ther., 2005, 18 (3), 187-197.
Woolf C.J., et al., "Implications of recent advances in the understanding of pain pathophysiology for the assessment of pain in patients," Pain, 1999, Suppl 6, S141-S147.
Woolf C.J., et al., "Neuronal Plasticity: Increasing the Gain in Pain," Science, 2000, 1765-1768, 288.
Woolf C.J., et al., "Neuropathic pain: aetiology, symptoms, mechanisms, and management," Lancet, 1999, 1959-1964, 353.
Yamashita K. et al., "Mild hypothermia ameliorates ubiquitin synthesis and prevents delayed neuronal death in the gerbil hippocampus.," Stroke , 1991, pp. 1574-1581, vol. 22.
Zhang F., et al., "Transient receptor potential vanilloid 1 activation induces inflammatory cytokine release in corneal epithelium through MAPK signaling.," J. Cell. Physiol., 2007, 213, 730-739.
Zhang Y. et al., "The effect of intraischemic mild hypothermia on focal cerebral ischemia/reperfusion injury.," Acta Anaesthesiol. Sin., 2001, pp. 65-69, vol. 39.
Kort, et al., "2 TRPV1 Antagonists: Clinical Setbacks and Prospects for Future Development," Abbott Laboratories, Neuroscience Disease Research, Abbott Park, IL, pp. 57-70, (2012).
Voight, et al., "Efficient and general asymmetric syntheses of (R)-chroman-4-amine salts,", Tetrahedron Letters, 51 (2010), pp. 5904-5907.
Voight, et al., "Transient receptor potential vanilloid-1 antagonists: a survey of recent patent literature," Expert Opinion Ther. Patents, (2010), 20(9), pp, 1107-1122.
Watabiki, et al., "Amelioration of Neuropathic Pain by Novel Transient Receptor Pot . . . ," Journal of Pharmacology and Experimental Therapeutics, (2011) 336(3), pp. 743-750.
Reilly, et al., "Pharmacology of Modality-Specific Transient Receptor Potential Van . . . ," Journal of Pharmacology and Experimental Therapeutics, (2012) 342(2), pp. 416-428.
International Search Report for PCT/US2009/060732 dated Feb. 18, 2010.

\* cited by examiner

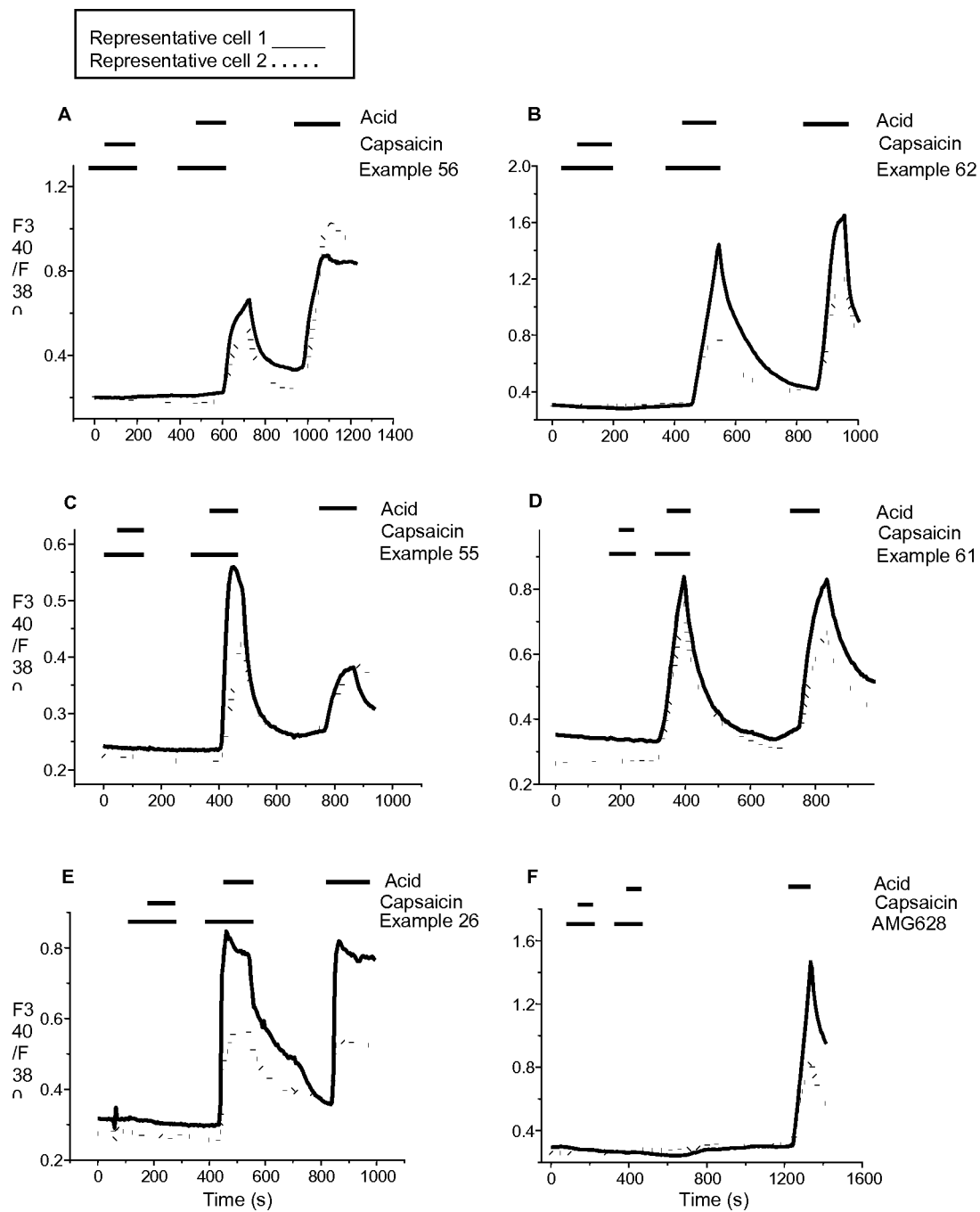

TRPV1 ANTAGONISTS

This application claims priority from U.S. provisional application Ser. No. 61/106,369, filed Oct. 17, 2008 and to U.S. provisional application Ser. No. 61/220,075, filed Jun. 24, 2009, the disclosures of which are incorporated herein as if set forth in their entirety.

TECHNICAL FIELD

Described herein are ureas which are useful for treating pain, cough, bladder overactivity, urinary incontinence, or conditions and disorders modulated by the TRPV1 channel. Pharmaceutical compositions comprising said compounds and methods for treating pain, cough, bladder overactivity, urinary incontinence, or conditions and disorders modulated by the TRPV1 channel are also included.

BACKGROUND

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as the transient receptor potential vanilloid-1 (TRPV1). TRPV1 is also known as vanilloid receptor-1 (VR1). The intradermal administration of capsaicin is characterized by an initial burning or hot sensation followed by a prolonged period of analgesia. The analgesic component of the TRPV1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist can reduce inflammation-induced hyperalgesia in animal models. TRPV1 receptors are also localized on sensory afferents, which innervate the bladder. Capsaicin or resiniferatoxin has been shown to ameliorate incontinence symptoms upon injection into the bladder.

The TRPV1 receptor has been called a "polymodal detector" of noxious stimuli since it can be activated in several ways. The receptor channel is activated by capsaicin and other vanilloids, and thus is classified as a ligand-gated ion channel. The TRPV1 receptor activation by capsaicin can be blocked by the competitive TRPV1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the TRPV1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knock-out mice were insensitive to the noxious effects of intradermal capsaicin, exposure to intense heat (50-55° C.), and failed to develop thermal hyperalgesia following the intradermal administration of carrageenan.

In the course of characterizing analgesic properties of structurally distinct TRPV1 antagonists multiple investigators have observed core body temperature elevating ("hyperthermic") attributes of these compounds in rodent behavioral models of pain (Swanson, D. M. et al. *J. Med. Chem.* 2005, 48, 1857; Gavva, N. R. et al. *J. Pharmacol. Exp. Ther.* 2007, 323, 128; Steiner, A. A. et al. *J. Neurosci.* 2007, 27, 7459; Tamayo, N. et al. *J. Med. Chem.* 2008, 51, 2744; Gavva, N. R. et al. *J. Neurosci.* 2007, 27, 3366). Often modest (0.5° C.), the associated temperature elevation can be considerably more robust (1-2° C.), and also has been reported preclinically in dogs and monkeys (Gavva, N. R. et al. *J. Pharmacol. Exp. Ther.* 2007, 323, 128; Gavva, N. R. et al. *J. Neurosci.* 2007, 27, 3366) and in human subjects in the course of clinical trials (Gavva, N. R. et al. *Pain* 2008, 136, 202). These effects have the potential to be self-limiting; they are generally transient and attenuate with repeat dosing (Gavva, N. R. et al. *J. Pharmacol. Exp. Ther.* 2007, 323, 128). Since TRPV1 null mice show no deficits in thermoregulation, the temperature effects are considered to be mechanism based (Iida, T. et al. *Neurosci. Lett.* 2005, 378, 28). Finding that antagonism of TRPV1 elicits increased body temperature is not wholly unanticipated. The channel's canonical agonist, capsaicin, has been known to cause profound hypothermia for more than 130 years (reviewed in Jancso-Gabor. A. et al. *J. Physiol.* 1970, 206, 495), and more recent work demonstrated that this decreased body temperature is TRPV1-dependent (Caterina, M. J. et al. *Science* 2000, 288, 306). The response is generally attributed to cutaneous vasodilation and hypersalivation. The extent of hyperthermia elicited by TRPV1 antagonists is independent of route of administration, suggesting that thermal effects associated with modulation of TRPV1 are not primarily autonomic hypothalamic responses. Instead, accumulating evidence suggests that the temperature elevation signaling pathway initiates in the periphery and is triggered by abdominal TRPV1 that induces vasoconstriction and increased thermogenesis (Steiner, A. A. et al. *J. Neurosci.* 2007, 27, 7459; Gavva, N. R. et al. *Pain* 2008, 136, 202).

Efforts to understand and separate the nociceptive and thermoregulatory functions of TRPV1 have led to directed research to identify antagonists that afford analgesic benefit without affecting core body temperature (Lehto, S. G. et al. *J. Pharmacol. Exp. Ther.* 2008, 326, 218). The polymodal character of TRPV1 offers opportunities to examine whether antagonists exhibit distinctive blockade profiles in response to activation by different stimuli (e.g., capsaicin, extracellular protons, heat >42° C., endogenous lipid ligands) that may portend their ability to modulate channel activity with or without hyperthermic effects.

Certain chromane derivatives that are TRPV1 modulators are discussed in the following publications: WO 2007/042906, WO 2008/059339, US 2006/0128689, WO 2007/121299, US 2008/0153871, and WO 2008/110863.

We describe herein TRPV1 antagonists that possess distinctive blockade profiles in response to activation by different stimuli and exhibit little or no hyperthermic effects.

SUMMARY

One aspect is directed towards compounds of formula (I) or pharmaceutical salts, solvates, prodrugs, salts of prodrugs, or combinations thereof,

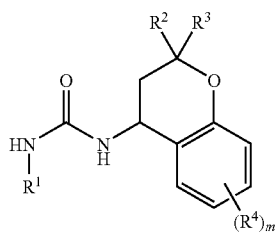

(I)

wherein $R^1$ represents a group of formula (a), (b), (c), or (d)

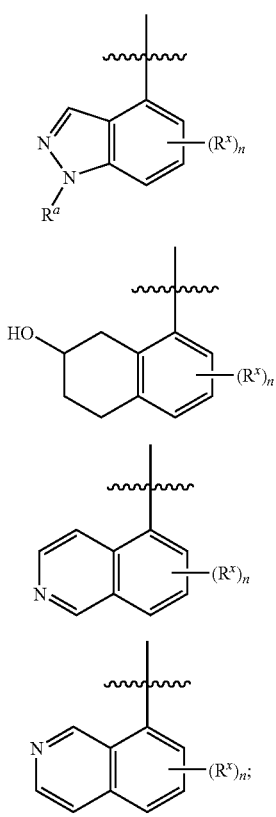

$R^x$, at each occurrence, represents optional substituent(s) on any substitutable position of the bicyclic ring, and is selected from the group consisting of alkyl, halogen, haloalkyl, OH, O(alkyl), O(haloalkyl), $NH_2$, N(H)(alkyl), and $N(alkyl)_2$;

$R^a$ is hydrogen or methyl;

$R^2$ and $R^3$ are the same or different and are each independently hydrogen, $C_1$-$C_5$ alkyl, or haloalkyl; or $R^2$ and $R^3$, together with the carbon atom to which they are attached, form a $C_3$-$C_6$ monocyclic cycloalkyl ring, optionally substituted with 1, 2, or 3 substituents selected from the group consisting of alkyl and halogen;

$R^4$, at each occurrence, represents optional substituent(s) on any substitutable position of the bicyclic ring, and is selected from the group consisting of alkyl, halogen, haloalkyl, O(alkyl), O(haloalkyl), piperidinyl, and $SCF_3$; and m and n are each independently 0, 1, 2, or 3;

with the proviso that the compound is other than
N-(7-tert-butyl-3,4-dihydro-2H-chromen-4-yl)-N'-1H-indazol-4-ylurea;
N-1H-indazol-4-yl-N'-[7-(trifluoromethyl)-3,4-dihydro-2H-chromen-4-yl]urea;
N-isoquinolin-5-yl-N'-[7-(trifluoromethyl)-3,4-dihydro-2H-chromen-4-yl]urea;
N-1H-indazol-4-yl-N'-(6-methyl-3,4-dihydro-2H-chromen-4-yl)urea;
N-isoquinolin-5-yl-N'-(6-methyl-3,4-dihydro-2H-chromen-4-yl)urea;
N-(6-fluoro-3,4-dihydro-2H-chromen-4-yl)-N'-1H-indazol-4-ylurea;
N-(6-fluoro-3,4-dihydro-2H-chromen-4-yl)-N'-isoquinolin-5-ylurea;
N-(6-chloro-7-methyl-3,4-dihydro-2H-chromen-4-yl)-N'-1H-indazol-4-ylurea;
N-(6-chloro-7-methyl-3,4-dihydro-2H-chromen-4-yl)-N'-isoquinolin-5-ylurea;
N-3,4-dihydro-2H-chromen-4-yl-N'-1H-indazol-4-ylurea;
N-(7-tert-butyl-3,4-dihydro-2H-chromen-4-yl)-N'-(3-methylisoquinolin-5-yl)urea;
N-(6-fluoro-3,4-dihydro-2H-chromen-4-yl)-N'-(3-methylisoquinolin-5-yl)urea;
N-(6-methyl-3,4-dihydro-2H-chromen-4-yl)-N'-(3-methylisoquinolin-5-yl)urea;
N-isoquinolin-5-yl-N'-(8-piperidin-1-yl-3,4-dihydro-2H-chromen-4-yl)urea;
N-3,4-dihydro-2H-chromen-4-yl-N'-isoquinolin-5-ylurea;
(+)-N-isoquinolin-5-yl-N'-[7-(trifluoromethyl)-3,4-dihydro-2H-chromen-4-yl]urea;
(−)-N-isoquinolin-5-yl-N'-[7-(trifluoromethyl)-3,4-dihydro-2H-chromen-4-yl]urea;
N-1H-indazol-4-yl-N'-[8-(trifluoromethyl)-3,4-dihydro-2H-chromen-4-yl]urea;
(−)-N-1H-indazol-4-yl-N'-[7-(trifluoromethyl)-3,4-dihydro-2H-chromen-4-yl]urea;
(+)-N-1H-indazol-4-yl-N'-[7-(trifluoromethyl)-3,4-dihydro-2H-chromen-4-yl]urea;
N-1H-indazol-4-yl-N'-(8-piperidin-1-yl-3,4-dihydro-2H-chromen-4-yl)urea;
N-(8-tert-butyl-3,4-dihydro-2H-chromen-4-yl)-N'-1H-indazol-4-ylurea;
N-[8-chloro-7-(trifluoromethyl)-3,4-dihydro-2H-chromen-4-yl]-N'-1H-indazol-4-ylurea;
(+)-N-(8-tert-butyl-3,4-dihydro-2H-chromen-4-yl)-N'-1H-indazol-4-ylurea;
(−)-N-(8-tert-butyl-3,4-dihydro-2H-chromen-4-yl)-N'-1H-indazol-4-ylurea;
N-1H-indazol-4-yl-N'-[8-(trifluoromethoxy)-3,4-dihydro-2H-chromen-4-yl]urea;
N-[8-fluoro-7-(trifluoromethyl)-3,4-dihydro-2H-chromen-4-yl]-N'-1H-indazol-4-ylurea;
N-1H-indazol-4-yl-N'-[7-(trifluoromethoxy)-3,4-dihydro-2H-chromen-4-yl]urea;
N-(6-fluoro-2-methyl-3,4-dihydro-2H-chromen-4-yl)-N'-1H-indazol-4-ylurea;

N-1H-indazol-4-yl-N'-(7-methoxy-2,2-dimethyl-3,4-dihydro-2H-chromen-4-yl)urea;
N-1H-indazol-4-yl-N'-(7-methoxy-2,2,8-trimethyl-3,4-dihydro-2H-chromen-4-yl)urea;
N-1H-indazol-4-yl-N'-(2,2,8-trimethyl-3,4-dihydro-2H-chromen-4-yl)urea;
N-1H-indazol-4-yl-N'-(7-methoxy-2,2-dimethyl-8-propyl-3,4-dihydro-2H-chromen-4-yl)urea;
N-(2,2-dimethyl-3,4-dihydro-2H-chromen-4-yl)-N'-1H-indazol-4-ylurea;
N-(7-fluoro-2,2-dimethyl-3,4-dihydro-2H-chromen-4-yl)-N'-1H-indazol-4-ylurea;
N-(7-fluoro-2,2-diethyl-3,4-dihydro-2H-chromen-4-yl)-N'-1H-indazol-4-ylurea;
N-(7,8-difluoro-2,2-dimethyl-3,4-dihydro-2H-chromen-4-yl)-N'-1H-indazol-4-ylurea;
N-(7-(3,3-dimethylbutyl)-3,4-dihydro-2H-chromen-4-yl)-N'-1H-indazol-4-ylurea;
N-(7-tert-butyl-2,2-dimethyl-3,4-dihydro-2H-chromen-4-yl)-N'-1H-indazol-4-ylurea;
N-(2,2-diethyl-7-fluoro-3,4-dihydro-2H-chromen-4-yl)-N'-(1-methyl-1H-indazol-4-yl)urea;
N-(7,8-difluoro-3,4-dihydro-2H-chromen-4-yl)-N'-1H-indazol-4-ylurea;
N-(7-fluoro-2,2-dipropyl-3,4-dihydro-2H-chromen-4-yl)-N'-1H-indazol-4-ylurea;
N-(2,2-dibutyl-7-fluoro-3,4-dihydro-2H-chromen-4-yl)-N'-1H-indazol-4-ylurea;
N-(2-tert-butyl-7-fluoro-3,4-dihydro-2H-chromen-4-yl)-N'-1H-indazol-4-ylurea;
N-(2-tert-butyl-7-fluoro-3,4-dihydro-2H-chromen-4-yl)-N'-(1-methyl-1H-indazol-4-yl)urea;
N-(8-tert-Butyl-3,4-dihydro-2H-chromen-4-yl)-N'-(7-hydroxy-5,6,7,8-tetrahydronaphthalen-1-yl)urea;
N-(7-Hydroxy-5,6,7,8-tetrahydronaphthalen-1-yl)-N'-(6-methyl-3,4-dihydro-2H-chromen-4-yl)urea;
N-[(4R)-3,4-Dihydro-2H-chromen-4-yl]-N'-(7-hydroxy-5,6,7,8-tetrahydronaphthalen-1-yl)urea;
N-[(4S)-3,4-Dihydro-2H-chromen-4-yl]-N'-(7-hydroxy-5,6,7,8-tetrahydronaphthalen-1-yl)urea;
1-(1H-indazol-4-yl)-3-(spiro[chroman-2,1'-cyclohexane]-4-yl)urea;
1-(7-fluorospiro[chroman-2,1'-cyclohexane]-4-yl)-3-(1H-indazol-4-yl)urea;
1-(7-fluorospiro[chroman-2,1'-cyclobutane]-4-yl)-3-(1H-indazol-4-yl)urea;
1-(7-fluorospiro[chroman-2,1'-cyclobutane]-4-yl)-3-(1-methyl-1H-indazol-4-yl)urea;
1-(6,7-dimethylspiro[chroman-2,1'-cyclohexane]-4-yl)-3-(1H-indazol-4-yl)urea;
1-(6,8-dichlorospiro[chroman-2,1'-cyclohexane]-4-yl)-3-(1H-indazol-4-yl)urea;
1-(6-chlorospiro[chroman-2,1'-cyclohexane]-4-yl)-3-(1H-indazol-4-yl)urea;
1-(7-tert-butylspiro[chroman-2,1'-cyclobutane]-4-yl)-3-(1H-indazol-4-yl)urea;
1-(6,8-difluorospiro[chroman-2,1'-cyclohexane]-4-yl)-3-(1H-indazol-4-yl)urea;
1-(6-ethoxyspiro[chroman-2,1'-cyclohexane]-4-yl)-3-(1H-indazol-4-yl)urea;
1-(1H-indazol-4-yl)-3-(6-methylspiro[chroman-2,1'-cyclopentane]-4-yl)urea;
1-(7-ethoxyspiro[chroman-2,1'-cyclopentane]-4-yl)-3-(1H-indazol-4-yl)urea;
1-(6,7-dimethylspiro[chroman-2,1'-cyclopentane]-4-yl)-3-(1H-indazol-4-yl)urea;
1-(7-fluorospiro[chroman-2,1'-cyclohexane]-4-yl)-3-(1-methyl-1H-indazol-4-yl)urea;
1-(1-methyl-1H-indazol-4-yl)-3-(spiro[chroman-2,1'-cyclohexane]4-yl)urea;
1-(1H-indazol-4-yl)-3-(7-methoxyspiro[chroman-2,1'-cyclohexane]-4-yl)urea;
(±)1-(3,4-dihydro-2,2-dimethyl-2H-1-benzopyran-4-yl)-3-(isoquinolin-5-yl)urea;
(±)1-(7-chloro-3,4-dihydro-2,2-dimethyl-2H-1-benzopyran-4-yl)-3-(isoquinolin-5-yl)urea;
(±)1-(6-bromo-3,4-dihydro-2,2-dimethyl-2H-1-benzopyran-4-yl)-3-(isoquinolin-5-yl)urea;
(±)1-(6-methoxy-3,4-dihydro-2,2-dimethyl-2H-1-benzopyran-4-yl)-3-(isoquinolin-5-yl)urea;
(±)1-(7-methoxy-3,4-dihydro-2,2-dimethyl-2H-1-benzopyran-4-yl)-3-(isoquinolin-5-yl)urea;
(±)1-(6-methyl-3,4-dihydro-2,2-dimethyl-2H-1-benzopyran-4-yl)-3-(isoquinolin-5-yl)urea;
(±)1-(7-methoxy-3,4-dihydro-2,2-dimethyl-2H-1-benzopyran-4-yl)-3-(1-methylisoquinolin-5-yl)urea;
(±)1-(6-bromo-3,4-dihydro-2,2-dimethyl-2H-1-benzopyran-4-yl)-3-(1-methylisoquinolin-5-yl)urea;
(±)1-(6-methyl-3,4-dihydro-2,2-dimethyl-2H-1-benzopyran-4-yl)-3-(1-methylisoquinolin-5-yl)urea;
(±)1-(3,4-dihydro-2,2-dimethyl-2H-1-benzopyran-4-yl)-3-(1-methylisoquinolin-5-yl)urea;
(±)1-(3,4-dihydro-spiro-[2H-1-benzopyran-2,1'-cyclobutan]-4-yl)-3-(isoquinolin-5-yl)urea;
(+)1-(3,4-dihydro-spiro-[2H-1-benzopyran-2,1'-cyclobutan]-4-yl)-3-(isoquinolin-5-yl)urea;
(−)1-(3,4-dihydro-spiro-[2H-1-benzopyran-2,1'-cyclobutan]-4-yl)-3-(isoquinolin-5-yl)urea;
(±)1-(3,4-dihydro-spiro-[2H-1-benzopyran-2,1'-cyclobutan]-4-yl)-3-(8-chloroisoquinolin-5-yl)urea;
(±)1-(3,4-dihydro-spiro-[2H-1-benzopyran-2,1'-cyclobutan]-4-yl)-3-(3-methylisoquinolin-5-yl)urea;
(±)1-(3,4-dihydro-spiro-[2H-1-benzopyran-2,1'-cyclobutan]-4-yl)-3-(1-methylisoquinolin-5-yl)urea;
(±)1-(3,4-dihydro-6-methyl-spiro-[2H-1-benzopyran-2,1'-cyclobutan]-4-yl)-3-(isoquinolin-5-yl)urea;
(±)1-(3,4-dihydro-7-methyl-spiro-[2H-1-benzopyran-2,1'-cyclobutan]-4-yl)-3-(isoquinolin-5-yl)urea;
(±)1-(3,4-dihydro-6-fluoro-spiro-[2H-1-benzopyran-2,1'-cyclobutan]-4-yl)-3-(isoquinolin-5-yl)urea;
(+)1-(3,4-dihydro-6-fluoro-spiro-[2H-1-benzopyran-2,1'-cyclobutan]-4-yl)-3-(isoquinolin-5-yl)urea;
(−)1-(3,4-dihydro-6-fluoro-spiro-[2H-1-benzopyran-2,1'-cyclobutan]-4-yl)-3-(isoquinolin-5-yl)urea;
(±)1-(3,4-dihydro-7-methoxy-spiro-[2H-1-benzopyran-2,1'-cyclobutan]-4-yl)-3-(isoquinolin-5-yl)urea;
1-(6,8-difluoro-3,4-dihydro-spiro-[2H-1-benzopyran-2,1'-cyclobutan]-4-yl)-3-(isoquinolin-5-yl)urea;
(±)1-(8-chloro-3,4-dihydro-spiro-[2H-1-benzopyran-2,1'-cyclobutan]-4-yl)-3-(isoquinolin-5-yl)urea;
(±)1-(3,4-dihydro-6-methoxy-spiro-[2H-1-benzopyran-2,1'-cyclobutan]-4-yl)-3-(isoquinolin-5-yl)urea;
(±)1-(7-difluoromethoxy-3,4-dihydro-spiro-[2H-1-benzopyran-2,1'-cyclobutan]-4-yl)-3-(isoquinolin-5-yl)urea hydrochloride;
(±)1-(7-difluoromethoxy-3,4-dihydro-spiro-[2H-1-benzopyran-2,1'-cyclobutan]-4-yl)-3-(3-methylisoquinolin-5-yl)urea;
(±)1-(7-chloro-3,4-dihydro-spiro-[2H-1-benzopyran-2,1'-cyclobutan]-4-yl)-3-(3-methylisoquinolin-5-yl)urea;
(+)1-(6,8-difluoro-3,4-dihydro-spiro-[2H-1-benzopyran-2,1'-cyclobutan]-4-yl)-3-(isoquinolin-5-yl)urea;

(−)1-(6,8-difluoro-3,4-dihydro-spiro-[2H-1-benzopyran-2,1'-cyclobutan]-4-yl)-3-(isoquinolin-5-yl)urea;
(±)1-(3,4-dihydro-8-difluoromethoxy-spiro-[2H-1-benzopyran-2,1'-cyclobutan]-4-yl)-3-(isoquinolin-5-yl)urea;
(±)1-(6-chloro-3,4-dihydro-spiro-[2H-1-benzopyran-2,1'-cyclobutan]-4-yl)-3-(isoquinolin-5-yl)urea;
(−)1-(6-chloro-3,4-dihydro-spiro-[2H-1-benzopyran-2,1'-cyclobutan]-4-yl)-3-(isoquinolin-5-yl)urea;
(±)1-(6-bromo-3,4-dihydro-spiro-[2H-1-benzopyran-2,1'-cyclobutan]-4-yl)-3-(isoquinolin-5-yl)urea;
(±)1-(6,8-dichloro-3,4-dihydro-spiro-[2H-1-benzopyran-2,1'-cyclobutan]-4-yl)-3-(isoquinolin-5-yl)urea;
(±)1-(6-bromo-3,4-dihydro-7-methylspiro-[2H-1-benzopyran-2,1'-cyclobutan]-4-yl)-3-(isoquinolin-5-yl)urea;
(±)1-(6,7-dichloro-3,4-dihydro-spiro-[2H-1-benzopyran-2,1'-cyclobutan]-4-yl)-3-(isoquinolin-5-yl)urea;
(±)1-(6-chloro-3,4-dihydro-7-methylspiro-[2H-1-benzopyran-2,1'-cyclobutan]-4-yl)-3-(isoquinolin-5-yl)urea;
(±)1-(6-chloro-3,4-dihydro-spiro-[2H-1-benzopyran-2,1'-cyclobutan]-4-yl)-3-(8-chloroisoquinolin-5-yl)urea;
(±)1-(6-fluoro-3,4-dihydro-spiro-[2H-1-benzopyran-2,1'-cyclobutan]-4-yl)-3-(8-chloroisoquinolin-5-yl)urea;
(±)1-(3,4-dihydro-6-fluoro-spiro-[2H-1-benzopyran-2,1'-cyclobutan]-4-yl)-3-(3-methylisoquinolin-5-yl)urea;
(±)1-(6-chloro-3,4-dihydro-spiro-[2H-1-benzopyran-2,1'-cyclobutan]-4-yl)-3-(3-methylisoquinolin-5-yl)urea;
(±)1-(6-chloro-3,4-dihydro-spiro-[2H-1-benzopyran-2,1'-cyclobutan]-4-yl)-3-(1-methylisoquinolin-5-yl)urea;
(±)1-(3,4-dihydro-6-fluoro-spiro-[2H-1-benzopyran-2,1'-cyclobutan]-4-yl)-3-(1-methylisoquinolin-5-yl)urea;
(±)1-(7-chloro-3,4-dihydro-spiro-[2H-1-benzopyran-2,1'-cyclobutan]-4-yl)-3-(isoquinolin-5-yl)urea;
(±)1-(3,4-dihyrospiro[chromene-2,1'-cyclobutan]-4-yl)-3-(1H-indazol-4-yl)urea;
(−)-1-(3,4-dihyrospiro[chromene-2,1'-cyclobutan]-4-yl)-3-(1H-indazol-4-yl)urea;
(+)-1-(3,4-dihyrospiro[chromene-2,1'-cyclobutan]-4-yl)-3-(1H-indazol-4-yl)urea;
(±)1-(6-fluoro-3,4-dihyrospiro[chromene-2,1'-cyclobutan]-4-yl)-3-(1H-indazol-4-yl)urea;
(±)1-(7-fluoro-3,4-dihyrospiro[chromene-2,1'-cyclobutan]-4-yl)-3-(1H-indazol-4-yl)urea;
(±)1-(6,8-difluoro-3,4-dihyrospiro[chromene-2,1'-cyclobutan]-4-yl)-3-(1H-indazol-4-yl)urea;
(+)-1-(6,8-difluoro-3,4-dihyrospiro[chromene-2,1'-cyclobutan]-4-yl)-3-(1H-indazol-4-yl)urea;
(±)1-(1H-indazol-4-yl)-3-(7-methyl-3,4-dihydrospiro[chromene-2,1'-cyclobutan]-4-yl)urea;
(±)1-(1H-indazol-4-yl)-3-(7-methoxy-3,4-dihydrospiro[chromene-2,1'-cyclobutan]-4-yl)urea;
(±)1-(1H-indazol-4-yl)-3-(7-chloro-3,4-dihydrospiro[chromene-2,1'-cyclobutan]-4-yl)urea;
(±)1-(3,4-dihyrospiro[chromene-2,1'-cyclobutan]-4-yl)-3-(6-bromo-1H-indazol-4-yl)urea;
(±)1-(3,4-dihyrospiro[chromene-2,1'-cyclobutan]-4-yl)-3-(6-fluoro-1H-indazol-4-yl)urea;
(+)-1-(3,4-dihyrospiro[chromene-2,1'-cyclobutan]-4-yl)-3-(6-fluoro-1H-indazol-4-yl)urea;
(±)1-(3,4-dihyrospiro[chromene-2,1'-cyclobutan]-4-yl)-3-(6-methoxy-1H-indazol-4-yl)urea; or
(−)-1-(6,8-difluoro-3,4-dihyrospiro[chromene-2,1'-cyclobutan]-4-yl)-3-(1H-indazol-4-yl)urea.

Another aspect is related to methods for treating ischemia such as acute cerebral ischemia, cerabrovascular ischemia; pain such as chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain; bladder disease such as incontinence, bladder overactivity, micturition disorder, renal colic and cystitis; inflammation such as burns, rheumatoid arthritis and osteoarthritis; neurodegenerative disease such as stroke and multiple sclerosis; pulmonary disease such as asthma, cough, chronic obstructive pulmonary disease (COPD) and broncho constriction; gastrointestinal disease such as gastroesophageal reflux disease (GERD), dysphagia, ulcer, irritable bowel syndrome (IBS), inflammatory bowel disease (IBD), colitis and Crohn's disease; emesis such as cancer chemotherapy-induced emesis, or obesity, said method comprising the step of administering therapeutically effective amounts of one or more compounds described herein, or pharmaceutically acceptable salts or solvates thereof, to a subject in need thereof, alone or in combination with one or more analgesics (e.g. acetaminophen), or one or more nonsteroidal anti-inflammatory drug (NSAID), or combinations thereof, and with or without one or more pharmaceutically acceptable carriers.

Further, included herein are uses of present compounds or pharmaceutically acceptable salts or solvates thereof, in the manufacture of medicaments for the treatment of the diseases or conditions described above, with or without one or more pharmaceutically acceptable carrier, and alone, or in combination with one or more analgesics (e.g. acetaminophen, opioids), or with one or more nonsteroidal anti-inflammatory drug (NSAID), or combinations thereof.

These and other objectives of the invention are described in the following paragraphs. These objects should not be deemed to narrow the scope of the invention.

BRIEF DESCRIPTION OF THE DRAWINGS

FIG. 1 shows the effects of the compound of (A) Example 56, (B) Example 62, (C) Example 55, (D) Example 61, (E) Example 26, and (F) AMG628 on intracellular calcium level responses in two individual representative cells (designated by solid or dotted line) to capsaicin or acid, as measured using ratiometric calcium imaging. The black bars above the traces designate addition and duration of different solution applications. Spaces between horizontal bars represent periods in which cells were perfused with D-PBS, pH 7.4 alone.

DETAILED DESCRIPTION

Disclosed herein are compounds of formula (I)

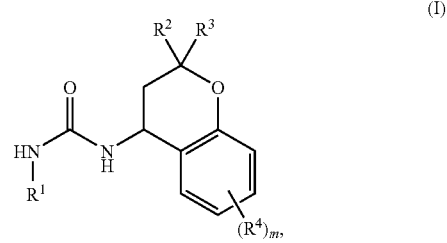

(I)

wherein $R^1$, $R^2$, $R^3$, $R^4$, and m are as defined above in the Summary of the Invention and below in the Detailed Description. Compositions comprising such compounds and methods for treating conditions and disorders using such compounds and compositions are also disclosed.

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds, which can be isolated from a reaction mixture.

a). DEFINITIONS

As used in the specification and the appended claims, unless specified to the contrary, the following terms have the meaning indicated:

The term "alkyl" as used herein, means a saturated, straight or branched hydrocarbon chain containing from 1 to 10 carbon atoms. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_5$ alkyl" refers to an alkyl substituent containing from 1 to 5 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "$C_3$-$C_6$ monocyclic cycloalkyl" means an optionally substituted monocyclic ring selected from the group consisting of cyclopropyl, cyclobutyl, cyclopentyl, and cyclohexyl, each of which is optionally substituted.

The term "haloalkyl" as used herein, means an alkyl group, as defined herein, in which one, two, three, four, five, six, or seven hydrogen atoms are replaced by halogen. The term "lower haloalkyl" means a $C_1$-$C_6$ alkyl group in which one, two, three, four, five, six, or seven hydrogen atoms are replaced by halogen. Representative examples of haloalkyl and lower haloalkyl include, but are not limited to, chloromethyl, fluoromethyl, 2-fluoroethyl, 2,2-difluoroethyl, trifluoromethyl, 2,2,2-trifluoroethyl, difluoromethyl, pentafluoroethyl, 2-chloro-3-fluoropentyl, and 2-iodoethyl.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

b) COMPOUNDS

TRPV1 antagonists have formula (I) as described above.

Particular values of variable groups in compounds of formula (I) are as follows. Such values may be used where appropriate with any of the other values, definitions, claims or embodiments defined hereinbefore or hereinafter.

In compounds of formula (I), $R^1$ represents formula (a), (b), (c), or (d)

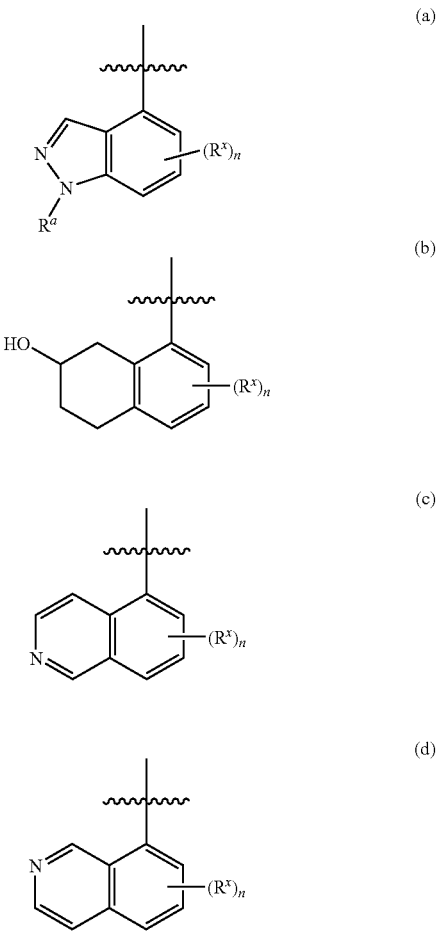

wherein $R^a$, $R^x$, and n are as defined in the Summary. In one embodiment, $R^1$ represents formula (a). In another embodiment, $R^1$ represents formula (b). In yet another embodiment, $R^1$ represents formula (c). In a further embodiment, $R^1$ represents formula (d).

$R^x$, if present, includes, but not limited to, alkyl (e.g. $C_1$-$C_3$ alkyl such as, but not limited to, methyl), halogen (including, but not limited to, Cl), and $NH_2$. In certain embodiments, $R^x$, if present, is alkyl (e.g. $C_1$-$C_3$ alkyl such as, but not limited to, methyl) or halogen. In certain embodiments, $R^x$, if present, is alkyl (e.g. $C_1$-$C_3$ alkyl such as, but not limited to, methyl). n, for example, is 0, 1, or 2. In certain embodiments, n is 0 or 1. In certain embodiment, n is 0. In yet other embodiments, n is 1. In the embodiments wherein n is 1 or 2, and $R^1$ is formula (c), it is preferred that at least one of the $R^x$ groups is attached to the 3-position of the isoquinoline ring. Thus, include herein are compounds of formula (I-i) and salts or solvates thereof

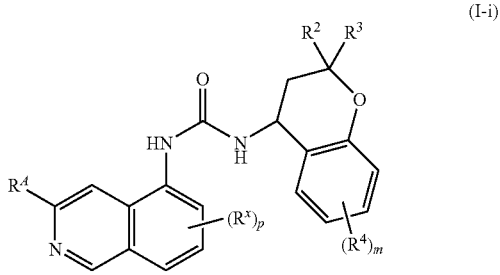

(I-i)

wherein $R^4$ is methyl, $NH_2$, or Cl, p is 0 or 1, and $R^x$, $R^2$, $R^3$, $R^4$, and m have meanings as disclosed for formula (I) in the Summary and Detailed Description sections.

$R^2$ and $R^3$ have values as described in the Summary and in embodiments herein. In certain embodiments, $R^2$ and $R^3$ are each independently hydrogen, $C_1$-$C_5$ alkyl (e.g. $C_1$-$C_3$ alkyl such as, but not limited to, methyl, ethyl, n-propyl), or haloalkyl (e.g. fluoromethyl, difluoromethyl). For example, in certain embodiments, $R^2$ and $R^3$ are the same or different, and can be each independently hydrogen, methyl, ethyl, n-propyl, fluoromethyl, or difluoromethyl. Included are, for example, compounds of formula (I) or (I-i) wherein $R^2$ and $R^3$ are hydrogen. In certain embodiments, at least one of $R^2$ and $R^3$ is other than hydrogen. In certain embodiments, $R^2$ and $R^3$ are the same or different, and can be each independently $C_1$-$C_5$ alkyl (e.g. $C_1$-$C_3$ alkyl such as, but not limited to, methyl, ethyl, n-propyl) or haloalkyl (e.g. fluoromethyl, difluoromethyl). In yet other embodiments, $R^2$ and $R^3$ are the same or different, and are each independently $C_1$-$C_5$ alkyl (e.g. $C_1$-$C_3$ alkyl such as, but not limited to, methyl, ethyl, n-propyl) or haloalkyl (e.g. fluoromethyl, difluoromethyl), with the proviso that at least one of them is haloalkyl. In certain embodiments, one of $R^2$ and $R^3$ is $C_1$-$C_5$ alkyl (e.g. $C_1$-$C_3$ alkyl such as, but not limited to, methyl, ethyl, n-propyl), and the other is haloalkyl (e.g. fluoromethyl, difluoromethyl). In yet other embodiments, $R^2$ and $R^3$ are the same or different, and are each haloalkyl (e.g. fluoromethyl, difluoromethyl).

In other embodiments, $R^2$ and $R^3$, together with the carbon atom to which they are attached, form a $C_3$-$C_6$ monocyclic cycloalkyl ring, optionally substituted with 1, 2, or 3 substituents selected from the group consisting of alkyl and halogen. Contemplated, but not limited to, are compounds of formula (I) or (I-i) wherein $R^2$ and $R^3$, together with the carbon atom to which they are attached, form an unsubstituted cyclobutyl ring.

$R^4$ has values as generally described in the Summary and the embodiments herein. For example, $R^4$, if present, is alkyl (e.g. $C_1$-$C_5$ alkyl including, but not limited to, methyl, tert-butyl), halogen (including, but not limited to, F, Cl, Br), haloalkyl (including, but not limited to, trifluoromethyl), O(haloalkyl) (e.g. $OCF_3$), or piperidinyl. In certain embodiments, $R^4$, if present, is alkyl (e.g. $C_1$-$C_5$ alkyl including, but not limited to, methyl, tert-butyl), halogen (including, but not limited to, F, Cl, Br), haloalkyl (including, but not limited to, trifluoromethyl), or O(haloalkyl) (e.g. $OCF_3$). In certain embodiments, $R^4$, if present, is halogen (e.g., F, Cl) or haloalkyl (e.g., trifluoromethyl). m, for example, is 0, 1, or 2. In certain embodiments, m is 0. In certain embodiments, m is 1. In certain embodiments, m is 2.

The present compounds may contain an asymmetrically substituted carbon atom in the 3,4-dihydrochromene ring of formula (I) wherein the configuration of the carbon atom bearing the NH group is assigned as (4R) (as depicted by formula (Ia)) or (4S) (as depicted by formula (Ib)) as defined by the IUPAC 1974 Recommendations for Section E, Fundamental Stereochemistry, Pure Appl. Chem. 1976 45, 13-30.

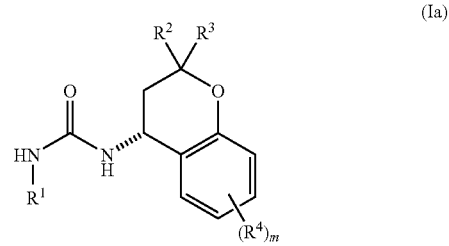

(Ia)

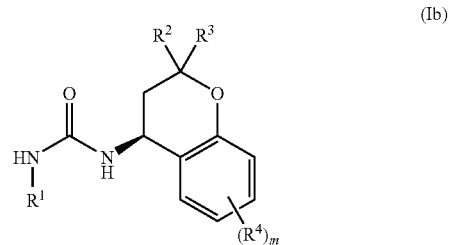

(Ib)

wherein $R^1$, $R^2$, $R^3$, $R^4$, and m have values as described generally in the Summary and in the embodiments for compounds of formula (I).

It will be appreciated two or more asymmetric centers may be present in the compounds of the invention, as exemplified by, but not limited to, formula (Ic) and (Id)

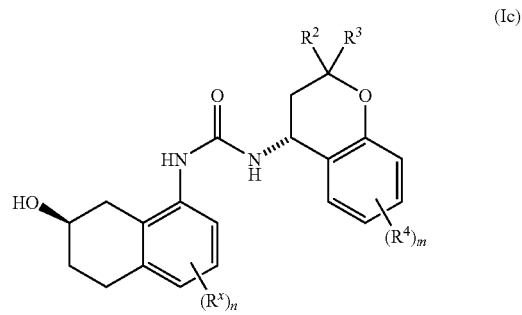

(Ic)

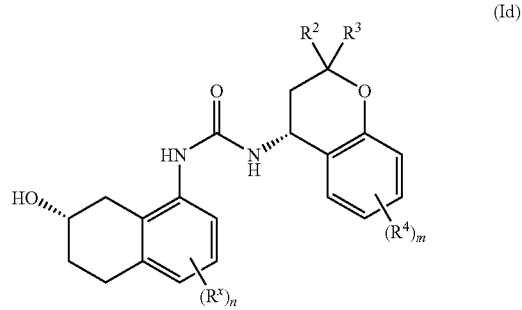

(Id)

wherein $R^2$, $R^3$, $R^4$, $R^x$, m, and n have values as described generally in the Summary and in the embodiments herein.

It is understood that embodiments for $R^1$, $R^2$, $R^3$, $R^4$, $R^x$, m, and n, and combinations of embodiments, including particular, and more particular embodiments as described for formula (I) are also contemplated for compounds of formula (Ia), (Ib), (Ic), and (Id).

It is intended that pure diasteromers, pure enantiomers, and mixtures thereof, are within the scope of the invention.

The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers and mixtures thereof are included in the scope of the invention.

The compounds of the invention also include those compounds in which one or more atoms have been replaced by their stable, non-radioactive isotopes, for example, a hydrogen atom by deuterium.

Stable isotopes (e.g., deuterium, $^{13}C$, $^{15}N$, $^{18}O$) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 1975, 64, 367-391). Such metabolic studies are important in the design of safe, effective therapeutic drugs, either because the in vivo active compound administered to the patient or because the metabolites produced from the parent compound prove to be toxic or carcinogenic (Foster et al. Advances in Drug Research Vol. 14, pp. 2-36, Academic press, London, 1985; Kato et al. *J. Labelled Comp. Radiopharmaceut.* 1995, 36(10), 927-932; Kushner et al. *Can. J. Physiol. Pharmacol.* 1999, 77, 79-88).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a carbon-deuterium bond can be up to 700 percent slower than a similar reaction involving breaking a carbon-hydrogen bond. If the carbon-deuterium bond is not involved in any of the steps leading to the metabolite, there may not be any effect to alter the behavior of the drug. If a deuterium is placed at a site involved in the metabolism of a drug, an isotope effect will be observed only if breaking of the carbon-deuterium bond is the rate limiting step. There is evidence to suggest that whenever cleavage of an aliphatic carbon-hydrogen bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons, G. and Rey, E. *Pediatrics* 1999, 104, 633; Coward, W. A. et al. *Lancet* 1979, 7, 13; Schwarcz, H. P. *Control. Clin. Trials* 1984, 5(4 Suppl), 573; Rodewald. L. E. et al. *J. Pediatr.* 1989, 114, 885; Butte, N. F. et al. *Br. J. Nutr.* 1991, 65, 3; MacLennan, A. H. et al. *Am. J. Obstet. Gynecol.* 1981, 139, 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka, D. M. and Finkel, A. J. *Ann. N.Y. Acad. Sci.* 1960, 84, 770; Thomson, J. F. *Ann. New York Acad. Sci.* 1960, 84, 736; Czakja, D. M. et al. *Am. J. Physiol.* 1961, 201, 357). Higher deuterium concentrations, usually in excess of 20%, can be toxic in animals. However, acute replacement of as high as 15%-23% of the hydrogen in humans' fluids with deuterium was found not to cause toxicity (Blagojevic, N. et al. in "Dosimetry & Treatment Planning for Neutron Capture Therapy", Zamenhof, R., Solares, G. and Harling, O., Eds., 1994. Advanced Medical Publishing, Madison, Wis. pp. 125-134; No authors listed *Diabetes Metab.* 1997, 23: 251).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J. et al. *Drug Future*, 1996, 21(11), 1116; Brickner, S. J. et al. *J. Med. Chem.* 1996, 39(3), 673; Mallesham, B. et al. *Org. Lett.* 2003, 5(7), 963 (2003); PCT publications WO1997/010223, WO2005/099353, WO1995/007271, WO2006/008754; U.S. Pat. Nos. 7,538,189, 7,534,814, 7,531,685, 7,528,131, 7,521,421, 7,514,068, 7,511,013; and US Patent Application Publication Nos. 2009/0137457; 2009/0131485; 2009/0131363; 2009/0118238; 2009/0111840; 2009/0105338; 2009/0105307; 2009/0105147; 2009/0093422; 2009/0088416; 2009/0082471, the methods are hereby incorporated by reference.

It is appreciated that the present application contemplates compounds of formula (I), (Ia)-(Id) with combinations of the above embodiments, including particular, more particular and preferred embodiments.

Accordingly, one aspect relates to a group of compounds of formula (I), (Ia) or (Ib), or pharmaceutically acceptable salts or solvates thereof, wherein $R^2$ and $R^3$ are the same or different and are each independently hydrogen, $C_1$-$C_5$ alkyl, or haloalkyl; and $R^1$ is formula (a).

Another aspect relates to a group of compounds of formula (I), (Ia) or (Ib), or pharmaceutically acceptable salts or solvates thereof, wherein $R^2$ and $R^3$ are the same or different, and are each independently $C_1$-$C_5$ alkyl or haloalkyl, with the proviso that at least one of $R^2$ and $R^3$ is haloalky; and $R^1$ is formula (a).

Another aspect of the invention relates to a group of compounds of formula (I), (Ia), or (Ib), or pharmaceutically acceptable salts or solvates thereof, wherein $R^2$ and $R^3$ are the same or different, and are each independently $C_1$-$C_5$ alkyl or haloalkyl, and $R^1$ is formula (b).

Yet another aspect relates to a group of compounds of formula (I), (Ia), or (Ib), or pharmaceutically acceptable salts or solvates thereof, wherein $R^2$ and $R^3$ are the same or different, and are each independently $C_1$-$C_5$ alkyl or haloalkyl, and $R^1$ is formula (c).

Yet another aspect relates to a group of compounds of formula (I), (Ia), or (Ib), or pharmaceutically acceptable salts or solvates thereof, wherein $R^2$ and $R^3$ are the same or different, and are $C_1$-$C_5$ alkyl, and $R^1$ is formula (c).

Yet another aspect relates to a group of compounds of formula (I), (Ia), or (Ib), or pharmaceutically acceptable salts or solvates thereof, wherein one of $R^2$ and $R^3$ is $C_1$-$C_5$ alkyl and the other is haloalkyl, and $R^1$ is formula (c).

Yet another aspect relates to a group of compounds of formula (I), (Ia), or (Ib), or pharmaceutically acceptable salts or solvates thereof, wherein $R^2$ and $R^3$ are the same or different, and are haloalkyl, and $R^1$ is formula (c).

Yet another aspect relates to a group of compounds of formula (I), (Ia), or (Ib), or pharmaceutically acceptable salts or solvates thereof, wherein $R^2$ and $R^3$ are the same or different, and are each independently $C_1$-$C_5$ alkyl or haloalkyl, and $R^1$ is formula (d).

A further aspect relates to a group of compounds of formula (I), (Ia), or (Ib), or pharmaceutically acceptable salts or solvates thereof, wherein $R^2$ and $R^3$, together with the carbon atom to which they are attached, form a $C_3$-$C_6$ monocyclic cycloalkyl ring, optionally substituted with 1, 2, or 3 substituents selected from the group consisting of alkyl and halogen, and $R^1$ is formula (a). In certain embodiments $R^2$ and $R^3$, together with the carbon atom to which they are attached, form an unsubstituted cyclobutyl ring.

Another aspect relates to a group of compounds of formula (I), (Ia), or (Ib), or pharmaceutically acceptable salts or solvates thereof, wherein $R^2$ and $R^3$, together with the carbon atom to which they are attached, form a $C_3$-$C_6$ monocyclic cycloalkyl ring, optionally substituted with 1, 2, or 3 substituents selected from the group consisting of alkyl and halogen, and $R^1$ is formula (b). In certain embodiments $R^2$ and $R^3$, together with the carbon atom to which they are attached, form an unsubstituted cyclobutyl ring.

Yet another aspect relates to a group of compounds of formula (I), or (Ia), or (Ib), or pharmaceutically acceptable salts or solvates thereof, wherein $R^2$ and $R^3$, together with the carbon atom to which they are attached, form a $C_3$-$C_6$ monocyclic cycloalkyl ring, optionally substituted with 1, 2, or 3 substituents selected from the group consisting of alkyl and halogen, and $R^1$ is formula (c). In certain embodiments $R^2$ and $R^3$, together with the carbon atom to which they are attached, form an unsubstituted cyclobutyl ring.

Yet another aspect relates to a group of compounds of formula (I), (Ia), or (Ib), or pharmaceutically acceptable salts or solvates thereof, wherein $R^2$ and $R^3$, together with the carbon atom to which they are attached, form a $C_3$-$C_6$ monocyclic cycloalkyl ring, optionally substituted with 1, 2, or 3 substituents selected from the group consisting of alkyl and halogen, and $R^1$ is formula (d). In certain embodiments $R^2$ and $R^3$, together with the carbon atom to which they are attached, form an unsubstituted cyclobutyl ring.

Within each group of compounds of formula (I), (Ia)-(Id), and (I-i) as described in the preceding paragraphs, $R^x$, $R^4$, m, and n have values as disclosed in the Summary and Detailed Description sections.

Thus, for all the foregoing groups of compounds of formula (I), (Ia)-(Id), and (I-i) as described above, examples of a subgroup include, but are not limited to, those wherein $R^4$, if present, is alkyl (e.g. $C_1$-$C_5$ alkyl including, but not limited to, methyl, tert-butyl), halogen (including, but not limited to, F, Cl, Br), haloalkyl (including, but not limited to, trifluoromethyl), O(halolakyl) (e.g. $OCF_3$), or piperidinyl.

Other examples of a subgroup include, but are not limited to, those wherein $R^4$, if present, is alkyl, halogen, haloalkyl, or O(halolakyl).

Yet other examples of a subgroup include, but are not limited to, those wherein $R^4$, if if present, is halogen or haloalkyl.

$R^x$, m, and n for each group and subgroup of compounds described above are as described generally in the Summary and in the embodiments described herein above.

For example, one aspect is directed to compounds of formula (I), (Ia), or (Ib) wherein $R^2$ and $R^3$ are the same or different, and are each independently $C_1$-$C_5$ alkyl or haloalkyl, $R^4$ is halogen or haloalkyl, $R^1$ is formula (c), and $R^x$, if present, is alkyl or halogen.

Another aspect is directed to compounds of formula (I), (Ia), or (Ib) wherein one of $R^2$ and $R^3$ is $C_1$-$C_5$ alkyl and the other is haloalkyl, $R^4$ is halogen or haloalkyl, $R^1$ is formula (c), and $R^x$, if present, is alkyl or halogen.

Another aspect is directed to compounds of formula (I), (Ia), or (Ib) wherein $R^2$ and $R^3$ are the same or different, and are each independently $C_1$-$C_5$ alkyl, $R^4$ is halogen or haloalkyl, $R^1$ is formula (c), and $R^x$, if present, is alkyl or halogen.

Another aspect is directed to compounds of formula (I), (Ia), or (Ib) wherein $R^2$ and $R^3$ are the same or different, and are each independently haloalkyl, $R^4$ is halogen or haloalkyl, $R^1$ is formula (c), and $R^x$, if present, is alkyl or halogen.

Included, but not limited to, are compounds of formula (I-i) wherein $R^2$ and $R^3$ are the same or different, and are each independently $C_1$-$C_5$ alkyl or haloalkyl, $R^4$ is alkyl, halogen, haloalkyl, or O(haloalkyl), and $R^x$, if present, is alkyl or halogen. In certain embodiments, $R^x$, if present, is halogen such as, but not limited to, F. In certain embodiments, $R^x$ is absent.

Other examples of compounds of formula (I-i) include, but are not limited to, those wherein one of $R^2$ and $R^3$ is $C_1$-$C_5$ alkyl and the other is haloalkyl, $R^4$ is alkyl, halogen, haloalkyl, or O(haloalkyl), and $R^x$, if present, is alkyl or halogen. In certain embodiments, $R^x$, if present, is halogen such as, but not limited to, F. In certain embodiments, $R^x$ is absent.

Yet other non limiting examples of compounds of formula (I-i) include those wherein $R^2$ and $R^3$ are the same or different, and are each independently $C_1$-$C_5$ alkyl, $R^4$ is alkyl, halogen, haloalkyl, or O(haloalkyl), and $R^x$, if present, is alkyl or halogen. In certain embodiments, $R^x$, if present, is halogen such as, but not limited to, F. In certain embodiments, $R^x$ is absent.

Further examples of compounds of formula (I-i) include, but are not limited to, those wherein $R^2$ and $R^3$ are the same or different, and are each independently haloalkyl, $R^4$ is alkyl, halogen, haloalkyl, or O(haloalkyl), and $R^x$, if present, is alkyl or halogen. In certain embodiments, $R^x$, if present, is halogen such as, but not limited to, F. In certain embodiments, $R^x$ is absent.

For each of the groups and subgroups of compounds described above, m and n have values as described in the Summary and the Detailed Description sections.

Exemplary compounds include, but are not limited to:

N-[(4R)-6-fluoro-3,3',4,4'-tetrahydro-2'H-spiro[chromene-2,1'-cyclobutan]-4-yl]-N'-[(7R)-7-hydroxy-5,6,7,8-tetrahydronaphthalen-1-yl]urea;

N-[(4R)-6-fluoro-3,3',4,4'-tetrahydro-2'H-spiro[chromene-2,1'-cyclobutan]-4-yl]-N'-(1-methyl-1H-indazol-4-yl)urea;

N-[(4R)-6-fluoro-3,3',4,4'-tetrahydro-2'H-spiro[chromene-2,1'-cyclobutan]-4-yl]-N'-1H-indazol-4-ylurea;

N-[(4R)-6-fluoro-2,2-dimethyl-3,4-dihydro-2H-chromen-4-yl]-N'-isoquinolin-5-ylurea;

N-[(4R)-6,8-difluoro-2,2-dimethyl-3,4-dihydro-2H-chromen-4-yl]-N'-isoquinolin-5-ylurea;

N-[(4R)-7-fluoro-2,2-dimethyl-3,4-dihydro-2H-chromen-4-yl]-N'-isoquinolin-5-ylurea;

N-[(4R)-2,2-diethyl-6-fluoro-3,4-dihydro-2H-chromen-4-yl]-N'-(1-methyl-1H-indazol-4-yl)urea;

N-[(4R)-2,2-dimethyl-3,4-dihydro-2H-chromen-4-yl]-N'-isoquinolin-5-ylurea;

N-[(4R)-2,2-diethyl-6-fluoro-3,4-dihydro-2H-chromen-4-yl]-N'-isoquinolin-5-ylurea;

N-[(4R)-2,2-dimethyl-7-(trifluoromethyl)-3,4-dihydro-2H-chromen-4-yl]-N'-isoquinolin-5-ylurea;

N-[(4R)-2,2-dimethyl-7-(trifluoromethyl)-3,4-dihydro-2H-chromen-4-yl]-N'-1H-indazol-4-ylurea;

N-[(4R)-2,2-diethyl-8-fluoro-3,4-dihydro-2H-chromen-4-yl]-N'-(1-methyl-1H-indazol-4-yl)urea;

N-[(4R)-2,2-diethyl-8-(trifluoromethoxy)-3,4-dihydro-2H-chromen-4-yl]-N'-(1-methyl-1H-indazol-4-yl)urea;

N-[(4R)-2,2-diethyl-6-fluoro-3,4-dihydro-2H-chromen-4-yl]-N'-(3-methylisoquinolin-5-yl)urea;

N-[(4R)-2,2-diethyl-6-fluoro-3,4-dihydro-2H-chromen-4-yl]-N'-1H-indazol-4-ylurea;

N-[(4R)-6-fluoro-2,2-dipropyl-3,4-dihydro-2H-chromen-4-yl]-N'-(1-methyl-1H-indazol-4-yl)urea;

N-[(4R)-2,2-diethyl-8-fluoro-3,4-dihydro-2H-chromen-4-yl]-N'-(3-methylisoquinolin-5-yl)urea;

N-[(4R)-6-fluoro-2,2-bis(fluoromethyl)-3,4-dihydro-2H-chromen-4-yl]-N'-(3-methylisoquinolin-5-yl)urea;

N-(3-methylisoquinolin-5-yl)-N'-[(4R)-8-(trifluoromethoxy)-3,4-dihydro-2H-chromen-4-yl]urea;

N-[(4R)-8-fluoro-2,2-dipropyl-3,4-dihydro-2H-chromen-4-yl]-N'-(1-methyl-1H-indazol-4-yl)urea;

N-[(4R)-8-fluoro-2,2-dipropyl-3,4-dihydro-2H-chromen-4-yl]-N'-(3-methylisoquinolin-5-yl)urea;

N-[(4R)-7-chloro-2,2-diethyl-3,4-dihydro-2H-chromen-4-yl]-N'-(3-methylisoquinolin-5-yl)urea;

N-1H-indazol-4-yl-N'-[(4R)-8-(trifluoromethoxy)-3,4-dihydro-2H-chromen-4-yl]urea;

N-(3-chloroisoquinolin-5-yl)-N'-[(4R)-2,2-diethyl-8-fluoro-3,4-dihydro-2H-chromen-4-yl]urea;

N-[(4R)-7-chloro-2,2-bis(fluoromethyl)-3,4-dihydro-2H-chromen-4-yl]-N'-(3-methylisoquinolin-5-yl)urea;

N-[(4R)-8-fluoro-2,2-bis(fluoromethyl)-3,4-dihydro-2H-chromen-4-yl]-N'-(3-methylisoquinolin-5-yl)urea;

N-[(4R)-2,2-diethyl-6-fluoro-3,4-dihydro-2H-chromen-4-yl]-N'-(1-methylisoquinolin-5-yl)urea;

N-[(4R)-2,2-bis(fluoromethyl)-8-(trifluoromethoxy)-3,4-dihydro-2H-chromen-4-yl]-N'-(3-methylisoquinolin-5-yl)urea;

N-[(4R)-2,2-bis(fluoromethyl)-8-(trifluoromethoxy)-3,4-dihydro-2H-chromen-4-yl]-N'-(1-methyl-1H-indazol-4-yl)urea;

N-[(4R)-8-chloro-2,2-bis(fluoromethyl)-3,4-dihydro-2H-chromen-4-yl]-N'-(3-methylisoquinolin-5-yl)urea;

N-[(4R)-2,2-dimethyl-8-(trifluoromethoxy)-3,4-dihydro-2H-chromen-4-yl]-N'-(3-methylisoquinolin-5-yl)urea;

N-[(4R)-7-fluoro-2,2-dimethyl-3,4-dihydro-2H-chromen-4-yl]-N'-(3-methylisoquinolin-5-yl)urea;

N-[(4R)-7-fluoro-2,2-bis(fluoromethyl)-3,4-dihydro-2H-chromen-4-yl]-N'-(3-methylisoquinolin-5-yl)urea;

N-[(4R)-7-chloro-2,2-dimethyl-3,4-dihydro-2H-chromen-4-yl]-N'-(3-methylisoquinolin-5-yl)urea;

N-[(4R)-6,8-difluoro-2,2-dimethyl-3,4-dihydro-2H-chromen-4-yl]-N'-(3-methylisoquinolin-5-yl)urea;

N-[(4R)-2,2-bis(fluoromethyl)-3,4-dihydro-2H-chromen-4-yl]-N'-(3-methylisoquinolin-5-yl)urea;

N-[(4R)-7-bromo-2,2-bis(fluoromethyl)-3,4-dihydro-2H-chromen-4-yl]-N'-(3-methylisoquinolin-5-yl)urea;

N-(3-aminoisoquinolin-5-yl)-N'-[(4R)-7-fluoro-2,2-dimethyl-3,4-dihydro-2H-chromen-4-yl]urea;

N-[(4R)-8-chloro-7-fluoro-2,2-dimethyl-3,4-dihydro-2H-chromen-4-yl]-N'-(3-methylisoquinolin-5-yl)urea;

N-[(4R)-7-fluoro-2,2,8-trimethyl-3,4-dihydro-2H-chromen-4-yl]-N'-(3-methylisoquinolin-5-yl)urea;

N-[(4R)-7,8-difluoro-2,2-dimethyl-3,4-dihydro-2H-chromen-4-yl]-N'-(3-methylisoquinolin-5-yl)urea;

N-[(4R)-2,2-dimethyl-7-(trifluoromethyl)-3,4-dihydro-2H-chromen-4-yl]-N'-(3-methylisoquinolin-5-yl)urea;

N-[(4R)-8-fluoro-2,2-dimethyl-3,4-dihydro-2H-chromen-4-yl]-N'-(3-methylisoquinolin-5-yl)urea;

N-[(4R)-6,8-difluoro-2,2-bis(fluoromethyl)-3,4-dihydro-2H-chromen-4-yl]-N'-(3-methylisoquinolin-5-yl)urea;

N-[(2R,4R)-7-chloro-2-(fluoromethyl)-2-methyl-3,4-dihydro-2H-chromen-4-yl]-N'-(3-methylisoquinolin-5-yl)urea;

N-[(2R,4R)-7-chloro-2-(fluoromethyl)-2-methyl-3,4-dihydro-2H-chromen-4-yl]-N'-(3-methylisoquinolin-5-yl)urea;

N-[(4R)-7-fluoro-2,2-dimethyl-3,4-dihydro-2H-chromen-4-yl]-N'-(6-fluoro-3-methylisoquinolin-5-yl)urea;

N-[(2R,4R)-7-chloro-2-(difluoromethyl)-2-methyl-3,4-dihydro-2H-chromen-4-yl]-N'-(3-methylisoquinolin-5-yl)urea;

N-[(2R,4R)-8-fluoro-2-(fluoromethyl)-2-methyl-3,4-dihydro-2H-chromen-4-yl]-N'-(3-methylisoquinolin-5-yl)urea; and N-[(2R,4R)-8-fluoro-2-(fluoromethyl)-2-methyl-3,4-dihydro-2H-chromen-4-yl]-N'-(3-methylisoquinolin-5-yl)urea;

or pharmaceutically acceptable salts or solvates thereof.

Other compounds contemplated include, but are not limited to:

N-[(4R)-6-fluoro-2,2-dimethyl-3,4-dihydro-2H-chromen-4-yl]-N'-1H-indazol-4-ylurea;

N-[(4S)-6-fluoro-3,3',4,4'-tetrahydro-2'H-spiro[chromene-2,1'-cyclobutan]-4-yl]-N'-[(7S)-7-hydroxy-5,6,7,8-tetrahydronaphthalen-1-yl]urea;

N-[(4S)-6-fluoro-3,3',4,4'-tetrahydro-2'H-spiro[chromene-2,1'-cyclobutan]-4-yl]-N'-[(7R)-7-hydroxy-5,6,7,8-tetrahydronaphthalen-1-yl]urea;

N-[(4R)-6-fluoro-3,4-dihydro-2H-chromen-4-yl]-N'-(1-methyl-1H-indazol-4-yl)urea;

N-[(4R)-6-fluoro-3,4-dihydro-2H-chromen-4-yl]-N'-isoquinolin-5-ylurea;

N-[(4R)-6-fluoro-3,4-dihydro-2H-chromen-4-yl]-N'-[(7R)-7-hydroxy-5,6,7,8-tetrahydronaphthalen-1-yl]urea;

N-[(4R)-6-fluoro-3,4-dihydro-2H-chromen-4-yl]-N'-[(7S)-7-hydroxy-5,6,7,8-tetrahydronaphthalen-1-yl]urea;

N-[(4R)-6,8-difluoro-2,2-dimethyl-3,4-dihydro-2H-chromen-4-yl]-N'-(1-methyl-1H-indazol-4-yl)urea;

N-[(4R)-6,8-difluoro-2,2-dimethyl-3,4-dihydro-2H-chromen-4-yl]-N'-[(7S)-7-hydroxy-5,6,7,8-tetrahydronaphthalen-1-yl]urea;

N-[(4R)-8-fluoro-2,2-dimethyl-3,4-dihydro-2H-chromen-4-yl]-N'-[(7R)-7-hydroxy-5,6,7,8-tetrahydronaphthalen-1-yl]urea;

N-[(4R)-8-fluoro-2,2-dimethyl-3,4-dihydro-2H-chromen-4-yl]-N'-[(7S)-7-hydroxy-5,6,7,8-tetrahydronaphthalen-1-yl]urea;

N-[(4R)-8-fluoro-2,2-dimethyl-3,4-dihydro-2H-chromen-4-yl]-N'-isoquinolin-5-ylurea;

N-[(4R)-8-fluoro-2,2-dimethyl-3,4-dihydro-2H-chromen-4-yl]-N'-(1-methyl-1H-indazol-4-yl)urea;

N-[(4R)-8-fluoro-2,2-dimethyl-3,4-dihydro-2H-chromen-4-yl]-N'-1H-indazol-4-ylurea;

N-[(4R)-6-fluoro-2,2-dimethyl-3,4-dihydro-2H-chromen-4-yl]-N'-(3-methylisoquinolin-5-yl)urea;

N-[(4R)-2,2-dimethyl-3,4-dihydro-2H-chromen-4-yl]-N'-[(7S)-7-hydroxy-5,6,7,8-tetrahydronaphthalen-1-yl]urea;

N-[(4R)-6-fluoro-2,2-dimethyl-3,4-dihydro-2H-chromen-4-yl]-N'-isoquinolin-8-ylurea;

N-[(4R)-2,2-dimethyl-8-(trifluoromethyl)-3,4-dihydro-2H-chromen-4-yl]-N'-isoquinolin-5-ylurea;

N-[(4R)-2,2-dimethyl-8-(trifluoromethyl)-3,4-dihydro-2H-chromen-4-yl]-N'-[(7R)-7-hydroxy-5,6,7,8-tetrahydronaphthalen-1-yl]urea;

N-[(4R)-2,2-diethyl-7-fluoro-3,4-dihydro-2H-chromen-4-yl]-N'-isoquinolin-5-ylurea;

N-[(4R)-2,2-diethyl-7-(trifluoromethyl)-3,4-dihydro-2H-chromen-4-yl]-N'-isoquinolin-5-ylurea;

N-[(4R)-2,2-dimethyl-7-(trifluoromethyl)-3,4-dihydro-2H-chromen-4-yl]-N'-[(7R)-7-hydroxy-5,6,7,8-tetrahydronaphthalen-1-yl]urea;

N-[(4R)-2,2-diethyl-8-fluoro-3,4-dihydro-2H-chromen-4-yl]-N'-isoquinolin-5-ylurea; and N-isoquinolin-5-yl-N'-[(4R)-8-(trifluoromethyl)-3,4-dihydro-2H-chromen-4-yl]urea;

or pharmaceutically acceptable salts or solvates thereof.

c) GENERAL SYNTHESIS

This invention is intended to encompass compounds of the invention when prepared by synthetic processes or by metabolic processes. Preparation of the compounds of the invention by metabolic processes includes those occurring in the human or animal body (in vivo) or processes occurring in vitro.

The compounds may be prepared by a variety of processes well known for the preparation of compounds of this class. For example, compounds of formula (I) wherein the groups $R^1$, $R^2$, $R^3$, $R^4$, m, and n have the meanings as set forth in the summary and detailed description sections unless otherwise noted, can be synthesized as shown in the accompanying Schemes 1-14.

As used in the descriptions of the schemes and the examples, certain abbreviations are intended to have the following meanings: AcCl for acetyl chloride; Boc for tert-butoxycarbonyl, (Boc)$_2$O for di-tert-butyl dicarbonate; dba for dibenzylideneacetone; DBU for 1,8-diazabicyclo[5.4.0]undec-7-ene; Cl$_2$Pd(PPh$_3$)$_2$ for dichlorobis(triphenylphosphine)palladium; Et$_3$N for triethylamine; THF for tetrahydrofuran; DCE for dichloroethane; DSC for disuccinyl carbonate; DME for dimethoxyethane; i-PrOH for isopropanol; MeOH for methanol; Me-THF for 2-methyl tetrahydrofuran; MTBE for methyl tert-butyl ether; Ms$_2$O for methanesulfonic anhydride; MOM for methoxymethyl; NaBH(OAc)$_3$ for sodium tricacetoxyborohydride; n-BuLi for n-butyllithium; Ac$_2$O for acetic anhydride; DMF for dimethylformamide; DMSO for dimethyl sulfoxide; EtOAc for ethyl acetate; Et$_2$O for diethyl ether; Ra—Ni for Raney nickel; Eaton's reagent for 7.7% phosphorus pentoxide solution in methanesulfonic acid; THF for tetrahydrofuran; Ti(OEt)$_4$ for titatium(IV) ethoxide; and HPLC for high performance liquid chromatography.

Ureas of general formula (I) may be prepared as described in Scheme 1 Amines of formula (1) can be reacted with disuccinyl carbonate in the presence of a base such as, but not limited to, pyridine, and in a solvent such as dichloromethane to provide activated carbamates of general formula (2). Treatment of succinyl carbamates (2) with nucleophiles of formula (3) in the presence of an amine base such as, but not limited to, diisopropylethylamine, provides ureas of general formula (I).

Scheme 1

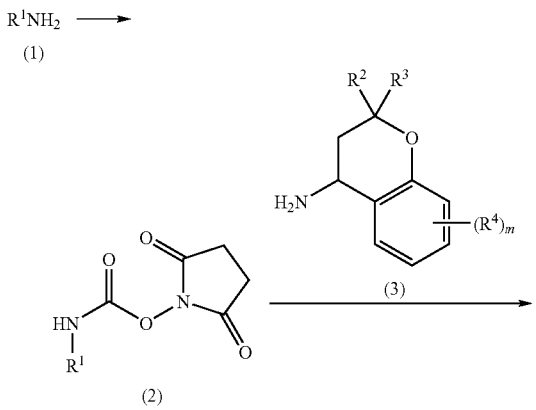

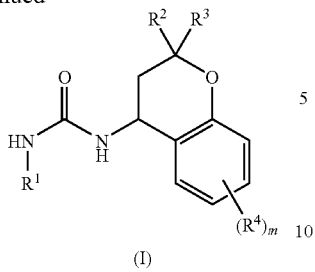

(I)

Ureas of general formula (I) may also be prepared utilizing general procedures as described in Scheme 2 Amines of formula (I) can be treated with trichloroactylchloride and a base such as, but not limited to, triethylamine in a solvent such as dichloromethane to provide trichloroacetamides of general formula (4). Trichloroacetamides of general formula (4) can be treated with amines of general formula (3), and a non-nucleophilic base such as, but not limited to, DBU or diisopropylethylamine, in a solvent such as, but not limited to, acetonitrile to provide ureas of general formula (I).

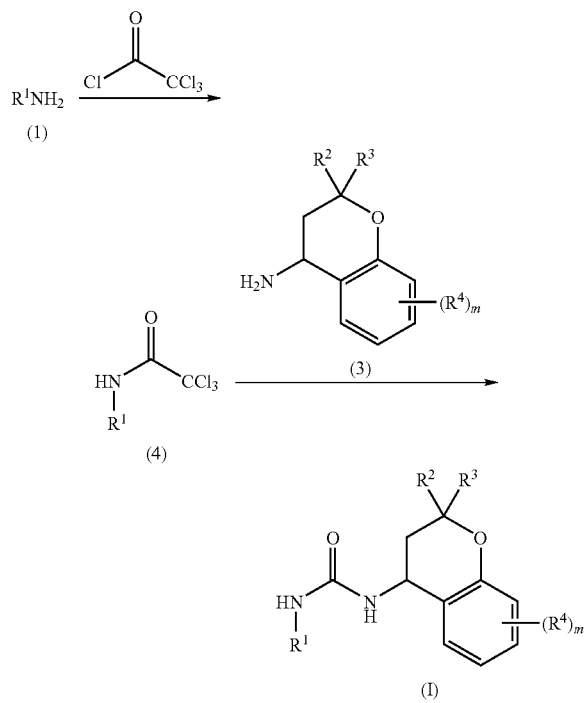

Alternatively, ureas of general formula (I) may be prepared by direct formation of a carbon-nitrogen between a primary urea and $R^1$ as described in Scheme 3 Amines of general formula (3) may be reacted with phenyl carbamate (5) in the presence of a non-nucleophilic amine base such as, but not limited to diisopropyethylamine, at an elevated temperature (e.g. at about 50 to about 80° C.) in a solvent such as, but not limited to, THF to provide primary ureas of general formula (6). Thereafter (6) can be transformed to compounds of general formula (I) by reaction of aryl chlorides of general formula (7) which are either commercially available or may be prepared by one skilled in the art from commercially available materials using methods described in the chemical literatures. The reaction is generally performed in the presence of a palladium catalyst such as $Pd_2$ $dba_3$, a trivalent phosphine ligand such as, but not limited to, 5-(di-tert-butylphosphino)-1',3',5'-triphenyl-1'H-1,4'-bipyrazole (CAS #894086-00-1, Aldrich), a base such as potassium carbonate, at an elevated temperature and in the solvent of choice (for example, DME at 40-60° C.).

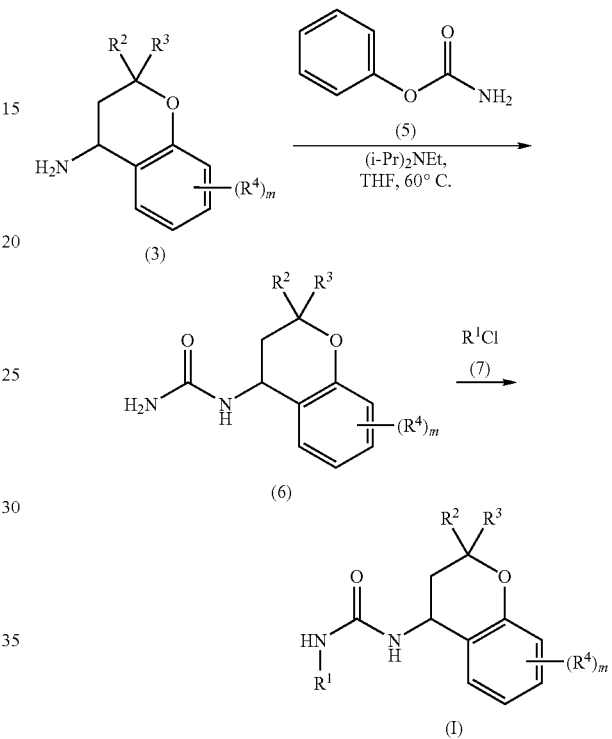

The requisite amines of general formula (3) may be prepared by any of several methods and synthetic intermediates selected by one of ordinary skill in the art as described in Schemes 4 or 5. As shown in Scheme 4, hydroxy benzoic acids of general formula (8) can be reacted with excess methyllithium in a solvent such as diethyl ether at reduced temperatures (less than 20° C.) to provide methyl ketones of general formula (9). Methyl ketones (9) can be reacted with ketones of general formula (10) to provide chromanones of general formula (10). Non-limiting examples of ketones (10) include acetone and 3-pentanone. The reaction is generally performed in the presence of an amine base such as pyrrolidine, in a protic solvent such as, but not limited to methanol. Ketones of general formula (11) may be treated with a variety of chiral hydride sources known to those skilled in the art (Corey, E. J. et al. *J. Org. Chem.* 1988, 53, 2861; Kawanami, S. et al. *Tetrahedron* 2003, 59, 8411; Corey, E. J. et al. *Tetrahedron Asymm.* 2002, 13, 1347) to provide chiral alcohols of general formula (12). Alcohols (12) may be converted to azides of general formula (13) by activation with a sulfonylating agenet such as, but not limited to, methanesulfonic anhydride, followed by displacement with a nucleophile azide source such as, but not limited to, tetrabutylammonium azide (Burgard, A. et al. *Tetrahedron* 1999, 55, 7555). It is to be noted that the transformation of (12) to (13) proceeds with net overall inversion of absolute stereochemistry. Finally, amines of general formula (14) may be obtained by reduction of azides (13) by treatment with a phosphine agent such as triphenylphosphine under aqueous conditions with an appropriate water-miscible organic co-solvent such as but not limited to THF (Gololobov, Y. G. et al. *Tetrahedron* 1981, 37, 437). Chiral amines of formula (14) can be converted to compounds of formula (Ia) using synthetic methods as outlined in Schemes 1-3.

be reduced using methodologies known by one skilled in the art, for example, by hydrogenolysis in the presence of a catalyst such as palladium on carbon to provide the amines of general formula (3).

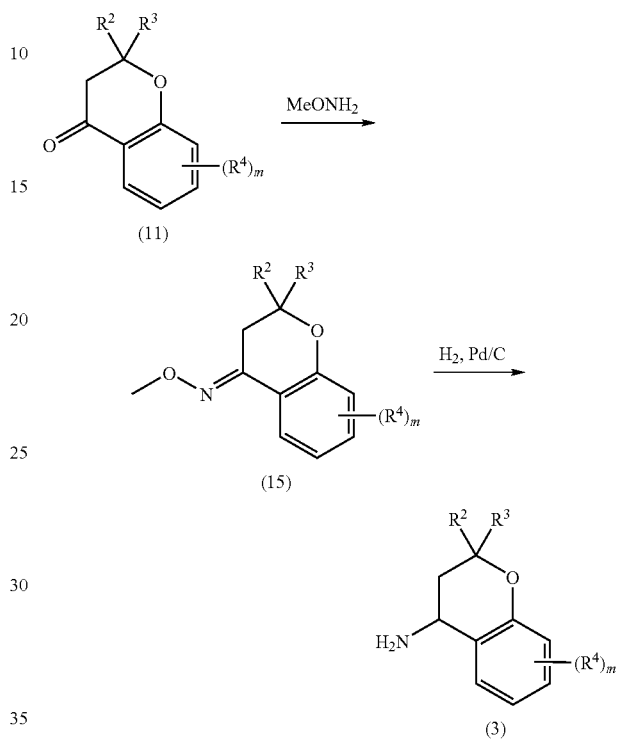

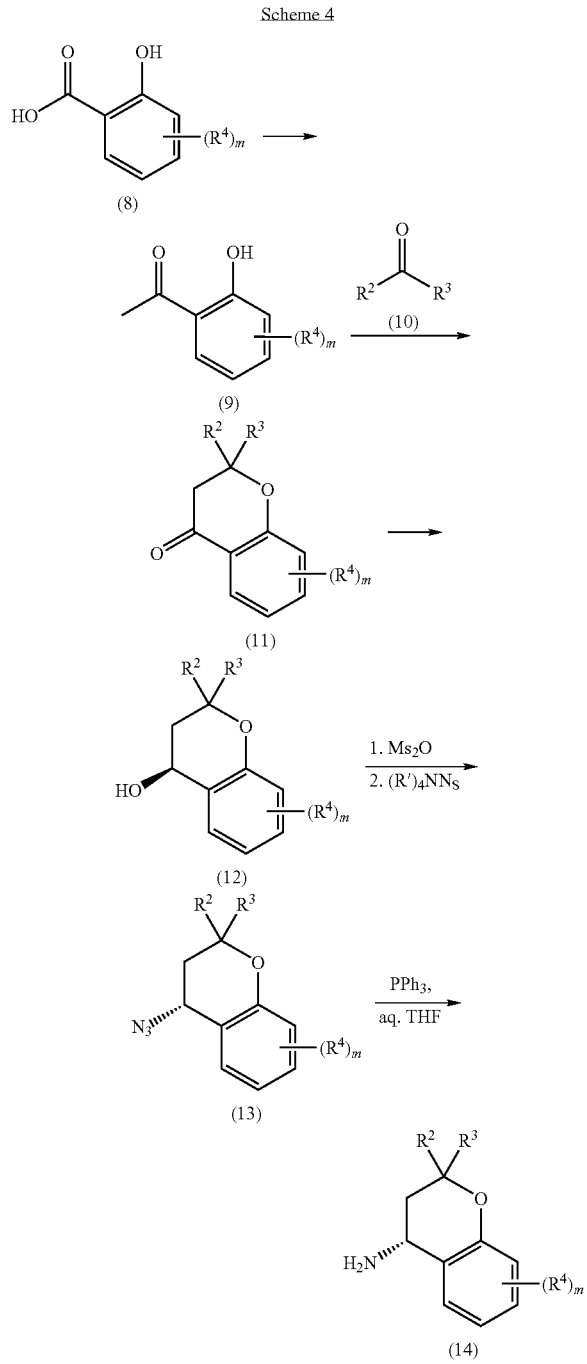

The requisite substituted methyl ketones (9) shown in Scheme 4 may be prepared by the methods described in Schemes 6 and 7. For example, phenols of general formula (16) may be protected and subsequently subjected to direct ortho-metalation. Treatment of (16) with methoxymethyl chloride in the presence of a non-nucleophilic amine base such as diisopropylethylamine in an aprotic solvent such as dichloromethane provides protect phenols of general formula (17). Other examples of suitable phenol oxygen protecting groups are known in the art. Reaction of (17) with an organolithium base such as n-butyllithium in a solvent at reduced temperature (such as THF at −78° C.) followed by quenching with carbon dioxide and subsequent exposure to mineral acid provides hydroxy benzoic acids of general formula (8). Hydroxyl benzoic acids (8) can be transformed to methyl ketones (9) using the chemistry described in Scheme 4.

Racemic amines of general formula (3) may be prepared from the corresponding chromanones (11) as shown in Scheme 5. Chromanones (11) may be treated with hydroxylamines or alkoxyamines such as methoxyamine to provide oximes of general formula (15). The oxime group of (15) can

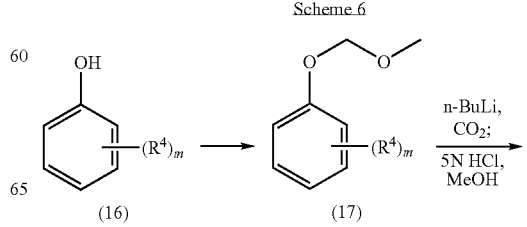

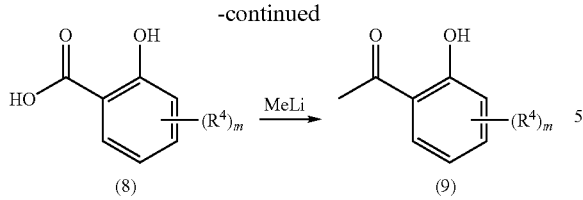

In a related approach shown in Scheme 7, phenols of general formula (16) can be treated with a methylating reagent such as, but not limited to, methyl iodide in the presence of a base such as, but not limited to potassium carbonate to provide anisole derivatives of general formula (18). Reaction of methyl ethers of general formula (18) with acetic anhydride and a mineral acid such as, but not limited to triflic acid provides methyl ketones of general formula (19). Removal of the methyl group in (19) to provide hydroxyl methyl ketones of general formula (9) may be effected by treatment with a sulfur nucleophile such as sodium ethanethiolate. The reaction is generally performed in a solvent such as dimethylformamide, and at elevated temperature, for example, at about 60 to about 150° C.

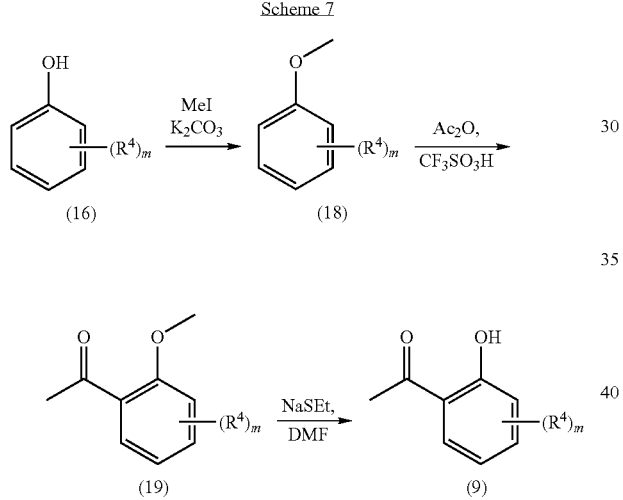

Another approach to the synthesis of chromanones is shown in Scheme 8. Phenols of general formula (16) may be reacted with unsaturated carboxylic acids of general formula (20) in the presence of a suitable activating agent such as Eaton's reagent (Eaton, P. et al. *J. Org. Chem.* 1973, 38, 4071) to provide chromanones of general formula (11).

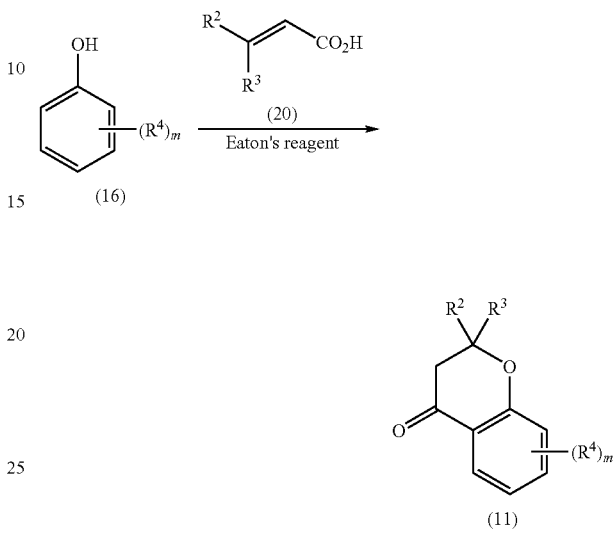

Schemes 9-12 describe the preparation of a variety of nucleophiles containing $R^1$ as defined in formula (I). As shown in Scheme 9, nitroaniline (21) can be reacted with sodium nitrite and an acid including, but not limited to, acetic acid in water to provide indazoles of general formula (22) (see Gomtsyan, A. et al. U.S. Pat. No. 7,015,233). Incorporation of a nitrogen protecting group can be accomplished by reaction of indazole (22) with chloroformates of formula R″OC(O)Cl wherein R″ is an alkyl such as, but not limited to, methyl, to provide carbamates of general formula (23). The nitro group of (23) can be reduced by hydrogenolysis in the presence of a catalyst such as palladium on carbon to provide the anilines of general formula (24) which can be reacted subsequently with DSC and amines of general formula (3) or (14) as described in Scheme 1 to give compounds of general formula (25) or (26). Removal of the nitrogen protecting group can be accomplished by reaction of (25) or (26) with aqueous sodium hydroxide in an alcoholic solvent such as methanol to provide indazoles of general formula (27) or (28), respectively.

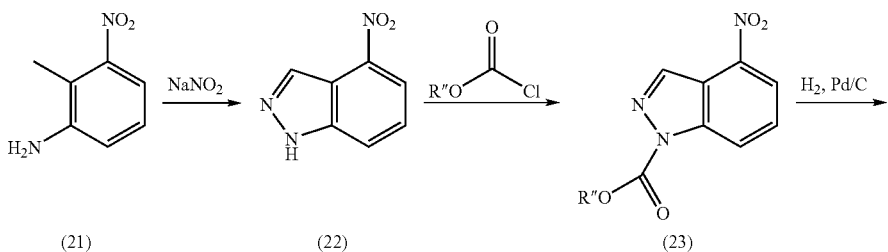

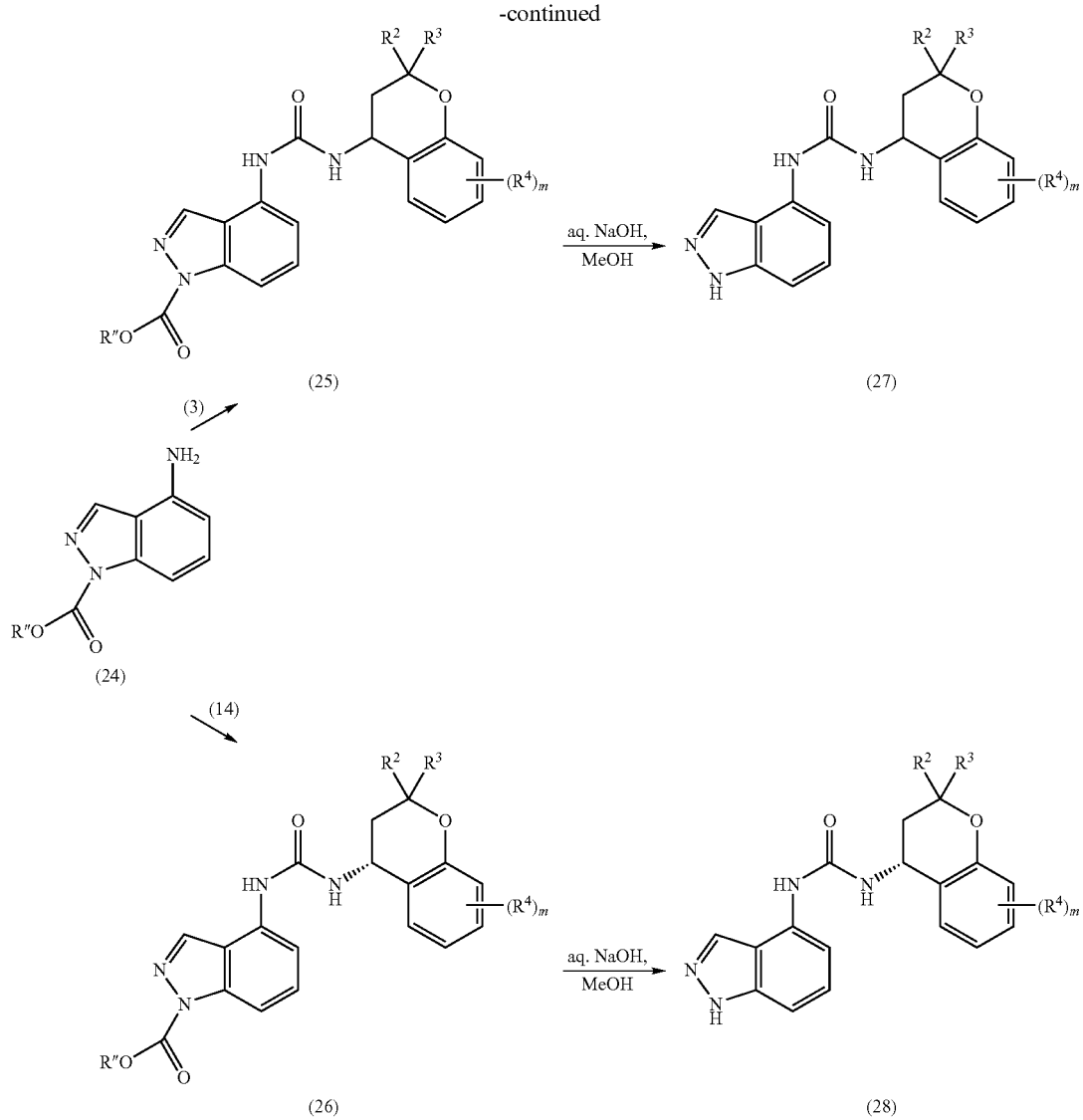

Methyl indazole precursors may be prepared via the methods described in Scheme 10. Nitrobenzaldehydes of general formula (29) where X may be a fluorine or bromine atom can be heated with hydrazines such as methylhydrazine to provide indazoles of general formula (30). The nitro group of (30) can be reduced by hydrogenolysis in the presence of a catalyst such as palladium on carbon to provide aminoindazoles of formula (31).

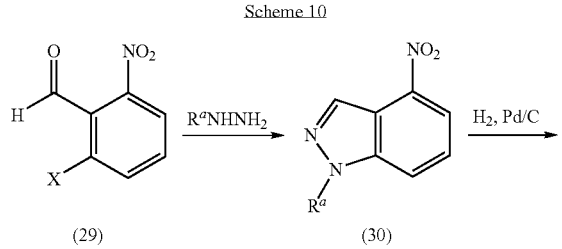

Scheme 10

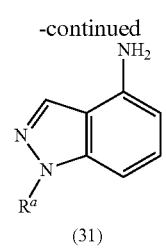

As shown in Scheme 11, aminonaphthol (32) may be partially saturated by hydrogenolysis in the presence of a suitable catalyst such as, but not limited to, Raney nickel in a protic solvent such as ethanol at elevated temperature, for example, at about 60 to about 85° C., to give the hydroxyaniline (33). Single enantiomers (34) and (35) can be separated from racemic alcohol (33) by chiral HPLC using a chiral column such as, but not limited to, a Chiralpak IC or Chiralcel AS column (Chiral Technologies Inc., West Chester, Pa.) and solvent mixtures containing methanol, hexane, and dichloromethane. Either (34) or (35) may be reacted further with amines (3) or (14) in the presence of DSC, as exemplified by the conversion of (34) to ureas of general formula (36) or (37) using the coupling methods described in Scheme 1.

Scheme 11

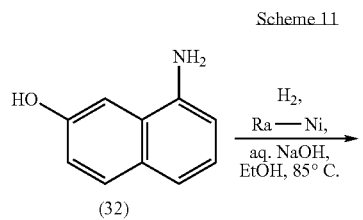

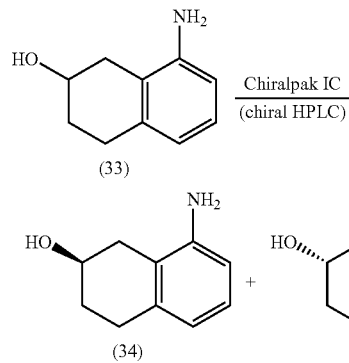

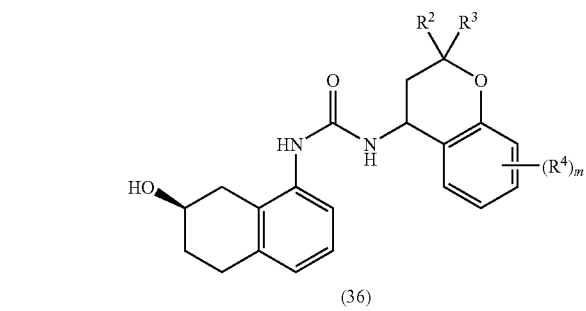

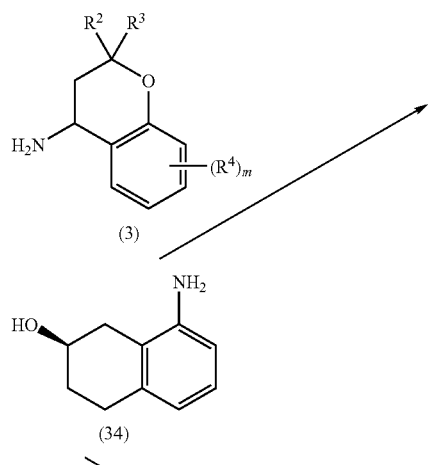

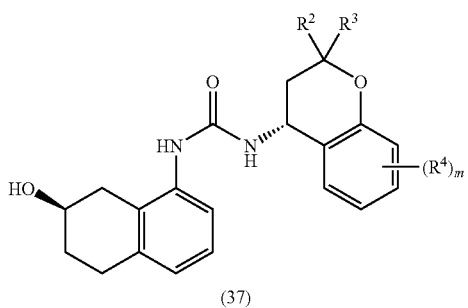

Ureas of general formula (I) may also be prepared utilizing the general procedure described in Scheme 12. Amines of general formula (1) may be reacted with phenyl chloroformate in the presence of a non-nucleophilic base such as, but not limited to, DBU or diisopropylethylamine, in a solvent such as, but not limited to, pyridine. Subsequent treatment with amines of general formula (3) provides ureas of general formula (I).

Scheme 12

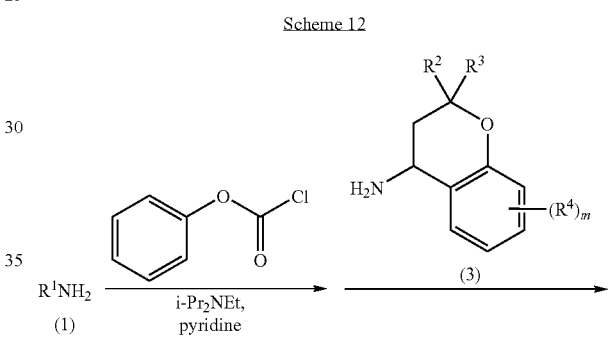

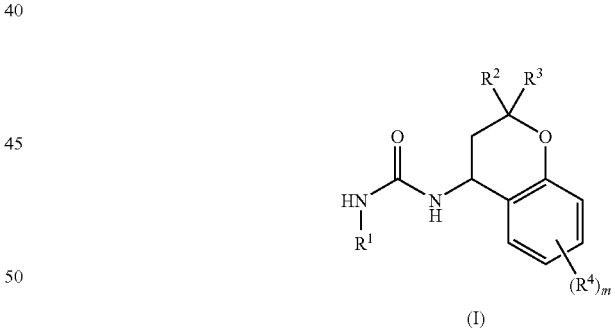

As shown in Scheme 13, chromanyl amines of general formula (I) may be prepared according to the general procedure described by Ellman and co-workers (Tanuwidjaja, J.; Ellman, J. A. et al. *J. Org. Chem.* 2007, 72, 626). Ketones of general formula (11) can be condensed with a chiral sulfinamide such as tert-butanesulfinamide in the presence of a Lewis acid such as Ti(OEt)$_4$ to provide N-sulfinyl imine intermediates that can undergo a subsequent in situ reduction with reagents such as sodium borohydride to provide sufinamides of general formula (38). Treatment of sulfinamides of general formula (38) with acetyl chloride and methanol in a solvent such as, but not limited to, methyl tert-butyl ether provides amine hydrochloride salts of general formula (39).

Scheme 13

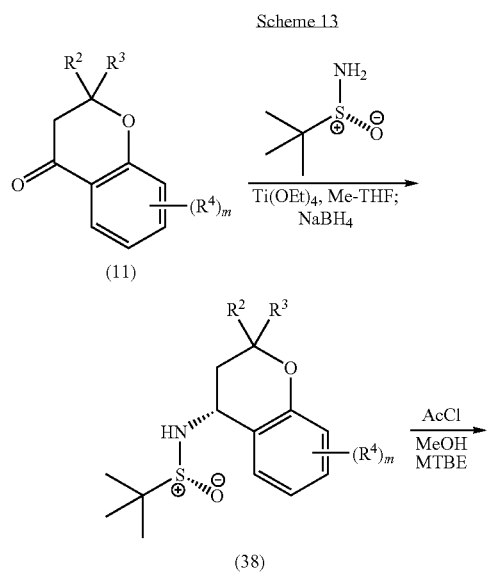

Construction of substituted isoquinolines can be accomplished using the method of Blurton, P. et al. WO2004/046133 as described in Scheme 14. Benzylamines of general formula (40) can be reacted with pyruvic aldehyde dimethyl acetal and a reducing agent such as, but not limited to, sodium tricacetoxyborohydride in a halogenated solvent such as dichloroethane to provide acetal derivatives of general formula (41). Subsequent treatment of acetals of general formula (41) with an acid such as, but not limited to, chlorosulfonic acid provides substituted 3-methylisoquinolines of general formula (42). In another approach to the synthesis of functionalized methylisoqinolines, substituted 2-bromo benzaldehydes of general formula (43) can be reacted with propyne and copper(I) iodide in the presence of a catalyst such as $Cl_2Pd(PPh_3)_2$ and a base such as, but not limited to, triethylamine in a solvent such as dimethylformamide to provide alkynyl aldehydes of general formula (44). Reaction of alkynes of general formula (44) with ammonia in a solvent such as, but not limited to, methanol also provides substituted 3-methylisoquinolines of general formula (42).

Scheme 14

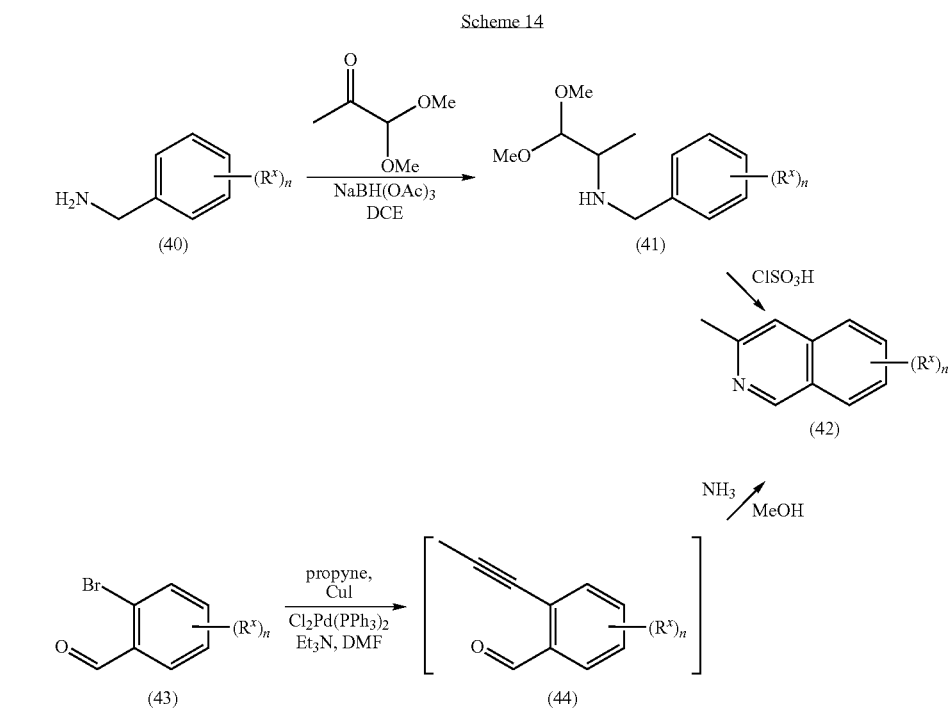

-continued

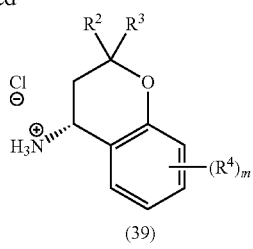

It will be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it may be prepared by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

d) EXAMPLES

Example 1

N-[(4R)-6-fluoro-2,2-dimethyl-3,4-dihydro-2H-chromen-4-yl]-N'-(1-methyl-1H-indazol-4-yl)urea Example 1A 6-fluoro-2,2-dimethylchroman-4-one In a 500 mL round-bottomed flask was added 1-(5-fluoro-2-hydroxyphenyl)ethanone (20.0 g, 130 mmol, Aldrich Chemical), propan-2-one (19.0 mL, 260 mmol), and pyrrolidine (21.5 mL, 260 mmol) in methanol (150 mL) to give a orange solution. The reaction mixture was stirred at ambient temperature for 48 h. The reaction mixture was poured into EtOAc (200 mL) and washed with 1N HCl (50 mL), saturated $NaHCO_3$ (50 mL), and brine (50 mL). The organic portion was dried ($Na_2SO_4$), filtered, and concentrated to provide an orange residue which was purified by silica gel chromatography (gradient elution, 0-20% EtOAc/hexanes) to provide the title compound (14.2 g, 73.1 mmol, 56%) as a white solid. MS (DCI/$NH_3$) m/z 208 $(M+NH_4)^+$.

Example 1B (S)-6-fluoro-2,2-dimethylchroman-4-ol

A solution of methyl tert-butylether (34 mL), (R)-diphenyl(pyrrolidin-2-yl)methanol (1.10 g, 4.35 mmol), and borane-N,N-diethylaniline complex (18.5 mL, 104 mmol) was heated to 45° C. and Example 1A (16.9 g, 87.0 mmol) in methyl tert-butylether (136 mL) was added over 75 min via addition funnel. After the addition, LCMS showed complete reaction. After 15 min of additional stirring at 45° C., the reaction mixture was cooled to 10° C. and treated with MeOH (85 mL) over 10 min, keeping the temperature≤15° C. ($H_2$ evolution). After stirring for 30 min at ambient temperature, 2 N HCl (85 mL) was added and the reaction mixture was stirred for 10 min. Methyl tert-butylether (170 mL) was added and the reaction mixture was partitioned. The orgaic portion was washed with 2 N HCl (85 mL) and brine (35 mL). The aqueous extracts were back-extracted with methyl tert-butylether (85 mL). The combined organic portions were dried ($Na_2SO_4$), filtered, and concentrated, to provide Example 1B (17.4 g, 89.0 mmol). Analysis by analytical chiral HPLC (Chiralcel OJ 4.6×25 mm, 20% isopropanol/hexane, 23° C., 0.5 mL/min) showed 99% ee versus a racemic reference (prepared as described above using sodium borohydride as the reducing agent). MS (DCI/$NH_3$) m/z 197 $(M+H)^+$.

Example 1C (R)-6-fluoro-2,2-dimethylchroman-4-amine

A mixture of Example 1B (17.1 g, 87.0 mmol) in THF (340 mL) was cooled to −30° C. followed by addition of methanesulfonic anhydride (16.7 mL, 131 mmol). N,N-Diisopropylethylamine (21.3 mL, 122 mmol) was slowly added (internal temperature ≤−24° C.) to the reaction mixture. After 30 min, ~50% conversion was observed by LC/MS, thus the reaction mixture was warmed to −10° C. After 20 min, the reaction mixture was warmed further to 0° C. After 20 min, additional $Ms_2O$ (3.00 g, 0.2 equiv) and N,N-diisopropylethylamine (2.8 mL, 0.2 equiv) were added and the reaction mixture was stirred for 20 min. At 0° C., additional N,N-diisopropylethylamine (1.40 mL, 0.1 equiv) was added, the reaction mixture was stirred for 10 min, then was cooled to −30° C. and treated with tetra-N-butylammonium azide (49.5 g, 174 mmol). The resulting slurry was allowed to slowly warm to ambient temperature overnight. After 14 h, methanol (85 mL) was added followed by 2 N NaOH (85 mL; slight exotherm to 27° C.). The reaction was stirred for 30 min, then diluted with MTBE (340 mL) and water (170 mL). The layers were separated and the organic layer was washed with water (85 mL), 2 N HCl (2×85 mL), water (85 mL), and brine (34 mL). The acidic washes were back-extracted with MTBE (85 mL). The combined organic portions were dried ($Na_2SO_4$), filtered, and concentrated to give a yellow residue that was used without further purification.

The crude azide product above was suspended in THF (305 mL) and water (34 mL) and treated with triphenylphosphine (25.1 g, 96.0 mmol). The yellow solution was heated to 60° C.

for 2.5 h. The reaction mixture was cooled and concentrated to remove THF. Dichloromethane (170 mL), 2 N HCl (85 mL), and water (425 mL) were added to form a homogeneous biphasic mixture. The layers were partitioned and the aqueous portion was washed with dichloromethane (85 mL). 2 N NaOH (100 mL) was added to the aqueous layer which was then extracted with dichlormethane (5×85 mL), dried ($Na_2SO_4$), filtered, and concentrated to give the title compound (12.6 g, 64.3 mmol, 74%). Analytical chiral HPLC (Chiralcel OJ 4.6×25 mm, 20% isopropanol/hexane, 23° C., 0.5 mL/min) showed 91% ee versus a racemic reference standard. MS (DCI/$NH_3$) m/z 196 (M+H)$^+$.

Example 1D (R)-6-fluoro-2,2-dimethylchroman-4-amine, (R)-2-hydroxy-2-phenylacetic acid salt Example 1C (12.6 g, 64.3 mmol) and isopropanol (126 mL) were heated to 50° C. while (R)-(–)-mandelic acid (9.79 g, 64.3 mmol) was added. At 43° C., solids were observed, and heating continued was up to 50° C. The mixture was aged at 50° C. for 10 min, then hexanes (126 mL) were added over 45 min at 50° C. Following the addition, the reaction mixture was cooled gradually to ambient temperature over 90 min, precipitated solids were filtered, and were washed with 1:1 isopropol-hexanes. The solid was dried in an oven at 45° C. overnight with air bleed, to give the title compound (17.2 g, 49.5 mmol, 77%) as a crystalline white solid. The solid had no detectable minor isomer by Analytical chiral HPLC (Chiralcel OJ 4.6×25 mm, 20% isopropanol/hexane, 0.5 mL/min) and the mother liquor showed ~50% ee in favor of the desired isomer. $^1$H NMR (300 MHz, DMSO-$d_6$) δ 7.44-7.37 (m, 3H), 7.30-7.17 (m, 3H), 7.01 (td, J=8.5, 3.1 Hz, 1H), 6.78-6.73 (m, 1H), 4.70 (s, 1H), 4.21 (dd, J=11.5, 6.3 Hz, 1H), 2.13 (dd, J=13.2, 6.3 Hz, 1H), 1.65 (t, J=12.3 Hz, 1H), 1.37 (s, 3H), 1.17 (s, 3H); MS (DCI/$NH_3$) m/z 179 (M−16)$^+$.

Example 1E 2-bromo-6-fluorobenzaldehyde

1-Bromo-3-fluorobenzene (17.3 g, 100 mmol) was added over 5 min to a solution of lithium diisopropylamide (prepared from the addition of 40 mL of 2.5 N-butyllithium in hexanes to 11.5 g of 0.1 M diisopropylamine at 0° C.) in THF at −70° C. The mixture was stirred cold for 1 h, after which DMF (8 mL) was added over 10 min. The mixture was stirred at −70° C. for an additional 40 min, then was treat with acetic acid (26 g). The mixture was allowed to warm to ambient temperature, transferred into a mixture of MTBE (200 mL), water (200 mL), and 4 N hydrochloric acid (150 mL). The layers were partitioned and the organic portion was concentrated under reduced pressure to provide the title compound. MS (DCI/$NH_3$) m/z 202 (M+H)$^+$.

Example 1F 4-bromo-1-methyl-1H-indazole

A solution of Example 1E (2.00 g, 9.95 mmol) in DMSO (3.5 mL) was added to methylhydrazine (98%, 3.20 g of 98% reagent, 69.6 mmol). The mixture was heated at 85° C. for 24 h, then cooled to ambient temperature and diluted with water (50 mL). The solution was extracted with $CH_2Cl_2$ (2×50 mL) and the combined organic layers were dried ($MgSO_4$), filtered, and concentrated under reduced pressure to provide the title compound which was used without further purification. MS (DCI/$NH_3$) m/z 202 (M+H)$^+$.

Example 1G 1-methyl-1H-indazol-3-amine

A mixture of palladium(II) acetate (82 mg, 2 mol %) and Xantphos (287 mg, 3 mol %) in toluene (10 mL) was stirred for 5 min at ambient temperature. To the solution was added a solution of Example 1F (3.68 g, 17.4 mmol) and benzophenone imine (3.00 g, 17.4 mmol) in toluene (30 mL). The mixture was evacuated and purged with nitrogen two times, then stirred at ambient temperature for 15 min Sodium tert-butoxide (1.90 g, 24.4 mmol) was added and the mixture was evacuated and purged with nitrogen. The mixture was heated to between 80 and 85° C. for 2 h, cooled to ambient temperature, and diluted with water (30 mL). The layers were partitioned and the aqueous layer was extracted with additional toluene (20 mL). The combined organic layers were stirred with 6 N HCl (10 mL) for 1 h, then 40 mL of water was added to dissolve the solids. The toluene layer was discarded and aqueous layer filtered to remove insoluble material. The aqueous layer was adjusted to pH 14 with the addition of 50% NaOH and the resulting solid was filtered and dried to provide the title compound. MS (DCI/$NH_3$) m/z 202 (M+H)$^+$.

Example 1H

N-[(4R)-6-fluoro-2,2-dimethyl-3,4-dihydro-2H-chromen-4-yl]-N'-(1-methyl-1H-indazol-4-yl)urea To a 100 mL round-bottomed flask was added N,N'-disuccinyl carbonate (1.38 g, 5.38 mmol), pyridine (0.435 mL, 5.38 mmol) and Example 1G (0.754 g, 5.12 mmol) in acetonitrile (15 mL). The brown solution was stirred at room temperature for 30 min and treated with a solution of Example 1D (1.00 g, 5.12 mmol) in acetonitrile (10 mL) followed by N,N-diisopropylethylamine (2.66 mL, 15.4 mmol). The reaction was stirred for 1 h, then poured into EtOAc (200 mL) and washed with saturated $NaHCO_3$ (50 mL) and 1N HCl (50 mL). The solution was dried ($Na_2SO_4$), filtered, and concentrated. The resulting residue was purified by silica gel chromatography (gradient elution, 0-50% EtOAc/hexanes) to provide the title compound (1.54 g, 4.18 mmol, 82%) as an off-white solid. $^1$H NMR (300 MHz, DMSO-$d_6$) δ 8.76 (s, 1H), 8.05 (d, J=0.9 Hz, 1H), 7.70 (dd, J=7.5, 0.7 Hz, 1H), 7.27 (d, J=7.7 Hz, 1H), 7.18 (dt, J=8.3, 0.8 Hz, 1H), 7.09 (ddd, J=9.4, 3.1, 0.9 Hz, 1H), 7.05-6.97 (m, 1H), 6.78 (dd, J=8.8, 4.8 Hz, 2H), 5.03-4.94 (m, 1H), 4.01 (s, 3H), 2.29-2.16 (m, 1H), 1.77 (dd, J=13.2, 10.9 Hz, 1H), 1.40 (s, 3H), 1.29 (s, 3H); MS (DCI/$NH_3$) m/z 369 (M+H)$^+$.

Example 2

N-[(4R)-6-fluoro-2,2-dimethyl-3,4-dihydro-2H-chromen-4-yl]-N'-1H-indazol-4-ylurea

Example 2A 4-nitro-1H-indazole

2-Methyl-3-nitroaniline (20.0 g, 131 mmol) in acetic acid (200 mL) was treated with $NaNO_2$ (20.0 g, 289 mmol) in water (50 mL) at 4° C. (mechanical stirring). The reaction mixture was allowed to warm to ambient temperature and was stirred for 16 h. Solvent was removed under reduced pressure, and the residue was treated with water (700 mL), and filtered. The filtered solid was dried at 45° C. in a vacuum oven for 10 h to provide the title compound which was used without further purification.

Alternatively, a 4-necked 5-L jacketed round bottom flask fitted with a mechanical stirrer and a thermocouple was charged with 2-methyl-3-nitroaniline (100 g, 658 mmol) and acetic acid (2000 mL). The solution was cooled to 14° C. and treated with a chilled (~1° C.; ice-water bath) solution of NaNO$_2$ (100 g, 1450 mmol) in water (250 mL) added in one portion. The internal temperature rose from 14° C. to 28° C. over 5 min and remained at this temperature for 5 min. before gradually cooling to 15° C. The mixture was stirred for 24 h after and was then concentrated under reduced pressure to an approximate volume of 500 mL. The residue was resuspended in water (1800 mL) at ambient temperature for 21 h. The resulting orange solid was filtered, washed with water (3×250 mL), and dried in a vacuum oven at 70° C. to afford 97.0 g of the title compound as a bright orange solid which was used without further purification.

Example 2B methyl 4-nitro-1H-indazole-1-carboxylate

NaH (300 mg, 12.5 mmol) in N,N-dimethylformamide (5 mL) was treated with Example 2A (1.33 g, 10.0 mmol) at 0° C. The reaction mixture was allowed to warm to ambient temperature and stir for 1 h. The mixture was then treated with methyl chloroformate (0.90 mL) and stirred at room temperature for 3 h. The reaction was quenched with water and filtered to provide the title compound as an off white solid.

Alternatively, to a 3-necked 2-L jacketed flask fitted with a mechanical stirrer, a thermocouple, and an addition funnel was charged with Example 2A (95.2 g, 716 mmol) and N,N-dimethylformamide (650 mL). The dark solution was cooled to 10° C. and DBU (96.0 g, 788 mmol) was added via addition funnel so that the internal temperature did not go beyond 15° C. After cooling the mixture back to 10° C., methyl chloroformate (108 g, 1430 mmol) was added via addition funnel so that the internal temperature did not go beyond 25° C. After 1 h of stirring at 10° C., aqueous 10% potassium phosphate diacid in water (500 mL) was added and the mixture was stirred for 15 h. The resulting brown solid was filtered and the reaction mixture vessel rinsed with aqueous 10% potassium phosphate diacid in water (2×150 mL). The rinses were added to the solid on the filter. The resulting solid was washed with aqueous 10% potassium phosphate diacid in water (2×200 mL) and water (2×200 mL), then was dried in a vacuum oven at 70° C. to afford 122 g of a dark brown solid. The solid was resuspended in isopropyl acetate (2000 mL) for 2 h. The solid was filtered, washed with fresh isopropyl acetate (2×250 mL), and dried in a vacuum oven at 70° C. to afford the title compound (110 g, 495 mmol) as a light brown solid. MS (DCI/NH$_3$) m/z 222 (M+H)$^+$.

Example 2C methyl 4-amino-1H-indazole-1-carboxylate

Example 2B (1.66 g, 7.50 mmol) and 10% Pd/C were combined in ethanol (20 mL) and exposed to hydrogen gas (1 atm pressure). The reaction mixture was heated at 80° C. for 20 min, allowed to cool to ambient temperature, and filtered through Celite. The filtrate was evaporated to provide title compound (1.22 g, 6.35 mmol). MS (DCI/NH$_3$) m/z 192 (M+H)$^+$.

Example 2D

N-[(4R)-6-fluoro-2,2-dimethyl-3,4-dihydro-2H-chromen-4-yl]-N'-1H-indazol-4-ylurea To a 100 mL round-bottomed flask was added N,N'-disuccinyl carbonate (1.38 g, 5.38 mmol), pyridine (0.435 mL, 5.38 mmol) and Example 2C (983 mg, 5.12 mmol) in acetonitrile (15 mL). The brown solution was stirred at room temperature for 30 min and the treated with a solution of Example 1D (1.00 g, 5.12 mmol) in acetonitrile (10 mL) followed by N,N-diisopropylethylamine (2.66 mL, 15.4 mmol). The reaction was stirred for 1 h, then poured into ethyl acetate (200 mL) and washed with saturated NaHCO$_3$ (50 mL) and 1N HCl (50 mL). The solution was dried (Na$_2$SO$_4$), filtered, and concentrated.

The resulting residue was dissolved in tetrahydrofuran (15 mL) and MeOH (15 mL) to give a yellow solution. To the solution was added 5N NaOH (4.8 mL) and the reaction mixture was stirred at ambient temperature for 2 h. The reaction mixture was poured into EtOAc (200 mL) and washed with saturated sodium bicarbonate (50 mL). The organic portion was dried (Na$_2$SO$_4$), filtered, and concentrated. Purified on by silica gel chromatography (gradient elution, with 0-10% MeOH/CH$_2$Cl$_2$) provided the title compound (1.10 g, 3.11 mmol, 83%) as a white amorphous solid. $^1$H NMR (300 MHz, DMSO-d$_6$) δ 13.06-13.04 (br s, 1H), 8.76 (s, 1H), 8.08 (t, J=1.1 Hz, 1H), 7.68 (d, J=7.2 Hz, 1H), 7.23 (d, J=7.76 Hz, 1H), 7.11-6.98 (m, 3H), 6.81-6.76 (m, 2H), 5.04-4.94 (m, 1H), 2.19 (dd, J=13.2, 6.2 Hz, 1H), 1.77 (dd, J=13.2, 10.9 Hz, 1H), 1.40 (s, 3H), 1.29 (s, 3H). MS (DCI/NH$_3$) m/z 355 (M+H)$^+$; [α]$^{23}_D$ +39.2° (c 1.0, MeOH).

Example 3

N-[(4R)-6-fluoro-2,2-dimethyl-3,4-dihydro-2H-chromen-4-yl]-N'-[(7S)-7-hydroxy-5,6,7,8-tetrahydronaphthalen-1-yl]urea Example 3A 8-amino-1,2,3,4-tetrahydronaphthalen-2-ol Ethanol (1 L) was added to 8-amino-2-naphthol (100 g, 610 mmol), Raney nickel (40 g, water wet), and sodium hydroxide (4.00 g, 8 mol % aqueous) in a stirred reactor. The reactor was sealed and sparged with hydrogen. The reaction mixture was stirred for 13 h at 85° C. and then an additional 8 h at 100° C. The mixture was then filtered through a pad of Celite. The resulting solution was treated with Darco G-60 (35 g) and heated to reflux for 1 h, then cooled to ambient temperature and stirred an additional 3 h. This mixture was filtered through Celite (350 g), and the pad washed with EtOAc (1.5 L). The solvent was removed in vacuo and methyl tert-butyl ether (1 L) was added. This was heated for 15 min at 50° C., stirred for 1 h at ambient temperature, filtered, and the solvent removed in vacuo. Approximately half of the resulting crude solid was purified by chromatography on silica gel (gradient elution, 2-30% MeOH/CH$_2$Cl$_2$) to give 37 g of the title compound as a light brown solid. $^1$H NMR (300 MHz, CDCl$_3$) δ 6.96 (t, J=7.6 Hz, 1H), 6.55 (dd, J=10.7, 7.6 Hz, 2H), 4.44-4.24 (m, 1H), 2.95-2.80 (m, 3H), 2.38 (dd, J=16.1, 7.6 Hz, 1H), 2.09-1.96 (m, 1H), 1.85-1.70 (m, 1H).

Example 3B (2S)-8-amino-1,2,3,4-tetrahydronaphthalen-2-ol

Example 3A was dissolved in isopropanol, loaded on a Chiralpak IC chiral HPLC column (30 cm ID×250 cm), and eluted with 32% isopropanol/hexane at 25° C. with a flow rate of 20 mL/min. The earlier eluting peak (retention time=16 min) was collected and the solvent evaporated to afford the title compound as an off-white solid in 99.2% ee. MS (DCI/NH$_3$) m/z 164 (M+H)$^+$, 181 (M+NH$_4$)$^+$.

Example 3C

N-[(4R)-6-fluoro-2,2-dimethyl-3,4-dihydro-2H-chromen-4-yl]-N'-[(7S)-7-hydroxy-5,6,7,8-tetrahydronaphthalen-1-yl]urea To a suspension of di(N-succinimidyl) carbonate (703 mg, 2.75 mmol) in acetonitrile (5 mL) was added Example 3B (427 mg, 2.62 mmol) dissolved in acetonitrile (10 mL) and pyridine (0.222 mL, 2.75 mmol). The reaction was stirred for 20 min whereupon Example 1C (510.6 mg, 2.62 mmol) in acetonitrile (10 mL) and N,N-diisopropylethylamine (1.37 mL, 7.85 mmol) was added. The reaction was stirred for 16 h at ambient temperature. EtOAc (200 mL) was added and the reaction mixture was washed with water (2×200 mL) and brine (200 mL), and partitioned. The organic portion was dried (Na$_2$SO$_4$) and filtered. Solvent was evaporated under reduced pressure and a white solid precipitated from solution. The solid was collected, triturated with diethyl ether, and filtered. The solid was rinsed with diethyl ether, then hexanes, and air-dried to provide the title compound (737 mg, 1.92 mmol, 73% yield) as a beige powder. $^1$H NMR (300 MHz, DMSO-d$_6$) δ 7.70 (d, J=7.9 Hz, 1H), 7.60 (s, 1H), 7.08-6.94 (m, 4H), 6.81-6.71 (m, 2H), 4.93 (dd, J=18.0, 7.2 Hz 1H), 4.86 (d, J=4.2 Hz, 1H), 3.98-3.87 (m, 1H), 2.91-2.63 (m, 3H), 2.37 (dd, J=16.5, 7.7 Hz, 1H), 2.15 (dd, J=13.2, 6.2 Hz, 1H), 1.93-1.83 (m, 1H), 1.69 (dd, J=13.0, 11.1 Hz, 1H), 1.63-1.52 (m, 1H), 1.39 (s, 3H), 1.26 (s, 3H); MS (ESI) m/z 385 (M+H)$^+$; [α]$^{23}_D$ +38.0° (c 1.0, CH$_3$OH).

Example 4

N-[(4R)-6-fluoro-2,2-dimethyl-3,4-dihydro-2H-chromen-4-yl]-N'-[(7R)-7-hydroxy-5,6,7,8-tetrahydronaphthalen-1-yl]urea

Example 4A (2R)-8-amino-1,2,3,4-tetrahydronaphthalen-2-ol

Example 3A was dissolved in isopropanol, loaded on a Chiralpak IC chiral HPLC column (30 cm ID×250 cm), and eluted with 32% isopropanol/hexane at 25° C. with a flow rate of 20 mL/min. The later eluting peak (retention time=19 min) was collected and the solvent evaporated to afford the title compound as an off-white solid in 99.6% ee. MS (DCI/NH$_3$) m/z 164 (M+H)$^+$, 181 (M+NH$_4$)$^+$.

Example 4B

N-[(4R)-6-fluoro-2,2-dimethyl-3,4-dihydro-2H-chromen-4-yl]-N'-[(7R)-7-hydroxy-5,6,7,8-tetrahydronaphthalen-1-yl]urea The title compound was prepared according to the procedure of Example 3C, substituting Example 4A for Example 3B. $^1$H NMR (300 MHz, DMSO-d$_6$) δ 7.69 (d, J=7.9 Hz, 1H), 7.61 (s, 1H), 7.08-6.94 (m, 4H), 6.81-6.71 (m, 2H), 4.99-4.88 (m, 1H), 4.86 (d, J=4.1 Hz, 1H), 4.00-3.88 (m, 1H), 2.90-2.64 (m, 3H), 2.35 (dd, J=16.5, 7.7 Hz, 1H), 2.15 (dd, J=13.2, 6.2 Hz, 1H), 1.93-1.81 (m, 1H), 1.69 (dd, J=13.0, 11.1 Hz, 1H), 1.64-1.51 (m, 1H), 1.39 (s, 3H), 1.27 (s, 3H); MS (DCI/NH$_3$) m/z 385 (M+H)$^+$; [α]$^{23}_D$ +34.6° (c 1.0, CH$_3$OH).

Example 5

N-[(4R)-6-fluoro-2,2-dimethyl-3,4-dihydro-2H-chromen-4-yl]-N'-isoquinolin-5-ylurea In a 500 mL round-bottomed flask was added N,N'-disuccinimidyl carbonate (1.38 g, 5.38 mmol), pyridine (0.435 mL, 5.38 mmol) and isoquinolin-5-amine (0.738 g, 5.12 mmol, Acros) in acetonitrile (15 mL) to give a brown solution. The reaction was stirred at ambient temperature for 30 min. To the mixture was added Example 1C (1.00 g, 5.12 mmol) in acetonitrile (10 mL) and N,N-diisopropylethylamine (2.66 mL, 15.4 mmol). The reaction was stirred for 90 min then was concentrated. The mixture was diluted with EtOAc (300 mL) and was washed with saturated NaHCO$_3$ (100 mL) dried (Na$_2$SO$_4$), filtered and concentrated. The residue was purified by silica gel chromatography (gradient elution, 0-10% MeOH/CH$_2$Cl$_2$) to give the title compound (1.12 g, 3.07 mmol, 60%) as a white solid. $^1$H NMR (300 MHz, DMSO-d$_6$) δ 9.29 (d, J=0.8 Hz, 1H), 8.76 (s, 1H), 8.56 (d, J=6.0 Hz, 1H), 8.34 (dd, J=7.7, 1.1 Hz, 1H), 7.94 (d, J=6.1 Hz, 1H), 7.77 (d, J=8.1 Hz, 1H), 7.64 (t, J=7.9 Hz, 1H), 7.12 (ddd, J=9.4, 3.2, 0.9 Hz, 1H), 7.06-6.98 (m, 2H), 6.79 (dd, J=8.9, 4.9 Hz, 1H), 5.05-4.95 (m, 1H), 2.21 (dd, J=13.2, 6.2 Hz, 1H), 1.78 (dd, J=13.2, 10.9 Hz, 1H), 1.41 (s, 3H), 1.29 (s, 3H); MS (DCI/NH$_3$) m/z 366 (M+H)$^+$; [α]$^{23}_D$ +32.6° (c 0.65, CH$_3$OH).

Example 6

N-[(4R)-6-fluoro-3,3',4,4'-tetrahydro-2'H-spiro[chromene-2,1'-cyclobutan]-4-yl]-N'-[(7R)-7-hydroxy-5,6,7,8-tetrahydronaphthalen-1-yl]urea

Example 6A 6-fluorospiro[chroman-2,1'-cyclobutan]-4-one

The title compound was prepared according to the procedure of Example 1A, using 1-(5-fluoro-2-hydroxyphenyl)ethanone and substituting cyclobutanone for propan-2-one. MS (DCI/NH$_3$) m/z 207 (M+H)$^+$.

Example 6B (E)-6-fluorospiro[chroman-2,1'-cyclobutan]-4-one O-methyl oxime

In a 500 mL round-bottomed flask was added Example 6A (19.4 g, 94.9 mmol) and O-methylhydroxylamine hydrochloride (8.53 mL, 112 mmol) in pyridine (150 mL) to give a yellow solution. The reaction mixture was stirred for 54 h at ambient temperature, concentrated, diluted with EtOAc (1 L), and washed with water (400 mL). The organic portion was dried (Na$_2$SO$_4$), filtered and concentrated. The resulting yellow residue was purified by silica gel chromatography (gradient elution, 0-30% EtOAc/hexanes) to provide the title compound (21.8 g, 94.0 mmol, 99%) as a pale yellow solid. MS (DCI/NH$_3$) m/z 224 (M+NH$_4$)$^+$.

Example 6C 6-fluorospiro[chroman-2,1'-cyclobutan]-4-amine

Example 6B (21.8 g, 94.0 mmol) and Raney nickel (5.49 g, water wet) were stirred in EtOH containing 7 M ammonia (150 mL). The reactor was sealed and sparged with hydrogen. The reaction mixture was stirred for 3 h at 32° C., cooled, diluted with EtOAc (250 mL) and filtered through a pad of Celite (50 g). The resulting solution was filtered through a plug of silica gel (50 g) and the filtrate evaporated to give the title compound (10.8 g, 52.1 mmol, 56%) as a pale oil. MS (DCI/NH$_3$) m/z 208 (M+H)$^+$.

Example 6D (R)-6-fluorospiro[chroman-2,1'-cyclobutan]-4-amine

Example 6C was resolved by semi-preparative chiral HPLC (Chiralcel OD 5×50 cm, 5% isopropanol/hexane+ 0.1% diethylamine, 23° C., 100 mL/min). The later of the two eluting peaks (retention time=26.0 min) was collected and the solvent evaporated to afford the title compound as an off-white solid in 99% ee versus a racemic reference (prepared as described above using sodium borohydride as the reducing agent). MS (DCI/NH$_3$) m/z 208 (M+H)$^+$.

Example 6E

N-[(4R)-6-fluoro-3,3',4,4'-tetrahydro-2'H-spiro[chromene-2,1'-cyclobutan]-4-yl]-N'-[(7R)-7-hydroxy-5,6,7,8-tetrahydronaphthalen-1-yl]urea The title compound was prepared according to the procedure of Example 3C, substituting Example 6D for Example 1C, and substituting Example 4A for Example 3B. $^1$H NMR (300 MHz, DMSO-d$_6$) δ 7.70 (d, J=7.8 Hz, 1H), 7.62 (s, 1H), 7.06-6.96 (m, 4H), 6.81 (dd, J=9.6, 4.9 Hz, 1H), 6.74 (d, J=7.4 Hz, 1H), 4.93 (dd, J=14.8, 9.1 Hz 1H), 4.86 (d, J=4.1 Hz, 1H), 3.99-3.88 (m, 1H), 2.91-2.64 (m, 3H), 2.42-2.03 (m, 6H), 1.93-1.67 (m, 4H), 1.67-1.52 (m, 1H); MS (ESI) m/z 397 (M+H)$^+$; [α]$^{23}_D$ +62.8° (c 1.0, CH$_3$OH)

Example 7

N-[(4R)-6-fluoro-3,3',4,4'-tetrahydro-2'H-spiro[chromene-2,1'-cyclobutan]-4-yl]-N'-(1-methyl-1H-indazol-4-yl)urea The title compound was prepared according to the procedure of Example 1H, substituting Example 6D for Example 1D. $^1$H NMR (300 MHz, DMSO-d$_6$) δ 8.79 (s, 1H), 8.05 (d, J=0.9 Hz, 1H), 7.72 (dd, J=7.5, 0.7 Hz, 1H), 7.28 (d, J=7.7 Hz, 1H), 7.20-7.16 (m, 1H), 7.09-6.99 (m, 2H), 6.83 (dd, J=8.7, 4.7 Hz, 2H), 5.03-4.94 (m, 1H), 4.01 (s, 3H), 2.51-2.38 (m, 1H), 2.36-2.04 (m, 4H), 2.00-1.68 (m, 3H); MS (DCI/NH$_3$) m/z 381 (M+H)$^+$; [α]$^{23}_D$ +34.4° (c 0.50, CH$_3$OH).

Example 8

N-[(4R)-6-fluoro-3,3',4,4'-tetrahydro-2'H-spiro[chromene-2,1'-cyclobutan]-4-yl]-N'-1H-indazol-4-ylurea The title compound was prepared according to the procedure of Example 2D, substituting Example 6D for Example 1D. $^1$H NMR (300 MHz, DMSO-d$_6$) δ 13.03-13.01 (br s, 1H), 8.75 (s, 1H), 8.08 (s, 1H), 7.68 (d, J=7.2 Hz, 1H), 7.22 (d, J=7.8 Hz, 1H), 7.11-6.94 (m, 3H), 6.86-6.81 (m, 2H), 5.03-4.94 (m, 1H), 2.45-2.06 (m, 5H), 1.95-1.69 (m, 3H); MS (DCI/NH$_3$) m/z 367 (M+H)$^+$; [α]$^{23}_D$ +24.1° (c 0.70, CH$_3$OH).

Example 9

N-[(4R)-6-fluoro-3,3',4,4'-tetrahydro-2'H-spiro[chromene-2,1'-cyclobutan]-4-yl]-N'-[(7S)-7-hydroxy-5,6,7,8-tetrahydronaphthalen-1-yl]urea The title compound was prepared according to the procedure of Example 3C, substituting Example 6D for Example 1C. $^1$H NMR (300 MHz, DMSO-d$_6$) δ 7.71 (d, J=7.3 Hz, 1H), 7.61 (s, 1H), 7.07-6.95 (m, 4H), 6.86-6.77 (m, 1H), 6.74 (d, J=7.4 Hz, 1H), 4.92 (dd, J=14.5, 9.2 Hz, 1H), 4.85 (d, J=4.3 Hz, 1H), 3.99-3.87 (m, 1H), 2.91-2.64 (m, 3H), 2.42-2.03 (m, 6H), 1.93-1.67 (m, 4H), 1.67-1.52 (m, 1H); MS (ESI) m/z 397 (M+H)$^+$; [α]$^{23}_D$ +68.4° (c 1.0, CH$_3$OH).

Example 10

N-[(4S)-6-fluoro-3,3',4,4'-tetrahydro-2'H-spiro[chromene-2,1'-cyclobutan]-4-yl]-N'-[(7S)-7-hydroxy-5,6,7,8-tetrahydronaphthalen-1-yl]urea Example 10A (S)-6-fluorospiro[chroman-2,1'-cyclobutan]-4-amine Example 6C was resolved by semi-preparative chiral HPLC (Chiralcel OD 5×50 cm, 5% isopropanol/hexane+ 0.1% diethylamine, 23° C., 100 mL/min). The earlier of the two eluting peaks (retention time=20.9 min) was collected and the solvent evaporated to afford the title compound as an off-white solid in 99% ee versus a racemic reference (prepared as described above using sodium borohydride as the reducing agent). MS (DCI/NH$_3$) m/z 208 (M+H)$^+$.

Example 10B

N-[(4S)-6-fluoro-3,3',4,4'-tetrahydro-2'H-spiro[chromene-2,1'-cyclobutan]-4-yl]-N'-[(7S)-7-hydroxy-5,6,7,8-tetrahydronaphthalen-1-yl]urea The title compound was prepared according to the procedure of Example 3C, substituting Example 10A for Example 1C. $^1$H NMR (300 MHz, DMSO-d$_6$) δ 7.71 (d, J=7.4 Hz, 1H), 7.62 (s, 1H), 7.07-6.96 (m, 4H), 6.81 (dd, J=9.6, 4.8 Hz, 1H), 6.74 (d, J=7.0 Hz, 1H), 4.98-4.89 (m, 1H), 4.87 (d, J=4.1 Hz, 1H), 3.99-3.89 (m, 1H), 2.90-2.64 (m, 3H), 2.41-2.02 (m, 6H), 1.92-1.67 (m, 4H), 1.66-1.51 (m, 1H); MS (ESI) m/z 397 (M+H)$^+$; [α]$^{23}_D$ −59.5° (c 1.0, CH$_3$OH).

Example 11

N-[(4S)-6-fluoro-3,3',4,4'-tetrahydro-2'H-spiro[chromene-2,1'-cyclobutan]-4-yl-]-N'-[(7R)-7-hydroxy-5,6,7,8-tetrahydronaphthalen-1-yl]urea The title compound was prepared according to the procedure of Example 3C, substituting Example 4A for Example 3B, and substituting Example 10A for Example 1C. $^1$H NMR (300 MHz, DMSO-d$_6$) δ 7.71 (d, J=7.4 Hz, 1H), 7.61 (s, 1H), 7.06-6.95 (m, 4H), 6.85-6.77 (m, 1H), 6.74 (d, J=7.5 Hz, 1H), 4.92 (dd, J=15.0, 9.1 Hz, 1H), 4.85 (d, J=5.3 Hz, 1H), 3.99-3.87 (m, 1H), 2.90-2.64 (m, 3H), 2.43-2.03 (m, 6H), 1.92-

1.66 (m, 4H), 1.66-1.52 (m, 1H); MS (ESI) m/z 397 (M+H)+; [α]$^{23}_D$ −63.0° (c 1.0, CH$_3$OH).

Example 12

N-[(4R)-6-fluoro-3,4-dihydro-2H-chromen-4-yl]-N'-(1-methyl-1H-indazol-4-yl)urea

Example 12A 6-fluorochroman-4-one

The title compound was prepared according to the procedure of Example 1A, substituting paraformaldehyde for propan-2-one. MS (DCI/NH$_3$) m/z 183 (M+NH$_4$)+.

Example 12B (R)-6-fluorochroman-4-amine, (R)-2-hydroxy-2-phenylacetic acid salt

The title compound was prepared from Example 12A according to the methods described in Example 1B, Example 1C, and Example 1D. MS (DCI/NH$_3$+) m/z 168 (M+H)+.

Example 12C

N-[(4R)-6-fluoro-3,4-dihydro-2H-chromen-4-yl]-N'-(1-methyl-1H-indazol-4-yl)urea

The title compound was prepared according to the procedure of Example 1H, substituting Example 12B for Example 1D. $^1$H NMR (300 MHz, DMSO-d$_6$) δ 8.63 (s, 1H), 8.00 (d, J=0.9 Hz, 1H), 7.70 (d, J=7.5 Hz, 1H), 7.43-7.25 (m, 2H), 7.18-6.79 (m, 5H), 5.01-4.88 (m, 1H), 4.20-4.00 (m, 4H), 2.20-1.84 (m, 2H); MS (DCI/NH$_3$) m/z 341 (M+H)+; [α]$^{23}_D$ +37.0° (c 0.15, MeOH).

Example 13

N-[(4R)-6-fluoro-3,4-dihydro-2H-chromen-4-yl]-N'-isoquinolin-5-ylurea

The title compound was prepared according to the procedure of Example 5, substituting Example 12B for Example 1C. $^1$H NMR (300 MHz, DMSO-d$_6$) δ 9.28 (s, 1H), 8.62 (s, 1H), 8.54 (d, J=6.0 Hz, 1H), 8.36 (d, J=8.1 Hz, 1H), 7.90 (d, J=6.1 Hz, 1H), 7.76 (d, J=8.1 Hz, 1H), 7.63 (t, J=7.9 Hz, 1H), 7.24-6.99 (m, 3H), 6.85 (dd, J=9.0, 4.9 Hz, 1H), 4.97-4.90 (m, 1H), 4.33-4.23 (m, 1H), 4.18 (ddd, J=11.3, 8.3, 3.0 Hz, 1H), 2.28-1.96 (m, 2H); MS (DCI/NH$_3$) m/z 338 (M+H)+; [α]$^{23}_D$ +29.0° (c 0.25 CH$_3$OH).

Example 14

N-[(4R)-6-fluoro-3,4-dihydro-2H-chromen-4-yl]-N'-[(7R)-7-hydroxy-5,6,7,8-tetrahydronaphthalen-1-yl]urea N,N'-Disuccinimidyl carbonate (842 mg, 3.29 mmol) was suspended in acetonitrile (10 mL) and treated with a solution of Example 4A (511 mg, 3.13 mmol) dissolved in acetonitrile (10 mL) and pyridine (0.265 mL, 3.29 mmol). The brown solution was stirred for 20 min at ambient temperature. Example 12B (1.00 g, 3.13 mmol) was added, followed by acetonitrile (15 mL) and N,N-diisopropyethylamine (2.19 mL, 12.5 mmol). The resulting slurry was stirred at ambient temperature for 3 hours; analysis by LC/MS indicated complete reaction. EtOAc (200 mL) was added, and the organic portion was washed with aq. K$_2$CO$_3$ (200 mL), 1N NaOH (200 mL), water (200 mL), and brine (200 mL). The combined aqueous washes were extracted with EtOAc (200 mL), and the combined organic portions were dried (Na$_2$SO$_4$), filtered, and concentrated. The crude residue was suspended in MeOH (50 mL), ane the suspension was sonicated. Water (300 mL) was added with rapidly stirring, and the resulting precipitate was collected, washed with water, and lyophilized for 12 h to provide the title compound (1.05 g, 2.96 mmol, 94%) as a gray powder. $^1$H NMR (300 MHz, DMSO-d$_6$) δ 7.73 (d, J=8.0 Hz, 1H), 7.49 (s, 1H), 7.13 (d, J=7.7 Hz, 1H), 7.10-6.96 (m, 3H), 6.82 (dd, J=8.9, 4.9 Hz, 1H), 6.72 (d, J=7.3 Hz, 1H), 4.89-4.82 (m, 2H), 4.26 (ddd, J=10.1, 6.8, 3.2 Hz, 1H), 4.13 (ddd, J=11.2, 8.4, 2.9 Hz, 1H), 3.98-3.87 (m, 1H), 2.88-2.62 (m, 3H), 2.31 (dd, J=16.8, 8.0 Hz, 1H), 2.18-2.04 (m, 1H), 2.01-1.81 (m, 2H), 1.66-1.50 (m, 1H); MS (ESI) m/z 357 (M+H)+; [α]$^{23}_D$ +66.1° (c 1.0, 1:1 DMSO:CH$_3$OH).

Example 15

N-[(4R)-6-fluoro-3,4-dihydro-2H-chromen-4-yl]-N'-[(7S)-7-hydroxy-5,6,7,8-tetrahydronaphthalen-1-yl]urea The title compound was prepared according to the procedure of Example 14, substituting Example 3B for Example 4A. $^1$H NMR (300 MHz, DMSO-d$_6$) δ 7.74 (d, J=8.0 Hz, 1H), 7.49 (s, 1H), 7.13 (d, J=7.7 Hz, 1H), 7.10-6.96 (m, 3H), 6.82 (dd, J=8.9, 4.9 Hz, 1H), 6.72 (d, J=7.5 Hz, 1H), 4.90-4.81 (m, 2H), 4.26 (ddd, J=10.2, 6.6, 3.1 Hz, 1H), 4.13 (ddd, J=11.3, 8.4, 2.9 Hz, 1H), 3.98-3.85 (m, 1H), 2.90-2.62 (m, 3H), 2.32 (dd, J=16.5, 7.7 Hz, 1H), 2.17-2.03 (m, 1H), 2.01-1.81 (m, 2H), 1.67-1.50 (m, 1H); MS (ESI) m/z 357 (M+H)+; [α]$^{23}_D$ +62.0° (c 1.0, 1:1 DMSO:CH$_3$OH).

Example 16

N-[(4R)-6,8-difluoro-2,2-dimethyl-3,4-dihydro-2H-chromen-4-yl]-N'-(1-methyl-1H-indazol-4-yl)urea Example 16A 6,8-difluoro-2,2-dimethylchroman-4-one The title compound was prepared according to the procedure of Example 1A, substituting 1-(3,5-difluoro-2-hydroxyphenyl)ethanone for 1-(5-fluoro-2-hydroxyphenyl)ethanone. MS (DCI/NH$_3$) m/z 230 (M+NH$_4$)+.

Example 16B (R)-6,8-difluoro-2,2-dimethylchroman-4-amine, (R)-2-hydroxy-2-phenylacetic acid salt The title compound was prepared from Example 16A according to the methods described in Example 1B, Example 1C, and Example 1D. MS (DCI/NH$_3$) m/z 214 (M+H)+.

Example 16C

N-[(4R)-6,8-difluoro-2,2-dimethyl-3,4-dihydro-2H-chromen-4-yl]-N'-(1-methyl-1H-indazol-4-yl)urea The title compound was prepared according to the procedure of Example 1H, substituting Example 16B for Example 1D. ¹H NMR (300 MHz, DMSO-d$_6$) δ 8.80 (s, 1H), 8.05 (d, J=0.9 Hz, 1H), 7.69 (dd, J=7.5, 0.8 Hz, 1H), 7.32-7.15 (m, 3H), 6.99-6.94 (m, 1H), 6.80 (d, J=8.3 Hz, 1H), 5.06-4.96 (m, 1H), 4.01 (s, 3H), 2.23 (dd, J=13.3, 6.2 Hz, 1H), 2.00-1.81 (m, 1H), 1.45 (s, 3H), 1.32 (s, 3H); MS (DCI/NH$_3$) m/z 387 (M+H)$^+$; [α]$^{23}_D$ +19.3° (c 0.73, MeOH).

Example 17

N-[(4R)-6,8-difluoro-2,2-dimethyl-3,4-dihydro-2H-chromen-4-yl]-N'-isoquinolin-5-ylurea In a 200 mL round-bottomed flask was added N,N'-disuccinimidyl carbonate (736 mg, 2.87 mmol), pyridine (0.232 mL, 2.87 mmol) and isoquinolin-5-amine (395 mg, 2.74 mmol) in acetonitrile (15 mL) to give a brown solution. The reaction was stirred at ambient temperature for 30 minutes. To the mixture was added Example 16B (1.00 g, 2.74 mmol) in acetonitrile (10 mL) and N,N-diisopropyethylamine (1.42 mL, 8.21 mmol). The reaction was stirred for 90 minutes and concentrated. The mixture was diluted with ethyl acetate (300 mL) and washed with saturated. NaHCO$_3$ (100 mL), dried (Na$_2$SO$_4$), filtered, and concentrated. The resulting residue was purified purified by silica gel chromatography (gradient elution, 0-10% MeOH/CH$_2$Cl$_2$) to provide the title compound (869 mg, 2.27 mmol, 83%) as an off-white solid. ¹H NMR (300 MHz, DMSO-d$_6$) δ 9.29 (d, J=0.8 Hz, 1H), 8.77 (s, 1H), 8.56 (d, J=6.0 Hz, 1H), 8.35 (dd, J=7.7, 1.1 Hz, 1H), 7.93 (d, J=6.1 Hz, 1H), 7.77 (d, J=8.1 Hz, 1H), 7.64 (t, J=7.9 Hz, 1H), 7.18-7.07 (m, 2H), 7.04 (d, J=8.4 Hz, 1H), 6.89 (td, J=7.9, 5.0 Hz, 1H), 5.10-5.01 (m, 1H), 2.24 (dd, J=13.3, 6.2 Hz, 1H), 2.00-1.81 (m, 1H), 1.46 (s, 3H), 1.33 (s, 3H). MS (DCI/NH$_3$) m/z 366 (M+H)$^+$; [α]$^{23}_D$ +26.7° (c 0.70, CH$_3$OH).

Example 18

N-[(4R)-6,8-difluoro-2,2-dimethyl-3,4-dihydro-2H-chromen-4-yl]-N'-[(7R)-7-hydroxy-5,6,7,8-tetrahydronaphthalen-1-yl]urea The title compound was prepared according to the procedure of Example 14, substituting Example 16B for Example 12B. ¹H NMR (300 MHz, DMSO-d$_6$) δ 7.71-7.61 (m, 2H), 7.17 (ddd, J=11.5, 8.8, 3.0 Hz, 1H), 7.06-6.97 (m, 2H), 6.91 (d, J=9.3 Hz, 1H), 6.75 (d, J=7.2 Hz, 1H), 5.02-4.89 (m, 1H), 4.86 (d, J=4.1 Hz, 1H), 4.00-3.87 (m, 1H), 2.90-2.64 (m, 3H), 2.35 (dd, J=16.5, 7.7 Hz, 1H), 2.19 (dd, J=13.2, 6.2 Hz, 1H), 1.93-1.82 (m, 1H), 1.77 (dd, J=13.2, 11.2 Hz, 1H), 1.68-1.51 (m, 1H), 1.43 (s, 3H), 1.30 (s, 3H); MS (ESI) m/z 403 (M+H)$^+$; [α]$^{23}_D$ +39.4° (c 1.0, CH$_3$OH).

Example 19

N-[(4R)-6,8-difluoro-2,2-dimethyl-3,4-dihydro-2H-chromen-4-yl]-N'-[(7S)-7-hydroxy-5,6,7,8-tetrahydronaphthalen-1-yl]urea The title compound was prepared according to the procedure of Example 14, substituting Example 3B for Example 4A, and substituting Example 16B for Example 12B. ¹H NMR (300 MHz, DMSO-d$_6$) δ 7.72-7.62 (m, 2H), 7.17 (ddd, J=11.4, 8.7, 3.0 Hz, 1H), 7.06-6.97 (m, 2H), 6.91 (d, J=9.3 Hz, 1H), 6.75 (d, J=7.4 Hz, 1H), 5.02-4.88 (m, 1H), 4.86 (d, J=4.1 Hz, 1H), 3.98-3.86 (m, 1H), 2.91-2.61 (m, 3H), 2.37 (dd, J=16.5, 7.8 Hz, 1H), 2.19 (dd, J=13.3, 6.2 Hz, 1H), 1.93-1.82 (m, 1H), 1.77 (dd, J=13.2, 11.3 Hz, 1H), 1.67-1.52 (m, 1H), 1.43 (s, 3H), 1.30 (s, 3H); MS (ESI) m/z 403 (M+H)$^+$; [α]$^{23}_D$ +42.8° (c 1.0, CH$_3$OH).

Example 20

N-[(4R)-8-fluoro-2,2-dimethyl-3,4-dihydro-2H-chromen-4-yl]-N'-[(7R)-7-hydroxy-5,6,7,8-tetrahydronaphthalen-1-yl]urea Example 20A 8-fluoro-2,2-dimethylchroman-4-one The title compound was prepared according to the procedure of Example 1A, substituting 1-(3-fluoro-2-hydroxyphenyl)ethanone for 1-(5-fluoro-2-hydroxyphenyl)ethanone and using propan-2-one. MS (DCI/NH$_3$) m/z 212 (M+NH$_4$)$^+$.

Example 20B (R)-8-fluoro-2,2-dimethylchroman-4-amine, (R)-2-hydroxy-2-phenylacetic acid salt The title compound was prepared from Example 20A according to the methods described in Example 1B, Example 1C, and Example 1D. MS (DCI/NH$_3$) m/z 196 (M+H)$^+$.

Example 20C

N-[(4R)-8-fluoro-2,2-dimethyl-3,4-dihydro-2H-chromen-4-yl]-N'-[(7R)-7-hydroxy-5,6,7,8-tetrahydronaphthalen-1-yl]urea The title compound was prepared according to the procedure of Example 14, substituting Example 20B for Example 12B. ¹H NMR (300 MHz, DMSO-d$_6$) δ 7.70 (d, J=7.4 Hz, 1H), 7.60 (s, 1H), 7.14-6.94 (m, 4H), 6.87 (td, J=8.0, 5.0 Hz, 1H), 6.74 (d, J=7.1 Hz, 1H), 5.04-4.92 (m, 1H), 4.86 (d, J=4.2 Hz, 1H), 3.99-3.86 (m, 1H), 2.90-2.63 (m, 3H), 2.36 (dd, J=16.6, 7.8 Hz, 1H), 2.18 (dd, J=13.3, 6.2 Hz, 1H), 1.93-1.82 (m, 1H), 1.76 (dd, J=13.3, 10.9 Hz, 1H), 1.67-1.51 (m, 1H), 1.44 (s, 3H), 1.31 (s, 3H); MS (ESI) m/z 385 (M+H)$^+$; [α]$^{23}_D$ +35.8° (c 1.0, CH$_3$OH).

Example 21

N-[(4R)-8-fluoro-2,2-dimethyl-3,4-dihydro-2H-chromen-4-yl]-N'-[(7S)-7-hydroxy-5,6,7,8-tetrahydronaphthalen-1-yl]urea The title compound was prepared according to the procedure of Example 14, substituting Example 3B for Example 4A, and substituting Example 20B for Example 12B. ¹H NMR (300 MHz, DMSO-d$_6$) δ 7.69 (d, J=7.4 Hz, 1H), 7.60 (s, 1H), 7.14-6.94 (m, 2H), 6.87 (td, J=8.0, 5.0 Hz, 1H), 6.74 (d, J=7.3 Hz, 1H), 5.04-4.92 (m, 1H), 4.86 (d, J=4.2 Hz, 1H), 3.99-3.87 (m, 1H), 2.89-2.64 (m, 3H), 2.34 (dd, J=16.5, 7.8 Hz, 1H), 2.19 (dd, J=13.4, 6.2 Hz, 1H), 1.93-1.82 (m, 2H), 1.76 (dd, J=13.3, 11.0 Hz, 1H), 1.61 (d, J=5.4 Hz, 1H), 1.44 (s, 3H), 1.31 (s, 3H); MS (ESI) m/z 385 (M+H)$^+$; [α]$^{23}_D$ +30.7° (c 1.0, CH$_3$OH).

Example 22

N-[(4R)-8-fluoro-2,2-dimethyl-3,4-dihydro-2H-chromen-4-yl]-N'-isoquinolin-5-ylurea The title compound was prepared according to the procedure of Example 17 substituting Example 20B for Example 16B. ¹H NMR (300 MHz, DMSO-d₆) δ 9.29 (d, J=0.9 Hz, 1H), 8.78 (s, 1H), 8.56 (d, J=6.0 Hz, 1H), 8.32 (dd, J=7.7, 1.1 Hz, 1H), 7.94 (d, J=6.1 Hz, 1H), 7.78 (d, J=8.1 Hz, 1H), 7.64 (t, J=7.9 Hz, 1H), 7.20 (ddd, J=11.3, 8.5, 2.9 Hz, 1H), 7.07-6.97 (m, 2H), 5.08-4.91 (m, 1H), 2.31-2.03 (m, 1H), 1.91-1.82 (m, 1H), 1.45 (s, 3H), 1.32 (s, 3H). MS (DCI/NH₃) m/z 384 (M+H)⁺; [α]²³_D +32.5° (c 0.63, CH₃OH).

Example 23

N-[(4R)-7-fluoro-2,2-dimethyl-3,4-dihydro-2H-chromen-4-yl]-N'-isoquinolin-5-ylurea

Example 23A 7-fluoro-2,2-dimethylchroman-4-one

The title compound was prepared according to the procedure of Example 1A, substituting 1-(4-fluoro-2-hydroxyphenyl)ethanone for 1-(5-fluoro-2-hydroxyphenyl)ethanone. MS (DCI/NH₃) m/z 212 (M+NH₄)⁺.

Example 23B (R)-7-fluoro-2,2-dimethylchroman-4-amine, (R)-2-hydroxy-2-phenylacetic acid salt The title compound was prepared from Example 23A according to the methods described in Example 1B, Example 1C, and Example 1D. MS (DCI/NH₃) m/z 196 (M+H)⁺.

Example 23C

N-[(4R)-7-fluoro-2,2-dimethyl-3,4-dihydro-2H-chromen-4-yl]-N'-isoquinolin-5-ylurea The title compound was prepared according to the procedure of Example 17 substituting Example 23B for Example 16B. ¹H NMR (300 MHz, DMSO-d₆) δ 9.29 (s, 1H), 8.72 (s, 1H), 8.56 (d, J=6.0 Hz, 1H), 8.35 (d, J=7.7 Hz, 1H), 7.93 (d, J=6.1 Hz, 1H), 7.77 (d, J=8.1 Hz, 1H), 7.63 (t, J=7.9 Hz, 1H), 7.39-7.34 (m, 1H), 6.98 (d, J=8.3 Hz, 1H), 6.76 (td, J=8.5, 2.7 Hz, 1H), 6.62 (dd, J=10.6, 2.6 Hz, 1H), 5.05-4.95 (m, 1H), 2.21 (dd, J=13.3, 6.1 Hz, 1H), 1.79 (dd, J=13.2, 10.7 Hz, 1H), 1.42 (s, 3H), 1.32 (m, 3H). MS (DCI/NH₃) m/z 366 (M+H)⁺; [α]²³_D +28.5° (c 0.82, CH₃OH).

Example 24

N-[(4R)-7-fluoro-2,2-dimethyl-3,4-dihydro-2H-chromen-4-yl]-N'-(1-methyl-1H-indazol-4-yl)urea The title compound was prepared according to the procedure of Example 1H, substituting Example 23B for Example 1D. ¹H NMR (300 MHz, DMSO-d₆) δ 8.74 (s, 1H), 8.04 (s, 1H), 7.71 (d, J=7.5 Hz, 1H), 7.37-7.25 (m, 2H), 7.17 (d, J=8.3 Hz, 1H), 6.76 (dd, J=8.6, 2.7 Hz, 1H), 6.72 (d, J=8.2 Hz, 1H), 6.61 (dd, J=10.6, 2.6 Hz, 1H), 5.03-4.93 (m, 1H), 4.01 (s, 3H), 2.20 (dd, J=13.3, 6.1 Hz, 1H), 2.00-1.73 (m, 1H), 1.42 (s, 3H), 1.31 (s, 3H); MS (DCI/NH₃) m/z 369 (M+H)⁺; [α]²³_D +11.0° (c 0.61, CH₃OH).

Example 25

N-[(4R)-8-fluoro-2,2-dimethyl-3,4-dihydro-2H-chromen-4-yl]-N'-(1-methyl-1H-indazol-4-yl)urea The title compound was prepared according to the procedure of Example 1H, substituting Example 20B for Example 1D. ¹H NMR (300 MHz, DMSO-d₆) δ 8.76 (s, 1H), 8.04 (d, J=0.9 Hz, 1H), 7.70 (dd, J=7.5, 0.8 Hz, 1H), 7.27 (d, J=7.7 Hz, 1H), 7.19-7.06 (m, 3H), 6.88 (td, J=7.9, 5.0 Hz, 1H), 6.76 (d, J=8.4 Hz, 1H), 5.09-4.99 (m, 1H), 4.01 (s, 3H), 2.22 (dd, J=13.3, 6.2 Hz, 1H), 1.84 (dd, J=13.3, 10.8 Hz, 1H), 1.45 (s, 3H), 1.33 (s, 3H); MS (DCI/NH₃) m/z 369 (M+H)⁺; [α]²³_D +13.0° (c 0.67, CH₃OH).

Example 26

N-[(4R)-2,2-diethyl-6-fluoro-3,4-dihydro-2H-chromen-4-yl]-N'-(1-methyl-1H-indazol-4-yl)urea

Example 26A 2,2-diethyl-6-fluorochroman-4-one 1-(5-Fluoro-2-hydroxyphenyl)ethanone (30.2 g, 196 mmol) and MeOH (300 mL) were stirred at ambient temperature and 3-pentanone (41.6 mL, 392 mmol) and pyrrolidine (17.8 mL, 216 mmol) were added. The mixture was heated to 60° C. for 62 h at which point LCMS analysis showed clean conversion to product. The reaction was cooled, concentrated to a minimal volume of MeOH, and MTBE (300 mL) was added. The organics were washed with 2N HCl (150 mL), brine (60 mL), 2N NaOH (150 mL), and brine (60 mL). The solution was passed through a plug of silica gel (30 g), washing with MTBE (150 mL). The filtrate was concentrated, giving the title compound (38.8 g, 175 mmol, 89%) as a light brown oil. MS (DCI/NH₃) m/z 240 (M+NH₄)⁺.

Example 26B (R)-6-fluoro-2,2-diethylchroman-4-amine

The title compound was prepared from Example 26A according to the methods described in Example 1B and Example 1C. MS (DCI/NH₃) m/z 224 (M+H)⁺.

Example 26C

N-[(4R)-2,2-diethyl-6-fluoro-3,4-dihydro-2H-chromen-4-yl]-N'-(1-methyl-1H-indazol-4-yl)urea The title compound was prepared according to the procedure of Example 1H, substituting Example 26B for Example 1D. ¹H NMR (300 MHz, DMSO-d₆) δ 8.75 (s, 1H), 8.05 (s, 1H), 7.70 (d, J=7.5 Hz, 1H), 7.28 (t, J=7.9 Hz, 1H), 7.18 (d, J=8.3 Hz, 1H), 7.09 (dd, J=9.4, 3.2 Hz, 1H), 7.01 (td, J=8.6, 3.2 Hz, 1H), 6.83-6.77 (m, 1H), 6.77 (d, J=8.2 Hz, 1H), 5.01-4.91 (m, 1H), 4.01 (s, 3H), 2.19 (dd, J=13.4, 6.1 Hz, 1H), 1.76-1.52 (m, 5H), 0.94-0.85 (m, 6H); MS (DCI/NH₃) m/z 397 (M+H)⁺; [α]²³_D +9.2° (c 0.61, CH₃OH).

Example 27

N-[(4R)-2,2-dimethyl-3,4-dihydro-2H-chromen-4-yl]-N'-isoquinolin-5-ylurea

Example 27A 2,2-dimethylchroman-4-one

The title compound was prepared according to the procedure of Example 1A, substituting 1-(2-hydroxyphenyl)ethanone for 1-(5-fluoro-2-hydroxyphenyl)ethanone and using propan-2-one. MS (DCI/NH$_3$) m/z 194 (M+NH$_4$)$^+$.

Example 27B (R)-2,2-dimethylchroman-4-amine, (R)-2-hydroxy-2-phenylacetic acid salt The title compound was prepared from Example 27A according to the methods described in Example 1B, Example 1C, and Example 1D. MS (APCI) m/z 178 (M+H)$^+$.

Example 27C

N-[(4R)-2,2-dimethyl-3,4-dihydro-2H-chromen-4-yl]-N-isoquinolin-5-ylurea

The title compound was prepared according to the procedure of Example 17 substituting Example 27B for Example 16B. $^1$H NMR (300 MHz, DMSO-d$_6$) δ 9.28 (s, 1H), 8.72 (s, 1H), 8.55 (d, J=6.0 Hz, 1H), 8.36 (d, J=8.1 Hz, 1H), 7.94 (d, J=6.1 Hz, 1H), 7.76 (d, J=8.1 Hz, 1H), 7.63 (t, J=7.9 Hz, 1H), 7.34 (d, J=7.8 Hz, 1H), 7.20-7.13 (m, 1H), 7.01-6.88 (m, 2H), 6.76 (dd, J=8.2, 1.2 Hz, 1H), 5.07-4.98 (m, 1H), 2.21 (dd, J=13.2, 6.2 Hz, 1H), 1.86-1.74 (m, 1H), 1.41 (s, 3H), 1.30 (s, 3H). MS (DCI/NH$_3$) m/z 348 (M+H)$^+$; [α]$^{23}_D$ +34.1° (c 0.65, CH$_3$OH).

Example 28

N-[(4R)-2,2-diethyl-6-fluoro-3,4-dihydro-2H-chromen-4-yl]-N'-isoquinolin-5-ylurea The title compound was prepared according to the procedure of Example 17 substituting Example 26B for Example 16B. $^1$H NMR (300 MHz, DMSO-d$_6$) δ 9.29 (d, J=0.8 Hz, 1H), 8.73 (s, 1H), 8.56 (d, J=6.0 Hz, 1H), 8.34 (dd, J=7.7, 1.1 Hz, 1H), 7.94 (d, J=6.1 Hz, 1H), 7.77 (d, J=8.1 Hz, 1H), 7.63 (t, J=7.9 Hz, 1H), 7.09-7.14 (m, 1H), 6.98-7.05 (m, 2H), 6.81 (dd, J=8.9, 4.9 Hz, 1H), 4.93-5.02 (m, 1H), 2.20 (dd, J=13.4, 6.1 Hz, 1H), 1.52-1.77 (m, 5H), 0.85-0.94 (m, 6H); MS (DCI/NH$_3$) m/z 394 (M+H)$^+$; [α]$^{23}_D$ +34.1° (c 0.46, CH$_3$OH).

Example 29

N-[(4R)-7-fluoro-2,2-dimethyl-3,4-dihydro-2H-chromen-4-yl]-N'-1H-indazol-4-ylurea The title compound was prepared according to the procedure of Example 2D, substituting Example 23B for Example 1D. $^1$H NMR (300 MHz, DMSO-d$_6$) δ 13.02 (br s, 1H), 8.71 (s, 1H), 8.07 (s, 1H), 7.68 (d, J=7.5 Hz, 1H), 7.37-7.32 (m, 1H), 7.23 (t, J=7.9 Hz, 1H), 7.09 (d, J=8.2 Hz, 1H), 6.79-6.71 (m, 2H), 6.61 (dd, J=10.6, 2.6 Hz, 1H), 5.03-4.93 (m, 1H), 2.20 (dd, J=13.3, 6.1 Hz, 1H), 1.78 (dd, J=13.2, 10.8 Hz, 1H), 1.42 (s, 3H), 1.31 (s, 3H); MS (DCI/NH$_3$) m/z 355 (M+H)$^+$; [α]$^{23}_D$ +34.7° (c 1.0, CH$_3$OH).

Example 30

N-[(4R)-7-fluoro-2,2-dimethyl-3,4-dihydro-2H-chromen-4-yl]-N'-[(7R)-7-hydroxy-5,6,7,8-tetrahydronaphthalen-1-yl]urea The title compound was prepared according to the procedure of Example 14, substituting Example 23B for Example 12B. $^1$H NMR (300 MHz, DMSO-d$_6$) δ 7.70 (d, J=7.9 Hz, 1H), 7.59 (s, 1H), 7.34-7.25 (m, 1H), 7.01 (t, J=7.8 Hz, 1H), 6.94 (d, J=8.4 Hz, 1H), 6.80-6.69 (m, 2H), 6.59 (dd, J=10.6, 2.6 Hz, 1H), 4.98-4.88 (m, 1H), 4.86 (d, J=4.1 Hz, 1H), 4.00-3.88 (m, 1H), 2.90-2.63 (m, 3H), 2.34 (dd, J=16.6, 7.7 Hz, 1H), 2.16 (dd, J=13.3, 6.1 Hz, 1H), 1.94-1.81 (m, 1H), 1.70 (dd, J=13.2, 10.9 Hz, 1H), 1.65-1.51 (m, 1H), 1.40 (s, 3H), 1.29 (s, 3H); MS (ESI) m/z 385 (M+H)$^+$; [α]$^{23}_D$ +20.2° (c 1.0, CH$_3$OH).

Example 31

N-[(4R)-7-fluoro-2,2-dimethyl-3,4-dihydro-2H-chromen-4-yl]-N'-[(7S)-7-hydroxy-5,6,7,8-tetrahydronaphthalen-1-yl]urea To a suspension of di(N-succinimidyl) carbonate (807 mg, 3.15 mmol) in acetonitrile (10 mL) was added Example 3B (490 mg, 3.00 mmol) dissolved in acetonitrile (10 mL) and pyridine (0.254 mL, 3.15 mmol). The reaction was stirred for 30 min whereupon Example 23B (670 mg, 3.00 mmol) in acetonitrile (10 mL) and N,N-diisopropylethylamine (1.57 mL, 9.00 mmol) was added. The reaction was stirred for 16 h at ambient temperature. EtOAc (300 mL) was added and the reaction mixture was washed with 1.5 N NaOH (200 mL), water (200 mL) and brine (200 mL). The organic portion was dried (Na$_2$SO$_4$) and filtered. Solvent was evaporated under reduced pressure and a white solid precipitated from solution. The solid was collected, triturated with diethyl ether, and filtered. The residue was purified by silica gel chromatography (gradient elution, 2-10% MeOH/CH$_2$Cl$_2$) to provide the title compound (1.05 g, 2.54 mmol, 85% yield) as a beige powder. $^1$H NMR (300 MHz, DMSO-d$_6$) δ 7.70 (d, J=7.5 Hz, 1H), 7.58 (s, 1H), 7.35-7.25 (m, 1H), 7.01 (t, J=7.8 Hz, 1H), 6.94 (d, J=8.3 Hz, 1H), 6.79-6.69 (m, 2H), 6.59 (dd, J=10.6, 2.6 Hz, 1H), 4.98-4.88 (m, 1H), 4.86 (d, J=4.1 Hz, 1H), 3.99-3.86 (m, 1H), 2.90-2.63 (m, 3H), 2.35 (dd, J=16.3, 7.5 Hz, 1H), 2.15 (dd, J=13.2, 6.1 Hz, 1H), 1.93-1.82 (m, 1H), 1.70 (dd, J=13.4, 10.9 Hz, 1H), 1.65-1.51 (m, 1H), 1.40 (s, 3H), 1.28 (s, 3H); MS (ESI) m/z 385 (M+H)$^+$; [α]$^{23}_D$ +26.0° (c 1.0, CH$_3$OH).

Example 32

N-[(4R)-8-fluoro-2,2-dimethyl-3,4-dihydro-2H-chromen-4-yl]-N'-1H-indazol-4-ylurea The title compound was prepared according to the procedure of Example 2D, substituting Example 20B for Example 1D. $^1$H NMR (300 MHz, DMSO-d$_6$) δ 13.02 (br s, 1H), 8.74 (s, 1H), 8.08 (s, 1H), 7.67 (d, J=7.5 Hz, 1H), 7.23 (t, J=7.9 Hz, 1H), 7.14 (d, J=7.4 Hz, 1H), 7.11-7.07 (m, 2H), 6.88 (td, J=8.0, 5.0 Hz, 1H), 6.77 (d, J=8.4 Hz, 1H), 5.09-4.99 (m, 1H), 2.23 (dd, J=13.3, 6.2 Hz, 1H), 1.84 (dd, J=13.3, 10.9 Hz, 1H), 1.46 (s, 3H), 1.33 (s, 3H); MS (DCI/NH$_3$) m/z 355 (M+H)$^+$; [α]$^{23}_D$ +28.7° (c 0.32, CH$_3$OH).

Example 33

N-[(4R)-2,2-dimethyl-7-(trifluoromethyl)-3,4-dihydro-2H-chromen-4-yl]-N (1-methyl-1H-indazol-4-yl)urea Example 33A 2,2-dimethyl-7-(trifluoromethyl)chroman-4-one A solution of 2-hydroxy-4-(trifluoromethyl)benzoic acid (10.0 g, 48.5 mmol) and THF (100 mL) was cooled to <5° C.

(internal temperature) and methyllithium (95 mL of a 1.6M solution in Et$_2$O, 152 mmol) was added, keeping the internal temperature≤20° C. (slow addition, methane generation). Following methyllithium addition, the solution was warmed to ambient temperature and stirred for 1 h. The solution was then re-cooled to 10° C. and treated carefully with EtOAc (100 mL) and 2N HCl (100 mL). The reaction mixture was further diluted with EtOAc (100 mL) then washed with water (100 mL) and brine (20 mL). The organic portion was dried (Na$_2$SO$_4$), filtered, and concentrated to give 1-(2-hydroxy-4-(trifluoromethyl)phenyl)ethanone (10.3 g) which was used without further purification.

The crude 1-[2-hydroxy-4-(trifluoromethyl)phenyl]ethanone (9.90 g, 48.5 mmol) from above was dissolved in methanol (100 mL) and acetone (3.56 mL, 48.5 mmol), and pyrrolidine (8.02 mL, 97.0 mmol) were added. The reaction was stirred at ambient temperature for 14 h; LCMS showed reaction completion. The reaction mixture was concentrated and diluted with EtOAc (300 mL), then washed with water (100 mL), 2N HCl (2×100 mL), water (50 mL), 2N NaOH (2×100 mL), water (50 mL), and brine (20 mL). The organic portion was dried (Na$_2$SO$_4$), filtered, concentrated, and the residue purified by silica gel chromatography (gradient elution, 0-20% EtOAc/hexanes) to give the title compound (8.93 g, 36.6 mmol, 75%) as a white solid. MS (ESI) m/z 245 (M+H)$^+$.

Example 33B (R)-7-(trifluoromethyl)-2,2-dimethylchroman-4-amine, (R)-2-hydroxy-2-phenylacetic acid salt The title compound was prepared from Example 33A according to the methods described in Example 1B, Example 1C, and Example 1D. MS (DCI/NH$_3$) m/z 246 (M+H)$^+$.

Example 33C

N-[(4R)-2,2-dimethyl-7-(trifluoromethyl)-3,4-dihydro-2H-chromen-4-yl]-N'-(1-methyl-1H-indazol-4-yl)urea The title compound was prepared according to the procedure of Example 1H, substituting Example 33B for Example 1D. $^1$H NMR (300 MHz, DMSO-d$_6$) δ 8.81 (s, 1H), 8.05 (d, J=0.9 Hz, 1H), 7.70 (d, J=7.5 Hz, 1H), 7.54 (d, J=8.1 Hz, 1H), 7.32-7.23 (m, 2H), 7.18 (d, J=8.3 Hz, 1H), 7.07 (d, J=1.7 Hz, 1H), 6.80 (d, J=8.4 Hz, 1H), 5.12-5.03 (m, 1H), 3.28 (s, 3H), 2.23 (dd, J=13.2, 6.2 Hz, 1H), 1.86 (dd, J=13.2, 11.2 Hz, 1H), 1.42 (s, 3H), 1.32 (s, 3H); MS (DCI/NH$_3$) m/z 419 (M+H)$^+$; [α]$^{23}_D$ +16.0° (c 0.78, CH$_3$OH).

Example 34

N-[(4R)-2,2-dimethyl-7-(trifluoromethyl)-3,4-dihydro-2H-chromen-4-yl]-N'-isoquinolin-5-ylurea The title compound was prepared according to the procedure of Example 17 substituting Example 33B for Example 16B. $^1$H NMR (300 MHz, DMSO-d$_6$) δ 9.29 (d, J=0.8 Hz, 1H), 8.78 (s, 1H), 8.56 (d, J=6.0 Hz, 1H), 8.33 (dd, J=7.7, 1.1 Hz, 1H), 7.94 (d, J=6.1 Hz, 1H), 7.78 (d, J=8.1 Hz, 1H), 7.64 (t, J=7.9 Hz, 1H), 7.56 (d, J=8.1 Hz, 1H), 7.26 (dd, J=8.1, 1.8 Hz, 1H), 7.08-7.04 (m, 2H), 5.14-5.04 (m, 1H), 2.25 (dd, J=13.3, 6.2 Hz, 1H), 1.87 (dd, J=13.2, 11.1 Hz, 1H), 1.45 (s, 3H), 1.33 (s, 3H); MS (DCI/NH$_3$) m/z 416 (M+H)$^+$; [α]$^{23}_D$ +26.8° (c 0.50, CH$_3$OH).

Example 35

N-[(4R)-6-fluoro-2,2-dimethyl-3,4-dihydro-2H-chromen-4-yl]-N'-(3-methylisoquinolin-5-yl)urea Example 35A 3-methyl-5-nitroisoquinoline To a 0° C. solution of 3-methylisoquinoline (3.00 g, 20.9 mmol) in concentrated sulfuric acid (35 mL) was added solid potassium nitrate (2.33 g, 23.0 mmol) in four portions. The mixture was stirred 2 hours at 0° C. then was diluted with ice. This mixture was basified (pH 10) with 50% aqueous NaOH extracted with CH$_2$Cl$_2$ (60 mL). The organic phase was washed with brine (25 mL), dried (Na$_2$SO$_4$), filtered, and the volatiles were removed in vacuo. The resulting solid was triturated with 1:1 EtOAc-hexanes, filtered and air-dried to provide the title compound (1.60, 8.78 mmol, 42%) as a yellow solid. $^1$H NMR (300 MHz, CDCl$_3$) δ 9.30 (s, 1H), 8.53 (dd, J=7.7, 1.1 Hz, 1H), 8.35 (s, 1H), 8.26 (d, J=8.1 Hz, 1H), 7.64 (dd, J=9.9, 5.9 Hz, 1H), 2.80 (s, 3H); MS (ESI) m/z 189 (M+H)$^+$.

Example 35B 3-methylisoquinolin-5-amine

To a solution of Example 35A (1.60 g, 8.82 mmol) in ethanol (45 mL) and THF (45 mL) was added 10% Pd/C (100 mg). The solution was hydrogenated under 1 atmosphere of hydrogen for 16 hours at ambient temperature. The mixture was filtered through a plug of Celite and the volatiles were evaporated in vacuo. The resulting solid was triturated with 1:1 CH$_2$Cl$_2$-hexanes and air-dried to provide the title compound (1.31 g, 8.29 mmol, 94% yield) as a light green solid. $^1$H NMR (300 MHz, DMSO-d$_6$) δ 9.00 (s, 1H), 7.78 (d, J=0.6 Hz, 1H), 7.25 (d, J=7.5 Hz, 1H), 7.18 (d, J=8.0 Hz, 1H), 6.80 (dd, J=7.4, 1.2 Hz, 1H), 5.84 (s, 2H), 2.58 (s, 3H); MS (ESI) m/z 159 (M+H)$^+$.

Example 35C

N-[(4R)-6-fluoro-2,2-dimethyl-3,4-dihydro-2H-chromen-4-yl]-N'-(3-methylisoquinolin-5-yl)urea The title compound was prepared according to the procedure of Example 17 substituting Example 35B for 5-aminoisoquinoline, and substituting Example 1D for Example 16B. $^1$H NMR (300 MHz, DMSO-d$_6$) δ 9.19 (s, 1H), 8.65 (s, 1H), 8.27 (d, J=7.6 Hz, 1H), 7.72 (d, J=8.2 Hz, 1H), 7.53 (t, J=7.9 Hz, 1H), 7.12 (dd, J=9.5, 3.0 Hz, 1H), 7.02 (td, J=8.4, 3.3 Hz, 2H), 6.79 (dd, J=8.9, 4.9 Hz, 1H), 5.00 (dd, J=17.8, 7.4 Hz, 1H), 2.59 (d, J=14.2 Hz, 3H), 2.20 (dd, J=13.2, 6.2 Hz, 1H), 1.83-1.71 (m, 1H), 1.38 (d, J=19.2 Hz, 3H), 1.30-1.19 (m, 3H); MS (ESI) m/z 380 (M+H)$^+$.

Example 36

N-[(4R)-2,2-dimethyl-3,4-dihydro-2H-chromen-4-yl]-N'-[(7R)-7-hydroxy-5,6,7,8-tetrahydronaphthalen-1-yl]urea The title compound was prepared according to the procedure of Example 14, substituting Example 27B for Example 12B. $^1$H NMR (300 MHz, DMSO-d$_6$) δ 7.71 (d, J=7.8 Hz, 1H), 7.58 (s, 1H), 7.28 (d, J=7.6 Hz, 1H), 7.14 (t, J=7.7 Hz, 1H), 7.01 (t, J=7.8 Hz, 1H), 6.94 (d, J=8.4 Hz, 1H), 6.89 (td, J=7.6, 1.1 Hz, 1H), 6.77-6.70 (m, 2H), 5.01-4.89 (m, 1H), 4.86 (d, J=4.1 Hz, 1H), 3.99-3.87 (m, 1H), 2.90-2.64 (m, 3H), 2.34 (dd, J=16.5, 7.7 Hz, 1H), 2.15 (dd, J=613.2, 6.2 Hz, 1H), 1.93-1.82 (m, 1H), 1.69 (dd, J=13.2, 10.8 Hz, 1H), 1.63-1.51 (m, 1H), 1.39 (s, 3H), 1.28 (s, 3H); MS (ESI) m/z 367 (M+H)$^+$; $[\alpha]^{23}_D$ +28.0° (c 1.0, CH$_3$OH).

Example 37

N-[(4R)-2,2-dimethyl-3,4-dihydro-2H-chromen-4-yl]-N'-[(7S)-7-hydroxy-5,6,7,8-tetrahydronaphthalen-1-yl]urea The title compound was prepared according to the procedure of Example 14, substituting Example 3B for Example 4A, and substituting Example 27B for Example 12B $^1$H NMR (300 MHz, DMSO-d$_6$) δ 7.72 (d, J=7.3 Hz, 1H), 7.57 (s, 1H), 7.28 (d, J=7.6 Hz, 1H), 7.14 (td, J=7.5, 1.2 Hz, 1H), 7.01 (t, J=7.8 Hz, 1H), 6.96-6.84 (m, 2H), 6.73 (dd, J=8.2, 1.2 Hz, 2H), 5.01-4.89 (m, 1H), 4.85 (d, J=4.2 Hz, 1H), 3.98-3.87 (m, 1H), 2.89-2.64 (m, 3H), 2.35 (dd, J=16.4, 7.7 Hz, 1H), 2.15 (dd, J=13.2, 6.2 Hz, 1H), 1.92-1.82 (m, 1H), 1.69 (dd, J=13.1, 10.9 Hz, 1H), 1.64-1.52 (m, 1H), 1.39 (s, 3H), 1.27 (s, 3H); MS (ESI) m/z 367 (M+H)$^+$; $[\alpha]^{23}_D$ +33.5° (c 1.0, CH$_3$OH).

Example 38

N-[(4R)-6-fluoro-2,2-dimethyl-3,4-dihydro-2H-chromen-4-yl]-N'-isoquinolin-8-ylurea The title compound was prepared according to the procedure of Example 17 substituting 8-aminoisoquinoline (Combi-Blocks) for 5-aminoisoquinoline, and substituting Example 1D for Example 16B. $^1$H NMR (300 MHz, DMSO-d$_6$) δ 9.52 (s, 1H), 9.00 (s, 1H), 8.51 (d, J=5.7 Hz, 1H), 8.18 (dd, J=7.6, 0.8 Hz, 1H), 7.80 (d, J=5.2 Hz, 1H), 7.71 (t, J=7.9 Hz, 1H), 7.60 (d, J=8.1 Hz, 1H), 7.13 (dd, J=9.5, 2.5 Hz, 1H), 7.01 (dd, J=13.4, 3.6 Hz, 1H), 6.79 (dd, J=8.9, 4.9 Hz, 1H), 5.01 (dd, J=17.9, 7.3 Hz, 1H), 2.21 (dd, J=13.2, 6.2 Hz, 1H), 1.79 (dd, J=13.1, 11.0 Hz, 1H), 1.41 (s, 3H), 1.29 (s, 3H); MS (ESI) m/e 366 (M+H)$^+$.

Example 39

N-[(4R)-2,2-dimethyl-7-(trifluoromethoxy)-3,4-dihydro-2H-chromen-4-yl]-N'-(1-methyl-1H-indazol-4-yl)urea Example 39A 2,2-dimethyl-7-(trifluoromethoxy)chroman-4-one Eaton's reagent (225 mL) was heated to 70° C. and 3-methylbut-2-enoic acid (28.1 g, 281 mmol) and 3-(trifluoromethoxy)phenol (25.0 g, 140 mmol) were added. After 30 min, additional 3-methylbut-2-enoic acid (1 equiv, 14 g) was added and heating was continued. After 30 min, additional Eaton's reagent (150 mL) was added and heating was continued for 35 min. The dark solution was cooled and poured into ice. The aqueous suspension was extracted with Et$_2$O (300 mL), and the organic portion was washed with water (75 mL) and brine (50 mL). The organic portion was dried (Na$_2$SO$_4$), filtered, concentrated, and purified by silica gel chromatography (gradient elution, 0-20% EtOAc/hexanes) to give the title compound (11.7 g, 45.0 mmol, 32%) as a white solid. MS (ESI) m/z 261 (M+H)$^+$.

Example 39B (R)-7-(trifluoromethoxy)-2,2-dimethylchroman-4-amine, (R)-2-hydroxy-2-phenylacetic acid salt The title compound was prepared from Example 39A according to the methods described in Example 1B, Example 1C, and Example 1D. MS (DCI/NH$_3$+) m/z 262 (M+H)$^+$.

Example 39C

N-[(4R)-2,2-dimethyl-7-(trifluoromethoxy)-3,4-dihydro-2H-chromen-4-yl]-N'-(1-methyl-1H-indazol-4-yl)urea The title compound was prepared according to the procedure of Example 1H, substituting Example 39B for Example 1D. $^1$H NMR (300 MHz, DMSO-d$_6$) δ 8.75 (s, 1H), 8.04 (d, J=0.9 Hz, 1H), 7.70 (dd, J=7.5, 0.8 Hz, 1H), 7.43 (dd, J=8.5, 1.0 Hz, 1H), 7.27 (d, J=7.7 Hz, 1H), 7.17 (dt, J=8.4, 0.8 Hz, 1H), 6.91 (ddd, J=8.5, 2.5, 1.2 Hz, 1H), 6.78-6.73 (m, 2H), 5.06-4.97 (m, 1H), 4.01 (s, 3H) 2.28-2.18 (m, 1H), 1.82 (dd, J=13.3, 10.9 Hz, 1H), 1.43 (s, 3H), 1.32 (s, 3H); MS (DCI/NH$_3$) m/z 435 (M+H)$_+$; $[\alpha]^{23}_D$ +6.2° (c 0.53, CH$_3$OH).

Example 40

N-[(4R)-2,2-dimethyl-7-(trifluoromethoxy)-3,4-dihydro-2H-chromen-4-yl]-N'-isoquinolin-5-ylurea The title compound was prepared according to the procedure of Example 17, substituting Example 39B for Example 16B. $^1$H NMR (300 MHz, DMSO-d$_6$) δ 9.29 (d, J=0.8 Hz, 1H), 8.78 (s, 1H), 8.56 (d, J=6.0 Hz, 1H), 8.34 (dd, J=7.7, 1.1 Hz, 1H), 7.93 (d, J=6.1 Hz, 1H), 7.77 (d, J=8.1 Hz, 1H), 7.63 (t, J=7.9 Hz, 1H), 7.45 (dd, J=8.5, 1.0 Hz, 1H), 7.02 (d, J=8.3 Hz, 1H), 6.92 (ddd, J=8.5, 2.5, 1.3 Hz, 1H), 6.75 (dd, J=2.5, 1.1 Hz, 1H), 5.08-4.99 (m, 1H), 2.22 (dd, J=13.3, 6.1 Hz, 1H), 1.83 (dd, J=13.3, 10.8 Hz, 1H), 1.45 (s, 3H), 1.33 (s, 3H); MS (DCI/NH$_3$) m/z 432 (M+H)$^+$; $[\alpha]^{23}_D$ +7.5° (c 0.45, CH$_3$OH).

Example 41

N-[(4R)-2,2-dimethyl-7-(trifluoromethyl)-3,4-dihydro-2H-chromen-4-yl]-N'-1H-indazol-4-ylurea The title compound was prepared according to the procedure of Example 2D, substituting Example 33B for Example 1D. $^1$H NMR (300 MHz, DMSO-d$_6$) δ 13.02 (br s, 1H), 8.77 (s, 1H), 8.09 (s, 1H), 7.67 (d, J=7.2 Hz, 1H), 7.54 (d, J=8.1 Hz, 1H), 7.24 (t, J=8.0 Hz, 2H), 7.10 (d, J=8.2 Hz, 1H), 7.07 (d, J=1.8 Hz, 1H), 6.81 (d, J=8.4 Hz, 1H), 5.12-5.03 (m, 1H), 2.23 (dd, J=13.2, 6.1 Hz, 1H), 1.90-1.81 (m, 1H), 1.44 (s, 3H), 1.33 (s, 3H); MS (DCI/NH$_3$) m/z 405 (M+H)$^+$; $[\alpha]^{23}_D$ +21.4° (c 0.30, CH$_3$OH).

Example 42

N-[(4R)-2,2-dimethyl-8-(trifluoromethyl)-3,4-dihydro-2H-chromen-4-yl]-N'-(1-methyl-1H-indazol-4-yl)urea Example 42A 1-(methoxymethoxy)-2-(trifluoromethyl)benzene A solution of 2-(trifluoromethyl)phenol (12.0 g, 74.0 mmol) in dichloromethane (49 mL) was cooled to 5° C., and N,N-diisopropylethylamine (25.9 mL, 148 mmol) and methoxymethyl chloride (8.43 mL, 111 mmol) were added dropwise, keeping the internal temperature≤15° C. After stirring for 15 min at ambient temperature, the reaction mixture was diluted with MTBE (250 mL) and washed with 2N HCl (2×50 mL), water (50 mL), 2N NaOH (2×30 mL), water (30 mL), and brine (30 mL). The organic portion was dried ($Na_2SO_4$), filtered, and concentrated to give the title compound (14.1 g, 68.4 mmol, 92%) which was used without further purification. MS ($DCI/NH_3$) m/z 207 (M+H)+.

Example 42B 2-hydroxy-3-(trifluoromethyl)benzoic acid

A solution of Example 42A (14.1 g, 68.4 mmol) in THF (68 mL) was cooled to −20° C. and n-butyllithium (30.1 mL of a 2.5 M solution in hexanes, 75.0 mmol) was added slowly, keeping the temperature at 0° C. After 70 min at −5 to 5° C., the reaction mixture was cooled to −20° C. and $CO_2$ gas was bubbled through the brown slurry, keeping the temperature ≤−10° C. The reaction went from a brown slurry to a dark purple solution to a yellow solution. After 10 min, the reaction mixture was cooled further to −20° C. and treated with 2N HCl (68 mL, 140 mmol). To facilitate the reaction mixture, additional concentrated HCl (17 mL, total 5 equiv of 4M HCl) was added. After 30 min, MTBE (70 mL) was added, and the organic portion was extracted with 2N NaOH (70 mL) and water (70 mL). The aqueous layer was acidified with 2N HCl (98 mL) and extracted with dichloromethane (2×140 mL). The organic portion was dried ($Na_2SO_4$), filtered, and concentrated to give the title compound (14.8 g, 71.8 mmol, 99%) as a yellow solid which was used without further purification. MS ($DCI/NH_3$) m/z 207 (M+H)+.

Example 42C 1-(2-hydroxy-3-(trifluoromethyl)phenyl)ethanone

A solution of Example 42B (14.1 g, 68.4 mmol) in THF (70 mL) was cooled to 5° C. and methyllithium (133 mL of a 1.6M solution in $Et_2O$, 212 mmol) was added, keeping the temperature≤20° C. (slow addition, methane generation). The cooling bath was removed and after 10 min, the reaction mixture was complete by LCMS. The reaction was cooled to 10° C. and EtOAc (140 mL) and 2N HCl (140 mL) were added. The layers were partitioned and the organic portion was washed with water (70 mL) and brine (28 mL). The organic portion was dried ($Na_2SO_4$), filtered, and concentrated, to give the title compound (14.0 g, 68.6 mmol, 99%) as an orange oil that was used without further purification. MS ($DCI/NH_3$) m/z 222 ($M+NH_4$)+.

Example 42D 2,2-dimethyl-8-(trifluoromethyl)chroman-4-one

A solution of crude Example 42C (13.9 g, 68.4 mmol), methanol (140 mL), 2-propanone (10.1 mL, 137 mmol), and pyrrolidine (6.22 ml, 75.0 mmol) were stirred at ambient temperature for 16 h. EtOAc (430 mL) was added and the solution was washed with water (140 mL), 2N HCl (2×70 mL), water (70 mL), 2N NaOH (2×70 mL), water (70 mL), and brine (30 mL). The organic portion was dried ($Na_2SO_4$), filtered, and concentrated. The resulting residue was purified by silica gel chromatography (gradient elution, 0-25% EtOAc/hexanes) to give the title compound (9.04 g, 37.0 mmol, 54% overall yield) as an off-white solid. MS (DCI/$NH_3$) m/z 262 ($M+NH_4$)+.

Example 42E (R)-8-(trifluoromethyl)-2,2-dimethylchroman-4-amine, (R)-2-hydroxy-2-phenylacetic acid salt The title compound was prepared from Example 42D according to the methods described in Example 1B, Example 1C, and Example 1D. MS ($DCI/NH_3$+) m/z 246 (M+H)+.

Example 42F

N-[(4R)-2,2-dimethyl-8-(trifluoromethyl)-3,4-dihydro-2H-chromen-4-yl]-N'-(1-methyl-1H-indazol-4-yl)urea The title compound was prepared according to the procedure of Example 1H, substituting Example 42E for Example 1D. $^1$H NMR (300 MHz, DMSO-$d_6$) δ 8.79 (s, 1H), 8.05 (d, J=0.9 Hz, 1H), 7.69 (dd, J=7.5, 0.7 Hz, 1H), 7.59-7.63 (m, 1H), 7.51 (d, J=7.8 Hz, 1H), 7.27 (d, J=7.7 Hz, 1H), 7.19-7.16 (m, 1H), 7.06 (t, J=7.7 Hz, 1H), 6.79 (d, J=8.4 Hz, 1H), 5.11-5.01 (m, 1H), 4.01 (s, 3H), 2.25 (dd, J=13.3, 6.3 Hz, 1H), 1.90 (dd, J=13.3, 10.8 Hz, 1H), 1.44 (s, 3H), 1.33 (s, 3H); MS ($DCI/NH_3$) m/z 419 (M+H)+; $[\alpha]^{23}_D$ +14.0° (c 0.68, $CH_3OH$).

Example 43

N-[(4R)-2,2-dimethyl-7-(trifluoromethyl)-3,4-dihydro-2H-chromen-4-yl]-N'-isoquinolin-8-ylurea The title compound was prepared according to the procedure of Example 17, substituting 8-aminoisoquinoline for isoquinolin-5-amine, and substituting Example 33B for Example 16B. $^1$H NMR (300 MHz, DMSO-$d_6$) δ 9.52 (s, 1H), 9.04 (s, 1H), 8.51 (d, J=5.7 Hz, 1H), 8.21-8.15 (m, 1H), 7.80 (dd, J=5.7, 0.5 Hz, 1H), 7.71 (t, J=7.9 Hz, 1H), 7.64-7.55 (m, 2H), 7.29-7.23 (m, 1H), 7.06 (d, J=8.5 Hz, 2H), 5.07 (d, J=8.3 Hz, 1H), 2.25 (dd, J=13.3, 6.2 Hz, 1H), 1.94-1.82 (m, 1H), 1.45 (s, 3H), 1.33 (s, 3H); MS ($DCI/NH_3$) m/z 416 (M+H)+.

Example 44

N-[(4R)-2,2-dimethyl-8-(trifluoromethyl)-3,4-dihydro-2H-chromen-4-yl]-N'-isoquinolin-5-ylurea The title compound was prepared according to the procedure of Example 17, substituting Example 42E for Example 16B. $^1$H NMR (300 MHz, DMSO-$d_6$) δ 9.31 (s, 1H), 8.75 (s, 1H), 8.56 (d, J=6.0 Hz, 1H), 8.33 (d, J=7.7 Hz, 1H), 7.94 (d, J=6.1 Hz, 1H), 7.78 (d, J=8.1 Hz, 1H), 7.60-7.66 (m, 2H), 7.52 (d, J=7.8 Hz, 1H), 7.06 (t, J=8.3 Hz, 2H), 5.13-5.03 (m, 1H), 2.27 (dd, J=13.3, 6.3 Hz, 1H), 2.00-1.86 (m, 1H), 1.44 (s, 3H), 1.33 (s, 3H); MS ($DCI/NH_3$) m/z 416 (M+H)+; $[\alpha]^{23}_D$ +23.8° (c 0.65, $CH_3OH$).

Example 45

N-[(4R)-2,2-dimethyl-8-(trifluoromethyl)-3,4-dihydro-2H-chromen-4-yl]-N'-1H-indazol-4-ylurea The title compound was prepared according to the procedure of Example 2D, substituting Example 42E for Example 1D. $^1$H NMR (300 MHz, DMSO-d$_6$) δ 13.02 (br s, 1H), 8.77 (s, 1H), 8.09 (s, 1H), 7.66 (d, J=7.5 Hz, 1H), 7.63-7.59 (m, 1H), 7.51 (d, J=7.8 Hz, 1H), 7.23 (t, J=7.9 Hz, 1H), 7.16-6.94 (m, 2H), 6.81 (d, J=8.4 Hz, 1H), 5.11-5.02 (m, 1H), 2.26 (dd, J=13.3, 6.2 Hz, 1H), 1.90 (dd, J=13.3, 10.9 Hz, 1H), 1.44 (s, 3H), 1.33 (s, 3H); MS (DCI/NH$_3$) m/z 405 (M+H)$^+$; [α]$^{23}_D$ +13.8° (c 0.45, CH$_3$OH).

Example 46

N-[(4R)-2,2-diethyl-7-fluoro-3,4-dihydro-2H-chromen-4-yl]-N'-(1-methyl-1H-indazol-4-yl)urea

Example 46A 2,2-diethyl-7-fluorochroman-4-one

The title compound was prepared according to the procedure of Example 26A, substituting 1-(4-fluoro-2-hydroxyphenyl)ethanone for 1-(5-fluoro-2-hydroxyphenyl)ethanone. MS (ESI) m/z 240 (M+NH$_4$)$^+$.

Example 46B (R)-2,2-diethyl-7-fluorochroman-4-amine

The title compound was prepared from Example 46A according to the methods described in Example 1B and Example 1C. MS (DCI/NH$_3$) m/z 224 (M+H)$^+$.

Example 46C

N-[(4R)-2,2-diethyl-7-fluoro-3,4-dihydro-2H-chromen-4-yl]-N'-(1-methyl-1H-indazol-4-yl)urea The title compound was prepared according to the procedure of Example 1H, substituting Example 46B for Example 1D. $^1$H NMR (300 MHz, DMSO-d$_6$) δ 8.73 (s, 1H), 8.04 (d, J=0.9 Hz, 1H), 7.70 (dd, J=7.5, 0.7 Hz, 1H), 7.37-7.25 (m, 2H), 7.17 (d, J=8.3 Hz, 1H), 6.78-6.70 (m, 2H), 6.63 (dd, J=10.6, 2.6 Hz, 1H), 5.00-4.90 (m, 1H), 4.01 (s, 3H), 2.23-2.14 (m, 1H), 1.77-1.51 (m, 5H), 0.99-0.86 (m, 6H); MS (DCI/NH$_3$) m/z 397 (M+H)$^+$; [α]$^{23}_D$ +1.0° (C. 0.58, CH$_3$OH).

Example 47

N-[(4R)-2,2-dimethyl-8-(trifluoromethyl)-3,4-dihydro-2H-chromen-4-yl]-N'-[(7R)-7-hydroxy-5,6,7,8-tetrahydronaphthalen-1-yl]urea The title compound was prepared according to the procedure of Example 31, substituting Example 4A for Example 3B, and substituting Example 42E for Example 23B. $^1$H NMR (300 MHz, DMSO-d$_6$) δ 7.69 (d, J=7.8 Hz, 1H), 7.63 (s, 1H), 7.56 (d, J=7.7 Hz, 1H), 7.50 (d, J=7.6 Hz, 1H), 7.10-6.97 (m, 3H), 6.74 (d, J=7.4 Hz, 1H), 5.07-4.94 (m, 1H), 4.86 (d, J=4.2 Hz, 1H), 4.00-3.87 (m, 1H), 2.91-2.64 (m, 3H), 2.35 (dd, J=16.5, 7.7 Hz, 1H), 2.22 (dd, J=13.3, 6.3 Hz, 1H), 1.93-1.75 (m, 2H), 1.67-1.50 (m, 1H), 1.43 (s, 3H), 1.31 (s, 3H); MS (ESI) m/z 435 (M+H)$^+$; [α]$^{23}_D$ +28.2° (c 1.0, CH$_3$OH).

Example 48

N-[(4R)-2,2-diethyl-7-fluoro-3,4-dihydro-2H-chromen-4-yl]-N'-isoquinolin-5-ylurea The title compound was prepared according to the procedure of Example 5 substituting Example 46B for Example 1C. $^1$H NMR (300 MHz, DMSO-d$_6$) δ 9.28 (d, J=0.8 Hz, 1H), 8.71 (s, 1H), 8.56 (d, J=6.0 Hz, 1H), 8.35 (dd, J=7.7, 1.1 Hz, 1H), 7.93 (d, J=6.1 Hz, 1H), 7.76 (d, J=8.1 Hz, 1H), 7.66-7.57 (m, 1H), 7.39-7.33 (m, 1H), 6.98 (d, J=8.2 Hz, 1H), 6.76 (td, J=8.5, 2.6 Hz, 1H), 6.66-6.56 (m, 1H), 5.01-4.92 (m, 1H), 2.20 (dd, J=13.5, 6.0 Hz, 1H), 1.79-1.54 (m, 5H), 0.95-0.84 (m, 6H); MS (DCI/NH$_3$) m/z 394 (M+H)$^+$; [α]$^{23}_D$ +8.8°(c 0.25, CH$_3$OH).

Example 49

N-[(4R)-2,2-diethyl-7-(trifluoromethyl)-3,4-dihydro-2H-chromen-4-yl]-N'-(1-methyl-1H-indazol-4-yl)urea

Example 49A 2,2-diethyl-7-(trifluoromethyl)chroman-4-one

The title compound was prepared according to the procedure of Example 26A, substituting 1-[2-hydroxy-4-(trifluoromethyl)phenyl]ethanone (prepared as described in Example 33A) for 1-(5-fluoro-2-hydroxyphenyl)ethanone. MS (ESI) m/z 273 (M+H)$^+$.

Example 49B (R)-2,2-diethyl-7-(trifluoromethyl)chroman-4-amine

The title compound was prepared from Example 49A according to the methods described in Example 1B and Example 1C. MS (DCI/NH$_3$) m/z 274 (M+H)$^+$.

Example 49C

N-[(4R)-2,2-diethyl-7-(trifluoromethyl)-3,4-dihydro-2H-chromen-4-yl]-N'-(1-methyl-1H-indazol-4-yl)urea The title compound was prepared according to the procedure of Example 1H, substituting Example 49B for Example 1D. $^1$H NMR (300 MHz, DMSO-d$_6$) δ 8.80 (s, 1H), 8.05 (d, J=0.9 Hz, 1H), 7.70 (d, J=7.5 Hz, 1H), 7.54 (d, J=8.1 Hz, 1H), 7.29 (d, J=8.1 Hz, 1H), 7.27-7.22 (m, 1H), 7.18 (d, J=8.3 Hz, 1H), 7.08 (d, J=1.8 Hz, 1H), 6.80 (d, J=8.4 Hz, 1H), 5.09-4.99 (m, 1H), 4.01 (s, 3H), 2.28-2.19 (m, 1H), 1.85-1.53 (m, 5H), 0.96-0.87 (m, 6H); MS (DCI/NH$_3$) m/z 447 (M+H)$^+$; [α]$^{23}_D$ +8.6° (c 0.57, CH$_3$OH).

Example 50

N-[(4R)-2,2-diethyl-8-fluoro-3,4-dihydro-2H-chromen-4-yl]-N'-(1-methyl-1H-indazol-4-yl)urea

Example 50A 2,2-diethyl-8-fluorochroman-4-one

The title compound was prepared according to the procedure of Example 26A, substituting 1-(3-fluoro-2-hydroxyphenyl)ethanone for 1-(5-fluoro-2-hydroxyphenyl)ethanone. MS (DCI/NH$_3$) m/z 240 (M+NH$_4$)$^+$.

Example 50B (R)-2,2-diethyl-8-fluorochroman-4-amine

The title compound was prepared from Example 50A according to the methods described in Example 1B and Example 1C. MS (DCI/NH$_3$+) m/z 224 (M+H)$^+$.

Example 50C

N-[(4R)-2,2-diethyl-8-fluoro-3,4-dihydro-2H-chromen-4-yl]-N'-(1-methyl-1H-indazol-4-yl)urea The title compound was prepared according to the procedure of Example 1H, substituting Example 50B for Example 1D. $^1$H NMR (300 MHz, DMSO-d$_6$) δ 8.75 (s, 1H), 8.04 (d, J=0.9 Hz, 1H), 7.70 (dd, J=7.5, 0.8 Hz, 1H), 7.27 (d, J=7.7 Hz, 1H), 7.06-7.19 (m, 3H), 6.88 (td, J=7.9, 5.0 Hz, 1H), 6.76 (d, J=8.3 Hz, 1H), 4.01 (s, 3H), 2.28-2.19 (m, 1H), 1.83-1.58 (m, 6H), 0.96-0.87 (m, 6H); MS (DCI/NH$_3$) m/z 397 (M+H)$^+$; [α]$^{23}_D$ +7.2° (c 0.57, CH$_3$OH).

Example 51

N-[(4R)-2,2-diethyl-7-(trifluoromethyl)-3,4-dihydro-2H-chromen-4-yl]-N'-isoquinolin-5-ylurea The title compound was prepared according to the procedure of Example 5 substituting Example 49B for Example 1C. $^1$H NMR (300 MHz, DMSO-d$_6$) δ 9.29 (d, J=0.6 Hz, 1H), 8.76 (s, 1H), 8.56 (d, J=6.0 Hz, 1H), 8.33 (dd, J=7.6, 1.0 Hz, 1H), 7.94 (d, J=6.1 Hz, 1H), 7.78 (d, J=8.1 Hz, 1H), 7.68-7.49 (m, 2H), 7.25 (d, J=8.1 Hz, 1H), 7.07 (dd, J=11.8, 4.9 Hz, 2H), 5.04 (s, 1H), 2.24 (dd, J=13.6, 6.2 Hz, 1H), 1.80-1.50 (m, 5H), 1.00-0.80 (m, 6H); MS (DCI/NH$_3$) m/z 444 (M+H)$^+$; [α]$^{23}_D$ +24.3° (c 0.14, CH$_3$OH).

Example 52

N-[(4R)-2,2-diethyl-8-fluoro-3,4-dihydro-2H-chromen-4-yl]-N'-[(7R)-7-hydroxy-5,6,7,8-tetrahydronaphthalen-1-yl]urea The title compound was prepared according to the procedure of Example 3C, substituting Example 4A for Example 3B, and substituting Example 50B for Example 1C. $^1$H NMR (300 MHz, DMSO-d$_6$) δ 7.70 (d, J=7.5 Hz, 1H), 7.59 (s, 1H), 7.13-6.95 (m, 4H), 6.86 (dt, J=8.0, 5.0 Hz, 1H), 6.73 (d, J=7.4 Hz, 1H), 5.01-4.88 (m, 1H), 4.86 (d, J=4.2 Hz, 1H), 3.97-3.87 (m, 1H), 2.90-2.65 (m, 3H), 2.34 (dd, J=16.5, 7.6 Hz, 1H), 2.18 (dd, J=13.5, 6.1 Hz, 1H), 1.94-1.81 (m, 1H), 1.78-1.50 (m, 6H), 0.90 (dt, J=12.1, 7.4 Hz, 6H); MS (ESI) m/z 413 (M+H)$^+$; [α]$^{23}_D$ +22.1° (c 1.0, CH$_3$OH).

Example 53

N-[(4R)-2,2-dimethyl-7-(trifluoromethyl)-3,4-dihydro-2H-chromen-4-yl]-N'-[(7R)-7-hydroxy-5,6,7,8-tetrahydronaphthalen-1-yl]urea The title compound was prepared according to the procedure of Example 31, substituting Example 4A for Example 3B, and substituting Example 33B for Example 23B. $^1$H NMR (300 MHz, DMSO-d$_6$) δ 7.69 (d, J=7.9 Hz, 1H), 7.63 (s, 1H), 7.50 (d, J=8.1 Hz, 1H), 7.24 (dd, J=8.0, 1.2 Hz, 1H), 7.07-6.97 (m, 3H), 6.74 (d, J=7.5 Hz, 1H), 5.08-4.95 (m, 1H), 4.87 (d, J=4.1 Hz, 1H), 4.00-3.86 (m, 1H), 2.91-2.64 (m, 3H), 2.35 (dd, J=16.5, 7.7 Hz, 1H), 2.20 (dd, J=13.3, 6.2 Hz, 1H), 1.93-1.83 (m, 1H), 1.77 (dd, J=13.0, 11.5 Hz, 1H), 1.67-1.51 (m, 1H), 1.43 (s, 3H), 1.31 (s, 3H); MS (ESI) m/z 435 (M+H)$^+$; [α]$^{23}_D$ +34.8° (c 1.0, CH$_3$OH).

Example 54

N-[(4R)-2,2-diethyl-6-fluoro-3,4-dihydro-2H-chromen-4-yl]-N'-[(7R)-7-hydroxy-5,6,7,8-tetrahydronaphthalen-1-yl]urea The title compound was prepared according to the procedure of Example 3C, substituting Example 4A for Example 3B, and substituting Example 26B for Example 1C. $^1$H NMR (300 MHz, DMSO-d$_6$) δ 7.70 (d, J=7.8 Hz, 1H), 7.60 (s, 1H), 7.08-6.94 (m, 4H), 6.83-6.70 (m, 2H), 4.96-4.84 (m, 2H), 3.98-3.87 (m, 1H), 2.90-2.64 (m, 3H), 2.34 (dd, J=16.4, 7.7 Hz, 1H), 2.15 (dd, J=13.5, 6.2 Hz, 1H), 1.93-1.82 (m, 1H), 1.72-1.47 (m, 6H), 0.88 (dt, J=11.9, 7.4 Hz, 6H); MS (ESI) m/z 413 (M+H)$^+$; [α]$^{23}_D$ +26.4° (c 1.0, CH$_3$OH); MS (DCI/NH$_3$) m/z 394 (M+H)$^+$; [α]$^{23}_D$ +8.8° (c 0.25, CH$_3$OH).

Example 55

N-[(4R)-2,2-diethyl-8-(trifluoromethoxy)-3,4-dihydro-2H-chromen-4-yl]-N'(1-methyl-1H-indazol-4-yl)urea Example 55A 1-(methoxymethoxy)-2-(trifluoromethoxy)benzene A solution of 2-(trifluoromethyloxy)phenol (12.0 g, 67.4 mmol) in dichloromethane (45 mL) was cooled to 5° C., and N,N-diisopropylethylamine (23.5 mL, 135 mmol) and methoxymethyl chloride (7.68 mL, 135 mmol) were added dropwise, keeping the internal temperature≤15° C. The reaction mixture was warmed to ambient temperature, stirred for 15 min at ambient temperature, then diluted with MTBE (250 mL) and washed with 2N HCl (2×50 mL), water (50 mL), 2N NaOH (2×30 mL), water (30 mL), and brine (30 mL). The organic portion was dried (Na$_2$SO$_4$), filtered, and concentrated to give the title compound (13.9 g, 62.6 mmol, 93%). which was used without further purification. MS (DCI/NH$_3$) m/z 222 (M+H)$^+$.

Example 55B 2-hydroxy-3-(trifluoromethoxy)benzoic acid

A solution of Example 55A (13.4 g, 60.3 mmol) in diethyl ether (135 mL) was cooled to −20° C. and n-butyllithium (26.5 mL of a 2.5 M solution in hexanes, 66.3 mmol) was added slowly, keeping the temperature at 0° C. The reaction mixture was warmed to ambient temperature and the resulting yellow slurry was stirred for 15 min. The reaction was cooled to −25° C. and CO$_2$ gas was bubbled through the reaction mixture for 10 min, keeping the temperature≤−20° C. After 10 min, the reaction mixture was warmed to ambient temperature and quenched by addition of water (220 mL). The mixture was acidified with 5N HCl (pH 2) and stirred vigorously for 15 min. The resulting white solid was collected by filtration, washed with water, and dried in a vacuum oven for 12 h.

The dried product from the reaction above was dissolved in methanol (65 mL) and 5N HCl (26 mL) was added. The reaction mixture was stirred for 20 min then concentrated to a volume of approximately 30 mL. The layers were partitioned and the aqueous portion was extracted with diethyl ether (25 mL). The combined organic portions were treated with 2N NaOH (100 mL) and stirred vigorously at ambient temperature for 15 min The reaction mixture was then acidified (pH 2) by addition of 2N HCl (120 mL) and extracted with dichloromethane (2×120 mL). The combined organic portions were dried ($Na_2SO_4$), filtered, and concentrated to give the title compound (10.3 g, 46.4 mmol, 77%) as an oil. MS (DCI/$NH_3$) m/z 223 $(M+H)^+$.

Example 55C 1-(2-hydroxy-3-(trifluoromethoxy)phenyl)ethanone

A solution of Example 55B (10.3 g, 46.4 mmol) in THF (100 mL) was cooled to −10° C. and methyllithium (90 mL of a 1.6M solution in $Et_2O$, 144 mmol) was added, keeping the temperature≤0° C. (slow addition, methane generation). After 90 min of stirring at 0° C., LCMS analysis indicated complete reaction. The reaction was cooled to −5° C. and treated with EtOAc (140 mL) followed by 2N HCl (100 mL) keeping the temperature≤10° C. The reaction mixture was diluted with EtOAc (100 mL) and partioned. The organic portion was washed with and brine (30 mL), dried ($Na_2SO_4$), filtered, and concentrated, to give the title compound (6.85 g, 31.1 mmol, 67%). MS (DCI/$NH_3$) m/z 238 $(M+NH_4)^+$.

Example 55D 2,2-diethyl-8-(trifluoromethoxy)chroman-4-one

A solution of Example 55C (3.52 g, 16.0 mmol) in methanol (35 mL) was stirred at room temperature and 3-pentanone (3.39 mL, 32.0 mmol) and pyrrolidine (1.45 ml, 17.6 mmol) were added. The reaction mixture was heated to 60° C. and stirred for 24 h. EtOAc (60 mL) was added and the solution was washed with water (35 mL), 2N HCl (2×25 mL), water (25 mL), 2N NaOH (2×20 mL), water (20 mL), and brine (20 mL). The organic portion was dried ($Na_2SO_4$), filtered, and concentrated. The resulting residue was purified by silica gel chromatography (gradient elution, 0-25% EtOAc/hexanes) to give the title compound (3.07 g, 10.6 mmol, 67% yield) as an off-white solid. MS (DCI/$NH_3$) m/z 306 $(M+NH_4)^+$.

Example 55E (R)-8-(trifluoromethyl)-2,2-dimethylchroman-4-amine, D-tartaric acid salt A solution of methyl tert-butylether (65 mL), (R)-diphenyl (pyrrolidin-2-yl)methanol (279 mg, 1.01 mmol), and borane-N,N-diethylaniline complex (4.70 mL, 26.4 mmol) was heated to 45° C. Example 55D (6.35 g, 22.0 mmol) in methyl tert-butylether (60 mL) was added over a 60 min period via addition funnel. The reaction was stirred an additional 15 min at 45° C.; LCMS analysis showed complete reaction. The reaction mixture was cooled to 5° C. and treated with MeOH (100 mL) was added keeping the temperature≤10° C. ($H_2$ evolution). The reaction was warmed to ambient temperature and stirred for 30 min The reaction was diluted with MTBE (100 mL) and washed with 2 N HCl (2×50 mL) and brine (50 mL). The organic portion was dried ($Na_2SO_4$), filtered, and concentrated and the resulting residue (6.22 g) was used without further purification.

To a solution of the crude (S)-2,2-diethyl-8-(trifluoromethoxy)chroman-4-ol (6.22 g, 21.4 mmol) described above in THF (50 mL) was added N,N-diisopropyethlyamine (7.79 mL, 45.0 mmol). The resulting yellow solution was cooled to −40° C. and solid methanesulfonic anhydride (8.59 g, 49.3 mmol) was added. The reaction mixture was warmed to −30° C. and stirred for 1 h. Tetrabutylammonium azide (14.6 g, 51.4 mmol) was added as a solid at −30° C. and the reaction was allowed to warm slowly to ambient temperature. MeOH (100 mL) was added followed by 2N NaOH (30 mL) and the reaction was stirred for 30 min. The reaction was diluted with MTBE (100 mL) and washed with 2N NaOH (30 mL), water (30 mL), 2N HCl (2×30 mL), and water (30 mL). The organic portion was dried ($Na_2SO_4$), filtered, and concentrated to give an oily residue (6.80 g) that was used without further purification.

The crude (R)-4-azido-8-trifluoromethoxy-2,2-diethylchroman described above was dissolved in MeOH (70 mL) and placed in a 250 mL stainless steel pressure bottle. 5% Pd—C (650 mg) was added and the reaction mixture was stirred for 3 h at 50° C. and 30 psi. Upon cooling, the reaction mixture was filtered through a nylon membrane and concentrated to give an oily residue (6.10 g) that was used without further purification.

The crude (R)-2,2-diethyl-8-(trifluoromethoxy)chroman-4-amine (6.10 g, 21.1 mmol) described above was dissolved in MeOH (60 mL), stirred rapidly at ambient temperature, and treated with D-(−)-tartaric acid (3.16 g, 21.1 mmol). After 15 min, MTBE (60 mL) was added and after 20 minutes a solid began to form. The reaction was stirred for another 20 min then cooled to 0° C. and stirred for 20 min. The resulting solid was collected by filtration, washed with MTBE (30 mL), and dried in vacuum oven for 8 h to provide the title compound (4.82 g, 11.0 mmol, 52% from Example 52D) as a white solid. MS (DCI/$NH_3$) m/z 290 $(M+H)^+$.

Example 55F

N-[(4R)-2,2-diethyl-8-(trifluoromethoxy)-3,4-dihydro-2H-chromen-4-yl]-N'-(1-methyl-1H-indazol-4-yl)urea To a 500 mL round-bottomed flask containing acetonitrile (30 mL) was added N,N'-disuccinyl carbonate (3.06 g, 12.0 mmol), Example 1G (1.76 g, 12.0 mmol), and then pyridine (0.435 mL, 5.38 mmol). The was stirred at ambient temperature for 10 min and treated with a solution of Example 55E (4.38 g, 9.97 mmol) in acetonitrile (10 mL) followed by N,N-diisopropylethylamine (4.38 mL, 9.97 mmol). The reaction was stirred for 1 h, then poured into EtOAc (200 mL) and washed with 2 N NaOH (2×50 mL), brine (50 mL), 2N HCl (2×50 mL), and brine (50 mL). The solution was dried ($Na_2SO_4$), filtered, and concentrated. The resulting residue was purified by silica gel chromatography (gradient elution, 25-80% EtOAc/hexanes) to provide the title compound (4.32 g, 9.34 mmol, 94%) as an off-white solid. $^1$H NMR (300 MHz, DMSO-$d_6$) δ 8.75 (s, 1H), 8.04 (d, J=0.9 Hz, 1H), 7.70 (d, J=7.5 Hz, 1H), 7.36 (d, J=7.9 Hz, 1H), 7.29 (d, J=8.1 Hz, 1H), 7.25 (d, J=6.7 Hz, 1H), 7.18 (d, J=8.3 Hz, 1H), 6.97 (t, J=7.9 Hz, 1H), 6.80 (d, J=8.3 Hz, 1H), 5.07-4.98 (m, 1H), 4.01 (s, 3H), 2.23 (dd, J=13.6, 6.0 Hz, 1H), 1.84-1.56 (m, 5H), 0.96-0.87 (m, 6H); MS (DCI/$NH_3$) m/z 463 $(M+H)^+$; $[α]^{23}_D$ +17.5° (c 0.6, $CH_3OH$).

Example 56

N-[(4R)-2,2-diethyl-6-fluoro-3,4-dihydro-2H-chromen-4-yl]-N-(3-methylisoquinolin-5-yl)urea The title compound was prepared according to the procedure of Example 17 substituting Example 35B for isoquinolin-5-amine, and substituting Example 26B for Example 16B. $^1$H NMR (300 MHz, DMSO-$d_6$) δ 9.19 (s, 1H), 8.64 (s, 1H), 8.27 (dd, J=7.7, 1.1 Hz, 1H), 7.72 (d, J=8.1 Hz, 1H), 7.53 (t, J=7.9 Hz 1H), 7.12 (dd, J=9.4, 3.2 Hz, 1H), 7.07-6.96 (m, 2H), 6.81 (dd, J=8.9, 4.9 Hz, 1H), 5.04-4.91 (m, 1H), 2.66 (s, 3H), 2.30-2.15 (m, 1H), 1.78-1.50 (m, 5H), 0.96-0.77 (m, 6H); MS (DCI/NH$_3$) m/z 407 (M+H)$^+$.

Example 57

N-[(4R)-2,2-diethyl-8-fluoro-3,4-dihydro-2H-chromen-4-yl]-N'-isoquinolin-5-ylurea The title compound was prepared according to the procedure of Example 5 substituting Example 50B for Example 1C. $^1$H NMR (300 MHz, DMSO-$d_6$) δ 9.28 (s, 1H), 8.73 (s, 1H), 8.55 (d, J=6.0 Hz, 1H), 8.34 (dd, J=7.7, 1.1 Hz, 1H), 7.93 (d, J=6.1 Hz, 1H), 7.77 (d, J=8.1 Hz, 1H), 7.63 (t, J=7.9 Hz, 1H), 7.18-7.07 (m, 2H), 7.02 (d, J=8.3 Hz, 1H), 6.89 (td, J=7.9, 5.0 Hz, 1H), 5.07-4.98 (m, 1H), 2.24 (dd, J=13.6, 6.1 Hz, 1H), 1.84-1.53 (m, 5H), 0.96-0.87 (m, 6H); MS (DCI/NH$_3$) m/z 394 (M+H)$^+$; [α]$^{23}_D$ +27.9° (c 0.51, CH$_3$OH).

Example 58

N-[(4R)-2,2-diethyl-6-fluoro-3,4-dihydro-2H-chromen-4-yl]-N'-1H-indazol-4-ylurea The title compound was prepared according to the procedure of Example 2D, using Example 2C and substituting Example 26B for Example 1D. $^1$H NMR (300 MHz, DMSO-$d_6$) δ 13.01 (br s, 1H), 8.72 (s, 1H), 8.08 (s, 1H), 7.67 (d, J=7.2 Hz, 1H), 7.22 (d, J=7.8 Hz, 1H), 6.97-7.11 (m, 3H), 6.83-6.76 (m, 2H), 5.01-4.91 (m, 1H), 2.19 (dd, J=13.4, 6.2 Hz, 1H), 1.76-1.52 (m, 5H), 0.94-0.85 (m, 6H); MS (DCI/NH$_3$) m/z 383 (M+H)$^+$; [α]$^{23}_D$ +31.6° (c 0.76, CH$_3$OH).

Example 59

N-(1-methyl-1H-indazol-4-yl)-N'-[(4R)-8-(trifluoromethyl)-3,4-dihydro-2H-chromen-4-yl]urea

Example 59A

8-(trifluoromethyl)chroman-4-one

The title compound was prepared according to the procedure of Example 42D, substituting paraformaldehyde for 2-propanone. MS (DCI/NH$_3$) m/z 234 (M+NH$_4$)$^+$.

Example 59B

(R)-8-(trifluoromethyl)chroman-4-amine, (R)-2-hydroxy-2-phenylacetic acid salt The title compound was prepared from Example 59A according to the methods described in Example 1B, Example 1C, and Example 1D. MS (DCI/NH$_3$) m/z 218 (M+H)$^+$.

Example 59C

N-(1-methyl-1H-indazol-4-yl)-N'-[(4R)-8-(trifluoromethyl)-3,4-dihydro-2H-chromen-4-yl]urea The title compound was prepared according to the procedure of Example 1H, substituting Example 59B for Example 1D. $^1$H NMR (300 MHz, DMSO-$d_6$) δ 8.61 (s, 1H), 8.00 (s, 1H), 7.70 (d, J=7.5 Hz, 1H), 7.62 (d, J=7.5 Hz, 1H), 7.55 (d, J=7.8 Hz, 1H), 7.33-7.23 (m, 1H), 7.16 (d, J=8.4 Hz, 1H), 7.08 (app t, J=7.7 Hz, 1H), 6.94 (d, J=7.7 Hz, 1H), 5.08-4.91 (m, 1H), 4.55-4.39 (m, 1H), 4.37-4.23 (m, 1H), 2.31-2.01 (m, 2H); MS (DCI/NH$_3$) m/z 391 (M+H)$^+$; [α]$^{23}_D$ +82.2° (c 0.55, MeOH).

Example 60

N-[(4R)-2,2-diethyl-6,8-difluoro-3,4-dihydro-2H-chromen-4-yl]-N'-(1-methyl-1H-indazol-4-yl)urea

Example 60A

2,2-diethyl-6,8-difluorochroman-4-one

The title compound was prepared according to the procedure of Example 26A, substituting 1-(3,5-difluoro-2-hydroxyphenyl)ethanone for 1-(5-fluoro-2-hydroxyphenyl)ethanone. MS (DCI/NH$_3$) m/z 258 (M-ENH$_4$)$^+$.

Example 60B

(R)-2,2-diethyl-6,8-difluorochroman-4-amine

The title compound was prepared from Example 60A according to the methods described in Example 1B and Example 1C. MS (DCI/NH$_3$) m/z 242 (M+H)$^+$.

Example 60C

N-[(4R)-2,2-diethyl-6,8-difluoro-3,4-dihydro-2H-chromen-4-yl]-N'-(1-methyl-1H-indazol-4-yl)urea The title compound was prepared according to the procedure of Example 1H, substituting Example 60B for Example 1D. $^1$H NMR (300 MHz, DMSO-$d_6$) δ 8.79 (s, 1H); 8.05 (d, J=0.9 Hz, 1H), 7.68 (d, J=7.0 Hz, 1H), 7.37-7.09 (m, 3H), 6.96 (d, J=9.3 Hz, 1H), 6.80 (d, J=8.3 Hz, 1H), 4.98 (t, J=12.6 Hz, 1H), 4.02 (d, J=10.5 Hz, 3H), 2.23 (dd, J=13.6, 6.2 Hz, 1H), 1.90-1.49 (m, 5H), 0.90 (dt, J=10.9, 7.5 Hz, 6H); MS (DCI/NH$_3$) m/z 415 (M+H)$^+$; [α]$^{23}_D$ +14.0° (c 0.58, CH$_3$OH).

Example 61

N-[(4R)-6-fluoro-2,2-dipropyl-3,4-dihydro-2H-chromen-4-yl]-N'-(1-methyl-1H-indazol-4-yl)urea

Example 61A

2,2-dipropyl-6-fluorochroman-4-one

The title compound was prepared according to the procedure of Example 26A, substituting 4-heptanone for 3-pentanone. MS (DCI/NH$_3$) m/z 268 (M+NH$_4$)$^+$.

Example 61B (R)-6-fluoro-2,2-dipropylchroman-4-amine

The title compound was prepared from Example 61A according to the methods described in Example 1B and Example 1C. MS (DCI/NH$_3$) m/z 252 (M+H)$^+$.

Example 61C

N-[(4R)-6-fluoro-2,2-dipropyl-3,4-dihydro-2H-chromen-4-yl]-N'-(1-methyl-1H-indazol-4-yl)urea The title compound was prepared according to the procedure of Example 1H, substituting Example 61B for Example 1D. $^1$H NMR (300 MHz, DMSO-d$_6$) δ 8.74 (s, 1H), 8.04 (d, J=0.9 Hz, 1H), 7.70 (d, J=7.2 Hz, 1H), 7.27 (d, J=7.7 Hz, 1H), 7.09-6.96 (m, 3H), 6.81-6.74 (m, 2H), 4.99-4.90 (m, 1H), 4.01 (s, 3H), 2.18 (dd, J=13.4, 6.1 Hz, 1H), 1.78-1.26 (m, 9H), 0.94-0.85 (m, 6H); MS (DCI/NH$_3$) m/z 425 (M+H)$^+$; [α]$^{23}_D$ +15.0° (c 0.62, CH$_3$OH).

Example 62

N-[(4R)-2,2-diethyl-8-fluoro-3,4-dihydro-2H-chromen-4-yl]-N-(3-methylisoquinolin-5-yl)urea The title compound was prepared according to the procedure of Example 5 substituting Example 35B for isoquinoline-5-amine, and substituting Example 50B for Example 1C. $^1$H NMR (300 MHz, DMSO-d$_6$) δ 9.18 (s, 1H), 8.64 (s, 1H), 8.29 (dd, J=7.7, 1.1 Hz, 1H), 7.78-7.68 (m, 2H), 7.53 (t, J=7.9 Hz, 1H), 7.13 (dd, J=20.6, 9.4 Hz, 2H), 7.00 (d, J=8.3 Hz, 1H), 6.89 (td, J=8.0, 5.0 Hz, 1H), 5.03 (s, 1H), 2.65 (s, 3H), 2.24 (dd, J=13.6, 6.1 Hz, 1H), 1.85-1.53 (m, 5H), 0.98-0.81 (m, 6H); MS (ESI) m/z 408 (M+H)$^+$.

Example 63

N-1H-indazol-4-yl-N'-[(4R)-8-(trifluoromethyl)-3,4-dihydro-2H-chromen-4-yl]urea

The title compound was prepared according to the procedure of Example 2D, substituting Example 59B for Example 1D. $^1$H NMR (300 MHz, DMSO-d$_6$) δ 13.01 (s, 1H), 8.58 (s, 1H), 8.03 (s, 1H), 7.67 (d, J=7.3 Hz, 1H), 7.62 (d, J=7.6 Hz, 1H), 7.55 (d, J=7.8 Hz, 1H), 7.28-7.16 (m, 1H), 7.13-7.03 (m, 2H), 5.07-4.91 (m, 1H), 4.52-4.39 (m, 1H), 4.35-4.21 (m, 1H), 2.32-1.97 (m, 2H); MS (DCI/NH$_3$) m/z 377 (M+H)$^+$; [α]$^{23}_D$ +83.3° (c 0.61, MeOH).

Example 64

N-isoquinolin-5-yl-N'-[(4R)-8-(trifluoromethyl)-3,4-dihydro-2H-chromen-4-yl]urea The title compound was prepared according to the procedure of Example 17 substituting Example 59B for Example 16B. $^1$H NMR (300 MHz, DMSO-d$_6$) δ 9.28 (s, 1H), 8.60 (s, 1H), 8.54 (d, J=6.0 Hz, 1H), 8.35 (dd, J=7.7, 0.8 Hz, 1H), 7.88 (d, J=6.1 Hz, 1H), 7.76 (d, J=8.2 Hz, 1H), 7.68-7.51 (m, 3H), 7.21 (d, J=7.7 Hz, 1H), 7.08 (app t, J=7.7 Hz, 1H), 5.10-4.91 (m, 1H), 4.54-4.40 (m, 1H), 4.38-4.22 (m, 1H), 2.31-2.01 (m, 2H); MS (DCI/NH$_3$) m/z 388 (M+H)$^+$; [α]$^{23}_D$ +78.9° (c 0.55, 1:1 CH$_2$Cl$_2$-MeOH).

Example 65

N-[(4R)-6-fluoro-2,2-bis(fluoromethyl)-3,4-dihydro-2H-chromen-4-yl]-N'-(3-methylisoquinolin-5-yl)urea

Example 65A 6-fluoro-2,2-bis(fluoromethyl)chroman-4-one

A solution of 1,3-difluoroacetone (4.90 g, 52.1 mmol), MeOH (100 mL), and 1-(5-fluoro-2-hydroxyphenyl)ethanone (6.69 g, 43.4 mmol, Aldrich Chemical) was stirred at ambient temperature and pyrrolidine (4.31 mL, 52.1 mmol) was added. The reaction was heated at 60° C. for 21 hours, then concentrated and purified by silica gel chromatography (gradient elution, 0-25% EtOAc/hexanes) to provide the title compound (6.70 g, 29.1 mmol, 67%) as a brown oil. MS (DCI) m/z 248 (M+NH$_4$)$^+$.

Example 65B (S)-6-fluoro-2,2-bis(fluoromethyl)chroman-4-ol

A solution of methyl tert-butylether (25 mL), (R)-diphenyl(pyrrolidin-2-yl)methanol (685 mg, 2.70 mmol), and borane-N,N-diethylaniline complex (11.5 mL, 64.9 mmol) was heated to 45° C. Example 65A (12.5 g, 54.1 mmol) in methyl tert-butylether (MTBE, 100 mL) was added over 70 min via addition funnel. After 15 min of additional stirring at 45° C., the reaction mixture was cooled to 10° C. and treated with MeOH (63 mL), keeping the temperature≤15° C. (H$_2$ evolution). After stirring for 30 min at ambient temperature, the reaction mixture was diluted with MTBE (125 mL) and washed with 2 N HCl (2×125 mL). The combined aqueous layers were back-extracted with MTBE (65 mL) and the organic layers combined and washed with brine (65 mL). The organic portion was dried (Na$_2$SO$_4$), filtered, and concentrated, to provide the title compound (13.4 g, >100%) as an off-white solid which was used without further purification. Analysis of the crude product by analytical chiral HPLC (Chiralcel OJ 4.6×25 mm, 5% isopropanol/hexane, 23° C., 0.5 mL/min) indicated >98% ee. MS (DCI) m/z 233 (M+H)$^+$.

Example 65C (R)-6-fluoro-2,2-bis(fluoromethyl)chroman-4-amine

A solution of Example 65B (54.1 mmol) in THF (190 mL) was cooled to <5° C. To this solution was added 1,8-diazabicyclo[5.4.0]undec-7-ene (12.1 mL, 81.0 mmol) followed by diphenylphosphoryl azide (15.2 mL, 70.3 mmol), keeping the temperature≤5° C. (no exotherm). After stirring for 2 hours at ≤5° C., the reaction mixture was warmed to ambient temperature and stirred for 14 hours. The reaction mixture was diluted with MTBE (250 mL), washed with 2N NaOH (2×125 mL), brine (50 mL), 2N HCl (2×125 mL), and brine (50 mL). The organic portion was dried (Na$_2$SO$_4$), filtered, and concentrated, giving (R)-4-azido-6-fluoro-2,2-bis(fluoromethyl)chroman (14.6 g, >100%) as a dark oil. The crude (R)-4-azido-6-fluoro-2,2-bis(fluoromethyl)chroman in MeOH (300 mL) was added to 5% Pd—C (4.38 g) in a 500 mL stainless steel pressure bottle. The mixture was stirred for 3 hours at 50° C. and 30 psi H$_2$. Upon cooling, the reaction mixture was filtered through a nylon membrane and concentrated. The resulting residue was used without further purification. MS (DCI) m/z 232 (M+H)$^+$.

Example 65D (R)-6-fluoro-2,2-bis(fluoromethyl)chroman-4-amine, D-tartaric acid salt Example 65C (54.1 mmol) in MeOH was concentrated, flushing with i-PrOH. The dark oil was diluted with i-PrOH (125 mL), heated to 50° C., and D-(−)-tartaric acid (8.12 g, 54.1 mmol) was added. The slurry was heated to 70° C., then cooled to ambient temperature over 1 hour. The white slurry was filtered and the solid washed with i-PrOH (20 mL). The white solid was dried in a vacuum oven at 60° C., to provide the title compound (15.7 g, 41.2 mmol, 76%). MS (DCI) m/z 232 (M+H)$^+$.

Example 65E

N-[(4R)-6-fluoro-2,2-bis(fluoromethyl)-3,4-dihydro-2H-chromen-4-yl]-N-(3-methylisoquinolin-5-yl)urea A slurry of 3-methylisoquinolin-5-amine (0.498 g, 3.15 mmol) in dichloromethane (10 mL), and pyridine (0.255 mL, 3.15 mmol) was cooled to <5° C. and phenyl chloroformate (0.395 mL, 3.15 mmol) was added dropwise. The light yellow slurry was stirred for 10 min, then diisopropylethylamine (1.83 mL, 10.5 mmol) and Example 65D (1.00 g, 2.62 mmol) were added. The solution was warmed to ambient temperature and stirred for 2.5 h. The reaction mixture was diluted with EtOAc (25 mL) and washed with 2N HCl (2×15 mL), brine (20 mL), 2N NaOH (2×15 mL), and brine (20 mL). The organic portion was dried (Na$_2$SO$_4$), filtered, and concentrated. The resulting residue was purified by silica gel chromatography (gradient elution, 0-10% MeOH/CH$_2$Cl$_2$, then 50-100% EtOAc/hexanes) to provide the title compound (758 mg, 1.82 mmol, 70%) as an off-white solid. $^1$H NMR (300 MHz, DMSO-d$_6$) δ 9.19 (s, 1H), 8.66 (s, 1H), 8.25 (d, J=7.5 Hz, 1H), 7.75 (s, 1H), 7.74 (d, J=9.5 Hz, 1H), 7.53 (t, J=7.9 Hz, 1H), 7.2-6.9 (m, 4H), 5.1-5.0 (m, 1H), 4.8-4.5 (m, 4H), 2.66 (s, 3H), 2.35 (dd, J=13.5, 6.0 Hz, 1H), 1.99 (dd, J=13.5, 2.0 Hz, 1H); MS (DCI/NH$_3$) m/z 416 (M+H)$^+$; [α]$^{23}_D$ +8.1° (c 0.57, CH$_3$OH).

Example 66

N-(3-methylisoquinolin-5-yl)-N'-[(4R)-8-(trifluoromethoxy)-3,4-dihydro-2H-chromen-4-yl]urea

Example 66A 1-(prop-2-ynyloxy)-2-(trifluoromethoxy)benzene

To a solution of 2-trifluoromethoxyphenol (10.0 g, 56.1 mmol) in acetonitrile (120 mL) was added potassium carbonate (9.31 g, 67.4 mmol) and propargyl bromide (80% in toluene, 10.0 g, 7.70 mL, 67.4 mmol). The reaction was stirred at ambient temperature for seven days, then diluted with water (150 mL) and extracted with diethyl ether (300 mL). The organic layer was separated and concentrated to obtain the title compound (13.05 g) which was used without further purification in the next step. $^1$H NMR (300 MHz, CDCl$_3$) δ 7.30-7.23 (m, 2H), 7.19-7.13 (m, 1H), 7.04-6.95 (m, 1H), 4.77 (d, J=2.4 Hz, 2H), 2.53 (t, J=2.4 Hz, 1H).

Example 66B 1-(3-chloroprop-2-ynyloxy)-2-(trifluoromethoxy)benzene

To a solution of the product of Example 66A (13.0 g, 56.1 mmol) in acetone (200 mL) was added N-chlorosuccinimide (8.99 g, 67.3 mmol) and silver acetate (0.936 g, 5.61 mmol). The reaction was heated at reflux for 16 hours, cooled to ambient temperature, and the solvent removed under reduced pressure. The residue was taken up in a mixture of diethyl ether and water, and filtered to remove the silver salts. The filtrate was extracted with diethyl ether (300 mL). The combined organic layers were washed with saturated sodium bicarbonate (75 mL) and concentrated to give the title compound (12.85 g) which was used without further purification in the next step. $^1$H NMR (300 MHz, CDCl$_3$) δ 7.30-7.24 (m, 2H), 7.15-7.09 (m, 1H), 7.01 (td, J=7.8, 1.4 Hz, 1H), 4.77 (s, 2H); MS (DCI) m/z 268 (M+NH$_4$)$^+$.

Example 66C 8-(trifluoromethoxy)chroman-4-one

A solution of the product of Example 66B (12.8 g, 51.2 mmol) in ethylene glycol (200 mL) was heated at reflux for 6 hours, cooled to ambient temperature, stirred for 16 hours at ambient temperature, then heated at reflux for an additional 3 hours. After cooling, the reaction mixture was poured into water (100 mL) and extracted with diethyl ether (250 mL). The mixture was partitioned and the organic portion was concentrated. The resulting residue was purified by silica gel chromatography (gradient elution, 0%-20% EtOAc/hexanes) to obtain the title compound (3.62 g, 28% for three steps). $^1$H NMR (300 MHz, CDCl$_3$) δ 7.86 (dd, J=8.1, 1.7 Hz, 1H), 7.44 (d, J=7.8 Hz, 1H), 7.05-6.98 (m, 1H), 4.66-4.60 (m, 2H), 2.90-2.84 (m, 2H).

Example 66D (S)-8-(trifluoromethoxy)chroman-4-ol

The title compound was prepared according to the procedure of Example 1B, substituting Example 66C for Example 1A. $^1$H NMR (300 MHz, DMSO-d$_6$) δ 7.42-7.12 (m, 2H), 6.98-6.89 (m, 1H), 5.52 (d, J=5.4 Hz, 1H), 4.72-4.61 (m, 1H), 4.35-4.19 (m, 2H), 2.11-1.96 (m, 1H), 1.95-1.83 (m, 1H); MS (DCI) m/z 217 (M−H$_2$O)$^+$.

Example 66E (R)-8-(trifluoromethoxy)chroman-4-amine

The title compound was prepared according to the procedure of Example 1C, substituting Example 66D for Example 1B. $^1$H NMR (300 MHz, DMSO-d$_6$) δ 7.41 (d, J=7.4 Hz, 1H), 7.15 (d, J=8.2 Hz, 1H), 6.96-6.84 (m, 1H), 4.39-4.15 (m, 2H), 3.92 (t, J=5.5 Hz, 1H), 2.10-1.87 (m, 3H), 1.83-1.67 (m, 1H); MS (DCI) m/z 234 (M+H)$^+$.

Example 66F (R)-8-(trifluoromethoxy)chroman-4-amine, D-tartaric acid salt

The title compound was prepared according to the procedure of Example 65D, substituting Example 66E for Example 65C. $^1$H NMR (300 MHz, DMSO-d$_6$) δ 7.46 (d, J=7.9 Hz, 1H), 7.32 (d, J=8.1 Hz, 1H), 7.13-6.95 (m, 1H), 4.50-4.24 (m, 2H), 3.94 (s, 2H), 2.30-2.13 (m, 1H), 2.09-1.87 (m, 1H); MS (DCI) m/z 234 (M+H)$^+$.

Example 66G

N-(3-methylisoquinolin-5-yl)-N'-[(4R)-8-(trifluoromethoxy)-3,4-dihydro-2H-chromen-4-yl]urea A suspension of 3-methylisoquinolin-5-amine (0.263 g, 1.66 mmol) and pyridine (0.134 mL, 1.66 mmol) in dichloromethane (6 mL) was cooled in an ice bath. A solution of phenyl chloroformate (0.260 g, 0.209 mL, 1.66 mmol) in dichloromethane (1 mL) was added slowly, and the reaction mixture was allowed to stir for 10 min before adding N,N-diisopropylethylamine (0.715 g, 0.966 mL, 5.53 mmol). Example 66F (0.530 g, 1.38 mmol) was added, and the reaction mixture was allowed to stir at 0° C. for 1 h and then at ambient temperature for 16 h. The reaction mixture was diluted with dichloromethane (10 mL), 1N aqueous sodium hydroxide (5 mL) was added and the precipitate filtered. The filtrate was treated with 1N NaOH (5 mL) and more of the precipitate was collected by filtration. The solids were combined, titurated with water, collected by filtration, and dried to give the title compound (298 mg, 52%). $^1$H NMR (300 MHz, DMSO-$d_6$) δ 9.17 (s, 1H), 8.51 (s, 1H), 8.31 (d, J=7.0 Hz, 1H), 7.74-7.66 (m, 2H), 7.57-7.48 (m, 1H), 7.38 (d, J=7.8 Hz, 1H), 7.29 (d, J=8.1 Hz, 1H), 7.18 (d, J=7.7 Hz, 1H), 7.05-6.96 (m, 1H), 5.05-4.95 (m, 1H), 4.49-4.38 (m, 1H), 4.32-4.21 (m, 1H), 2.63 (s, 3H), 2.26-2.01 (m, 2H); MS (DCI) m/z 418 (M+H)$^+$; $[α]^{23}_D$+49.6° (c 0.50, 1:1 MeOH—CH$_2$Cl$_2$).

Example 67

N-[(4R)-8-fluoro-2,2-dipropyl-3,4-dihydro-2H-chromen-4-yl]-N'-(1-methyl-1H-indazol-4-yl)urea

Example 67A 2,2-dipropyl-8-fluorochroman-4-one

The title compound was prepared according to the procedure of Example 26A, substituting 1-(3-fluoro-2-hydroxyphenyl)ethanone for 1-(5-fluoro-2-hydroxyphenyl)ethanone and 4-heptanone for 3-pentanone. MS (DCI/NH$_3$) m/z 268 (M+NH$_4$)$^+$.

Example 67B (R)-8-fluoro-2,2-dipropylchroman-4-amine

The title compound was prepared from Example 67A according to the methods described in Example 1B and Example 1C. MS (DCI/NH$_3$) m/z 252 (M+H)$^+$.

Example 67C

N-[(4R)-8-fluoro-2,2-dipropyl-3,4-dihydro-2H-chromen-4-yl]-N'-(1-methyl-1H-indazol-4-yl)urea The title compound was prepared according to the procedure of Example 1H, substituting Example 67B for Example 1D. $^1$H NMR (300 MHz, DMSO-$d_6$) δ 8.75 (s, 1H), 8.03 (d, J=0.9 Hz, 1H), 7.70 (d, J=7.5 Hz, 1H), 7.27 (d, J=7.8 Hz, 1H), 7.20-7.05 (m, 3H), 6.87 (td, J=7.9, 5.0 Hz, 1H), 6.75 (d, J=8.3 Hz, 1H), 5.07-4.94 (m, 1H), 4.01 (s, 3H), 2.21 (dd, J=13.5, 6.0 Hz, 1H), 1.80 (dd, J=13.5, 11.0 Hz, 1H), 1.73-1.28 (m, 8H), 1.02-0.81 (m, 6H); MS (ESI) m/z 425 (M+H)$^+$.

Example 68

N-[(4R)-8-fluoro-2,2-dipropyl-3,4-dihydro-2H-chromen-4-yl]-N'-(3-methylisoquinolin-5-yl)urea The title compound was prepared according to the procedure of Example 5 substituting Example 35B for isoquinoline-5-amine, and substituting Example 67B for Example 1C. $^1$H NMR (300 MHz, DMSO-$d_6$) δ 9.18 (s, 1H), 8.63 (s, 1H), 8.28 (dd, J=7.7, 1.1 Hz, 1H), 7.78-7.68 (m, 2H), 7.52 (t, J=7.9 Hz, 1H), 7.13 (dd, J=20.6, 9.4 Hz, 2H), 7.00 (d, J=8.3 Hz, 1H), 6.89 (td, J=8.0, 5.0 Hz, 1H), 5.07-4.93 (m, 1H), 2.65 (s, 3H), 2.23 (dd, J=13.6, 6.1 Hz, 1H), 1.85-1.25 (m, 7H), 0.98-0.81 (m, 6H); MS (ESI) m/z 436 (M+H)$^+$.

Example 69

N-[(4R)-7-chloro-2,2-diethyl-3,4-dihydro-2H-chromen-4-yl]-N'-(3-methylisoquinolin-5-yl)urea

Example 69A 7-chloro-2,2-diethylchroman-4-one

The title compound was prepared according to the procedure of Example 26A, substituting 1-(4-chloro-2-hydroxyphenyl)ethanone for 1-(5-fluoro-2-hydroxyphenyl)ethanone. MS (DCI/NH$_3$) m/z 256 (M+NH$_4$)$^+$.

Example 69B (R)-7-chloro-2,2-dimethylchroman-4-amine

The title compound was prepared according to the procedures of Examples 1B and 1C, substituting Example 69A for Example 1A.

Example 69C (R)-7-chloro-2,2-dimethylchroman-4-amine, D-tartaric acid salt

The title compound was prepared according to the procedure of Example 65D, substituting Example 69B for Example 65C. MS (DCI/NH$_3$) m/z 240 (M+H)$^+$.

Example 69D

N-[(4R)-7-chloro-2,2-diethyl-3,4-dihydro-2H-chromen-4-yl]-N-(3-methylisoquinolin-5-yl)urea The title compound was prepared according to the procedure of Example 65E substituting Example 69C for Example 65D. $^1$H NMR (300 MHz, DMSO-$d_6$) δ 9.19 (s, 1H), 8.64 (s, 1H), 8.28 (dd, J=7.7, 1.1 Hz, 1H), 7.75 (d, J=1.0 Hz, 1H), 7.71 (d, J=8.1 Hz, 1H), 7.53 (t, J=7.9 Hz, 1H), 7.35 (dd, J=8.3, 1.0 Hz, 1H), 6.97 (dd, J=8.3, 2.2 Hz, 2H), 6.86 (d, J=2.1 Hz, 1H), 5.03-4.91 (m, 1H), 2.65 (s, 3H), 2.20 (dd, J=13.5, 6.1 Hz, 1H), 1.80-1.49 (m, 5H), 1.04 (d, J=6.1 Hz, 1H), 0.97-0.84 (m, 6H); MS (ESI) m/z 424 (M+H)+.

Example 70

N-1H-indazol-4-yl-N'-[(4R)-8-(trifluoromethoxy)-3,4-dihydro-2H-chromen-4-yl]urea The title compound was prepared according to the procedure of Example 2D, substituting Example 66F for Example 1D. $^1$H NMR (300 MHz, DMSO-$d_6$) δ 13.01 (s, 1H), 8.59 (s, 1H), 8.03 (s, 1H), 7.67 (d, J=7.3 Hz, 1H), 7.37 (dd, J=7.8, 0.7 Hz, 1H), 7.33-7.16 (m, 2H), 7.08 (d, J=8.3 Hz, 1H), 7.00 (app t, J=7.9 Hz, 1H), 6.94 (d, J=7.7 Hz, 1H), 4.98 (app q, J=6.0 Hz, 1H), 4.54-4.33 (m, 1H), 4.25 (ddd, J=11.4, 8.8, 2.9 Hz, 1H), 2.25-1.97 (m, 2H); MS (DCI) m/z 393 (M+H)+; $[\alpha]^{23}_D$ +65.0° (c 0.54, 1:1 MeOH—CH$_2$Cl$_2$).

Example 71

N-[(4R)-2,2-diethyl-7-fluoro-3,4-dihydro-2H-chromen-4-yl]-N'-[(7S)-7-hydroxy-5,6,7,8-tetrahydronaphthalen-1-yl]urea To a suspension of di(N-succinimidyl) carbonate (807 mg, 3.15 mmol) in acetonitrile (10 mL) was added a solution of Example 3B (490 mg, 3.00 mmol) dissolved in acetonitrile (10 mL) and pyridine (0.254 mL, 3.15 mmol). The reaction was stirred the solution for 30 min, then Example 46B (670 mg, 3.00 mmol) in acetonitrile (10 mL) and N,N-diisopropylethylamine (1.572 mL, 9.00 mmol) was added. The reaction was stirred the solution overnight at ambient temperature then diluted with EtOAc (300 mL). The organic portion was washed with 1.5N sodium hydroxide (200 mL), water (200 mL), and brine (200 mL), dried (Na$_2$SO$_4$), filtered, and concentrated. The residue was purified by silica gel chromatography (gradient elution: 50-100% EtOAc/hexanes) to provide the title compound (1.05 g, 2.54 mmol, 85% yield) as a beige powder. $^1$H NMR (300 MHz, DMSO-$d_6$) δ 7.71 (d, J=7.9 Hz, 1H), 7.57 (s, 1H), 7.34-7.25 (m, 1H), 7.01 (t, J=7.8 Hz, 1H), 6.95 (d, J=8.3 Hz, 1H), 6.78-6.69 (m, 2H), 6.60 (dd, J=10.6, 2.6 Hz, 1H), 4.95-4.83 (m, 2H), 3.98-3.86 (m, 1H), 2.89-2.63 (m, 3H), 2.35 (dd, J=16.6, 7.7 Hz, 1H), 2.14 (dd, J=13.5, 6.1 Hz, 1H), 1.93-1.82 (m, 1H), 1.74-1.47 (m, 6H), 0.89 (dt, J=10.5, 7.5 Hz, 6H); MS (ESI) m/z 413 (M+H)+; $[\alpha]^{23}_D$ +20.7° (c 1.0, CH$_3$OH).

Example 72

N-[(4R)-6-fluoro-2,2-dipropyl-3,4-dihydro-2H-chromen-4-yl]-N'-[(7R)-7-hydroxy-5,6,7,8-tetrahydronaphthalen-1-yl]urea The title compound was prepared according to the procedure of Example 3C, substituting Example 4A for Example 3B, and substituting Example 61B for Example 1D. $^1$H NMR (300 MHz, DMSO-$d_6$) δ 7.69 (d, J=8.1 Hz, 1H), 7.59 (s, 1H), 7.06-6.95 (m, 4H), 6.89-6.70 (m, 2H), 4.86 (d, J=3.9 Hz, 1H), 3.97-3.85 (m, 1H), 2.89-2.64 (m, 3H), 2.34 (dd, J=16.4, 7.5 Hz, 1H), 2.13 (dd, J=13.3, 6.5 Hz, 1H), 1.92-1.84 (m, 1H), 1.74-1.46 (m, 5H), 1.44-1.22 (m, 6H), 0.92 (t, J=7.5 Hz, 3H), 0.87 (t, J=7.5 Hz, 3H); MS (ESI) m/z 441 (M+H)+.

Example 73

N-[(4R)-2,2-diethyl-6-fluoro-3,4-dihydro-2H-chromen-4-yl]-N'-[(7S)-7-hydroxy-5,6,7,8-tetrahydronaphthalen-1-yl]urea The title compound was prepared according to the procedure of Example 71, substituting Example 26B for Example 46B. $^1$H NMR (300 MHz, DMSO-d6) δ 7.71 (d, J=8.0 Hz, 1H), 7.59 (s, 1H), 7.08-6.93 (m, 4H), 6.82-6.70 (m, 2H), 4.96-4.82 (m, 2H), 3.99-3.87 (m, 1H), 2.91-2.63 (m, 3H), 2.37 (dd, J=16.4, 7.5 Hz, 1H), 2.14 (dd, J=13.5, 6.1 Hz, 1H), 1.93-1.81 (m, 1H), 1.74-1.46 (m, 6H), 0.88 (dt, J=12.3, 7.4 Hz, 6H); MS (ESI) m/z 413 (M+H)+; $[\alpha]^{23}_D$ +30.9° (c 1.0, CH$_3$OH).

Example 74

N-[(4R)-2,2-diethyl-7-fluoro-3,4-dihydro-2H-chromen-4-yl]-N'-[(7R)-7-hydroxy-5,6,7,8-tetrahydronaphthalen-1-yl]urea The title compound was prepared according to the procedure of Example 71, substituting Example 4A for Example 3B. $^1$H NMR (300 MHz, DMSO-$d_6$) δ 7.70 (d, J=7.4, 1H), 7.57 (s, 1H), 7.33-7.24 (m, 1H), 7.01 (t, J=7.8 Hz, 1H), 6.94 (d, J=8.3 Hz, 1H), 6.78-6.68 (m, 2H), 6.60 (dd, J=10.6, 2.6 Hz, 1H), 4.95-4.82 (m, 2H), 4.00-3.87 (m, 1H), 2.90-2.63 (m, 3H), 2.33 (dd, J=16.6, 7.5 Hz, 1H), 2.15 (dd, J=13.5, 6.1 Hz, 1H), 1.93-1.81 (m, 1H), 1.75-1.48 (m, 6H), 0.89 (dt, J=10.1, 7.5 Hz, 6H); MS (ESI) m/z 413 (M+H)+; $[\alpha]^{23}_D$+14.5° (c 1.0, CH$_3$OH).

Example 75

N-[(4R)-7-chloro-2,2-diethyl-3,4-dihydro-2H-chromen-4-yl]-N'-[(7R)-7-hydroxy-5,6,7,8-tetrahydronaphthalen-1-yl]urea The title compound was prepared according to the procedure of Example 14, substituting Example 69C for Example 12B. $^1$H NMR (300 MHz, DMSO-$d_6$) δ 7.70 (d, J=8.1 Hz, 1H), 7.59 (s, 1H), 7.28 (d, J=8.3 Hz, 1H), 7.05-6.91 (m, 3H), 6.83 (d, J=2.1 Hz, 1H), 6.73 (d, J=7.5 Hz, 1H), 4.96-4.84 (m, 2H), 4.13-3.88 (m, 1H), 3.17 (d, J=5.2 Hz, 1H), 2.78 (dd, J=39.5, 5.8 Hz, 1H), 2.85-2.72 (m, 1H), 2.34 (dd, J=16.5, 7.7 Hz, 1H), 2.15 (dd, J=13.5, 6.1 Hz, 1H), 2.01-1.83 (m, 1H), 1.73-1.49 (m, 6H), 0.95-0.83 (m, 6H); MS (DCI) m/z 429 (M+H)+.

Example 76

N-[(4R)-7-chloro-2,2-diethyl-3,4-dihydro-2H-chromen-4-yl]-N'-[(7S)-7-hydroxy-5,6,7,8-tetrahydronaphthalen-1-yl]urea The title compound was prepared according to the procedure of Example 14, substituting Example 3B for Example 4A, and Example 69C for Example 12B. $^1$H NMR (300 MHz, DMSO-$d_6$) δ 7.70 (d, J=8.1 Hz, 1H), 7.59 (s, 1H), 7.29 (d, J=8.3 Hz, 1H), 7.06-6.91 (m, 3H), 6.83 (d, J=2.1 Hz, 1H), 6.73 (d, J=7.5 Hz, 1H), 4.96-4.84 (m, 2H), 3.99-3.86 (m, 1H), 2.90-2.63 (m, 3H), 2.35 (dd, J=16.5, 7.8 Hz, 1H), 2.14 (dd, J=13.5, 6.1 Hz, 1H), 1.93-1.82 (m, 1H), 1.73-1.49 (m, 6H), 1.00-0.83 (m, 6H); MS (DCI) m/z 429 (M+H)+.

Example 77

N-[(4R)-2,2-diethyl-8-(trifluoromethyl)-3,4-dihydro-2H-chromen-4-yl]-N-(1-methyl-1H-indazol-4-yl)urea

Example 77A 2,2-diethyl-8-(trifluoromethyl)chroman-4-one

The title compound was prepared according to the procedure of Example 42D substituting 3-pentanone for 2-propanone. MS (DCI/NH$_3$) m/z 273 (M+H)$^+$.

Example 77B (S)-2,2-diethyl-8-(trifluoromethyl)chroman-4-ol

The title compound was prepared according to the procedure of Example 65B substituting Example 77A for Example 65A. MS (DCI/NH$_3$) m/z 292 (M+NH$_4$)$^+$.

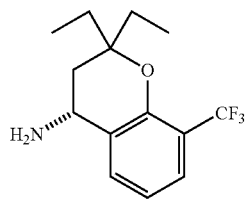 [SMILES: CCC1(CC)C[C@@H](N)c2cccc(C(F)(F)F)c2O1]

Example 77C (R)-2,2-diethyl-8-(trifluoromethyl)chroman-4-amine

The title compound was prepared according to the procedure of Example 65C substituting Example 77B for Example 65B. MS (DCI/NH$_3$) m/z 274 (M+H)$^+$.

Example 77D

N-[(4R)-2,2-diethyl-8-(trifluoromethyl)-3,4-dihydro-2H-chromen-4-yl]-N'-(1-methyl-1H-indazol-4-yl)urea The title compound was prepared according to the procedure of Example 1H, substituting Example 77C for Example 1D. $^1$H NMR (300 MHz, DMSO-d$_6$) δ 8.79 (s, 1H), 8.05 (d, J=0.5 Hz, 1H), 7.70 (d, J=7.4 Hz, 1H), 7.60 (d, J=7.7 Hz, 1H), 7.51 (d, J=7.6 Hz, 1H), 7.28 (app t, J=8.0 Hz, 1H), 7.18 (d, J=8.4 Hz, 1H), 7.05 (app t, J=7.7 Hz, 1H), 6.79 (d, J=8.4 Hz, 1H), 5.14-4.93 (m, 1H), 4.01 (s, 3H), 2.23 (dd, J=13.5, 6.1 Hz, 1H), 1.84 (dd, J=13.4, 11.2 Hz, 1H), 1.77-1.52 (m, 4H), 1.00-0.83 (m, 6H); MS (DCI/NH$_3$) m/z 447 (M+H)$^+$; [α]$^{23}_D$ +24.0° (c 0.55, CH$_3$OH).

Example 78

N-[(4R)-7-chloro-2,2-diethyl-3,4-dihydro-2H-chromen-4-yl]-N'-(1-methyl-1H-indazol-4-yl)urea The title compound was prepared according to the procedure of Example 55F, substituting Example 69C for Example 55E. $^1$H NMR (300 MHz, DMSO-d$_6$) δ 8.75 (s, 1H), 8.04 (d, J=0.9 Hz, 1H), 7.70 (d, J=7.5 Hz, 1H), 7.34-7.25 (m, 2H), 7.17 (d, J=8.3 Hz, 1H), 6.96 (dd, J=8.3, 2.2 Hz, 1H), 6.85 (d, J=2.1 Hz, 1H), 6.73 (d, J=8.3 Hz, 1H), 5.00-4.91 (m, 1H), 4.00 (s, 3H), 2.19 (dd, J=13.5, 6.1 Hz, 1H), 1.78-1.53 (m, 5H), 0.95-0.83 (m, 6H); MS (DCI/NH$_3$) m/z 413 (M+H); [α]$^{23}_D$ +2.0° (c 0.64, CH$_3$OH).

Example 79

N-(1-methyl-1H-indazol-4-yl)-N'-[(4R)-8-(trifluoromethoxy)-3,4-dihydro-2H-chromen-4-yl]urea The title compound was prepared according to the procedure of Example 55, substituting Example 66F for Example 55E. $^1$H NMR (300 MHz, DMSO-d$_6$) δ 8.61 (s, 1H), 7.99 (d, J=0.9 Hz, 1H), 7.70 (d, J=7.3 Hz, 1H), 7.37 (dd, J=7.8, 0.8 Hz, 1H), 7.33-7.23 (m, 2H), 7.16 (d, J=8.4 Hz, 1H), 7.05-6.85 (m, 2H), 4.98 (dd, J=12.7, 5.5 Hz, 1H), 4.42 (ddd, J=9.7, 6.2, 3.4 Hz, 1H), 4.24 (ddd, J=11.4, 8.7, 3.0 Hz, 1H), 4.00 (s, 3H), 2.24-2.00 (m, 2H); MS (DCI/NH$_3$) m/z 407 (M+H)$^+$; [α]$^{23}_D$ +67.1° (c 0.56, 1:1 CH$_3$OH—CH$_2$Cl$_2$).

Example 80

N-[(4R)-2,2-dimethyl-7-(trifluoromethoxy)-3,4-dihydro-2H-chromen-4-yl]-N'-(3-methylisoquinolin-5-yl)urea The title compound was prepared according to the procedure of Example 65E, substituting Example 39B for Example 65D. $^1$H NMR (300 MHz, DMSO-d$_6$) $^1$H NMR (300 MHz, DMSO-d$_6$) δ 9.19 (s, 1H), 8.65 (s, 1H), 8.29 (d, J=7.3 Hz, 1H), 7.75 (s, 1H), 7.72 (d, J=7.1 Hz, 1H), 7.53 (t, J=7.6 Hz, 1H), 7.46 (d, J=8.0 Hz, 1H), 7.01 (d, J=8.0 Hz, 1H), 6.93 (dd, J=8.0, 0.8 Hz, 1H), 6.76 (br s, 1H), 5.06-4.99 (m, 1H), 2.65 (s, 3H), 2.23 (dd, J=12.9, 5.7 Hz, 1H), 1.79 (dd, J=12.9, 10.9 Hz, 1H), 1.44 (s, 3H), 1.32 (s, 3H); MS (DCI/NH$_3$) m/z 444 (M+H)$^+$; [α]$^{23}_D$ +7.8° (c 0.5, CH$_3$OH).

Example 81

N-(3-chloroisoquinolin-5-yl)-N'-[(4R)-2,2-diethyl-8-fluoro-3,4-dihydro-2H-chromen-4-yl]urea

Example 81A 3-chloroisoquinoline

A mixture of 1,3-dichloroisoquinoline (5.00 g, 25.2 mmol), red phosphorus, (1.72 g, 55.5 mmol), and hydriodic acid (10.5 mL, 58.1 mmol) in acetic acid (25 mL) was heated to reflux for 24 hours. The reaction mixture was cooled and poured onto ice, and the resulting solution brought to pH 7 by the addition of 10N aqueous sodium hydroxide. The solution was extracted with dichloromethane (2×50 mL), and the organic layers concentrated. The residue was purified by silica gel chromatography (elution with 10% EtOAc/hexanes) to provide 1.01 g (24%) of the title compound. MS (DCI/NH$_3$) m/z 164 (M+H)$^+$.

Example 81B 3-chloro-5-nitroisoquinoline

To a solution of Example 81A (1.00 g, 6.11 mmol) in concentrated sulfuric acid (24 mL) at 0° C. was added a solution of potassium nitrate (0.655 g, 6.48 mmol) in concentrated sulfuric acid (6.48 mL). The reaction was stirred at 0°

C. for 2 hours, then allowed to warm to ambient temperature and stirred an additional 16 hours. The reaction mixture was poured onto ice. The precipitate that formed was collected by filtration and dried to provide 1.29 g (100%) of the title compound. MS (DCI/NH$_3$) m/z 208 (M+H)$^+$.

Example 81C 3-chloroisoquinolin-5-amine

A solution of Example 81B (10 mg, 0.048 mmol) in tetrahydrofuran (2 mL) was added to water-wet Ra—Ni (30.0 mg, 0.511 mmol) and exposed to hydrogen gas at 30 psi. The reaction was heated to 40° C. for 15 minutes. After filtration, the solution was concentrated to produce 0.84 g (76%) of the title compound. MS (DCI/NH$_3$) m/z 179 (M+H)$^+$.

Example 81D

N-(3-chloroisoquinolin-5-yl)-N'-[(4R)-2,2-diethyl-8-fluoro-3,4-dihydro-2H-chromen-4-yl]urea The title compound was prepared according to the procedure of Example 5, substituting Example 81C for isoquinolin-5-amine, and substituting Example 50B for Example 1C. $^1$H NMR (300 MHz, DMSO-d$_6$) δ 9.19 (s, 1H), 8.77 (s, 1H), 8.39 (d, J=7.6 Hz, 1H), 8.09 (s, 1H), 7.82 (d, J=8.1 Hz, 1H), 7.70-7.61 (m, 1H), 7.13 (dd, J=20.2, 9.6 Hz, 2H), 6.91 (ddd, J=13.0, 12.3, 6.7 Hz, 2H), 5.02 (dd, J=16.2, 8.8 Hz, 1H), 2.24 (dd, J=13.6, 6.1 Hz, 1H), 1.87-1.52 (m, 5H), 1.03-0.78 (m, 6H); MS (DCI/NH$_3$) m/z 428 (M+H)$^+$; [α]$^{23}_D$ +14.8° (c 0.53, CH$_3$OH).

Example 82

N-[(4R)-2,2-diethyl-7-fluoro-3,4-dihydro-2H-chromen-4-yl]-N'-isoquinolin-8-ylurea The title compound was prepared according to the procedure of Example 65E, substituting 8-aminoisoquinoline for 3-methylisoquinolin-5-amine and substituting Example 46B for Example 65D. $^1$H NMR (300 MHz, DMSO-d$_6$) δ 9.51 (s, 1H), 8.98 (s, 1H), 8.50 (d, J=5.6, 1H), 8.19 (dd, J=7.6, 0.9 Hz, 1H), 7.79 (d, J=5.9 Hz, 1H), 7.70 (t, J=7.8 Hz, 1H), 7.59 (d, J=8.2 Hz, 1H), 7.37 (t, J=6.8 Hz, 1H), 6.98 (d, J=8.1 Hz, 1H), 6.75 (td, J=6.6, 2.0 Hz, 1H), 6.63 (dd, J=8.2, 2.1 Hz, 1H), 5.03-4.92 (m, 1H), 2.21 (dd, J=13.6, 6.1 Hz, 1H), 1.88-1.52 (m, 5H), 0.93 (t, J=7.5 Hz, 3H), 0.88 (t, J=7.5 Hz, 3H); MS (ESI+) m/z 394 (M+H)$^+$; [α]$^{23}_D$ +11.0° (c 0.54, CH$_3$OH).

Example 83

N-[(4R)-2,2-diethyl-8-fluoro-3,4-dihydro-2H-chromen-4-yl]-N'-isoquinolin-8-ylurea The title compound was prepared according to the procedure of Example 65E, substituting 8-aminoisoquinoline for 3-methylisoquinolin-5-amine, and substituting Example 50B for Example 65D. $^1$H NMR (300 MHz, DMSO-d$_6$) δ 9.51 (s, 1H), 9.00 (s, 1H), 8.50 (d, J=5.6, 1H), 8.19 (dd, J=7.7, 0.9 Hz, 1H), 7.79 (dd, J=5.7, 0.6 Hz, 1H), 7.70 (t, J=7.9 Hz, 1H), 7.59 (d, J=8.2 Hz, 1H), 7.21-7.06 (m, 2H), 7.02 (d, J=8.3 Hz, 1H), 6.89 (td, J=8.0, 5.0 Hz, 1H), 5.10-4.96 (m, 1H), 2.24 (dd, J=13.6, 6.1 Hz, 1H), 1.88-1.52 (m, 5H), 0.94 (t, J=7.5 Hz, 3H), 0.90 (t, J=7.5 Hz, 3H); MS (ESI+) m/z 394 (M+H)$^+$; [α]$^{23}_D$ +24.0° (c 0.53, MeOH).

Example 84

N-[(4R)-7-chloro-2,2-bis(fluoromethyl)-3,4-dihydro-2H-chromen-4-yl]-N'-(3-methylisoquinolin-5-yl)urea Example 84A 7-chloro-2,2-bis(fluoromethyl)chroman-4-one The title compound was prepared according to the procedure of Example 65A substituting 1-(4-chloro-2-hydroxyphenyl)ethanone (AMRI) for 1-(5-fluoro-2-hydroxyphenyl)ethanone. MS (DCI/NH$_3$) m/z 264 (M+NH$_4$)$^+$.

Example 84B (S)-7-chloro-2,2-bis(fluoromethyl)chroman-4-ol

The title compound was prepared according to the procedure of Example 65B substituting Example 84A for Example 65A. MS (DCI/NH$_3$) m/z 249 (M+H)$^+$.

Example 84C (R)-7-chloro-2,2-bis(fluoromethyl)chroman-4-amine

The title compound was prepared according to the procedure of Example 65C substituting Example 84B for Example 65B. MS (DCI/NH$_3$) m/z 248 (M+H)$^+$.

Example 84D (R)-7-chloro-2,2-bis(fluoromethyl)chroman-4-amine, D-tartaric acid salt The title compound was prepared according to the procedure of Example 65D substituting Example 84C for Example 65C. MS (DCI/NH$_3$) m/z 248 (M+H)$^+$.

Example 84E

N-[(4R)-7-chloro-2,2-bis(fluoromethyl)-3,4-dihydro-2H-chromen-4-yl]-N'-(3-methylisoquinolin-5-yl)urea The title compound was prepared according to the procedure of Example 65E substituting Example 84D for Example 65D. $^1$H NMR (300 MHz, DMSO-d$_6$) δ 9.19 (s, 1H), 8.69-8.66 (br s, 1H), 8.26 (d, J=6.9 Hz, 1H), 7.76-7.70 (m, 2H), 7.54 (d, J=7.9 Hz, 1H), 7.37 (d, J=0.9 Hz, 1H), 7.07 (dd, J=8.3, 2.2 Hz, 2H), 7.00 (d, J=2.1 Hz, 1H), 5.08-5.01 (m, 1H), 4.72-4.74 (m, 2H), 4.56-4.58 (m, 2H), 2.66 (s, 3H), 2.31-2.42 (m, 1H), 1.96-2.07 (m, 1H); MS (DCI/NH$_3$) m/z 432 (M+H)$^+$; [α]$^{23}_D$ +1.3° (c 0.55, CH$_3$OH).

Example 85

N-[(4R)-8-fluoro-2,2-bis(fluoromethyl)-3,4-dihydro-2H-chromen-4-yl]-N'-(3-methylisoquinolin-5-yl)urea Example 85A 8-fluoro-2,2-bis(fluoromethyl)chroman-4-one The title compound was prepared according to the procedure of Example 65A substituting 1-(3-fluoro-2-hydroxyphenyl)ethanone for 1-(5-fluoro-2-hydroxyphenyl)ethanone. MS (DCI/NH$_3$) m/z 248 (M+NH$_4$)$^+$.

Example 85B (S)-8-fluoro-2,2-bis(fluoromethyl)chroman-4-ol

The title compound was prepared according to the procedure of Example 65B substituting Example 85A for Example 65A. MS (DCI) m/z 233 (M+H)$^+$.

Example 85C (R)-8-fluoro-2,2-bis(fluoromethyl)chroman-4-amine

The title compound was prepared according to the procedure of Example 65C substituting Example 85B for Example 65B. MS (DCI/NH$_3$) m/z 232 (M+H)$^+$.

Example 85D (R)-8-fluoro-2,2-bis(fluoromethyl)chroman-4-amine, D-tartaric acid salt The title compound was prepared according to the procedure of Example 65D substituting Example 85C for Example 65C. MS (DCI/NH$_3$) m/z 232 (M+H)$^+$.

Example 85E

N-[(4R)-8-fluoro-2,2-bis(fluoromethyl)-3,4-dihydro-2H-chromen-4-yl]-N'-(3-methylisoquinolin-5-yl)urea The title compound was prepared according to the procedure of Example 65E substituting Example 85D for Example 65D. $^1$H NMR (300 MHz, DMSO-d$_6$) δ 9.19 (s, 1H), 8.68 (s, 1H), 8.27 (dd, J=7.7, 1.1 Hz, 1H), 7.76-7.71 (m, 2H), 7.54 (t, J=7.9 Hz, 1H), 7.16-7.23 (m, 2H), 7.09-6.88 (m, 2H), 5.15-5.06 (m, 1H), 4.80-4.71 (m, 2H), 4.57-4.64 (m, 2H), 2.66 (s, 3H), 2.39 (dd, J=13.8, 5.9 Hz, 1H), 1.99-2.11 (m, 1H); MS (DCI/NH$_3$) m/z 416 (M+H)$^+$; [α]$^{23}$$_D$ +3.2° (c 0.65, CH$_3$OH).

Example 86

N-[(4R)-2,2-diethyl-6-fluoro-3,4-dihydro-2H-chromen-4-yl]-N'-(1-methylisoquinolin-5-yl)urea

Example 86A 1-methylisoquinolin-5-amine

1-Methyl-5-nitroisoquinoline (prepared according to Rathelot, P. et al. *Eur. J. Med. Chem.* 1995, 30, 503-508.) (2.19 g, 11.64 mmol) was dissolved in methanol (20 mL) and tetrahydrofuran (20 mL) in a 250 mL stainless steel pressure bottle to which was added 5% Pd—C (0.438 g, 4.12 mmol). The reaction mixture was stirred for 2 h under 30 psi hydrogen at ambient temperature. The mixture was filtered through a nylon membrane and the volatiles evaporated in vacuo. The resulting grayish solid was triturated with 1:1 hexanes-CH$_2$Cl$_2$ (50 mL) and the title compound (1.62 g, 10.24 mmol, 88%) was collected as an off white solid. MS (DCI/NH$_3$) m/z 159 (M+H)$^+$.

Example 86B

N-[(4R)-2,2-diethyl-6-fluoro-3,4-dihydro-2H-chromen-4-yl]-N'-(1-methylisoquinolin-5-yl)urea The title compound was prepared according to the procedure of Example 65E, substituting Example 86A for 3-methylisoquinolin-5-amine, and substituting Example 26B for Example 65D. $^1$H NMR (300 MHz, DMSO-d$_6$) δ 8.68 (s, 1H), 8.40 (d, J=5.7 Hz, 1H), 8.31 (dd, J=7.7, 0.9 Hz, 1H), 7.86 (d, J=7.9 Hz, 1H), 7.80 (d, J=5.9 Hz, 1H), 7.61 (t, J=7.8 Hz 1H), 7.12 (dd, J=8.9, 3.0 Hz, 1H), 7.05-6.96 (m, 2H), 6.81 (dd, J=8.8, 5.0 Hz, 1H), 5.03-4.92 (m, 1H), 2.89 (s, 3H), 2.20 (dd, J=9.3, 5.4 Hz, 1H), 1.76-1.50 (m, 5H), 0.92 (t, J=7.9 Hz, 3H), 0.87 (t, J=7.9 Hz, 3H); MS (DCI/NH$_3$) m/z 408 (M+H)$^+$; [α]$^{23}$$_D$ +40.0° (c 0.50, CH$_3$OH).

Example 87

N-[(4R)-2,2-bis(fluoromethyl)-8-(trifluoromethoxy)-3,4-dihydro-2H-chromen-4-yl]-N'-(3-methylisoquinolin-5-yl)urea

Example 87A 2,2-bis(fluoromethyl)-8-(trifluoromethoxy)chroman-4-one

The title compound was prepared according to the procedure of Example 65A substituting Example 55C for 1-(5-fluoro-2-hydroxyphenyl)ethanone. MS (DCI/NH$_3$) m/z 314 (M+NH$_4$)$^+$.

Example 87B (S)-2,2-bis(fluoromethyl)-8-(trifluoromethoxy)chroman-4-ol

The title compound was prepared according to the procedure of Example 65B substituting Example 87A for Example 65A. MS (DCI/NH$_3$) m/z 299 (M+H)$^+$.

Example 87C (R)-2,2-bis(fluoromethyl)-8-(trifluoromethoxy)chroman-4-amine

The title compound was prepared according to the procedure of Example 65C substituting Example 87B for Example 65B. MS (DCI/NH$_3$) m/z 315 (M+H)$^+$.

Example 87D (R)-2,2-bis(fluoromethyl)-8-(trifluoromethoxy)chroman-4-amine, D-tartaric acid salt The title compound was prepared according to the procedure of Example 65D substituting Example 87C for Example 65C. MS (DCI/NH$_3$) m/z 315 (M+H)$^+$.

Example 87E

N-[(4R)-2,2-bis(fluoromethyl)-8-(trifluoromethoxy)-3,4-dihydro-2H-chromen-4-yl]-N-(3-methylisoquinolin-5-yl)urea The title compound was prepared according to the procedure of Example 65E substituting Example 87D for Example 65D. $^1$H NMR (300 MHz, DMSO-d$_6$) δ 9.19 (s, 1H), 8.68 (s, 1H), 8.32-8.18 (m, 1H), 7.80-7.66 (m, 2H), 7.61-7.46 (m, 1H), 7.46-7.26 (m, 2H), 7.06 (ddd, J=20.1, 12.2, 5.3 Hz, 2H), 5.12 (dd, J=14.5, 9.5 Hz, 1H), 4.83-4.68 (m, 2H), 4.68-4.51 (m, 2H), 2.65 (s, 3H), 2.40 (dd, J=13.9, 5.9 Hz, 1H), 2.18-1.93 (m, 1H); MS (DCI/NH$_3$) m/z 482 (M+H)$^+$; [α]$^{23}_D$ +8.9° (c 0.53, CH$_3$OH).

Example 88

N-[(4R)-2,2-bis(fluoromethyl)-8-(trifluoromethoxy)-3,4-dihydro-2H-chromen-4-yl]-N'-(1-methyl-1H-indazol-4-yl)urea The title compound was prepared according to the procedure of Example 55F, substituting Example 87D for Example 55E. $^1$H NMR (300 MHz, DMSO-d$_6$) 8.78 (s, 1H), 8.05 (d, J=0.9 Hz, 1H), 7.68 (d, J=7.5 Hz, 1H), 7.38 (d, J=7.8 Hz, 1H), 7.34-7.26 (m, 2H), 7.18 (d, J=8.3 Hz, 1H), 7.07 (t, J=7.9 Hz, 1H), 6.86 (d, J=8.1 Hz, 1H), 5.15-5.06 (m, 1H), 4.84-4.73 (m, 2H), 4.65-4.57 (m, 1H), 4.61 (d, J=4.9 Hz, 1H), 4.01 (s, 3H), 2.39 (dd, J=13.8, 6.0 Hz, 1H), 2.12-1.90 (m, 1H); MS (DCI/NH$_3$) m/z 471 (M+H)$^+$; [α]$^{23}_D$ +5.8° (c 0.65, CH$_3$OH).

Example 89

N-[(4R)-7-fluoro-2,2-bis(fluoromethyl)-3,4-dihydro-2H-chromen-4-yl]-N'-[(7R)-7-hydroxy-5,6,7,8-tetrahydronaphthalen-1-yl]urea

Example 89A 7-fluoro-2,2-bis(fluoromethyl)chroman-4-one

The title compound was prepared according to the procedure of Example 65A substituting 1-(4-fluoro-2-hydroxyphenyl)ethanone for 1-(5-fluoro-2-hydroxyphenyl)ethanone. MS (DCI/NH$_3$) m/z 231 (M+H)$^+$.

Example 89B (S)-7-fluoro-2,2-bis(fluoromethyl)chroman-4-ol

The title compound was prepared according to the procedure of Example 65B substituting Example 89A for Example 65A. MS (DCI/NH$_3$) m/z 233 (M+H)$^+$.

Example 89C (R)-7-fluoro-2,2-bis(fluoromethyl)chroman-4-amine

The title compound was prepared according to the procedure of Example 65C substituting Example 89B for Example 65B. MS (DCI/NH$_3$) m/z 232 (M+H)$^+$.

Example 89D (R)-8-fluoro-2,2-bis(fluoromethyl)chroman-4-amine, D-tartaric acid salt The title compound was prepared according to the procedure of Example 65D substituting Example 89C for Example 65C. MS (DCI/NH$_3$) m/z 232 (M+H)$^+$.

Example 89E

N-[(4R)-7-fluoro-2,2-bis(fluoromethyl)-3,4-dihydro-2H-chromen-4-yl]-N'-[(7R)-7-hydroxy-5,6,7,8-tetrahydronaphthalen-1-yl]urea The title compound was prepared according to the procedure of Example 31, substituting Example 4A for Example 3B, and substituting Example 89D for Example 23B. $^1$H NMR (300 MHz, DMSO-d$_6$) δ 7.69 (d, J=8.0 Hz, 1H), 7.59 (s, 1H), 7.37-7.28 (m, 1H), 7.06-6.95 (m, 2H), 6.84 (td, J=8.6, 2.6 Hz, 1H), 6.79-6.70 (m, 2H), 5.01-4.89 (m, 1H), 4.86 (d, J=3.4 Hz, 1H), 4.78-4.65 (m, 2H), 4.63-4.50 (m, 2H), 3.99-3.87 (m, 1H), 2.90-2.64 (m, 3H), 2.40-2.25 (m, 2H), 2.01-1.81 (m, 2H), 1.67-1.52 (m, 1H); MS (ESI+) m/z 421 (M+H)$^+$; [α]$^{23}_D$ +12.1° (c 1.0, CH$_3$OH).

Example 90

N-(3-aminoisoquinolin-5-yl)-N'-[(4R)-2,2-dimethyl-7-(trifluoromethyl)-3,4-dihydro-2H-chromen-4-yl]urea

Example 90A

N-(isoquinolin-3-yl)acetamide

Acetic anhydride (5.92 mL, 62.6 mmol) was added to a suspension of isoquinolin-3-amine (3.01 g, 20.9 mmol) and triethylamine (3.18 mL, 23.0 mmol) in CH$_2$Cl$_2$ (80 mL) at ambient temperature. The mixture was stirred 3.5 hours, then the volatiles were evaporated in vacuo. The residue was chased with toluene and concentrated in vacuo (3×25 mL) to provide the title compound (3.89 g) as a yellow solid. This material, which was found to also contain small quantities of acetic acid, was used without further purification. $^1$H NMR (300 MHz, DMSO-d$_6$) δ 10.58 (s, 1H), 9.13 (s, 1H), 8.45 (s, 1H), 8.04 (d, J=7.8 Hz, 1H), 7.88 (d, J=8.2 Hz, 1H), 7.69 (ddd, J=8.2, 6.8, 1.2 Hz, 1H), 7.52 (ddd, J=7.9, 6.9, 1.0 Hz, 1H), 2.13 (s, 3H).

Example 90B

N-(5-nitroisoquinolin-3-yl)acetamide

A solution of N-(isoquinolin-3-yl)acetamide (3.89 g, 20.9 mmol) in concentrated H$_2$SO$_4$ (40 mL) was cooled to 0° C. and solid potassium nitrate (2.53 g, 25.1 mmol) was added slowly in portions over 10 min. After stiffing for 1 h at 0° C., the reaction mixture was poured over ice (50 g), and neutralized with concentrated NH$_4$OH solution. The resulting yellow solid was collected by vacuum filtration, washed with water, and dried in the vacuum oven at ambient temperature for 48 hours. This material was triturated with 1:1 CH$_3$OH—CH$_2$Cl$_2$, collected by filtration, washed with CH$_2$Cl$_2$, and dried under vacuum. This provided 4.14 g of the title compound as a yellow solid in approximately 60% purity. MS (ESI+) m/z 232 (M+H)$^+$.

Example 90C 1-(5-aminoisoquinolin-3-yl)acetamide

Example 90B (2.40 g, 10.4 mmol) was hydrogenated at 60 psi hydrogen with 10% Pd/C (240 mg) in methanol (200 mL) for 4 h at ambient temperature. The catalyst was removed by filteration through silica gel and the solvent was evaporated. The crude product was purified by chromatography on silica gel (elution with 5% MeOH/CH$_2$Cl$_2$) to give an orange solid. This material was triturated with Et$_2$O, and the solid was collected by vacuum filtration and dried in the vacuum oven at 50° C. for 1 h to provide the title compound (1.59 g, 7.90 mmol, 44%) as a light brown solid. $^1$H NMR (300 MHz, DMSO-d$_6$) δ 10.42 (s, 1H), 8.92 (d, J=0.7 Hz, 1H), 8.41 (s, 1H), 7.26-7.17 (m, 2H), 6.89-6.80 (m, 1H), 5.60 (s, 2H), 2.13 (s, 3H); MS (DCI/NH$_3$) m/z 202 (M+H)$^+$.

Example 90D (R)—N-(5-(3-(2,2-dimethyl-7-(trifluoromethyl)chroman-4-yl)ureido)isoquinolin-3-yl)acetamide Phenyl chloroformate (0.170 mL, 1.33 mmol) was added dropwise to a mixture of Example 90C (268 mg, 1.33 mmol) and pyridine (0.110 mL, 1.33 mmol) in CH$_2$Cl$_2$ (5 mL) at 0° C. After 10 min the thick mixture was diluted with THF (5 mL), and then diisopropylethylamine (0.770 mL, 4.44 mmol) was added, followed by Example 33B (441 mg, 1.11 mmol) as a solid all in one portion. The cooling bath was removed and the reaction was stirred for 2 h, and then 1:1 CH$_2$Cl$_2$-THF (5 mL) was added and stirring was continued for 27 hours. The mixture was diluted with CH$_2$Cl$_2$ (50 mL) and washed with 2 N aq NaOH solution, resulting in an intractable emulsion. The mixture was concentrated in vacuo, and the residue was taken up in EtOAc (125 mL) and separated from the aqueous phase. The organic layer was washed with 2 N aq NaOH solution (20 mL) and brine (25 mL), dried over Na$_2$SO$_4$, filtered, and concentrated in vacuo. The crude product was suspended in EtOAc (15 mL), and then triturated with 1:1 Et$_2$O-hexanes. The resulting solid was collected by vacuum filtration, washed with 1:1 Et$_2$O-hexanes, and dried in a vacuum oven at 50° C. for 30 min to afford the title compound (515 mg, 1.09 mmol, 98% yield) as a white solid. MS (ESI+) m/z 473 (M+H)$^+$.

Example 90E

N-(3-aminoisoquinolin-5-yl)-N'-[(4R)-2,2-dimethyl-7-(trifluoromethyl)-3,4-dihydro-2H-chromen-4-yl]urea A mixture of Example 90D (505 mg, 1.07 mmol) and NaOH (428 mg, 10.7 mmol) in MeOH (10 mL) and H$_2$O (3.5 mL) was heated to 85° C. After 24 h the reaction mixture was cooled to ambient temperature. The precipitate was collected by vacuum filtration, washed with minimal MeOH and then water, and dried in the vacuum oven at 50° C. for 4 h to provide the title compound (238 mg, 0.553 mmol, 52% yield) as a yellow solid. $^1$H NMR (300 MHz, DMSO-d$_6$) δ 8.79 (s, 1H), 8.35 (s, 1H), 7.89 (d, J=7.4 Hz, 1H), 7.52 (t, J=7.5 Hz, 2H), 7.26 (d, J=8.2 Hz, 1H), 7.11 (t, J=7.8 Hz, 1H), 7.06 (s, 1H), 6.95 (d, J=8.5 Hz, 1H), 6.71 (s, 1H), 5.99 (s, 2H), 5.14-5.00 (m, 1H), 2.21 (dd, J=13.3, 6.2 Hz, 1H), 1.82 (dd, J=13.1, 11.6 Hz, 1H), 1.44 (s, 3H), 1.32 (s, 3H); MS (ESI+) m/z 431 (M+H)$^+$; [α]$^{23}_D$ +35.7° (c 0.61, CH$_3$OH).

Example 91

N-[(4R)-8-chloro-2,2-bis(fluoromethyl)-3,4-dihydro-2H-chromen-4-yl]-N'-(3-methylisoquinolin-5-yl)urea

Example 91A 8-chloro-2,2-bis(fluoromethyl)chroman-4-one

The title compound was prepared according to the procedure of Example 65A substituting 1-(3-chloro-2-hydroxyphenyl)ethanone for 1-(5-fluoro-2-hydroxyphenyl)ethanone. MS (DCI/NH$_3$) m/z 264 (M+NH$_4$)$^+$.

Example 91B (S)-8-chloro-2,2-bis(fluoromethyl)chroman-4-ol

The title compound was prepared according to the procedure of Example 65B substituting Example 91A for Example 65A. MS (DCI/NH$_3$) m/z 249 (M+H)$^+$.

Example 91C (R)-8-chloro-2,2-bis(fluoromethyl)chroman-4-amine

The title compound was prepared according to the procedure of Example 65C substituting Example 91B for Example 65B. MS (DCI/NH$_3$) m/z 248 (M+H)$^+$.

Example 91D (R)-8-chloro-2,2-bis(fluoromethyl)chroman-4-amine, D-tartaric acid salt The title compound was prepared according to the procedure of Example 65D substituting Example 91C for Example 65C. MS (DCI/NH$_3$) m/z 248 (M+H)$^+$.

Example 91E

N-[(4R)-8-chloro-2,2-bis(fluoromethyl)-3,4-dihydro-2H-chromen-4-yl]-N'-(3-methylisoquinolin-5-yl)urea The title compound was prepared according to the procedure of Example 65E substituting Example 91D for Example 65D. $^1$H NMR (300 MHz, DMSO-d$_6$) δ 9.20 (s, 1H), 8.69 (s, 1H), 8.26 (dd, J=7.7, 1.1 Hz, 1H), 7.76-7.71 (m, 2H), 7.53 (t, J=7.9 Hz, 1H), 7.42-7.32 (m, 2H), 6.98-7.07 (m, 2H), 5.15-5.06 (m, 1H), 4.81-4.58 (m, 4H), 2.66 (s, 3H), 2.39 (dd, J=13.8, 5.9 Hz, 1H), 2.06 (ddd, J=13.6, 10.7, 2.8 Hz, 1H); MS (DCI/NH$_3$) m/z 432 (M+H)$^+$; [α]$^{23}$1)+14.0° (c 0.70, CH$_3$OH).

Example 92

N-[(4R)-2,2-bis(fluoromethyl)-7-(trifluoromethoxy)-3,4-dihydro-2H-chromen-4-yl]-N'-(1-methyl-1H-indazol-4-yl)urea

Example 92A 1-(2-hydroxy-4-(trifluoromethoxy)phenyl)ethanone

A solution of 1-(2-methoxy-4-(trifluoromethoxy)phenyl)ethanone (17.8 g, 76.0 mmol) in CH$_2$Cl$_2$ (178 mL) was cooled to −25° C. and boron trichloride (91.0 mL of a 1.0 M solution in CH₂Cl₂, 91 mmol) was added dropwise keeping the internal temperature ≤−18° C. Following addition, analysis by LCMS indicated complete reaction. The reaction mixture was poured into ice (75 g) and partitioned. The organic layer was washed with water (50 mL), dried (Na₂SO₄), filtered, and concentrated to give 16.2 g (73.6 mmol, 97% yield) of the title compound. MS (DCI/NH₃) m/z 238 (M+NH₄)⁺.

Example 92B 2,2-bis(fluoromethyl)-7-(trifluoromethoxy)chroman-4-one

The title compound was prepared according to the procedure of Example 65A substituting Example 92A for 1-(5-fluoro-2-hydroxyphenyl)ethanone. MS (DCI/NH₃) m/z 314 (M+NH₄)⁺.

Example 92C (S)-2,2-bis(fluoromethyl)-7-(trifluoromethoxy)chroman-4-ol

The title compound was prepared according to the procedure of Example 65B substituting Example 92B for Example 65A. MS (DCI/NH₃) m/z 299 (M+H)⁺.

Example 92D (R)-2,2-bis(fluoromethyl)-7-(trifluoromethoxy)chroman-4-amine

The title compound was prepared according to the procedure of Example 65C substituting Example 92C for Example 65B. MS (DCI/NH₃) m/z 315 (M+H)⁺.

Example 92E (R)-2,2-bis(fluoromethyl)-7-(trifluoromethoxy)chroman-4-amine, D-tartaric acid salt The title compound was prepared according to the procedure of Example 65D substituting Example 92D for Example 65C. MS (DCI/NH₃) m/z 315 (M+H)⁺.

Example 92F

N-[(4R)-2,2-bis(fluoromethyl)-7-(trifluoromethoxy)-3,4-dihydro-2H-chromen-4-yl]-N'-(1-methyl-1H-indazol-4-yl)urea The title compound was prepared according to the procedure of Example 55F, substituting Example 92E for Example 55E. ¹H NMR (300 MHz, DMSO-d₆) δ 8.76 (s, 1H), 8.04 (d, J=0.9 Hz, 1H), 7.68 (dd, J=7.5, 0.8 Hz, 1H), 7.46 (dd, J=8.5, 1.0 Hz, 1H), 7.27 (d, J=7.7 Hz, 1H), 7.18 (d, J=8.4 Hz, 1H), 7.00 (ddd, J=8.5, 2.5, 1.3 Hz, 1H), 6.91 (dd, J=2.4, 1.1 Hz, 1H), 6.82 (d, J=8.0 Hz, 1H), 5.02-5.11 (m, 1H), 4.81-4.57 (m, 4H), 4.01 (s, 3H), 2.36 (dd, J=13.8, 5.9 Hz, 1H), 2.09-1.99 (m, 1H); MS (DCI/NH₃) m/z 471 (M+H)⁺; [α]²³_D +2.9° (c 0.56, CH₃OH).

Example 93

N-[(4R)-2,2-bis(fluoromethyl)-7-(trifluoromethyl)-3,4-dihydro-2H-chromen-4-yl]-N'-isoquinolin-8-ylurea

Example 93A 2,2-bis(fluoromethyl)-7-(trifluoromethyl)chroman-4-one

The title compound was prepared according to the procedure of Example 33A substituting 1,3-difluoroacetone for acetone. MS (DCI/NH₃) m/z 298 (M+NH₄)⁺.

Example 93B (S)-2,2-bis(fluoromethyl)-7-(trifluoromethyl)chroman-4-ol

The title compound was prepared according to the procedure of Example 65B substituting Example 93A for Example 65A. MS (DCI/NH₃) m/z 283 (M+H)⁺.

Example 93C (R)-2,2-bis(fluoromethyl)-7-(trifluoromethyl)chroman-4-amine

The title compound was prepared according to the procedure of Example 65C substituting Example 93B for Example 65B. MS (DCI/NH₃) m/z 299 (M+H)⁺.

Example 93D (R)-2,2-bis(fluoromethyl)-7-(trifluoromethyl)chroman-4-amine, D-tartaric acid salt The title compound was prepared according to the procedure of Example 65D substituting Example 93C for Example 65C. MS (DCI/NH₃) m/z 299 (M+H)⁺.

Example 93E

N-[(4R)-2,2-bis(fluoromethyl)-7-(trifluoromethyl)-3,4-dihydro-2H-chromen-4-yl]-N'-isoquinolin-8-ylurea The title compound was prepared according to the procedure of Example 65E, substituting 8-aminoisoquinoline for 3-methylisoquinolin-5-amine, and substituting Example 93D for Example 65D. ¹H NMR (300 MHz, DMSO-d₆) δ 9.52 (s, 1H), 9.06 (s, 1H), 8.51 (d, J=5.7 Hz, 1H), 8.14 (d, J=7.6 Hz, 1H), 7.80 (d, J=5.3 Hz, 1H), 7.71 (t, J=7.9 Hz, 1H), 7.65-7.56 (m, 2H), 7.35 (d, J=8.1 Hz, 1H), 7.23 (s, 1H), 7.12 (d, J=8.2 Hz, 1H), 5.22-5.08 (m, 1H), 4.85-4.71 (m, 2H), 4.69-4.55 (m, 2H), 2.41 (dd, J=13.7, 6.0 Hz, 1H), 2.15-2.02 (m, 1H); MS (ESI+) m/z 452 (M+H)⁺; [α]²³_D +21.9° (c 0.79, CH₃OH).

Example 94

N-[(4R)-2,2-dimethyl-8-(trifluoromethoxy)-3,4-dihydro-2H-chromen-4-yl]-N'-(3-methylisoquinolin-5-yl)urea

Example 94A 2,2-dimethyl-8-(trifluoromethoxy)chroman-4-one

The title compound was prepared according to the procedure of Example 1A, substituting Example 55C for 1-(5- fluoro-2-hydroxyphenyl)ethanone and using propan-2-one. MS (DCI/NH₃) m/z 278 (M+NH₄)⁺.

Example 94B (S)-2,2-dimethyl-8-(trifluoromethoxy)chroman-4-ol

The title compound was prepared according to the procedure of Example 65B substituting Example 94A for Example 65A. MS (DCI/NH₃) m/z 263 (M+H)⁺.

Example 94C (R)-2,2-dimethyl-8-(trifluoromethoxy)chroman-4-amine

The title compound was prepared according to the procedure of Example 65C substituting Example 94B for Example 65B. MS (DCI/NH₃) m/z 262 (M+H)⁺.

Example 94D (R)-2,2-dimethyl-8-(trifluoromethoxy)chroman-4-amine, D-tartaric acid salt The title compound was prepared according to the procedure of Example 65D substituting Example 94C for Example 65C. MS (DCI/NH₃) m/z 262 (M+H)⁺.

Example 94E

N-[(4R)-2,2-dimethyl-8-(trifluoromethoxy)-3,4-dihydro-2H-chromen-4-yl]-N'-(3-methylisoquinolin-5-yl)urea The title compound was prepared according to the procedure of Example 65E substituting Example 94D for Example 65D. $^1$H NMR (300 MHz, DMSO-d$_6$) δ 9.18 (s, 1H), 8.62 (s, 1H), 8.28 (dd, J=7.7, 1.1 Hz, 1H), 7.70-7.75 (m, 2H), 7.53 (t, J=7.9 Hz, 1H), 7.39 (dt, J=7.8, 1.2 Hz, 1H), 7.26 (d, J=8.0 Hz, 1H), 7.05-6.96 (m, 2H), 5.12-5.02 (m, 1H), 2.65 (s, 3H), 2.26 (dd, J=13.4, 6.2 Hz, 1H), 1.92-1.82 (m, 1H), 1.45 (s, 3H), 1.32 (s, 3H); MS (DCI/NH₃) m/z 446 (M+H)⁺; $[α]^{23}_D$ +16° (c 0.65, CH₃OH).

Example 95

N-[(4R)-7-fluoro-2,2-dimethyl-3,4-dihydro-2H-chromen-4-yl]-N'-(3-methylisoquinolin-5-yl)urea The title compound was prepared according to the procedure of Example 65E substituting Example 23B for Example 65D. $^1$H NMR (300 MHz, DMSO-d$_6$) δ 9.18 (s, 1H), 8.62 (s, 1H), 8.30 (dd, J=7.7, 1.1 Hz, 1H), 7.76-7.69 (m, 2H), 7.53 (t, J=7.9 Hz, 1H), 7.40-7.34 (m, 1H), 6.96 (d, J=8.3 Hz, 1H), 6.76 (td, J=8.5, 2.6 Hz, 1H), 6.62 (dd, J=10.6, 2.6 Hz, 1H), 5.04-4.94 (m, 1H), 2.65 (s, 3H), 2.21 (dd, J=13.3, 6.1 Hz, 1H), 1.79 (dd, J=13.3, 10.7 Hz, 1H), 1.42 (s, 3H), 1.31 (s, 3H); MS (DCI/NH₃) m/z 380 (M+H)⁺; $[α]^{23}_D$ +4.4° (c 0.45, CH₃OH.

Example 96

N-[(4R)-7-fluoro-2,2-bis(fluoromethyl)-3,4-dihydro-2H-chromen-4-yl]-N'-(3-methylisoquinolin-5-yl)urea The title compound was prepared according to the procedure of Example 65E substituting Example 89D for Example 65D. $^1$H NMR (300 MHz, DMSO-d$_6$) δ 9.19 (s, 1H), 8.64 (s, 1H), 8.27 (d, J=7.5 Hz, 1H), 7.77-7.69 (m, 2H), 7.53 (t, J=7.9 Hz, 1H), 7.45-7.36 (m, 1H), 7.02 (d, J=7.9 Hz, 1H), 6.86 (td, J=8.5, 2.6 Hz, 1H), 6.79 (dd, J=10.4, 2.6 Hz, 1H), 5.03 (dd, J=14.8, 9.0 Hz, 1H), 4.80-4.68 (m, 2H), 4.64-4.53 (m, 2H), 2.65 (s, 3H), 2.36 (dd, J=13.7, 5.8 Hz, 1H), 2.08-1.96 (m, 1H); MS (ESI+) m/z 416 (M+H)⁺; $[α]^{23}_D$ +3.7° (c 1.0, CH₃OH).

Example 97

N-[(4R)-7-chloro-2,2-dimethyl-3,4-dihydro-2H-chromen-4-yl]-N'-(3-methylisoquinolin-5-yl)urea Example 97A 7-chloro-2,2-dimethylchroman-4-one The title compound was prepared according to the procedure of Example 1A, substituting 1-(4-chloro-2-hydroxyphenyl)ethanone for 1-(5-fluoro-2-hydroxyphenyl)ethanone. MS (DCI/NH₃) m/z 228 (M+NH₄)⁺.

Example 97B (R)-7-chloro-2,2-dimethylchroman-4-amine

The title compound was prepared according to the procedures of Examples 1B and 1C, substituting Example 97A for Example 1A. MS (DCI/NH₃) m/z 212 (M+H)⁺.

Example 97C (R)-7-chloro-2,2-dimethylchroman-4-amine, D-tartaric acid salt

The title compound was prepared according to the procedure of Example 65D, substituting Example 97B for Example 65C. MS (DCI/NH₃) m/z 212 (M+H)⁺.

Example 97D

N-[(4R)-7-chloro-2,2-dimethyl-3,4-dihydro-2H-chromen-4-yl]-N'-(3-methylisoquinolin-5-yl)urea The title compound was prepared according to the procedure of Example 65E substituting Example 97C for Example 65D. $^1$H NMR (300 MHz, DMSO-d$_6$) δ 9.19 (s, 1H), 8.65 (s, 1H), 8.28 (d, J=7.5 Hz, 1H), 7.77-7.69 (m, 2H), 7.53 (t, J=7.9 Hz, 1H), 7.35 (d, J=8.3 Hz, 1H), 6.97 (dd, J=8.3, 1.8 Hz, 2H), 6.84 (d, J=2.1 Hz, 1H), 5.06-4.94 (m, 1H), 2.65 (s, 3H), 2.21 (dd, J=13.3, 6.2 Hz, 1H), 1.79 (dd, J=13.2, 11.1 Hz, 1H), 1.42 (s, 3H), 1.31 (s, 3H); MS (ESI+) m/z 396 (M+H)⁺; $[α]^{23}_D$ +9.0° (c 1.0, CH₃OH).

Example 98

N-[(4R)-6,8-difluoro-2,2-dimethyl-3,4-dihydro-2H-chromen-4-yl]-N-(3-methylisoquinolin-5-yl)urea The title compound was prepared according to the procedure of Example 65E substituting Example 16B for Example 65D. $^1$H NMR (300 MHz, DMSO-d$_6$) δ 9.19 (s, 1H), 8.68 (s, 1H), 8.25 (dd, J=7.6, 1.0 Hz, 1H), 7.76-7.71 (m, 2H), 7.53 (t, J=7.9 Hz, 1H), 7.24-7.15 (m, 1H), 7.05-6.97 (m, 2H), 5.07-4.97 (m, 1H), 2.66 (s, 3H), 2.24 (dd, J=13.3, 6.2 Hz, 1H), 1.86

(dd, J=13.3, 11.0 Hz, 1H), 1.45 (s, 3H), 1.32 (s, 3H); MS (DCI/NH$_3$) m/z 398 (M+H)$^+$; [α]$^{23}_D$ +24° (c 0.50, CH$_3$OH).

Example 99

N-[(4R)-8-fluoro-2,2-dimethyl-7-(trifluoromethyl)-3,4-dihydro-2H-chromen-4-yl]-N'-(3-methylisoquinolin-5-yl)urea

Example 99A 2-fluoro-1-(methoxymethoxy)-3-(trifluoromethyl)benzene

The title compound was prepared as described in Example 42A, substituting 2-fluoro-3-(trifluoromethyl)phenol for 2-(trifluoromethyl)phenol. $^1$H NMR (300 MHz, DMSO-d$_6$) δ 7.66-7.54 (m, 1H), 7.43-7.29 (m, 2H), 5.33 (s, 2H), 3.43 (s, 3H).

Example 99B 3-fluoro-2-hydroxy-4-(trifluoromethyl)benzoic acid

The title compound was prepared as described in Example 42B, substituting Example 99A for Example 42A. $^1$H NMR (300 MHz, DMSO-d$_6$) δ 7.75 (d, J=8.4 Hz, 1H), 7.23 (dd, J=8.4, 6.3 Hz, 1H).

Example 99C 1-(3-fluoro-2-hydroxy-4-(trifluoromethyl)phenyl)ethanone

The title compound was prepared as described in Example 42C, substituting Example 99B for Example 42B. $^1$H NMR (300 MHz, DMSO-d$_6$) δ 11.86 (s, 1H), 7.81-7.76 (m, 1H), 7.29 (dd, J=8.5, 6.0 Hz, 1H), 2.68 (s, 3H).

Example 99D 8-fluoro-2,2-dimethyl-7-(trifluoromethyl)chroman-4-one

The title compound was prepared according to the procedure of Example 1A, Example 99C for 1-(5-fluoro-2-hydroxyphenyl)ethanone. MS (DCI/NH$_3$) m/z 280 (M+NH$_4$)$^+$.

Example 99E (R)-8-fluoro-2,2-dimethyl-7-(trifluoromethyl)chroman-4-amine

The title compound was prepared according to the procedures of Examples 1B and 1C, substituting Example 99D for Example 1A. MS (DCI/NH$_3$) m/z 264 (M+H)$^+$.

Example 99F (R)-8-fluoro-2,2-dimethyl-7-(trifluoromethyl)chroman-4-amine, D-tartaric acid salt The title compound was prepared according to the procedure of Example 65D, substituting Example 99E for Example 65C. MS (DCI/NH$_3$) m/z 264 (M+H)$^+$.

Example 99G

N-[(4R)-8-fluoro-2,2-dimethyl-7-(trifluoromethyl)-3,4-dihydro-2H-chromen-4-yl]-A T'-(3-methylisoquinolin-5-yl)urea The title compound was prepared according to the procedure of Example 65E substituting Example 99F for Example 65D. $^1$H NMR (300 MHz, DMSO-d$_6$) δ 9.19 (s, 1H), 8.73 (s, 1H), 8.25 (dd, J=7.6, 0.8 Hz, 1H), 7.78-7.70 (m, 2H), 7.58-7.49 (m, 1H), 7.36 (d, J=8.3 Hz, 1H), 7.30-7.21 (m, 1H), 7.06 (d, J=8.5 Hz, 1H), 5.11 (dd, J=16.7, 9.2 Hz, 1H), 2.66 (s, 3H), 2.27 (dd, J=13.4, 6.2 Hz, 1H), 2.01-1.87 (m, 1H), 1.50 (s, 3H), 1.37 (s, 3H); MS (DCI/NH$_3$) m/z 448 (M+H)$^+$; [α]$^{23}_D$ +30.2° (c 0.58, MeOH).

Example 100

N-[(4R)-8-tert-butyl-3,4-dihydro-2H-chromen-4-yl]-N'-(3-methylisoquinolin-5-yl)urea, hydrochloride salt

Example 100A 1-tert-butyl-2-(prop-2-ynyloxy)benzene

To a solution of 2-(tert-butyl)phenol (21.0 g, 140 mmol) and propargyl bromide (18.8 mL, 168 mmol) in acetonitrile (250 mL) was added potassium carbonate (23.3 g, 168 mmol). The reaction was stirred at ambient temperature for two days. The reaction mixture was diluted with water (50 mL) and extracted diethyl ether (2×150 mL). The combined organic extracts were concentrated to provide 23.7 g (90%) of the title compound which was used without further purification. $^1$H NMR (300 MHz, DMSO-d$_6$) δ 7.26-7.14 (m, 2H), 7.02 (d, J=8.0 Hz, 1H), 6.94-6.86 (m, 1H), 4.83 (d, J=2.4 Hz, 2H), 3.55 (t, J=2.4 Hz, 1H), 1.34 (s, 9H).

Example 100B 1-tert-butyl-2-(3-chloroprop-2-ynyloxy)benzene

To a solution of Example 100A (22.2 g, 118 mmol) in acetone (300 mL) was added N-chlorosuccinimide (18.8 g, 141 mmol) and silver acetate (1.96 g, 11.7 mmol). The reaction was heated to reflux for 24 h, cooled, and the solvent removed by evaporation. The residue was taken up in a mixture of water (125 mL) and diethyl ether (125 mL), and filtered to remove the undissolved silver salts. The filtrate was extracted with diethyl ether (150 mL), and the combined organic layers washed with brine (75 mL) and concentrated to produce 26.9 g of the crude title compound which was used without further purification. MS (DCI/NH$_3$) m/z 240 (M+NH$_4$)$^+$.

Example 100C 8-tert-butylchroman-4-one

Example 100B (26.9 g, 118 mmol) was heated in refluxing ethylene glycol (300 mL) for 6 h. The reaction mixture was cooled, diluted with water (100 mL), and extracted with diethyl ether (2×150 mL). The combined organic layers were washed with 1N aqueous sodium hydroxide (50 mL) and concentrated. The residue was purified by silica gel chromatography (gradient elution, 0-20% EtOAc/hexanes) to provide the title compound. MS (DCI/NH$_3$) m/z 205 (M+H)$^+$.

Example 100D (R)-8-tert-butylchroman-4-amine

The title compound was prepared according to the procedures of Examples 1B and 1C, substituting Example 100C for Example 1A. MS (DCI/NH$_3$) m/z 206 (M+H)$^+$.

Example 100E

N-[(4R)-8-tert-butyl-3,4-dihydro-2H-chromen-4-yl]-N'-(3-methylisoquinolin-5-yl)urea, hydrochloride salt 3-Methylisoquinolin-5-amine (0.949 g, 6.00 mmol) was suspended in CH$_2$Cl$_2$ (20 mL). Pyridine (0.485 mL, 6.00 mmol) was added and the reaction was cooled to 0° C. in an ice-water bath. Phenyl chloroformate (0.754 mL, 6.00 mmol) was added and the reaction was allowed to stir for 15 minutes. N,N-Diisopropyethylamine (1.747 mL, 10.00 mmol) was added, followed by Example 100D (1.03 g, 5.00 mmol) in CH$_2$Cl$_2$ (10 mL). The reaction was allowed to warm to ambient and stirred overnight. The reaction mixture was diluted with CH$_2$Cl$_2$ (50 mL), washed with 1N NaOH (2×15 mL), water (15 mL), and brine (2-mL). The organic portion was dried (MgSO$_4$), filtered, and concentrated. The residue was taken up in EtOAc (20 mL) and treated with 1N HCl (5 mL), which resulted in the formation of a yellow precipitate. This precipitate was collected by filtration and dried overnight in a vacuum oven to provide the title compound. $^1$H NMR (300 MHz, DMSO-d$_6$) δ 9.68 (s, 1H), 9.19 (s, 1H), 8.65 (d, J=7.7 Hz, 1H), 8.47 (s, 1H), 8.00 (d, J=8.2 Hz, 1H), 7.86-7.77 (m, 1H), 7.57 (d, J=7.7 Hz, 1H), 7.19 (d, J=7.6 Hz, 1H), 7.15 (d, J=7.8 Hz, 1H), 6.89-6.81 (m, 1H), 4.94 (dd, J=12.4, 5.1 Hz, 1H), 4.44-4.32 (m, 1H), 4.27-4.14 (m, 1H), 2.76 (s, 3H), 2.23-1.95 (m, 2H), 1.35 (s, 9H); MS (DCI/NH$_3$) m/z 390 (M+H)$^+$; [α]$^{23}_D$ +87.6° (c 0.50, MeOH).

Example 101

N-[(4R)-2,2-bis(fluoromethyl)-3,4-dihydro-2H-chromen-4-yl]-N'-(3-methylisoquinolin-5-yl)urea Example 101A 2,2-bis(fluoromethyl)chroman-4-one The title compound was prepared according to the procedure of Example 65A substituting 1-(2-hydroxyphenyl)ethanone for 1-(5-fluoro-2-hydroxyphenyl)ethanone. MS (DCI/NH$_3$) m/z 230 (M+NH$_4$)$^+$.

Example 101B (S)-2,2-bis(fluoromethyl)chroman-4-ol

The title compound was prepared according to the procedure of Example 65B substituting Example 101A for Example 65A. MS (DCI/NH$_3$) m/z 215 (M+H)$^+$.

Example 101C (R)-2,2-bis(fluoromethyl)chroman-4-amine

The title compound was prepared according to the procedure of Example 65C substituting Example 101B for Example 65B. MS (DCI/NH$_3$) m/z 214 (M+H)$^+$.

Example 101D (R)-2,2-bis(fluoromethyl)chroman-4-amine, D-tartaric acid salt

The title compound was prepared according to the procedure of Example 65D substituting Example 101C for Example 65C. MS (DCI/NH$_3$) m/z 248 (M+H)$^+$.

Example 101E

N-[(4R)-7-chloro-2,2-bis(fluoromethyl)-3,4-dihydro-2H-chromen-4-yl]-N'-(3-methylisoquinolin-5-yl)urea The title compound was prepared according to the procedure of Example 65E substituting Example 101D for Example 65D. $^1$H NMR (300 MHz, DMSO-d$_6$) δ 9.19 (s, 1H), 8.66 (s, 1H), 8.26 (d, J=7.2 Hz, 1H), 7.75-7.70 (m, 2H), 7.53 (t, J=7.9 Hz, 1H), 7.30 (s, 1H), 7.21 (d, J=2.0 Hz, 1H), 7.12 (d, J=1.9 Hz, 1H), 7.03 (d, J=8.0 Hz, 1H), 5.07-4.98 (m, 1H), 4.74-4.72 (br s, 2H), 4.58-4.56 (br s, 2H), 2.66 (s, 3H), 2.34 (d, J=5.9 Hz, 1H), 1.99 (s, 1H); MS (DCI/NH$_3$) m/z 398 (M+H)$^+$; [α]$^{23}_D$ +38.5° (c 0.50, MeOH).

Example 102

N-[(4R)-7-bromo-2,2-bis(fluoromethyl)-3,4-dihydro-2H-chromen-4-yl]-N'-(3-methylisoquinolin-5-yl)urea Example 102A 7-bromo-2,2-bis(fluoromethyl)chroman-4-one The title compound was prepared according to the procedure of Example 65A substituting 1-(4-bromo-2-hydroxyphenyl)ethanone for 1-(5-fluoro-2-hydroxyphenyl)ethanone. MS (DCI/NH$_3$) m/z 308 (M+NH$_4$)$^+$.

Example 102B (S)-7-bromo-2,2-bis(fluoromethyl)chroman-4-ol

The title compound was prepared according to the procedure of Example 65B substituting Example 102A for Example 65A. MS (DCI/NH$_3$) m/z 293 (M+H)$^+$.

Example 102C (R)-7-bromo-2,2-bis(fluoromethyl)chroman-4-amine

The title compound was prepared according to the procedure of Example 65C substituting Example 102B for Example 65B. MS (DCI/NH$_3$) m/z 292 (M+H)$^+$.

Example 102D

(R)-7-bromo-2,2-bis(fluoromethyl)chroman-4-amine, D-tartaric acid salt

The title compound was prepared according to the procedure of Example 65D substituting Example 102C for Example 65C. MS (DCI/NH$_3$) m/z 292 (M+H)$^+$.

Example 102E

N-[(4R)-7-bromo-2,2-bis(fluoromethyl)-3,4-dihydro-2H-chromen-4-yl]-N'-(3-methylisoquinolin-5-yl)urea The title compound was prepared according to the procedure of Example 65E substituting Example 102D for Example 65D. $^1$H NMR (300 MHz, DMSO-d$_6$) δ 9.19 (s, 1H), 8.62 (s, 1H), 8.29 (dd, J=7.7, 1.1 Hz, 1H), 7.76-7.68 (m, 2H), 7.54 (d, J=7.8 Hz, 1H), 7.37 (s, 1H), 7.24-7.20 (m, 1H), 7.06-6.97 (m, 2H), 6.90 (dd, J=8.2, 1.2 Hz, 1H), 5.10-5.02 (m, 1H), 4.73-4.62 (m, 2H), 4.61-4.52 (m, 2H), 2.65 (s, 3H), 2.33 (d, J=5.9 Hz, 1H), 2.06-1.96 (m, 1H); MS (DCI/NH$_3$) m/z 477 (M+H)$^+$; [α]$^{23}_D$ +14.5° (c 0.60, MeOH).

Example 103

N-[(4R)-7-chloro-2,2-dimethyl-3,4-dihydro-2H-chromen-4-yl]-N'-[(7S)-7-hydroxy-5,6,7,8-tetrahydronaphthalen-1-yl]urea The title compound was prepared according to the procedure of Example 31, and substituting Example 97C for Example 23B. $^1$H NMR (300 MHz, DMSO-d$_6$) δ 7.69 (d, J=8.0 Hz, 1H), 7.60 (s, 1H), 7.29 (d, J=8.3 Hz, 1H), 7.01 (t, J=7.8 Hz, 1H), 6.95 (dd, J=8.3, 1.7 Hz, 2H), 6.81 (d, J=2.1 Hz, 1H), 6.73 (d, J=7.4 Hz, 1H), 4.98-4.84 (m, 2H), 3.98-3.87 (m, 1H), 2.89-2.63 (m, 3H), 2.35 (dd, J=16.5, 7.7 Hz, 1H), 2.15 (dd, J=13.3, 6.2 Hz, 1H), 1.92-1.82 (m, 1H), 1.71 (dd, J=13.0, 11.2 Hz, 1H), 1.66-1.51 (m, 1H), 1.40 (s, 3H), 1.28 (s, 3H); MS (ESI+) m/z 401 (M+H)$^+$; [α]$^{23}_D$ +29.4° (c 1.0, CH$_3$OH).

Example 104

N-[(4R)-7-chloro-2,2-bis(fluoromethyl)-3,4-dihydro-2H-chromen-4-yl]-N'-[(7S)-7-hydroxy-5,6,7,8-tetrahydronaphthalen-1-yl]urea The title compound was prepared according to the procedure of Example 14, substituting Example 4A for Example 3B, and substituting Example 84D for Example 12B. $^1$H NMR (300 MHz, DMSO-d$_6$) δ 7.68 (d, J=7.4 Hz, 1H), 7.61 (s, 1H), 7.31 (dd, J=8.3, 1.0 Hz, 1H), 7.07-6.96 (m, 4H), 6.74 (d, J=7.5 Hz, 1H), 5.01-4.92 (m, 1H), 4.85 (d, J=4.2 Hz, 1H), 4.72 (m, 2H), 4.58-4.51 (m, 2H), 4.07-3.87 (m, 1H), 2.92-2.61 (m, 3H), 2.40-2.27 (m, 2H), 2.00-1.82 (m, 2H), 1.71-1.51 (m, 1H); MS (DCI/NH$_3$) m/z 437 (M+H)$^+$; [α]$^{23}_D$ +8.9° (c 0.54, CH$_3$OH).

Example 105

N-[(4R)-7-chloro-2,2-bis(fluoromethyl)-3,4-dihydro-2H-chromen-4-yl]-N'-[(7R)-7-hydroxy-5,6,7,8-tetrahydronaphthalen-1-yl]urea The title compound was prepared according to the procedure of Example 31, substituting Example 4A for Example 3B, and substituting Example 84D for Example 23B. $^1$H NMR (300 MHz, DMSO-d$_6$) δ 7.68 (d, J=8.0 Hz, 1H), 7.62 (s, 1H), 7.30 (s, 1H), 7.06-7.00 (m, 3H), 6.98 (d, J=2.1 Hz, 1H), 6.74 (d, J=7.5 Hz, 1H), 4.99-4.94 (m, 1H), 4.73-4.56 (m, 4H), 3.95-3.91 (m, 1H), 2.85-2.80 (m, 2H), 2.75-2.68 (m, 1H), 2.39-2.27 (m, 2H), 2.00-1.86 (m, 2H), 1.63-1.55 (m, 1H); MS (DCI/NH$_3$) m/z 437 (M+H)$^+$; [α]$^{23}_D$ +4.7° (c 0.40, CH$_3$OH).

Example 106

N-(3-aminoisoquinolin-5-yl)-N'-[(4R)-7-fluoro-2,2-dimethyl-3,4-dihydro-2H-chromen-4-yl]urea

Example 106A

(R)—N-(5-(3-(2,2-dimethyl-7-fluorochroman-4-yl)ureido)isoquinolin-3-yl)acetamide The title compound was prepared according to the procedure of Example 90D, substituting Example 23B for Example 33B. MS (DCI/NH$_3$) m/z 421 (M+H)$^+$.

Example 106B

N-(3-aminoisoquinolin-5-yl)-N'-[(4R)-7-fluoro-2,2-dimethyl-3,4-dihydro-2H-chromen-4-yl]urea The title compound was prepared according to the procedure of Example 90E substituting Example 106A for Example 90D. $^1$H NMR (300 MHz, DMSO-d$_6$) δ 7.68 (d, J=8.0 Hz, 1H), 7.62 (s, 1H), 7.30 (s, 1H), 7.06-7.00 (m, 3H), 6.98 (d, J=2.1 Hz, 1H), 6.74 (d, J=7.5 Hz, 1H), 4.99-4.94 (m, 1H), 4.73-4.56 (m, 4H), 3.95-3.91 (m, 1H), 2.85-2.80 (m, 2H), 2.75-2.68 (m, 1H), 2.39-2.27 (m, 2H), 2.00-1.86 (m, 2H), 1.63-1.55 (m, 1H); MS (DCI/NH$_3$) m/z 381 (M+H)$^+$; [α]$^{23}_D$ +5.8° (c 0.40, CH$_3$OH).

Example 107

N-[(4R)-8-fluoro-2,2-bis(fluoromethyl)-3,4-dihydro-2H-chromen-4-yl]-N'-[(7S)-7-hydroxy-5,6,7,8-tetrahydronaphthalen-1-yl]urea The title compound was prepared according to the procedure of Example 31, substituting Example 85D for Example 23B. $^1$H NMR (300 MHz, DMSO-d$_6$) δ 7.69 (d, J=8.1 Hz, 1H), 7.62 (s, 1H), 7.20-7.11 (m, 2H), 7.06-6.92 (m, 3H), 6.74 (d, J=7.5 Hz, 1H), 5.07-4.98 (m, 1H), 4.77-4.74 (m, 2H), 4.61-4.54 (m, 2H), 4.07-3.91 (m, 1H), 2.89-2.65 (m, 3H), 2.38 (d, J=8.7 Hz, 1H), 2.33 (d, J=7.8 Hz, 1H), 2.03-1.85 (m, 3H), 1.66-1.49 (m, 1H); MS (DCI/NH$_3$) m/z 421 (M+H)$^+$; [α]$^{23}_D$ +8.1° (c 1.0, CH$_3$OH).

Example 108

N-[(4R)-8-chloro-7-fluoro-2,2-dimethyl-3,4-dihydro-2H-chromen-4-yl]-N'-[(7R)-7-hydroxy-5,6,7,8-tetrahydronaphthalen-1-yl]urea

Example 108A

(R)-tert-butyl 7-fluoro-2,2-dimethylchroman-4-ylcarbamate

Example 23B (8.02 g, 14.84 mmol), THF (80 mL) and triethylamine (4.14 mL, 29.7 mmol) were stirred at ambient temperature and Boc$_2$O (6.89 mL, 29.7 mmol) was added. The resulting white slurry was heated to 50° C. After 110 min, the reaction mixture was cooled and concentrated and methyl tert-buthy ether (160 mL) was added. The reaction mixture was partitioned, and the organic portion was washed with water (40 mL), 2N HCl (40 mL), and brine (20 mL). The organic portion was dried ($Na_2SO_4$) and concentrated, to give the title compound (8.47 g, 28.7 mmol, 97% yield). MS (ESI+) m/z 295 (M+).

Example 108B (R)-8-chloro-7-fluoro-2,2-dimethylchroman-4-amine

A solution of Example 108A (4.00 g, 13.5 mmol) in THF (40 mL) was cooled to −70° C. and n-butyllithium (2.5 M in hexanes, 11.38 mL, 28.4 mmol) added at ≤−50° C. The mixture was cooled back to −70° C. and potassium tert-butoxide (14.9 mL, 14.9 mmol) was added at ≤−65° C. After 90 min, additonal n-butyl lithium (0.5 equiv, 2.7 mL) and potassium tert-butoxide (0.5 equiv, 6.8 mL) were added along with THF (20 mL) to facilitate stirring of the gelatinous slurry. After 1 h, hexachloroethane (3.07 mL, 27.1 mmol) was added (internal temperature at −45° C.); LCMS showed complete clean conversion to product. The reaction was quenched by addition of 2N HCl (60 mL), diluted with methyl tert-butyl ether (40 mL), and partitioned. The organic layer was washed with brine (20 mL), dried ($Na_2SO_4$), filtered, and concentrated. The crude product was used without further purification.

The crude (R)-tert-butyl 8-chloro-7-fluoro-2,2-dimethylchroman-4-ylcarbamate (4.47 g, 13.5 mmol), MeOH (36 mL), and concentrated HCl (4 mL) were heated to 50° C. After 2 h, complete deprotection observed by LCMS. The reaction mixture was cooled, stirred for 8 h, then diluted with methyl tert-buthy ether (60 mL) and water (40 mL). The mixture was paritioned and the organic layer was extracted with water (50 mL). The aqueous layer was basified with 2N NaOH (40 mL) and extracted with dichloromethane (2×40 mL). The organic extracts were dried ($Na_2SO_4$), filtered, and concentrated to give the title compound (2.87 g, 12.50 mmol, 92% yield). MS (ESI+) m/z 230 (M+H)+.

Example 108C

N-[(4R)-8-chloro-7-fluoro-2,2-dimethyl-3,4-dihydro-2H-chromen-4-yl]-N'-[(7R)-7-hydroxy-5,6,7,8-tetrahydronaphthalen-1-yl]urea The title compound was prepared according to the procedure of Example 31, substituting Example 4A for Example 3B, and substituting Example 108B for Example 23B. $^1$H NMR (300 MHz, DMSO-$d_6$) δ 7.68 (d, J=7.4 Hz, 1H), 7.63 (s, 1H), 7.27 (ddd, J=8.7, 6.5, 1.0 Hz, 1H), 7.04-6.92 (m, 3H), 6.74 (d, J=7.5 Hz, 1H), 5.02-4.92 (m, 1H), 4.85 (d, J=4.2 Hz, 1H), 3.97-3.89 (m, 1H), 2.89-2.64 (m, 3H), 2.35 (dd, J=16.5, 7.7 Hz, 1H), 2.19 (dd, J=13.3, 6.1 Hz, 1H), 1.82-1.76 (m, 2H), 1.68-1.51 (m, 1H), 1.46 (s, 3H), 1.32 (s, 3H); MS (DCI/$NH_3$) m/z 419 (M+H)+; $[\alpha]^{23}_D$ +18° (c 0.53, $CH_3OH$).

Example 109

N-[(4R)-8-chloro-7-fluoro-2,2-dimethyl-3,4-dihydro-2H-chromen-4-yl]-N'-[(7S)-7-hydroxy-5,6,7,8-tetrahydronaphthalen-1-yl]urea The title compound was prepared according to the procedure of Example 31, substituting Example 108B for Example 23B. $^1$H NMR (300 MHz, DMSO-$d_6$) δ 7.69 (d, J=7.4 Hz, 1H), 7.63 (s, 1H), 7.28 (ddd, J=8.7, 6.4, 1.0 Hz, 1H), 6.99-6.95 (m, 3H), 6.74 (d, J=7.5 Hz, 1H), 4.91-5.01 (m, 1H), 4.86 (d, J=4.2 Hz, 1H), 3.98-3.89 (m, 1H), 2.65-2.89 (m, 3H), 2.36 (dd, J=16.5, 7.7 Hz, 1H), 2.19 (dd, J=13.3, 6.1 Hz, 1H), 1.77 (dd, J=13.3, 11.1 Hz, 2H), 1.68-1.50 (m, 1H), 1.46 (s, 3H), 1.32 (s, 3H); MS (DCI/$NH_3$) m/z 419 (M+H)+; $[\alpha]^{23}_D$ +20° (c 0.65, $CH_3OH$).

Example 110

N-[(4R)-8-chloro-7-fluoro-2,2-dimethyl-3,4-dihydro-2H-chromen-4-yl]-N'-(3-methylisoquinolin-5-yl)urea The title compound was prepared according to the procedure of Example 65E substituting Example 108B for Example 65D. $^1$H NMR (300 MHz, DMSO-$d_6$) δ 9.19 (s, 1H), 8.68 (s, 1H), 8.27 (d, J=7.6 Hz, 1H), 7.75 (s, 1H), 7.72 (d, J=8.1 Hz, 1H), 7.54 (d, J=7.9 Hz, 1H), 7.38-7.32 (m, 1H), 7.01-6.97 (m, 2H), 5.06-4.99 (m, 1H), 2.65 (s, 3H), 2.22 (d, J=6.1 Hz, 1H), 2.00-1.84 (m, 1H), 1.49 (s, 3H), 1.34 (s, 3H); MS (DCI/$NH_3$) m/z 414 (M+H)+; $[\alpha]^{23}_D$ +18° (c 0.74, $CH_3OH$).

Example 111

N-[(4R)-7-fluoro-2,2,8-trimethyl-3,4-dihydro-2H-chromen-4-yl]-N-(3-methylisoquinolin-5-yl)urea Example 111A (R)-7-fluoro-2,2,8-trimethylchroman-4-amine The title compound was prepared according to the procedure of Example 108B substituting methyl iodide for hexachloroethane. MS (DCI/$NH_3$) m/z 210 (M+H)+.

Example 111B

N-[(4R)-7-fluoro-2,2,8-trimethyl-3,4-dihydro-2H-chromen-4-yl]-N-(3-methylisoquinolin-5-yl)urea The title compound was prepared according to the procedure of Example 65E substituting Example 111A for Example 65D. $^1$H NMR (300 MHz, DMSO-$d_6$) δ 9.18 (s, 1H), 8.63 (s, 1H), 8.30 (d, J=7.9 Hz, 1H), 7.75 (d, J=1.1 Hz, 1H), 7.71 (d, J=8.1 Hz, 1H), 7.53 (d, J=7.9 Hz, 1H), 7.23-7.17 (m, 1H), 6.92 (d, J=8.3 Hz, 1H), 6.75 (d, J=8.9 Hz, 1H), 5.04-4.95 (m, 1H), 2.65 (s, 3H), 2.21 (dd, J=13.2, 6.2 Hz, 1H), 2.04 (d, J=2.0 Hz, 3H), 1.79 (d, J=10.7 Hz, 1H), 1.45 (s, 3H), 1.31 (s, 3H); MS (DCI/$NH_3$) m/z 394 (M+H)+; $[\alpha]^{23}_D$ +11.0° (c 0.76, $CH_3OH$).

Example 112

N-[(4R)-2,2-bis(fluoromethyl)-7-(trifluoromethyl)-3,4-dihydro-2H-chromen-4-yl]-N'-[(7S)-7-hydroxy-5,6,7,8-tetrahydronaphthalen-1-yl]urea The title compound was prepared according to the procedure of Example 31, substituting Example 93D for Example 23B. $^1$H NMR (300 MHz, DMSO-$d_6$) δ 7.71-7.63 (m, 2H), 7.53 (d, J=8.1 Hz, 1H), 7.33 (dd, J=8.1, 1.3 Hz, 1H), 7.20 (s, 1H), 7.07 (d, J=8.1 Hz, 1H), 7.02 (t, J=7.8 Hz, 1H), 6.75 (d, J=7.5 Hz, 1H), 5.13-4.99 (m, 1H), 4.86 (d, J=4.2 Hz, 1H), 4.82-4.68 (m, 2H), 4.66-4.53 (m, 2H), 3.98-3.87 (m, 1H), 2.90-2.64 (m, 3H), 2.42-2.29 (m, 2H), 2.05-1.82 (m, 2H), 1.67-1.52 (m, 1H); MS (ESI+) m/z 471 (M+H)+; [α]$^{23}_D$+ 24.4° (c 1.0, CH$_3$OH).

Example 113

N-[(4R)-7,8-difluoro-2,2-dimethyl-3,4-dihydro-2H-chromen-4-yl]-N'-(3-methylisoquinolin-5-yl)urea Example 113A 2,3-difluorophenyl acetate To a solution of 2,3-difluorophenol (30.0 g, 231 mmol) and pyridine (18.6 mL, 231 mmol) in dichloromethane (230 mL) at 0° C. was carefully added acetyl chloride (16.4 mL, 231 mmol). The reaction was allowed to warm to ambient temperature and stirred for 16 h. The reaction mixture was then diluted with dichloromethane (100 mL), washed with 1N aqueous hydrochloric acid (2×50 mL) and brine (75 mL), and concentrated to produce 41.0 g (100%) of the title compound. MS (DCI/NH$_3$) m/z 190 (M+NH$_4$)+.

Example 113B 1-(3,4-difluoro-2-hydroxyphenyl)ethanone

To a slurry of aluminum trichloride (30.8 g, 231 mmol) in dichloroethane (25 mL) at 0° C. was added dropwise a solution of Example 113A (41.0 g, 231 mmol) in dichloroethane (25 mL). After addition was complete, the reaction was heated to reflux for 16 h. The reaction mixture was then cooled to 0° C. and the reaction quenched by the addition of water. The resulting mixture was extracted with dichloromethane (2×75 mL). The organic layer was washed with water (40 mL) and brine (60 mL), and concentrated to produce 35.8 g (90%) of the title compound. MS (DCI/NH$_3$) m/z 190 (M+NH$_4$)+.

Example 113C 7,8-difluoro-2,2-dimethylchroman-4-one

The title compound was prepared according to the procedure of Example 1A, substituting Example 113B for 1-(5-fluoro-2-hydroxyphenyl)ethanone. MS (DCI/NH$_3$) m/z 230 (M+NH$_4$)+.

Example 113D (R)-7,8-difluoro-2,2-dimethylchroman-4-amine

The title compound was prepared according to the procedures of Examples 1B and 1C, substituting Example 113C for Example 1A. MS (DCI/NH$_3$) m/z 214 (M+H)+.

Example 113E (R)-7,8-difluoro-2,2-dimethylchroman-4-amine, D-tartaric acid salt

The title compound was prepared according to the procedure of Example 65D, substituting Example 113D for Example 65C. MS (DCI/NH$_3$) m/z 214 (M+H)+.

Example 113F

N-[(4R)-7,8-difluoro-2,2-dimethyl-3,4-dihydro-2H-chromen-4-yl]-N'-(3-methylisoquinolin-5-yl)urea The title compound was prepared according to the procedure of Example 65E substituting Example 113E for Example 65D. $^1$H NMR (300 MHz, DMSO-d$_6$) δ 9.19 (s, 1H), 8.68 (s, 1H), 8.28 (d, J=7.6 Hz, 1H), 7.75 (s, 1H), 7.72 (d, J=8.1 Hz, 1H), 7.57-7.51 (m, 1H), 7.17 (t, J=7.1 Hz, 1H), 7.00 (d, J=8.4 Hz, 1H), 6.95 (dd, J=13.0, 5.7 Hz, 1H), 5.08-4.98 (m, 1H), 2.66 (s, 3H), 2.25 (dd, J=13.4, 6.1 Hz, 1H), 1.85 (dd, J=13.2, 11.2 Hz, 1H), 1.48 (s, 3H), 1.35 (s, 3H); MS (DCI/NH$_3$) m/z 398 (M+H)+; [α]$^{23}_D$ +17.1° (c 0.68, CH$_3$OH).

Example 114

N-[(4R)-7,8-difluoro-2,2-dimethyl-3,4-dihydro-2H-chromen-4-yl]-N'-[(7S)-7-hydroxy-5,6,7,8-tetrahydronaphthalen-1-yl]urea The title compound was prepared according to the procedure of Example 31, substituting Example 113E for Example 23B. $^1$H NMR (300 MHz, DMSO-d$_6$) δ 7.69 (d, J=7.9 Hz, 1H), 7.63 (s, 1H), 7.13-7.06 (m, 1H), 7.05-6.89 (m, 3H), 6.74 (d, J=7.5 Hz, 1H), 5.00-4.90 (m, 1H), 4.87 (d, J=4.2 Hz, 1H), 3.96-3.88 (m, 1H), 2.87-2.77 (m, 2H), 2.76-2.66 (m, 1H), 2.36 (dd, J=16.4, 7.7 Hz, 1H), 2.19 (dd, J=13.4, 6.1 Hz, 1H), 1.91-1.84 (m, 1H), 1.77 (dd, J=13.2, 11.2 Hz 1H), 1.65-1.50 (m, 1H), 1.46 (s, 3H), 1.32 (s, 3H); MS (DCI/NH$_3$) m/z 403 (M+H)+; [α]$^{23}_D$+24.1° (c 0.62, CH$_3$OH).

Example 115

N-[(4R)-2,2-dimethyl-7-(trifluoromethoxy)-3,4-dihydro-2H-chromen-4-yl]-N'-[(7R)-7-hydroxy-5,6,7,8-tetrahydronaphthalen-1-yl]urea The title compound was prepared according to the procedure of Example 31, substituting Example 4A for Example 3B, and substituting Example 39B for Example 23B. $^1$H NMR (300 MHz, DMSO-d$_6$) δ 7.70 (d, J=7.4 Hz, 1H), 7.61 (s, 1H), 7.38 (dd, J=8.6, 0.8 Hz, 1H), 7.06-6.96 (m, 2H), 6.91 (ddd, J=8.5, 2.3, 1.1 Hz, 1H), 6.77-6.70 (m, 2H), 5.01-4.86 (m, 2H), 3.99-3.86 (m, 1H), 2.89-2.64 (m, 3H), 2.33 (dd, J=16.6, 7.8 Hz, 1H), 2.17 (dd, J=13.3, 6.1 Hz, 1H), 1.93-1.82 (m, 1H), 1.73 (dd, J=13.2, 11.0 Hz, 1H), 1.66-1.50 (m, 1H), 1.41 (s, 3H), 1.30 (s, 3H); MS (ESI+) m/z 451 (M+H)+; [α]$^{23}_D$ +23.0° (c 1.0, CH$_3$OH).

Example 116

N-[(4R)-2,2-dimethyl-7-(trifluoromethoxy)-3,4-dihydro-2H-chromen-4-yl]-N'-[(7S)-7-hydroxy-5,6,7,8-tetrahydronaphthalen-1-yl]urea The title compound was prepared according to the procedure of Example 31, substituting Example 39B for Example 23B. $^1$H NMR (300 MHz, DMSO-d$_6$) δ 7.70 (d, J=7.4 Hz, 1H), 7.61 (s, 1H), 7.39 (dd, J=8.6, 0.8 Hz, 1H), 7.06-6.97 (m, 2H), 6.91 (ddd, J=8.6, 2.4, 1.1 Hz, 1H), 6.77-6.71 (m, 2H), 5.01-4.87 (m, 2H), 3.98-3.86 (m, 1H), 2.89-2.64 (m, 3H), 2.35 (dd, J=16.4, 7.7 Hz, 1H), 2.17 (dd, J=13.3, 6.1 Hz, 1H), 1.93-1.81 (m, 1H), 1.73 (dd, J=13.2, 11.1 Hz, 1H), 1.67-1.51 (m, 1H), 1.41 (s, 3H), 1.30 (s, 3H); MS (ESI+) m/z 451 (M+H)+; [α]$^{23}_D$ +27.1° (c 1.0, CH$_3$OH).

Example 117

N-(8-fluoro-2,2-dimethyl-7-piperidin-1-yl-3,4-dihydro-2H-chromen-4-yl)-N'-(3-methylisoquinolin-5-yl)urea

Example 117A 8-fluoro-2,2-dimethyl-7-(piperidin-1-yl)chroman-4-one

To a solution of the Example 113B (5.16 g, 30.0 mmol) in pyridine (20 mL) was added piperidine (5.94 mL, 60.0 mmol), and the reaction was heated to reflux for 2 h. The reaction was cooled to ambient temperature, and acetone (4.63 mL, 63.0 mmol) and pyrrolidine (1.240 mL, 15.00 mmol) were added. The reaction was stirred at ambient temperature for 16 hours, then heated to reflux for 4 h. The reaction mixture was then cooled and concentrated. The residue was taken up in diethyl ether (150 mL), washed with water (50 mL), 1N aqueous sodium hydroxide (2×25 mL), and concentrated to produce 5.02 g (60%) of the title compound. MS (DCI/NH$_3$) m/z 278 (M+H)$^+$.

Example 117B (E)-8-fluoro-2,2-dimethyl-7-(piperidin-1-yl)chroman-4-one O-methyl oxime To a solution of Example 117A (5.02 g, 18.1 mmol) in pyridine (20 mL) was added O-methylhydroxylamine hydrochloride (1.81 g, 21.7 mmol). The reaction was stirred at ambient temperature for 16 h and then was concentrated. The residue was taken up in diethyl ether (100 mL), washed with water (25 mL) and brine (25 mL), and concentrated to produce 5.55 g (100%) of the title compound. MS (DCI/NH$_3$) m/z 307 (M+H)$^+$.

Example 117C 8-fluoro-2,2-dimethyl-7-(piperidin-1-yl)chroman-4-amine

A solution of Example 117B (5.55 g, 18.1 mmol) in 7M ammonia in methanol (250 mL) was added to water wet R$^a$—Ni (27.8 g, 473 mmol) and exposed to hydrogen gas at 30 psi. The reaction was stirred at ambient temperature for 30 min. After filtration, the solution was concentrated. The residue was taken up in diethyl ether (75 mL) and extracted with 1N aqueous hydrochloric acid (2×50 mL). The combined acidic extracts were made basic with 50% aqueous NaOH, and extracted twice with diethyl ether (2×150 mL). The diethyl ether extracts were combined, dried (Na$_2$SO$_4$), filtered, and concentrated to produce 3.80 g (75%) of the title compound. MS (DCI/NH$_3$) m/z 279 (M+H)$^+$.

Example 117D

N-(8-fluoro-2,2-dimethyl-7-piperidin-1-yl-3,4-dihydro-2H-chromen-4-yl)-N'-(3-methylisoquinolin-5-yl)urea The title compound was prepared according to the procedure of Example 65E substituting Example 117C for Example 65D. $^1$H NMR (300 MHz, DMSO-d$_6$) δ 9.18 (s, 1H), 8.60 (s, 1H), 8.29 (dd, J=7.6, 0.9 Hz, 1H), 7.76-7.67 (m, 2H), 7.56-7.48 (m, 1H), 7.03 (d, J=8.3 Hz, 1H), 6.91 (d, J=8.3 Hz, 1H), 6.65-6.56 (m, 1H), 4.98 (dd, J=15.0, 9.9 Hz, 1H), 2.98-2.87 (m, 4H), 2.65 (s, 3H), 2.20 (dd, J=13.3, 6.2 Hz, 1H), 1.77 (dd, J=13.2, 10.6 Hz, 1H), 1.70-1.47 (m, 6H), 1.44 (s, 3H), 1.31 (s, 3H); MS (DCI) m/z 463 (M+H)$^+$.

Example 118

N-[(4R)-2,2-dimethyl-7-(trifluoromethyl)-3,4-dihydro-2H-chromen-4-yl]-N'-(3-methylisoquinolin-5-yl)urea The title compound was prepared according to the procedure of Example 65E substituting Example 33B for Example 65D. $^1$H NMR (300 MHz, DMSO-d$_6$) δ 9.19 (s, 1H), 8.68 (s, 1H), 8.28 (dd, J=7.7, 1.1 Hz, 1H), 7.76-7.70 (m, 2H), 7.58-7.50 (m, 2H), 7.26 (dd, J=8.1, 1.9 Hz, 1H), 7.07 (d, J=1.8 Hz, 1H), 7.03 (d, J=8.4 Hz, 1H), 5.14-5.04 (m, 1H), 2.66 (s, 3H), 2.23 (d, J=6.2 Hz, 1H), 1.86 (dd, J=13.3, 11.1 Hz, 1H), 1.45 (s, 3H), 1.33 (s, 3H); MS (DCI/NH$_3$) m/z 430 (M+H)$^+$; [α]$^{23}_D$ +2.4° (c 0.20, CH$_3$OH).

Example 119

N-[(4R)-8-fluoro-2,2-dimethyl-3,4-dihydro-2H-chromen-4-yl]-N'-(3-methylisoquinolin-5-yl)urea The title compound was prepared according to the procedure of Example 65E substituting Example 20B for Example 65D. $^1$H NMR (300 MHz, DMSO-d$_6$) δ 9.19 (s, 1H), 8.65 (s, 1H), 8.29 (dd, J=7.7, 1.1 Hz, 1H), 7.75 (d, J=1.1 Hz, 1H), 7.71 (d, J=8.1 Hz, 1H), 7.53 (t, J=7.9 Hz, 1H), 7.19-6.85 (m, 4H), 5.10-5.01 (m, 1H), 2.65 (s, 3H), 2.24 (dd, J=13.3, 6.2 Hz, 1H), 2.00-1.80 (m, 1H), 1.46 (s, 3H), 1.33 (s, 3H); MS (DCI/NH$_3$) m/z 380.

Example 120

N-[(4R)-6,8-difluoro-2,2-bis(fluoromethyl)-3,4-dihydro-2H-chromen-4-yl]-N'-(3-methylisoquinolin-5-yl)urea

Example 120A 6,8-difluoro-2,2-bis(fluoromethyl)chroman-4-one

The title compound was prepared according to the procedure of Example 65A substituting 1-(3,5-difluoro-2-hydroxyphenyl)ethanone for 1-(5-fluoro-2-hydroxyphenyl)ethanone. MS (DCI/NH$_3$) m/z 249 (M+NH$_4$)$^+$.

Example 120B (S)-6,8-difluoro-2,2-bis(fluoromethyl)chroman-4-ol

The title compound was prepared according to the procedure of Example 65B substituting Example 120A for Example 65A. MS (DCI/NH$_3$) m/z 251 (M+H)$^+$.

Example 120C (R)-6,8-difluoro-2,2-bis(fluoromethyl)chroman-4-amine

The title compound was prepared according to the procedure of Example 65C substituting Example 120B for Example 65B. MS (DCI/NH$_3$) m/z 250 (M+H)$^+$.

Example 120D (R)-6,8-difluoro-2,2-bis(fluoromethyl)chroman-4-amine, D-tartaric acid salt The title compound was prepared according to the procedure of Example 65D substituting Example 120C for Example 65C. MS (DCI/NH$_3$) m/z 250 (M+H)$^+$.

Example 120E

N-[(4R)-6,8-difluoro-2,2-bis(fluoromethyl)-3,4-dihydro-2H-chromen-4-yl]-N'-(3-methylisoquinolin-5-yl)urea The title compound was prepared according to the procedure of Example 65E substituting Example 120D for Example 65D. $^1$H NMR (300 MHz, DMSO-d$_6$) δ 9.19 (s, 1H), 8.70 (s, 1H), 8.23 (d, J=7.0 Hz, 1H), 7.76-7.75 (m, 1H), 7.74 (d, J=8.6 Hz, 1H), 7.54 (d, J=7.9 Hz, 1H), 7.28 (ddd, J=11.3, 8.5, 2.9 Hz, 1H), 7.10-7.01 (m, 2H), 5.13-5.03 (m, 1H), 4.83-4.52 (m, 4H), 2.66 (s, 3H), 2.38 (d, J=5.9 Hz, 1H), 1.99 (d, J=1.4 Hz, 1H); MS (DCI/NH$_3$) m/z 250 (M+H)$^+$.

Example 121

N-[(2R,4R)-7-chloro-2-(fluoromethyl)-2-methyl-3,4-dihydro-2H-chromen-4-yl]-N-(3-methylisoquinolin-5-yl)urea

Example 121A 7-chloro-2-(fluoromethyl)-2-methylchroman-4-one 1-(4-Chloro-2-hydroxyphenyl)ethanone (10.2 g, 59.8 mmol), MeOH (100 mL), fluoroacetone (5.00 g, 65.8 mmol), and pyrrolidine (5.44 ml, 65.8 mmol) were stirred at ambient temperature. After 3 days, LCMS showed complete reaction. The reaction mixture was diluted with MTBE (250 mL), washed with water (100 mL), 2N HCl (2×50 mL), brine (50 mL), 2N NaOH (2×50 mL), and brine (2×50 mL). The organic portion was dried (Na$_2$SO$_4$), filtered, and concentrated to provide the title compound (12.9 g, 56.4 mmol, 94% yield) as a brown oil. MS (DCI/NH$_3$) m/z 246 (M+NH$_4$)$^+$.

Example 121B

A solution of Example 121A (13.0 g, 56.8 mmol), (R)-2-methylpropane-2-sulfinamide (10.3 g, 85.0 mmol), 2-methyltetrahydrofuran (130 mL), and tetraethoxytitanium (47.6 mL, 227 mmol) was heated to 70° C. After 5 hours, approximately 70% conversion was observed by LCMS. An additional 0.5 equivalent of (R)-2-methylpropane-2-sulfinimide was added and the reaction was stirred with continued heating for 12 hours. The reaction was cooled to −10° C. and sodium borohydride (4.30 g, 114 mmol) was added. The reaction was allowed to warm gradually to ambient temperature over a period of 2 hours. Another 0.5 equivalent of sodium borohydride was added at ambient temperature. After 1 hour, the reaction was cooled to <5° C. and 10% aqueous citric acid (100 mL) was added; the reaction mixture was stirred vigorously for 2 h, then diluted with MTBE (300 mL). The layers were partitioned and the organic portion was washed with water (75 mL) and brine (75 mL). The organic portion was dried (Na$_2$SO$_4$), filtered, concentrated, and the residue purified by flash chromatograph (gradient elution, 20-100% EtOAc/hexanes) to give the title compound (13.9 g, 41.5 mmol, 73% yield). MS (DCI/NH$_3$) m/z 334 (M+H)$^+$.

Example 121C (4R)-7-chloro-2-(fluoromethyl)-2-methylchroman-4-amine, hydrochloride salt A yellow slurry of Example 121B (26.18 g, 78.0 mmol) in MTBE (120 mL) was stirred at ambient temperature and HCl in methanol, formed from addition of acetyl chloride (11.2 mL, 157 mmol) to methanol (28.6 mL, 706 mmol) at <5° C., was added. After 2 hours, the reaction mixture was filtered; the precipitate was collected and washed with MTBE. The resulting off-white solid was dried in a vacuum oven at 60° C. to give the title compound. MS (DCI/NH$_3$) m/z 213 (M-NH$_3$)$^+$.

Example 121D

N-[(4R)-7-chloro-2-(fluoromethyl)-2-methyl-3,4-dihydro-2H-chromen-4-yl]-N'-(3-methylisoquinolin-5-yl)urea The title compound was prepared according to the procedure of Example 65E substituting Example 121C for Example 65D. MS (DCI/NH$_3$) m/z 414 (M+H)$^+$.

Example 121E

N-[(2R,4R)-7-chloro-2-(fluoromethyl)-2-methyl-3,4-dihydro-2H-chromen-4-yl]-N'-(3-methylisoquinolin-5-yl)urea Example 121D was dissolved in a minimum volume of methanol, loaded on a Chiralpak AD-H chiral column (30 cm ID×250 cm column, 20 mg/injection), and eluted with methanol and supercritical carbon dioxide at 25° C. (flow rate ~50 mL/min. The earlier eluting peak (retention time=13.6 min) was collected and the solvent evaporated to afford the title compound as an off-white solid in 99.4% ee. $^1$H NMR (300 MHz, CDCl$_3$) δ 9.18 (s, 1H), 7.84 (d, J=8.2 Hz, 1H), 7.77 (d, J=7.4 Hz, 1H), 7.65 (s, 1H), 7.52 (t, J=7.8 Hz, 1H), 7.16 (d, J=8.2 Hz, 1H), 6.85-6.79 (m, 2H), 6.63 (br s, 1H), 5.22-5.13 (m, 1H), 4.81-4.77 (m, 1H), 4.41 (d, J=1.8 Hz, 1H), 4.25 (d, J=1.8 Hz, 1H), 2.72 (s, 3H), 2.42 (dd, J=13.8, 6.3 Hz, 1H), 1.73-1.63 (m, 1H), 1.34 (d, J=1.9 Hz, 3H); MS (DCI/NH$_3$) m/z 414 (M+H)$^+$.

Example 122

N-[(2S,4R)-7-chloro-2-(fluoromethyl)-2-methyl-3,4-dihydro-2H-chromen-4-yl]-N'-(3-methylisoquinolin-5-yl)urea Example 121D was dissolved in a minimum volume of methanol, loaded on a Chiralpak AD-H chiral column (30 cm ID×250 cm column, 20 mg/injection), and eluted with methanol and supercritical carbon dioxide at 25° C. (flow rate ~50 mL/min. The later eluting peak (retention time=15.0 min) was collected and the solvent evaporated to afford the title compound as an off-white solid in 99.1% ee. $^1$H NMR (300 MHz, CDCl$_3$) δ 9.18 (s, 1H), 7.82 (d, J=8.2 Hz, 1H), 7.76 (d, J=7.4 Hz, 1H), 7.62 (s, 1H), 7.50 (t, J=7.8 Hz, 1H), 7.18 (d, J=8.6 Hz, 1H), 6.79-6.85 (m, 2H), 6.67 (s, 1H), 5.21-5.31 (m, 1H), 4.88 (d, J=8.9 Hz, 1H), 4.12-4.46 (m, 2H), 2.71 (s, 3H), 2.17 (dd, J=13.3, 6.3 Hz, 1H), 1.76-1.84 (m, 1H), 1.28 (d, J=2.2 Hz, 3H); MS (DCI/NH$_3$) m/z 414 (M+H)$^+$.

Example 123

N-[(4R)-7-fluoro-2,2-dimethyl-3,4-dihydro-2H-chromen-4-yl]-N'-(6-fluoro-3-methylisoquinolin-5-yl)urea Example 123A N-(4-fluorobenzyl)-1,1-dimethoxypropan-2-amine 4-Fluorobenzylamine (3.00 mL, 26.2 mmol), pyruvic aldehyde dimethyl acetal (3.11 mL, 26.2 mmol), DCE (87 mL), and sodium triacetoxyborohydride (7.79 g, 36.7 mmol) were stirred at ambient temperature. After 14 hours, the reaction was complete as indicated by LCMS. To the reaction mixture was added 30% aqueous K$_3$PO$_4$ (pH=14; 60 mL). The layers were partitioned and the aqueous layer was, extracted with EtOAc (2×50 mL), and washed with brine (60 mL). The organic portion was dried (Na$_2$SO$_4$), filtered, and concentrated to give the title compound (5.83 g, 25.7 mmol, 98% yield). MS (DCI/NH$_3$) m/z 228 (M+H)$^+$.

Example 123B 6-fluoro-3-methylisoquinoline

Chlorosulfonic acid (17.2 mL, 257 mmol) cooled to −10° C. and Example 123A (5.83 g, 25.7 mmol) was added dropwise. The reaction mixture was heated to 100° C. (internal temperature) for 10 minutes, then cooled and poured into ice. The aqueous suspension was extracted with MTBE (50 mL), and the aqueous layer was neutralized with 2N NaOH (caution: exothermic reaction) and extracted with EtOAc (2×30 mL). The organic portion was washed with brine (40 mL), dried (Na$_2$SO$_4$), filtered, and concentrated to give the title compound (2.80 g, 17.37 mmol, 678% yield). MS (DCI/NH$_3$) m/z 162 (M+H)$^+$.

Example 123C 6-fluoro-3-methyl-5-nitroisoquinoline

Sulfuric acid (13.5 mL, 253 mmol) was treated with Example 123B (2.79 g, 17.3 mmol). The slurry was cooled to −10° C. and potassium nitrate (0.913 mL, 19.0 mmol) was added in five equal portions between −5 and −10° C. After 30 minutes, the reaction mixture was poured into ice, sodium hydroxide (26.4 mL, 505 mmol) was added (caution: exothermic reaction), and the suspension was extracted with EtOAc (30 mL). The organic portion was washed with brine (25 mL), dried (Na$_2$SO$_4$), filtered, and concentrated. Purification by silica gel chromatography (gradient elution: 20-100% EtOAc/hexanes) gave the title compound (1.44 g, 6.98 mmol, 40% yield) as a yellow solid. MS (DCI/NH$_3$) m/z 207 (M+H)$^+$.

Example 123D 5-amino-6-fluoro-3-methylisoquinoline

The title compound was prepared according to the procedure of Examples 86A, substituting Example 123C for 1-methyl-5-nitroisoquinoline. MS (DCI/NH$_3$) m/z 177 (M+H)$^+$.

Example 123E 2,2,2-trichloro-N-(6-fluoro-3-methylisoquinolin-5-yl)acetamide

A solution of Example 123D (410 mg, 2.33 mmol) in acetonitrile (8 mL), and pyridine (0.471 mL, 5.82 mmol) was cooled to −10° C. and trichloroacetic anhydride (0.553 mL, 3.03 mmol) was added dropwise between −5 and −10° C. Water (16 mL) was added in dropwise fashion dropwise giving a white slurry. The precipitate was collected by filtration, washed with water, and dried in a vacuum oven at 60° C. for 8 h to give the title compound (646 mg, 2.009 mmol, 86% yield). MS (DCI/NH$_3$) m/z 321 (M+H)$^+$.

Example 123F (S)-7-fluoro-2,2-dimethylchroman-4-ol

The title compound was prepared according to the procedure of Example 65B substituting Example 23A for Example 65A. MS (DCI/NH$_3$) m/z 198 (M+H)$^+$.

Example 123G (R)-7-fluoro-2,2-dimethylchroman-4-amine

The title compound was prepared according to the procedure of Example 65C substituting Example 123F for Example 65B. MS (DCI/NH$_3$) m/z 196 (M+H)$^+$.

Example 123H (R)-7-fluoro-2,2-dimethylchroman-4-amine (2S,3S)-2,3-dihydroxysuccinic acid salt The title compound was prepared according to the procedure of Example 65D substituting Example 123F for Example 65C and substituting (2S,3S)-2,3-dihydroxysuccinic acid for D-(−)-tartaric acid. MS (DCI/NH$_3$) m/z 196 (M+H)$^+$.

Example 123J

N-[(4R)-7-fluoro-2,2-dimethyl-3,4-dihydro-2H-chromen-4-yl]-N-(6-fluoro-3-methylisoquinolin-5-yl)urea Example 123E (700 mg, 2.18 mmol), Example 123H (706 mg, 1.31 mmol), and potassium carbonate (903 mg, 6.53 mmol) in DMF (7 mL) were heated to 100° C. After 1 h, the reaction mixture was cooled to ambient temperature, diluted with MTBE (20 mL), and washed sequentially with water (10 mL), brine (10 mL), 10% KH$_2$PO$_4$ (3×7 mL), brine (5 mL), 2N NaOH (5 mL), and brine (5 mL). The organic portion was dried (Na$_2$SO$_4$), filtered, and concentrated, and the resulting residue was purified by flash chromatography (gradient elution, 0-10% MeOH/CH$_2$Cl$_2$) to provide the title compound (551 mg, 1.39 mmol, 64% yield). $^1$H NMR (300 MHz, DMSO-d$_6$) δ 9.23 (s, 1H), 8.24 (s, 1H), 8.06 (dd, J=9.0, 5.1 Hz, 1H), 7.65 (s, 1H), 7.55 (t, J=9.5 Hz, 1H), 7.36 (t, J=7.7 Hz, 1H), 6.82-6.73 (m, 2H), 6.58 (dd, J=10.6, 2.6 Hz, 1H), 5.00-4.90 (m, 1H), 2.65 (s, 3H), 2.12 (dd, J=13.2, 6.2 Hz, 1H), 1.82 (d, J=12.1 Hz, 1H), 1.40 (s, 3H), 1.27 (s, 3H); MS (DCI/NH$_3$) m/z 398 (M+H)$^+$.

Example 124

N-[(2S,4R)-7-chloro-2-(difluoromethyl)-2-methyl-3,4-dihydro-2H-chromen-4-yl]-N'-(3-methylisoquinolin-5-yl)urea

Example 124A 7-chloro-2-(difluoromethyl)-2-methylchroman-4-one 1-(4-Chloro-2-hydroxyphenyl)ethanone (8.07 g, 47.3 mmol), MeOH (81 mL), 1,1-difluoroacetone (4.89 g, 52.0 mmol), and pyrrolidine (4.30 ml, 52.0 mmol) were stirred at ambient temperature for 45 hours, at 35° C. for 7 hours, then at 50° C. for 3 hours. The reaction mixture was concentrated, diluted with MTBE (75 mL), then washed with water (40 mL), 2N HCl (2×25 mL), brine (20 mL), 2N NaOH (2×20 mL), and brine (2×20 mL). The organic portion was dried ($Na_2SO_4$), filtered, and concentrated to give the title compound (9.78 g, 39.7 mmol, 84% yield) as a brown oil. MS (DCI/$NH_3$) m/z 264 (M+$NH_4$)$^+$.

Example 124B

A solution of Example 124A (9.78 g, 39.7 mmol), (R)-2-methylpropane-2-sulfinamide (7.21 g, 59.5 mmol), 2-methyltetrahydrofuran (100 mL), and tetraethoxytitanium (433.3 mL, 159 mmol) was heated to 75° C. After 7 hours, the reaction was cooled to −30° C. and sodium borohydride (3.00 g, 79.0 mmol) was added. The reaction flask was wrapped with aluminum foil and allowed to warm gradually to ambient temperature with continued stiffing over a period of 12 hours. The reaction was cooled to <5° C. and 10% aqueous citric acid (200 mL) was added; the reaction mixture was stirred vigorously for 2 hours, then diluted with MTBE (300 mL). The layers were partitioned and the organic portion was washed with water (75 mL). The aqueous layer was back-extracted with MTBE (75 mL) and the combined organic portions were washed with brine (75 mL). The organic portion was dried ($Na_2SO_4$), filtered, concentrated to give the title compound, a mixture of diastereomers, that was used without further purification. MS (DCI/$NH_3$) m/z 352 (M+H)$^+$.

Example 124C (4R)-7-chloro-2-(difluoromethyl)-2-methylchroman-4-amine, D-tartaric acid salt A yellow slurry of Example 124B (13.97 g, 39.70 mmol) in MTBE (140 mL) was stirred at ambient temperature and HCl in methanol, formed from addition of acetyl chloride (5.65 mL, 79.0 mmol) to methanol (14.5 mL, 357 mmol) at <5° C., was added. After 10 min, the reaction mixture was filtered; the precipitate was collected and washed with 10% MeOH/MTBE (2×10 mL). The resulting off-white solid was dried in a vacuum oven at 60° C. to and was used without subsequent purification.

D-(−)-Tartaric acid (5.33 g, 35.5 mmol) and isopropanol (90 mL) heated to 70° C., and a solution of crude (4R)-7-chloro-2-(difluoromethyl)-2-methylchroman-4-amine (8.80 g, 35.5 mmol) from above in isopropanol (45 mL) was added over 30 min. The reaction mixture was cooled to ambient temperature and the precipitate collected by filtration, washed with isopropanol, and dried in a vacuum oven at 60° C. for 6 hours to give the title compound (10.7 g, 26.9 mmol, 76% yield). MS (DCI/$NH_3$) m/z 248 (M+$NH_4$—$H_2O$)$^+$.

Example 124D

N-[(2S,4R)-7-chloro-2-(difluoromethyl)-2-methyl-3,4-dihydro-2H-chromen-4-yl]-N-(3-methylisoquinolin-5-yl)urea Step A: Example 124C (2.00 g, 5.03 mmol) was stirred in MTBE (10 mL) and 30% $K_3PO_4$ (10 mL). The mixture was added to a separatory funnel and partitioned. The organic portion was washed with brine (20 mL), dried ($Na_2SO_4$), filtered, and concentrated. The resulting residue was redissolved in acetonitrile (4 mL) and treated with diisopropylethylamine (1.84 mL, 10.6 mmol).

Step B: In a separate flask, a light yellow slurry of 3-methylisoquinolin-5-amine (0.835 g, 5.28 mmol), acetonitrile (20 mL), and pyridine (0.183 mL, 2.26 mmol) was cooled to −10° C. Phenyl chloroformate (0.695 mL, 5.53 mmol) was added dropwise between −5 and −10° C. and the reaction mixture was stirred for 30 minutes. To this mixture at −5° C. was added in a dropwise fashion the solution prepared in Step A. The reaction mixture was allowed to warm gradually to ambient temperature with continued stirring over a period of 1.5 hours. Water (12 mL) was added slowly until a slurry persisted. The mixture was aged for 30 minutes and the solids were then collected by filtration and washed with 5:3 acetonitrile-water. The white solid was dried in a vacuum oven at 60° C. for 6 hours to give the title compound (1.48 g, 3.43 mmol, 68% yield). MS (DCI/$NH_3$) m/z 432 (M+H)$^+$.

Example 124E

N-[(2S,4R)-7-chloro-2-(difluoromethyl)-2-methyl-3,4-dihydro-2H-chromen-4-yl]-N'-(3-methylisoquinolin-5-yl)urea Example 124D was dissolved in a minimum volume of methanol, loaded on a Chiralpak AD-H chiral column (30 cm ID×250 cm column, 20 mg/injection), and eluted with methanol and supercritical carbon dioxide at 25° C. (flow rate ~50 mL/min. The later eluting peak (retention time=14.8 min) was collected and the solvent evaporated to afford the title compound (351 mg, 0.813 mmol, 24% yield) as an off-white solid in 99.5% ee. $^1$H NMR (500 MHz, DMSO-$d_6$) δ 9.19 (s, 1H), 8.70 (s, 1H), 8.28 (d, J=7.7 Hz, 1H), 7.72 (d, J=8.1 Hz, 1H), 7.53 (t, J=7.9 Hz, 1H), 7.38 (d, J=8.3 Hz, 1H), 7.03-7.07 (m, 3H), 6.99 (d, J=2.1 Hz, 1H), 6.24 (t, J=64.6 Hz, 1H), 5.03-5.09 (m, 1H), 2.66 (s, 3H), 1.99-2.01 (m, 2H), 1.44 (s, 3H); MS (DCI/$NH_3$) m/z 432 (M+H)$^+$.

Example 125

N-[(4R)-2,2-dimethyl-7-(trifluoromethyl)-3,4-dihydro-2H-chromen-4-yl]-N'-(6-fluoro-3-methylisoquinolin-5-yl)urea Example 123E (0.411 g, 1.278 mmol), Example 33B (0.5053 g, 1.278 mmol), DMF (4.1 mL), and $K_2CO_3$ (0.707 g, 5.11 mmol) were heated in a 100° C. oil bath. After 45 minutes, the reaction mixture was cooled, diluted with EtOAc (15 mL) and MTBE (10 mL), washed with 10% aqueous $KH_2PO_4$ (2×15 mL), brine (10 mL), 2N NaOH (10 mL), and brine (10 mL). The organic portion was dried ($Na_2SO_4$), filtered, and concentrated. The mixture was by silica gel chromatorgraphy (gradient elution 20-90% EtOAc/hexanes)

to provide the title compound (283 mg, 0.633 mmol, 50% yield). $^1$H NMR (300 MHz, DMSO-$d_6$) δ 9.23 (s, 1H), 8.32 (s, 1H), 8.07 (dd, J=9.0, 5.1 Hz, 1H), 7.66 (d, J=1.1 Hz, 1H), 7.57 (d, J=4.3 Hz, 1H), 7.55 (d, J=2.8 Hz, 1H), 7.27 (dd, J=8.1 Hz, 1.8 Hz, 1H), 7.04 (d, J=1.8 Hz, 1H), 6.89 (d, J=8.7 Hz, 1H), 5.09-4.99 (m, 1H), 2.65 (s, 3H), 2.15 (dd, J=13.2, 6.2 Hz, 1H), 1.92-1.83 (m, 1H), 1.42 (s, 3H), 1.29 (s, 3H); MS (DCI/NH$_3$) m/z 448 (M+H)$^+$.

Example 126

N-[(2R,4R)-8-fluoro-2-(fluoromethyl)-2-methyl-3,4-dihydro-2H-chromen-4-yl]-N'-(3-methylisoquinolin-5-yl)urea Example 126A 8-fluoro-2-(fluoromethyl)-2-methylchroman-4-one The title compound was prepared according to the procedure of Example 121A, substituting 1-(3-fluoro-2-hydroxyphenyl)ethanone for 1-(4-chloro-2-hydroxyphenyl)ethanone. MS (DCI/NH$_3$) m/z 230 (M+NH$_4$)$^+$.

Example 126B (4S)-8-fluoro-2-(fluoromethyl)-2-methylchroman-4-ol

The title compound was prepared according to the procedure of Example 65B substituting Example 126A for Example 65A. MS (DCI/NH$_3$) m/z 232 (M+NH$_4$)$^+$.

Example 126C (2R,4S)-8-fluoro-2-(fluoromethyl)-2-methylchroman-4-ol

Example 126B (2.00 g, 9.34 mmol) and THF (20 mL) were stirred at ambient temperature and potassium tert-butoxide (14.0 mL, 14.0 mmol) was added slowly at <28° C. After 2 hours, the reaction was diluted with MTBE (20 mL), washed with saturated aqueous NH$_4$Cl (2×10 mL), dried (Na$_2$SO$_4$), filtered, concentrated. Purification of the resulting residue by silica gel chromatography (gradient elution: 0-50% EtOAc/hexanes) gave the title compound (905 mg, 4.22 mmol, 45.3% yield). MS (DCI/NH$_3$) m/z 232 (M+NH$_4$)$^+$.

Example 126D (2R,4R)-8-fluoro-2-(fluoromethyl)-2-methylchroman-4-amine

The title compound was prepared according to the procedure of Example 65C substituting Example 126C for Example 65B. MS (DCI/NH$_3$) m/z 214 (M+H)$^+$.

Example 126E (2R,4R)-8-fluoro-2-(fluoromethyl)-2-methylchroman-4-amine, D-tartaric acid salt Isopropanol (10 mL) and D-(−)-tartaric acid (0.617 g, 4.11 mmol) were heated to 70° C. and Example 126D (0.876 g, 4.11 mmol) in isopropanol (5 mL) added. The white slurry was slowly cooled to ambient temperature, and the solids were collected by filtration and washed with isoproanol. The solids were dried in a vacuum oven at 40° C. for 10 hours to give the title compound (1.15 g, 3.17 mmol, 77% yield). MS (DCI/NH$_3$) m/z 214 (M+NH$_4$—H$_2$O)$^+$.

Example 126F

N-[(2R,4R)-8-fluoro-2-(fluoromethyl)-2-methyl-3,4-dihydro-2H-chromen-4-yl]-N'-(3-methylisoquinolin-5-yl)urea The title compound was prepared according to the procedure of Example 65E substituting Example 126E for Example 65D. $^1$H NMR (300 MHz, DMSO-$d_6$) δ 9.19 (s, 1H), 8.66 (s, 1H), 8.27 (dd, J=7.6, 1.1 Hz, 1H), 7.72 (d, J=8.2 Hz, 1H), 7.53 (t, J=7.9 Hz, 1H), 7.21-7.11 (m, 2H), 7.04 (d, J=8.3 Hz, 1H), 6.94 (td, J=8.0, 5.0 Hz, 1H), 5.19-5.04 (m, 1H), 4.54 (dd, J=64.6, 2.0 Hz, 2H), 2.66 (s, 3H), 2.21 (dd, J=13.2, 6.0 Hz, 1H), 2.01-1.92 (m, 2H), 1.57-1.26 (m, 3H); MS (DCI/NH$_3$) m/z 398 (M+H)$^+$.

Example 127

N-[(2R,4R)-2-(fluoromethyl)-2-methyl-7-(trifluoromethyl)-3,4-dihydro-2H-chromen-4-yl]-N-(3-methylisoquinolin-5-yl)urea Example 127A 2-(fluoromethyl)-7-(trifluoromethyl)-2-methylchroman-4-one The title compound was prepared according to the procedure of Example 33A, substituting fluoroacetone for acetone. MS (DCI/NH$_3$) m/z 263 (M+H)$^+$.

Example 127B (4S)-2-(fluoromethyl)-2-methyl-7-(trifluoromethyl)chroman-4-ol

The title compound was prepared according to the procedure of Example 65B substituting Example 127A for Example 65A. MS (DCI/NH$_3$) m/z 265 (M+H)$^+$.

Example 127C (2R,4S)-2-(fluoromethyl)-2-methyl-7-(trifluoromethyl)chroman-4-ol

The title compound was prepared according to the procedure of Example 126C substituting Example 127B for Example 126B. MS (DCI/NH$_3$) m/z 265 (M+H)$^+$.

Example 127D (2R,4R)-2-(fluoromethyl)-2-methyl-7-(trifluoromethyl)chroman-4-amine The title compound was prepared according to the procedure of Example 65C substituting Example 127C for Example 65B. MS (DCI/NH$_3$) m/z 264 (M+H)$^+$.

Example 127E (2R,4R)-2-(fluoromethyl)-2-methyl-7-(trifluoromethyl)chroman-4-amine, D-tartaric acid salt The title compound was prepared according to the procedure of Example 126E substituting Example 127D for Example 126D. MS (DCI/NH$_3$) m/z 264 (M+H)$^+$.

Example 127F

N-[(2R,4R)-2-(fluoromethyl)-2-methyl-7-(trifluoromethyl)-3,4-dihydro-2H-chromen-4-yl]-N'-(3-methylisoquinolin-5-yl)urea The title compound was prepared according to the procedure of Example 65E substituting Example 127E for Example 65D. $^1$H NMR (300 MHz, DMSO-d$_6$) δ 9.19 (s, 1H), 8.71 (s, 1H), 8.26 (dd, J=7.7, 1.1 Hz, 1H), 7.76 (d, J=1.0 Hz, 1H), 7.73 (d, J=8.1 Hz, 1H), 7.60-7.50 (m, 2H), 7.30 (dd, J=8.1, 1.9 Hz, 1H), 7.14-7.08 (m, 2H), 5.19-5.04 (m, 1H), 4.53 (dd, J=47.8, 1.5 Hz, 2H), 2.66 (s, 3H), 2.03-1.93 (m, 2H), 1.33 (d, J=2.1 Hz, 3H); MS (DCI/NH$_3$) m/z 448 (M+H)$^+$.

Example 128

N-[(2S,4R)-8-fluoro-2-(fluoromethyl)-2-methyl-3,4-dihydro-2H-chromen-4-yl]-N'-(3-methylisoquinolin-5-yl)urea

Example 128A (4R)-8-fluoro-2-(fluoromethyl)-2-methylchroman-4-amine

The title compound was prepared according to the procedure of Example 65C substituting Example 126B for Example 65B. MS (LCMS) m/z 197 (M-NH$_2$)$^+$.

Example 128B (2S,4R)-8-fluoro-2-(fluoromethyl)-2-methylchroman-4-amine

A solution of Example 128A (1.99 g, 9.34 mmol) in THF (100 mL) was cooled to 0° C. and n-BuLi (3.74 mL of a 2.5M solution in hexanes, 9.34 mmol) was added while maintaining the internal temperature <0° C. The reaction was warmed to ambient temperature and n-BuLi was added twice more (2 mL for each addition). After 30 minutes, the reaction was quenched by addition of water (25 mL) and extracted with MTBE (50 mL). The organic portion was washed with brine (25 mL), dried (Na$_2$SO$_4$), filtered, and concentrated. The residue was purified by silica gel chromatorgraphy (gradient elution: 0-10% MeOH/EtOAc) to give the title compound (490 mg, 2.30 mmol, 25% yield). MS (LCMS) m/z 197 (M-NH$_2$)$^+$.

Example 128C (2S,4R)-8-fluoro-2-(fluoromethyl)-2-methylchroman-4-amine, D-tartaric acid salt The title compound was prepared according to the procedure of Example 126E substituting Example 128B for Example 126D. MS (LCMS) m/z 197 (M-NH$_2$)$^+$.

Example 128D

N-[(2S,4R)-8-fluoro-2-(fluoromethyl)-2-methyl-3,4-dihydro-2H-chromen-4-yl]-N-(3-methylisoquinolin-5-yl)urea The title compound was prepared according to the procedure of Example 65E substituting Example 128C for Example 65D. $^1$H NMR (300 MHz, DMSO-d$_6$) δ 9.19 (s, 1H), 8.68 (s, 1H), 8.29 (d, J=7.6 Hz, 1H), 7.71 (d, J=8.1 Hz, 1H), 7.53 (t, J=7.9 Hz, 1H), 7.19-7.11 (m, 3H), 7.05 (d, J=8.1 Hz, 1H), 6.94 (td, J=7.9, 5.0 Hz, 1H), 5.11-5.02 (m, 1H), 4.53 (dd, J=47.3, 3.7 Hz, 2H), 2.65 (s, 3H), 2.41 (dd, J=13.9, 6.0 Hz, 1H), 2.03-1.94 (m, 1H), 1.44 (d, J=2.0 Hz, 3H); MS (DCI/NH$_3$) m/z 398 (M+H)$^+$.

Example 129

N-[(2S,4R)-2-(fluoromethyl)-2-methyl-7-(trifluoromethyl)-3,4-dihydro-2H-chromen-4-yl]-N-(3-methylisoquinolin-5-yl)urea

Example 129A (4R)-2-(fluoromethyl)-2-methyl-7-(trifluoromethyl)chroman-4-amine The title compound was prepared according to the procedure of Example 65C substituting Example 127B for Example 65B. MS (DCI/NH$_3$) m/z 264 (M+NH$_4$)$^+$.

Example 129B (2S,4R)-2-(fluoromethyl)-2-methyl-7-(trifluoromethyl)chroman-4-amine The title compound was prepared according to the procedure of Example 128B substituting Example 129A for Example 128A. MS (DCI/NH$_3$) m/z 264 (M+NH$_4$)$^+$.

Example 129C (2S,4R)-2-(fluoromethyl)-2-methyl-7-(trifluoromethyl)chroman-4-amine, D-tartaric acid salt The title compound was prepared according to the procedure of Example 126E substituting Example 129B for Example 126D. MS (DCI/NH$_3$) m/z 264 (M+NH$_4$)$^+$.

Example 129D

N-[(2S,4R)-2-(fluoromethyl)-2-methyl-7-(trifluoromethyl)-3,4-dihydro-2H-chromen-4-yl]-N'-(3-methylisoquinolin-5-yl)urea The title compound was prepared according to the procedure of Example 65E substituting Example 129C for Example 65D. $^1$H NMR (300 MHz, DMSO-d$_6$) δ 9.19 (s, 1H), 8.68 (s, 1H), 8.29 (d, J=7.6 Hz, 1H), 7.78-7.70 (m, 2H), 7.61-7.50 (m, 2H), 7.32-7.27 (m, 1H), 7.16-7.15 (m, 1H), 7.05 (d, J=8.1 Hz, 1H), 5.11-5.02 (m, 1H), 4.66-4.42 (m, 2H), 2.65 (s, 3H), 2.41 (dd, J=13.9, 6.0 Hz, 1H), 2.03-1.94 (m, 1H), 1.44 (d, J=2.0 Hz, 3H); MS (DCI/NH$_3$) m/z 448 (M+H)$^+$.

e) BIOLOGICAL DATA (i) Capsaicin Activation Assay

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate, without phenol red), L-glutamine, hygromycin B, and Lipofectamine® were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methyl-phenoxy[ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human TRPV1 receptor (hTRPV1) were isolated by reverse transcriptase-polymerase chain reaction (RT-PCR) from human small intestine poly A+ RNA supplied by Clontech (Palo Alto, Calif.) using primers designed surrounding the initiation and termination codons identical to the published sequences (Hayes et al. Pain 2000, 88, 205-215). The resulting cDNA PCR products were subcloned into pClneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hTRPV1 cDNA were transfected individually into 1321N1 human astrocytoma cells using Lipofectamine®. Forty-eight hours after transfection, the neomycin-resistant cells were selected with growth medium containing 800 µg/mL Geneticin (Gibco BRL). Surviving individual colonies were isolated and screened for TRPV1 receptor activity. Cells expressing recombinant homomeric TRPV1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the TRPV1 receptor was determined with a $Ca^{2+}$ influx assay and measurement of intracellular $Ca^{2+}$ levels ($[Ca^{2+}]_i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the TRPV1 agonist capsaicin was also prepared in D-PBS. The fluorescent $Ca^{2+}$ chelating dye Fluo-4 AM was used as an indicator of the relative levels of $[Ca^{2+}]_i$ in a 96-well format using a Fluorescence Imaging Plate Reader (FLIPR)(Molecular Devices, Sunnyvale, Calif.). Cells were grown to confluency in 96-well black-walled tissue culture plates. Then, prior to the assay, the cells were loaded with 100 µL per well of Fluo-4 AM (2 µM, in D-PBS) for 1-2 hours at 23° C. Washing of the cells was performed to remove extracellular Fluo-4 AM (2×1 mL D-PBS per well), and afterward, the cells were placed in the reading chamber of the FLIPR instrument. 50 µL of the compound solutions were added to the cells at the 10 second time mark of the experimental run. Then, after a 3-minute time delay, 50 µL of the capsaicin solution was added at the, 190 second time mark (0.05 µM final concentration)(final volume=200 µL) to challenge the TRPV1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values (shown in Table 1) were calculated.

Compounds tested in the assay described above have $IC_{50}$ of about 4 nM to about 250 nM. For example, compounds described herein exhibited $IC_{50}$ of about 4 nM to about 230 nM, or between about 4 nM to about 100 nM, or even between about 4 nM to about 50 nM.

(ii) Acid Activation Assay—Ratiometric Imaging to Measure Intracellular Calcium Concentration as an Indication of TRPV1 Function The differential effects of TRPV1 antagonists on capsaicin- or acid-induced responses were verified by ratiometric calcium imaging. Transiently transfected HEK293-F cells expressing human TRPV1 were incubated with 5 µM Fura-2AM for 30 minutes at 37° C. Intracellular calcium concentration was measured on an imaging system consisting of the X-Cite™ 120 Fluorescence Illumination System (EXFO) and a Digital Camera (C4742-95, Hamamatsu Photonics) connected to an Olympus 1×71 microscope. Through the control of Slide Book 4.2 software, fluorescence was measured during excitation at 340 and 380 nm; the ratio of the fluorescence at both excitation wavelengths (F340/F380) was monitored. D-PBS, pH 7.4 (Invitrogen, catalog no. 14287) was used as the extracellular solution. Acidic buffer was prepared by titrating D-PBS, pH 7.4 with 7 N HCl to pH 5.5. Agonists and antagonists were prepared in the pH 7.4 or 5.5 solutions. Rapid solution switch was achieved by using a ValveLink system.

FIG. 1 panel A shows results of a typical experiment with Example 56 with F340/F380 traces from two individual, representative cells (designated by solid or dotted line). Over the time 1250-second course, the cells were challenged sequentially with solutions containing Example 56 (3 µM), Example 56 (3 µM) plus capsaicin (1 µM), Example 56 (3 µM) plus acid (pH 5.5), or acid (pH 5.5) alone. The black bars above the traces designate addition and duration of solution applications. Spaces between horizontal bars represent periods in which cells were perfused with D-PBS, pH 7.4 alone. As shown in FIG. 1, panel A, Example 56 (3 µM) completely blocked the TRPV1-mediated increase in intracellular calcium concentration in response to capsaicin (1 µM) treatment, but it did not completely block the TRPV1-mediated increase in intracellular calcium concentration in response to pH 5.5 treatment. Similarly, Examples 62, 55, 61, and 26 completely blocked increase in intracellular calcium concentration in response to treatment with 1 µM capsaicin but did not completely block the increase in intracellular calcium concentration observed with pH 5.5 treatment (FIG. 1, panels B-E). In contrast, the TRPV1 antagonist AMG 628 completely blocked both capsaicin and pH 5.5-mediated increase in intracellular calcium concentration (FIG. 1, panel F). Parallel experiments demonstrated that cells subjected to continuous perfusion with D-PBS, pH 7.4 exhibited consistent baselines in the assay, and cells perfused with 1 µM capsaicin responded with robust influx of calcium in the absence of TRPV1 antagonist.

Representative compounds described herein are potent TRPV1 antagonists that inhibit calcium flux following activation by the TRPV1 agonist capsaicin (1 µM), but are less effective in inhibiting calcium flux caused by acid activation of TRPV1 (particularly human TRPV1) at acidic pH 5.5. Compounds described herein at 3 µM concentration cause less than 95% inhibition of the proton (pH 5.5) induced response. For example, compounds described herein block about 0% to about 70% calcium flux caused by pH 5.5 induced activation of hTRPV1, or block about 0% to about 95% of calcium flux caused by pH 5.5 induced activation of hTRPV1. Present compounds may also potentiate pH 5.5 induced activation of hTRPV1 as described by Lehto, S. G. et al. *J. Pharmacol. Exp. Ther.* 2008, 326, 218.

(iii) Rat Telemetry Protocol

Male, Sprague Dawley rats, 225-250 grams were anesthetized with Sevoflurane (Abbott Laboratories). Rats were placed on a heating pad and covered with a sterile surgical drape. A ventral midline abdominal incision was made and sterile cotton tip applicators were used to gently move internal tissue and expose the abdominal aorta for implantation of the telemetry catheter (Data Sciences International; TL11M2-050-PXT). Blood flow was temporarily stopped to the lower extremities (5-7 min) with Diffenbach clamps to allow the insertion of the telemetry catheter into the abdominal aorta. Once inserted, a sterile cellulose patch was placed over the catheter/aorta and secured using a small amount of tissue adhesive (Vetbond, 3M). Once catheter placement was complete, the clamps were removed and blood flow was restored to the lower extremities. The transmitter was placed in the intraperitoneal cavity. The transmitter suture rib was sewn into the abdominal sutures to secure it in place. The skin was closed using sterile wound clips and the animal removed from Sevoflurane. Buprenex (0.01 mg/mL s.c.; Phoenix) was administered for post-operative analgesia. Animals were maintained on a heating pad until ambulatory, and then individually housed with food and water ad lib. Surgical staples were removed after 7-10 days post-implantation. Rats were allowed a 2-week post-surgical recovery period before treatment with test compound. Oral dosing (p.o.) was at time zero, with rats receiving a single dose of vehicle (10% EtOH, 20% Tween-80, 70% PEG-400) or a 100 µmol/kg dose of compound dissolved in vehicle. Temperature measurements were recorded every 15 minutes for the duration of the study (24 hours).

Table 1 showed the effect of compounds tested on core body temperature of rats at one hour post dosing (100 µmol/kg), relative to vehicle, as well as the $IC_{50}$ values for hTRPV1 (capsaicin).

TABLE 1

| Example Number | $IC_{50}$ (nM) | Δ Temp (° C.) |
|---|---|---|
| 5 | 23 | −0.2 |
| 6 | 28 | 0.2 |
| 7 | 78 | 0.1 |
| 8 | 76 | 0.1 |
| 17 | 32 | −1.5 |
| 23 | 6 | −0.7 |
| 26 | 50 | 0.1 |
| 27 | 32 | −1.0 |
| 28 | 10 | −0.2 |
| 34 | 5 | −1.6 |
| 41 | 16 | −2.5 |
| 50 | 35 | 0.1 |
| 55 | 16 | 0.3 |
| 56 | 15 | 0.2 |
| 58 | 19 | 0.3 |
| 61 | 31 | 0.3 |
| 62 | 4 | −0.5 |
| 65 | 40 | 0.0 |
| 66 | 4 | −0.9 |
| 67 | 18 | −0.2 |
| 68 | 16 | 0.1 |

TABLE 1-continued

| Example Number | $IC_{50}$ (nM) | Δ Temp (° C.) |
|---|---|---|
| 69 | 4 | 0.1 |
| 70 | 5 | 0.3 |
| 81 | 5 | −0.5 |
| 84 | 11 | 0.0 |
| 85 | 51 | 0.2 |
| 86 | 10 | −1.7 |
| 87 | 10 | −2.0 |
| 88 | 9 | −0.3 |
| 91 | 26 | −0.1 |
| 94 | 9 | −2.0 |
| 95 | 7 | 0.0 |
| 96 | 15 | 0.0 |
| 97 | 7 | 0.4 |
| 98 | 17 | 0.0 |
| 101 | 91 | 0.0 |
| 102 | 14 | −0.7 |
| 106 | 21 | 0.3 |
| 110 | 23 | −1.1 |
| 111 | 24 | −1.3 |
| 113 | 12 | 0.0 |
| 118 | 19 | 0.0 |
| 119 | 28 | 0.0 |
| 120 | 43 | −0.5 |
| 121 | 9 | 0.0 |
| 122 | 30 | 0.0 |
| 123 | 27 | 0.0 |
| 124 | 6 | 0.0 |
| 126 | 200 | 0.0 |
| 128 | 300 | −0.1 |

Representative compounds described herein have the novel property of having limited transient temperature effect on core body temperature of a mammal (e.g. rats). For example, compounds tested alter core body temperature of rats by less than about +0.5° C. at about 1 hour after administration of a single dose (100 µmol/kg) of the test compounds orally, for example, in the range from about −2.5° C. to less than about +0.5° C., from about −0.5° C. to less than about +0.5° C.; or from about −0.3° C. to about +0.3° C.

The term "core body temperature" as used herein, means the temperature measured in the intraperitoneal cavity.

(iv) Cytochrome P450 2C9 Subtype (CYP2C9), 2D6 Subtype (CYP2D6), and 3A4 Subtype (CYP3A4) Inhibition Assays Stock solutions of test compounds were assayed in 96-well format for their ability to inhibit CYP2C9, CYP2D6, or CYP3A4 mediated metabolism of test substrates. Luciferin-H was used as the substrate for CYP2C9; 3-[2-(N, N-diethyl-N-methylammonium)ethyl]-7-methoxy-4-methylcoumarin (AMMC) was used as the substrate for CYP2D6; 7-benzyloxyquiniline (BZQ) was used as the substrate for CYP3A4. For each subtype, positive controls (sulphaphenazole in the case of CYP2C9; quinidine in the case of CYP2D6, ketoconazole in the case of CYP3A4) were used to validate assay results run in duplicate.

Pre-Incubation Mixture Preparation for CYP2C9 and CYP2D6: A pre-incubation mixture was prepared by combining 100 mM phosphate buffer (9.12 mL; pH 7.4), human liver microsomes (BD Gentest, 240 itt; final concentration: 0.4 mg/mL), and 10 mM nicotinamide adenine dinucleotide phosphate in 65.4 mM $MgCl_2$ hexahydrate (120 µL; final concentration: 125 µM and 818 µM, respectively). To this was mixture is added a 'regeneration' mixture (120 µL) of 333 mM glucose-6-phosphate and 40 U/mL glucose-6-phosphate dehydrogenase in 5 mM sodium citrate (final concentration: 4 mM, 0.5 U/mL, and 0.06 mM, respectively).

Substrate Mixture Preparation for CYP2C9: To a solution of 25 mM phosphate buffer, (2.16 mL, pH 7.4) was added 5 mM Luciferin-H (Promega P450 Glo Assay V8792, 240 µL; final solution concentration 0.5 mM, final assay concentration 100 µM).

Substrate Mixture Preparation for CYP2D6: To a solution of 100 mM phosphate buffer, (2.80 mL, pH 7.4) was added 10 mM AMMC in acetonitrile (14 itt; final solution concentration 0.05 mM, final assay concentration 10 µM).

CYP2C9 Inhibiton Assay: To each well in the assay plate containing varying concentrations of test compound or control compound in DMSO (10 µL) Pre-Incubation Mixture (40 itt) was added to the wells and the assay plate was pre-incubated for 10 minutes at 37° C., with shaking or rocking. CYP2C9 Substrate Mixture (10 µL) was added to all wells and the assay plate was incubated for an additional 25 minutes at 37° C., with shaking or rocking. Final DMSO concentration was 1%. Luciferin-H detection reagent (Promega kit V8792, 50 µL) was added to all wells. The plate was then vortexed at ambient temperature for between 20 minutes and 2 hours, and the luminescence of each well was then read and recorded.

CYP2D6 Inhibiton Assay: To each well in the assay plate containing varying concentrations of test compound or control compound in DMSO (10 µL), Pre-Incubation Mixture (40 µL) was added to the wells and the assay plate was pre-incubated for 10 minutes at 37° C., with shaking or rocking. A pre-read of each well was performed at 390 nm and 460 nm extinction/emission. CYP2D6 Substrate Mixture (10 µL) was added to all wells and the assay plate was incubated for an additional 25 mM at 37° C., with shaking or rocking. Final DMSO concentration was 1%. A post-read of each well was then performed at 390 nm and 460 nm extinction/emission.

Pre-Incubation Mixture Preparation for CYP3A4: A pre-incubation mixture was prepared by combining 100 mM phosphate buffer (19.35 mL; pH 7.4), human liver microsomes (BD Gentest, 450 µL; final concentration: 0.4 mg/mL), and 10 mM nicotinamide adenine dinucleotide phosphate in 65.4 mM $MgCl_2$ hexahydrate (225 µL; final concentration: 100 µM and 654 µM, respectively). To this was mixture was added a 'regeneration' mixture (225 µL) of 333 mM glucose-6-phosphate and 40 U/mL glucose-6-phosphate dehydrogenase in 5 mM sodium citrate (final concentration: 3.3 mM, 0.4 U/mL, and 0.05 mM, respectively).

Substrate Mixture Preparation for CYP3A4: To a solution of 100 mM phosphate buffer, (2.36 mL, pH 7.4) was added 30 mM BZQ in acetonitrile (40 µL; final solution concentration 0.5 mM, final assay concentration 50 µM).

CYP3A4 Inhibiton Assay: To each well in the assay plate containing varying concentrations of test compound or control compound in DMSO (10 µL), CYP3A4 Pre-Incubation Mixture (90 µL) was added to the wells and the assay plate was pre-incubated for 10 minutes at 37° C., with shaking or rocking. A pre-read of each well was performed at 405 nm and 535 nm extinction/emission. CYP3A4 Substrate Mixture (10 µL) was added to all wells and the assay plate was incubated for an additional 25 mM at 37° C., with shaking or rocking. Final DMSO concentration was 1%. A post-read of each well was then performed at 405 nm and 535 nm extinction/emission.

TABLE 2

Table 2 compares the inhibition profile of compounds of formula (II) against CYP2C9, CYP2D6, and CYP3A4.

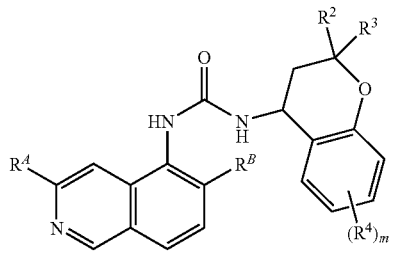

| Example Number | $R^A$ | $R^B$ | CYP2C9 % inh @ 2.2 µM | CYP2D6 % inh @ 2.2 µM) | CYP3A4 % inh @ 2.2 µM | Change in MAP or HR ≥ 15% ? ‡ |
|---|---|---|---|---|---|---|
| 5 | H | H | 55 | 100 | 61 | Yes* |
| 17 | H | H | 50 | 100 | 63 | |
| 23 | H | H | 56 | | 69 | |
| 27 | H | H | 48 | | 65 | |
| 28 | H | H | 35 | 98 | 19 | Yes |
| 34 | H | H | 39 | 97 | 36 | |
| 56 | Me | H | 20 | 14 | 17 | No |
| 62 | Me | H | 22 | 9.1 | 0 | No |
| 65 | Me | H | 0 | 12 | 0.57 | No |
| 66 | Me | H | 4.5 | 9.5 | 0 | No |
| 68 | Me | H | 13 | 0 | 6.4 | |
| 69 | Me | H | 5.3 | 0 | 0 | |
| 81 | Cl | H | 19 | 0.68 | 0 | |
| 84 | Me | H | 3.7 | 49 | 0 | No |
| 85 | Me | H | 7.2 | 10 | 0 | No |
| 87 | Me | H | 25 | 9 | 0 | |
| 91 | Me | H | 13 | 19 | 3.8 | |
| 94 | Me | H | 5.2 | 16 | 0 | |
| 95 | Me | H | 0 | 3.5 | 0 | Yes* |
| 96 | Me | H | 4.1 | 7.9 | 0 | Yes |
| 97 | Me | H | 17 | 19 | 0 | Yes* |
| 98 | Me | H | 8.4 | 3.7 | 0 | Yes |
| 101 | Me | H | 11 | 11 | | Yes |
| 102 | Me | H | 13 | 20 | | |
| 106 | $NH_2$ | H | 13 | | | |
| 110 | Me | H | 13 | 1.4 | 0.25 | Yes* |
| 111 | Me | H | 0.36 | 0.87 | 0 | |
| 113 | Me | H | 7.6 | 0 | 9 | Yes |
| 118 | Me | H | 7.8 | 21 | 0 | Yes |
| 119 | Me | H | 2.1 | 8.7 | 0 | Yes |
| 120 | Me | H | 11 | 6.2 | 25 | No |
| 121 | Me | H | 15 | 8 | 23 | Yes |
| 122 | Me | H | 20 | 5 | 20 | No |
| 123 | Me | F | 19 | 42 | 49 | No |
| 124 | Me | H | 1.2 | 8.4 | 21 | No |
| 126 | Me | H | 0 | 0 | 11 | |
| 128 | Me | H | 9 | 0.23 | 0 | |

‡Was an increase or decrease of greater than 15% in MAP (mean arterial pressure) or HR (heart rate) observed relative to the vehicle control group in one or more of the animals in the test group? ("Yes" or "No")
*Denotes animal lethality observed during the study.

These results clearly show distinct inhibition profile of compounds of formula (II) when $R^A$ is other than hydrogen. Substitution at the 3-position of isoquinoline (for example, when $R^A$ is methyl, Cl, or $NH_2$) provides compounds with superior profiles against all three subtypes of cytochrome P450. The data in Table 2 demonstrate that compounds of formula (II) wherein $R^A$ is methyl, Cl, or $NH_2$ have little or no effect on drug metabolizing enzymes such as cytochrome P450 subtypes: CYP2C9, CYP2D6, and CYP3A4. The majority of these compounds tested exhibit about 0% to about 49% inhibition at 2.2 µM against all three cytochrome P450 subtypes assayed. This property may result in better dosage quantities of the TRPV1 anatagonists, with which the same beneficial therapeutic effects can be induced without or at least with minimized undesirable side effects generally associated with the inhibition of cytochrome P450 enzymes.

(v) Assessment of Hemodynamic Profile in Anesthetized Rat

Male Sprague-Dawley rats were anesthetized with Inactin, instrumented, and allowed to stabilize. Following a 30 minute baseline period, test compound was infused via intravenous administration at 3, 10, and 30 mg/kg/30 minutes/dose in a low volume PEG-400 vehicle (1 mL/kg) or 20:40:40 dimethylacetamide:propylene glycol:PEG-400 vehicle (1 mL/kg). A separate group of animals received infusion of vehicle alone. Mean arterial pressure (MAP) and heart rate (HR) were observed and recorded. Table 2 summarizes the observed changes in cardiovascular parameters for compounds of formula (II). An observed increase or decrease of greater than 15% in MAP (mean arterial pressure) or HR (heart rate) in one or more of the animals in the test group relative to the vehicle control group is indicated as "Yes" in the table; an observed increase or decrease of less than or equal to 15% in MAP (mean arterial pressure) or HR (heart rate) in the test group of animals relative to the vehicle control group is indicated as "No" in the table. An asterisk (*) denotes an animal lethality was observed during the course of the experiment.

Compounds having favorable cardiovascular profile (for example, those that modify MAP or heart rate of less than or equal to about 15% in rat when administered intravenously at 3, 10, and 30 mg/kg/30 minutes/dose) are preferred.

One embodiment provides a method for treating a disorder that may be ameliorated by inhibiting vanilloid receptor subtype 1 (TRPV1) receptor in a host mammal in need of such treatment. The method comprises administering therapeutically effective amounts of one or more compound described herein or a pharmaceutically acceptable salts or solvates thereof, with or without one or more pharmaceutically acceptable carriers, and alone, or in combination with one or more analgesics (e.g. acetaminophen, opioids), or with one or more NSAIDs, or combinations thereof.

Another embodiment provides a method for treating pain in a mammal in need of such treatment. The method comprises administering therapeutically effective amounts of one or more compound described herein or a pharmaceutically acceptable salts or solvates thereof, with or without one or more pharmaceutically acceptable carriers, and alone, or in combination with one or more analgesics (e.g. acetaminophen, opioids), or with one or more NSAIDs, or combinations thereof.

Yet another embodiment provides a method for treating pain including, but not limited to, chronic pain, neuropathic pain, nociceptive pain, allodynia, inflammatory pain, inflammatory hyperalgesia, post herpetic neuralgia, post operative pain, post stroke pain, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, fibromyalgia, neuritis, sciatica, pelvic hypersensitivity, pelvic pain, menstrual pain, bladder disease, such as incontinence and bladder overactivity, micturition disorder, renal colic; and cystitis; inflammation such as burns, rheumatoid arthritis and osteoarthritis; neurodegenerative disease such as stroke and multiple sclerosis; pulmonary disease such as asthma, cough, chronic obstructive pulmonary disease (COPD) and bronchoconstriction; gastrointestinal disease such as gastroesophageal reflux disease (GERD), dysphagia, ulcer, irritable bowel syndrome (IBS), inflammatory bowel disease (IBD), colitis and Crohn's disease; ischemia such as cerebrovascular ischemia, acute cerebral ischemia; emesis such as cancer chemotherapy-induced emesis, and obesity, in mammals, especially humans. For example, the present compounds are useful for the treatment of pain, particularly nociceptive and inflammatory pain. The method comprises administering therapeutically effective amounts of one or more compound described herein or a pharmaceutically acceptable salts or solvates thereof, with or without one or more pharmaceutically acceptable carriers, and alone, or in combination with one or more analgesics (e.g. acetaminophen, opioids), or with one or more NSAIDs, or combinations thereof.

The present compounds can be used to treat pain as demonstrated by Nolano, M. et al. *Pain* 1999, 81, 135-145; Caterina, M. J. and Julius, D. *Annu. Rev. Neurosci.* 2001, 24, 487-517; Caterina, M. J. et al. *Science* 2000, 288, 306-313; Caterina, M. J. et al. *Nature* 1997, 389, 816-824.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan in *Prog. Neurobiol.* 1999, 57, 1-164 for a review). These sensory fibers are known as nociceptors and are characteristically small-diameter axons with slow conduction velocities. Nociceptors encode the intensity, duration and quality of noxious stimulus and by virtue of their topographically organized projection to the spinal cord, the location of the stimulus. The nociceptors are found on nociceptive nerve fibers of which there are two main types, A-delta fibers (myelinated) and C fibers (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain, these mechanisms can be useful in promoting protective behaviors that may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter *Science* 2000, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia: Meyer et al. Textbook of Pain, 13-44 (1994)). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury.

Pain afferents are activated by transduction of stimuli by nociceptors at the site of injury and activate neurons in the spinal cord at the level of their termination. This is then relayed up the spinal tracts to the brain where pain is perceived (Meyer et al. Textbook of Pain, 13-44 (1994). The activation of nociceptors activates two types of afferent nerve fibers. Myelinated A-delta fibers transmit rapidly and are responsible for sharp and stabbing pain sensations, whilst unmyelinated C fibers transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumor related pain (e.g. bone pain, headache, facial pain or visceral pain) or pain associated with cancer therapy (e.g. post-chemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition, which can be particularly debilitating.

Neuropathic pain is currently defined as pain initiated or caused by a primary lesion or dysfunction in the nervous system. Nerve damage can be caused by trauma and disease and thus the term neuropathic pain encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological, as it has no protective role. It is often present well after the original cause has dissipated, commonly lasting for years, significantly decreasing a patient's quality of life (Woolf and Mannion *Lancet* 1999, 353, 1959-1964). The symptoms of neuropathic pain are difficult to treat, as they are often heterogeneous even between patients with the same disease (Woolf and Decosterd *Pain Supp.* 1999, 6, S141-S147; Woolf and Mannion *Lancet* 1999, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, Textbook of Pain, 45-56 (1994)). Arthritic pain is the most common inflammatory pain.

Rheumatoid disease is one of the commonest chronic inflammatory conditions in developed countries and rheumatoid arthritis is a common cause of disability. The exact etiology of rheumatoid arthritis is unknown, but current hypotheses suggest that both genetic and microbiological factors may be important (Grennan & Jayson, Textbook of Pain, 397-407 (1994)). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder *Ann. Pharmacother.* 2002, 36, 679-686; McCarthy et al., Textbook of Pain, 387-395 (1994)). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs. Fernihough, J. et al. describe in *Neurosci. Lett.* 2005, 75-80 a potential role for TRPV1 in the manifestation of pain behavior accompanied by osteoarthritis changes in the knee.

Compounds described herein are TRPV1 antagonists and thus are useful in ameliorating acute and chronic inflammatory pain and postoperative pain as demonstrated in Honore, P. et al. *J. Pharmacol. Exp. Ther.* 2005, 410-421.

Another type of inflammatory pain is visceral pain, which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain.

Commonly encountered gastrointestinal (GI) disorders that cause pain include functional bowel disorder (FBD) and inflammatory bowel disease (IBD). These GI disorders include a wide range of disease states that are currently only moderately controlled, including, with respect to FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Elevated TRPV1 immunoreactivity has been observed in colonic sensory nerve fibers in patients with IBD (Szallasi, A. et al. *Nature Rev.* 2007, 6, 357-373).

Other types of visceral pain include the pain associated with dysmenorrhea, cystitis and pancreatitis and pelvic pain.

It should be noted that some types of pain have multiple etiologies and thus can be classified in more than one area, e.g. back pain and cancer pain have both nociceptive and neuropathic components.

Other types of pain include: pain resulting from musculoskeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardical infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain. It has been shown that CGRP-receptor antagonists block the vasodilation effects of CGRP and exhibits efficacy in patients with migraine and cluster headaches. CGRP is strongly co-expressed in many TRPV1 expressing nerve fibers, it is plausible that activation of TRPV1 could partially underlie a neurogenic-mediated component of headache.

Another type of pain is ocular pain (eye pain), which includes pain associated with dry eye syndrome, increased intraocular pressure, glaucoma, accidental trauma, and surgical procedures. intraocular pressure. Activation of TRPV1 induces inflammatory cytokine release in corneal epithelium in the eye (Zhang, F. et al. *J. Cell. Physiol* 2007, 213, 730; Murata, Y. et al. *Brain Res.* 2006, 1085, 87). Retinal ganglion cell apoptosis induced by elevated hydrostatic pressure arises substantially through TRPV1, likely through the influx of extracellular $Ca^{2+}$ (Sappington, R. M. et al. Invest. Ophth. Vis. Sci. 2009, 50, 717). TRPV1 antagonists can effectively reduce symptoms of dry eye without causing anesthesia effects on the ocular surface (US2009/0131449). Silencing of TRPV1 by administration of siRNA can be a useful therapy in the treatment of ocular pain associated with dry eye syndrome and could reduce side effects associated with medications currently used to treat patients suffering from this pathology. Investigators at Sylentis have reported data indicating that an siRNA targeting TRPV1 could be used to decrease the behavioral response of guinea pigs to ocular surface irritation (Association for Research in Vision and Opthalmology Meeting, 2008). Administration of the TRPV1 agonist capsaicin resulted in a significant increase in irritation parameters compared with saline and that topical administration of TRPV1 siRNA twice a day for three days resulted in reduced scratching and wiping movements for up to nine days in the treated eyes. The reported analgesic effect was greater than that observed using the reference standard capsazepine.

It is known that capsaicin, a TRPV1 agonist, induces cough and reduced airway conductance in human clinical trials. TRPV1 antagonists such as capsazepine have been shown to block capsaicin and citric acid-induced cough responses in guinea pigs as demonstrated by Geppetti, P. et al. *Eur. J. Pharmacol.* 2006, 533, 207-214. Thus, TRPV1 antagonists demonstrate potential in the treatment of asthma, cough, chronic obstructive pulmonary disease (COPD) and bronchoconstriction as demonstrated by Watanabe, N. et al. *Pulmonary Pharmacol. Ther.* 2005, 18, 187-197 and Jia, Y. et al. *Br. J. Pharmacol.* 2002, 137, 831-836.

Present compounds can be used to treat bladder overactivity and/or urinary incontinence as demonstrated by Fowler, C. *Urology* 2005, 65, 400-405.

Present compounds can be used to treat inflammatory thermal hyperalgesia as demonstrated by Davis, J. et al. *Nature* 2000, 405, 183-187.

Present compounds can be used for the treatment of anxiety-related disorders as demonstrated by Marsch, R. et al. *J. Neurosci.* 2007, 27, 832-839.

Present compounds can be used for the treatment of disorders associated with hyperdopaminergia such as psychosis, attention deficit hyperactivity disorder and schizophrenia as demonstrated by Tzavara, E. et al. *Biol. Psych.* 2006, 59, 508-515.

Present compounds can be used for the treatment of diabetes and obesity as demonstrated by Suni, A. and Sallazi, A. *Trends Pharmacol. Sci.* 2008, 29, 29-36.

Ischemia (e.g. cerebral ischemia) is the shortage or inadequate of oxygenated blood flow to body parts and organs, and often results in dysfunction or damage of tissue. The neuroprotective efficacy of induced hypothermia following or during cerebral ischemia is evident in experimental anima models of stroke (Barone, F. C. et al. *Neurosci. Biobehav. Rev.* 1997; 2(1), 31-44; Onesti, S. T. et al. *Neurosurgery* 1991, 29, 369; Coimbra, C. et al. *Acta Neuropathol. (Berl)* 1994; 87, 325; Zhang, Y. et al. *Acta Anaesthesiol. Sin.* 2001, 39, 65; Yamashita, K. et al. Stroke 1991, 22, 1574; Ooboshi, H. et al. *Brain Res.* 2000, 884, 23; Colbourne, F. et al. *J. Cereb. Blood Flow Metab.* 2000, 20(1-2), 1702; Kawai, N. et al. *Stroke* 2000, 3, 1982; Maier, C. M. et al. *J. Neurosurg.* 2001, 94, 90; Maier, C. M. et al. *Stroke* 1998, 29, 2171). Two trials conducted in cardiac arrest patients have demonstrated improved neurological outcome of inducing hypothermia (Mild therapeutic hypothermia to improve the neurologic outcome after cardiac arrest: Bernard, S. A. et al. *N. Engl. J. Med.* 2002, 346, 549 and *N. Engl. J. Med.* 2002, 346, 557). Induction of hypothermia by lowering of the core temperature has been attempted by mechanical devices such as surface cooling using catheters placed in a large vessel. However, such mechanical devices have been shown to have considerable side effects, including shivering, serious infections, and lung puncture. Regulation of the core body temperature by pharmaceutical compositions comprising TRPV1 agonists as a safer and less expensive alternative to the mechanical method was discussed in WO2008/040360 and WO2008/040361. Such treatments may have unintended side effects such as the sensation of burning pain, known to be elicited by TRPV1 agonists. TRPV1 antagonists that are capable of inducing hypothermia may be used for the treatment of ischemia without the pungent effects.

Present compounds may be administered alone, or in combination with one or more other compounds described herein, or in combination (i.e. co-administered) with one or more additional pharmaceutical agents. For example, a compound of formula (I), or a pharmaceutically acceptable salt or solvate thereof, may be administered in combination with one or more analgesics (e.g. acetaminophen, or an opioid such as morphine), or with one or more nonsteroidal anti-inflammatory drug (NSAID) such as, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac; or administered with a combination of one or more analgesic (e.g. acetaminophen, opioids) and one or more NSAID. In certain embodiments, the nonsteroidal anti-inflammatory drug (NSAID) is ibuprofen. In certain embodiments, the analgesic is acetaminophen. Combination therapy includes administration of a single pharmaceutical dosage formulation containing one or more of the compounds described herein and one or more additional pharmaceutical agents, as well as administration of the compounds of the invention and each additional pharmaceutical agent, in its own separate pharmaceutical dosage formulation. For example, a compound of formula (I) and one or more additional pharmaceutical agent(s) may be administered to the patient together, in a single oral dosage composition having a fixed ratio of each active ingredient, such as a tablet or capsule; or each agent may be administered in separate oral dosage formulations.

Where separate dosage formulations are used, the present compounds and one or more additional pharmaceutical agents may be administered at essentially the same time (e.g., concurrently) or at separately staggered times (e.g., sequentially).

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds can be employed in pure form or, where such forms exist, in pharmaceutically acceptable salts thereof. The present compounds can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds administered to a human or lower animal range from about 0.10 µg/kg body weight to about 25 mg/kg body weight. More preferable doses can be in the range of from about 0.10 µg/kg body weight to about 1 mg/kg body weight. If desired, the effective daily dose can be divided into multiple doses for purposes of administration. Consequently, single dose compositions may contain such amounts or submultiples thereof to make up the daily dose.

f) PHARMACEUTICAL COMPOSITIONS

Described herein are also pharmaceutical compositions comprising of compounds described herein, or pharmaceutically acceptable salts or solvates thereof, formulated together with one or more pharmaceutically acceptable carriers. The pharmaceutical compositions can be formulated for oral administration in solid or liquid form, for parenteral injection or for rectal administration.

The compounds identified by the methods described herein may be administered as the sole pharmaceutical agent or in combination with one or more other pharmaceutical agents. For example, the compounds or salts or solvate thereof can be combined with one or more analgesics, or with one or more nonsteroidal anti-inflammatory drug (NSAID, or with a combination of oneor more analgesic and one or more NSAID. Thus, the present invention also includes pharmaceutical compositions which are comprised of therapeutically effective amount of compounds identified by the methods described herein, or pharmaceutically acceptable salts or solvates thereof, one or more pharmaceutical agents as disclosed hereinabove, and one or more pharmaceutically acceptable carriers.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of interest, lactose, talc, silicic acid, aluminum hydroxide, calcium silicates and polyamide powder, or mixtures of these substances. Sprays can additionally contain customary propellants such as chlorofluorohydrocarbons.

The present compounds can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of interest, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., p 33 et seq (1976).

Dosage forms for topical administration include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds can be used in the form of pharmaceutically acceptable salts derived from inorganic or organic acids. The term "pharmaceutically acceptable salts" as used herein, include salts and zwitterions of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds or separately by mixing together solutions of the compounds of invention and a suitable acid or base. The salt may precipitate from the solution and be collected by filtration or may be recovered by evaporation of the solvent. The degree of ionization in the salt may vary from completely ionized to almost non-ionized.

Suitable acid addition salts are formed from acids which form non-toxic salts. Representative acid addition salts include, but are not limited to acetate, adipate, alginate, citrate, aspartate, benzoate, benzenesulfonate, bisulfate, bicarbonate, butyrate, camphorate, camphorsulfonate, carbonate, citrate, digluconate, glycerophosphate, hemisulfate, heptanoate, hexanoate, formate, fumarate, gluconate, glucuronate, glutamate, hydrochloride, hydrobromide, hydroiodide, 2-hydroxyethansulfonate (isethionate), lactate, maleate, malate, malonate, methanesulfonate, nicotinate, 2-naphthalenesulfonate, nicotinate, nitrate, orotate, oxalate, palmitate, pamoate, pectinate, persulfate, 3-phenylpropionate, picrate, pivalate, propionate, saccharate, stearate, succinate, sulfate, tartrate, thiocyanate, phosphate, hydrogenphosphate, dihydrogen phosphate, p-toluenesulfonate, trifluoroacetate, and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, zinc, and aluminum salts, and the like, and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable prodrug" or "prodrug" as used herein, represents those prodrugs of the compounds of the invention which are, within the scope of sound medical judgment, suitable for use in contact with the tissues of humans and animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need thereof may be converted through in vivo biotransformation into compounds of the invention.

The compounds of the invention may exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

We claim:

1. A compound having formula (I-i) or a pharmaceutically acceptable thereof,

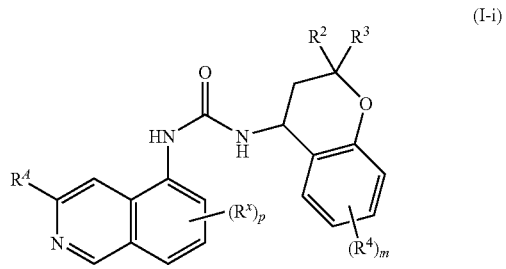

wherein $R^A$ is methyl, $NH_2$, or Cl;
p is 0 or 1;
$R^x$, at each occurrence, represents optional substituent(s) on any substitutable position of the bicyclic ring selected from the group consisting of alkyl, halogen, haloalkyl, OH, O(alkyl), O(haloalkyl), $NH_2$, N(H)(alkyl), and $N(alkyl)_2$;
$R^2$ and $R^3$ are the same or different, and are each independently hydrogen, $C_1$-$C_5$ alkyl, or haloalkyl; or
$R^2$ and $R^3$, together with the carbon atom to which they are attached, form a $C_3$-$C_6$ monocyclic cycloalkyl ring, optionally substituted with 1, 2, or 3 substituents selected from the group consisting of alkyl and halogen;

$R^4$, at each occurrence, represents optional substituent(s) on any substitutable position of the bicyclic ring selected from the group consisting of alkyl, halogen, haloalkyl, O(alkyl), O(haloalkyl), and $SCF_3$; and m and n are each independently 0, 1, 2, or 3;

with the proviso that the compound is other than

N-(7-tert-butyl-3,4-dihydro-2H-chromen-4-yl)-N'-(3-methylisoquinolin-5-yl)urea;

N-(6-fluoro-3,4-dihydro-2H-chromen-4-yl)-N'-(3-methylisoquinolin-5-yl)urea; or

N-(6-methyl-3,4-dihydro-2H-chromen-4-yl)-N'-(3-methylisoquinolin-5-yl)urea.

2. The compound of claim 1 having formula (I-i) or a pharmaceutically acceptable salt thereof, wherein m is 0, 1, or 2;

$R^x$ is alkyl or halogen; and $R^4$ is alkyl, halogen, haloalkyl, or O(haloalkyl).

3. The compound of claim 1 having formula (I-i) or a pharmaceutically acceptable salt thereof, wherein $R^2$ and $R^3$ are the same or different, and are each independently $C_1$-$C_5$ alkyl or haloalkyl.

4. The compound of claim 1 or a pharmaceutically acceptable salt thereof wherein said compound exhibits a limited transient temperature effect on core body temperature of a mammal.

5. The compound of claim 1 or a pharmaceutically acceptable salt thereof wherein said compound alters core body temperature of a mammal by less than about +0.5° C.

6. The compound of claim 1 or a pharmaceutically acceptable salt thereof wherein said compound alters core body temperature of a mammal from about −2.5° C. to less than about +0.5° C.

7. The compound of claim 1 or a pharmaceutically acceptable salt thereof wherein said compound alters core body temperature of a mammal from about −0.5° C. to less than about +0.5° C.

8. The compound of claim 1 or a pharmaceutically acceptable salt thereof wherein said compound alters core body temperature of a mammal from about −0.3° C. to about +0.3° C.

9. The compound of claim 1 or a pharmaceutically acceptable salt thereof wherein said compound at concentration of 3 μM blocks at least about 95% calcium flux caused by activation of human TRPV1 by addition of 1 μM capsaicin, and blocks less than about 95% calcium flux caused by activation of human TPRV1 at pH 5.5.

10. The compound of claim 1 or a pharmaceutically acceptable salt thereof wherein said compound at concentration of 3 μM blocks at least about 95% calcium flux caused by activation of human TRPV1 by addition of 1 μM capsaicin.

11. The compound of claim 1 or a pharmaceutically acceptable salt thereof wherein said compound exhibits about 0% inhibition to about 49% inhibition at 2.2 μM against CYP2C9, CYP2D6, and CYP3A4.

12. The compound of claim 1 or a pharmaceutically acceptable salt thereof wherein said compound modify the mean arterial pressure or heart beat in a mammal by less than or equal to about 15% when administered intravenously.

13. The compound of claim 1 or a pharmaceutically acceptable salt thereof wherein said compound has at least two of the following properties:

a) alters core body temperature of a mammal from about −2.5° C. to less than about +0.5° C., b) at concentration of 3 μM blocks at least about 95% calcium flux caused by activation of human TRPV1 by addition of 1 μM capsaicin, c) exhibits about 0% inhibition to about 49% inhibition at 2.2 μM against CYP2C9, CYP2D6, and CYP3A4.

14. The compound of claim 13 or a pharmaceutically acceptable salt thereof wherein said compound modify the mean arterial pressure or heart beat in a mammal by less than or equal to about 15% when administered intravenously.

15. The compound according to any one of claim 1, 4, 5, 6, 7, 8, 9, 10, 11, 12, 13, or 14, or a pharmaceutically acceptable salt thereof wherein $R^2$ and $R^3$ the same or different, and are each independently hydrogen, $C_1$-$C_5$ alkyl, or haloalkyl.

16. The compound according to claim 15, or a pharmaceutically acceptable salt thereof wherein $R^2$ and $R^3$ are the same or different, and are each independently $C_1$-$C_5$ alkyl or haloalkyl.

17. The compound according to claim 16 or a pharmaceutically acceptable salt thereof wherein m is 0, 1, or 2; and $R^4$ is alkyl, halogen, haloalkyl, or O(haloalkyl).

18. The compound according to any one of claim 1, 4, 5, 6, 7, 8, 9, 10, 11, 12, 13, or 14, or a pharmaceutically acceptable salt thereof wherein $R^2$ and $R^3$, together with the carbon atoms to which they are attached, form a $C_3$-$C_6$ monocyclic cycloalkyl ring, optionally substituted with 1, 2, or 3 substituents selected from the group consisting of alkyl and halogen.

19. The compound according to claim 18 or a pharmaceutically acceptable salt thereof wherein m is 0, 1 or 2; and $R^4$ is alkyl, halogen, haloalkyl, or O(haloalkyl).

20. The compound according to claim 1, or a pharmaceutically acceptable salt thereof, wherein the compound is selected from the group consisting of:

N-[(4R)-2,2-diethyl-6-fluoro-3,4-dihydro-2H-chromen-4-yl]-N'-(3-methylisoquinolin-5-yl)urea;

N-[(4R)-2,2-diethyl-8-fluoro-3,4-dihydro-2H-chromen-4-yl]-N'-(3-methylisoquinolin-5-yl)urea;

N-[(4R)-6-fluoro-2,2-bis(fluoromethyl)-3,4-dihydro-2H-chromen-4-yl]-N'-(3-methylisoquinolin-5-yl)urea;

N-(3-methylisoquinolin-5-yl)-N'-[(4R)-8-(trifluoromethoxy)-3,4-dihydro-2H-chromen-4-yl]urea;

N-[(4R)-8-fluoro-2,2-dipropyl-3,4-dihydro-2H-chromen-4-yl]-N'-(3-methylisoquinolin-5-yl)urea;

N-[(4R)-7-chloro-2,2-diethyl-3,4-dihydro-2H-chromen-4-yl]-N'-(3-methylisoquinolin-5-yl)urea;

N-(3-chloroisoquinolin-5-yl)-N'-[(4R)-2,2-diethyl-8-fluoro-3,4-dihydro-2H-chromen-4-yl]urea;

N-[(4R)-7-chloro-2,2-bis(fluoromethyl)-3,4-dihydro-2H-chromen-4-yl]-N'-(3-methylisoquinolin-5-yl)urea;

N-[(4R)-8-fluoro-2,2-bis(fluoromethyl)-3,4-dihydro-2H-chromen-4-yl]-N'-(3-methylisoquinolin-5-yl)urea;

N-[(4R)-2,2-bis(fluoromethyl)-8-(trifluoromethoxy)-3,4-dihydro-2H-chromen-4-yl]-N'-(3-methylisoquinolin-5-yl)urea;

N-[(4R)-8-chloro-2,2-bis(fluoromethyl)-3,4-dihydro-2H-chromen-4-yl]-N'-(3-methylisoquinolin-5-yl)urea;

N-[(4R)-2,2-dimethyl-8-(trifluoromethoxy)-3,4-dihydro-2H-chromen-4-yl]-N'-(3-methylisoquinolin-5-yl)urea;

N-[(4R)-7-fluoro-2,2-dimethyl-3,4-dihydro-2H-chromen-4-yl]-N'-(3-methylisoquinolin-5-yl)urea;

N-[(4R)-7-fluoro-2,2-bis(fluoromethyl)-3,4-dihydro-2H-chromen-4-yl]-N'-(3-methylisoquinolin-5-yl)urea;

N-[(4R)-7-chloro-2,2-dimethyl-3,4-dihydro-2H-chromen-4-yl]-N'-(3-methylisoquinolin-5-yl)urea;

N-[(4R)-6,8-difluoro-2,2-dimethyl-3,4-dihydro-2H-chromen-4-yl]-N'-(3-methylisoquinolin-5-yl)urea;

N-[(4R)-2,2-bis(fluoromethyl)-3,4-dihydro-2H-chromen-4-yl]-N'-(3-methylisoquinolin-5-yl)urea;

N-[(4R)-7-bromo-2,2-bis(fluoromethyl)-3,4-dihydro-2H-chromen-4-yl]-N'-(3-methylisoquinolin-5-yl)urea;

N-(3-aminoisoquinolin-5-yl)-N'-[(4R)-7-fluoro-2,2-dimethyl-3,4-dihydro-2H-chromen-4-yl]urea;

N-[(4R)-8-chloro-7-fluoro-2,2-dimethyl-3,4-dihydro-2H-chromen-4-yl]-N'-(3-methylisoquinolin-5-yl)urea;

N-[(4R)-7-fluoro-2,2,8-trimethyl-3,4-dihydro-2H-chromen-4-yl]-N'-(3-methylisoquinolin-5-yl)urea;

N-[(4R)-7,8-difluoro-2,2-dimethyl-3,4-dihydro-2H-chromen-4-yl]-N'-(3-methylisoquinolin-5-yl)urea;

N-[(4R)-2,2-dimethyl-7-(trifluoromethyl)-3,4-dihydro-2H-chromen-4-yl]-N'-(3-methylisoquinolin-5-yl)urea;

N-[(4R)-8-fluoro-2,2-dimethyl-3,4-dihydro-2H-chromen-4-yl]-N'-(3-methylisoquinolin-5-yl)urea;

N-[(4R)-6,8-difluoro-2,2-bis(fluoromethyl)-3,4-dihydro-2H-chromen-4-yl]-N'-(3-methylisoquinolin-5-yl)urea;

N-[(2R,4R)-7-chloro-2-(fluoromethyl)-2-methyl-3,4-dihydro-2H-chromen-4-yl]-N'-(3-methylisoquinolin-5-yl)urea;

N-[(2S,4R)-7-chloro-2-(fluoromethyl)-2-methyl-3,4-dihydro-2H-chromen-4-yl]-N'-(3-methylisoquinolin-5-yl)urea;

N-[(4R)-7-fluoro-2,2-dimethyl-3,4-dihydro-2H-chromen-4-yl]-N'-(6-fluoro-3-methylisoquinolin-5-yl)urea;

N-[(2S,4R)-7-chloro-2-(difluoromethyl)-2-methyl-3,4-dihydro-2H-chromen-4-yl]-N'-(3-methylisoquinolin-5-yl)urea;

N-[(2R,4R)-8-fluoro-2-(fluoromethyl)-2-methyl-3,4-dihydro-2H-chromen-4-yl]-N'-(3-methylisoquinolin-5-yl)urea; and N-[(2S,4R)-8-fluoro-2-(fluoromethyl)-2-methyl-3,4-dihydro-2H-chromen-4-yl]-N'-(3-methylisoquinolin-5-yl)urea.

21. The compound or salt according to claim 1, wherein the compound is N-[(4R)-7-chloro-2,2-bis(fluoromethyl)-3,4-dihydro-2H-chromen-4-yl]-N'-(3-methylisoquinolin-5-yl)urea.

22. The compound according to claim 21 that is N-[(4R)-7-chloro-2,2-bis(fluoromethyl)-3,4-dihydro-2H-chromen-4-yl]-N'-(3-methylisoquinolin-5-yl)urea.

23. The salt of claim 21 that is a pharmaceutically acceptable salt of N-[(4R)-7-chloro-2,2-bis(fluoromethyl)-3,4-dihydro-2H-chromen-4-yl]-N'-(3-methylisoquinolin-5-yl)urea.

24. A pharmaceutical composition comprising a compound of formula (I) according to any one of claim 1, 2, 3, 4, 5, 6, 7, 8, 9, 10, 11, 12, 13, 14, or 20, or a pharmaceutically acceptable salt thereof, and one or more pharmaceutically acceptable carriers.

25. The pharmaceutical composition according to claim 24 further comprising one or more analgesic or one or more nonsteroidal anti-inflammatory drug, or a combination thereof.

26. The pharmaceutical composition according to claim 24, wherein the composition comprises N-[(4R)-7-chloro-2,2-bis(fluoromethyl)-3,4-dihydro-2H-chromen-4-yl]-N'-(3-methylisoquinolin-5-yl)urea, or a pharmaceutically acceptable salt thereof.

27. A method for treating pain comprising administering a therapeutically effective amount of a compound of formula (I) according to any one of claim 1, 2, 3, 4, 5, 6, 7, 8, 9, 10, 11, 12, 13, 14, or 20, or a pharmaceutically acceptable salt thereof, to a subject in need thereof.

28. The method according to claim 27 further comprising the step of co-administering with one or more analgesics, or with one or more nonsteroidal anti-inflammatory drug, or combination thereof.

29. The method according to claim 28 wherein the nonsteroidal anti-inflammatory drug is ibuprofen.

30. A method for treating incontinence, micturition disorder, renal colic, cystitis, stroke, acute cerebral ischemia, ischemia, multiple sclerosis, asthma, cough, chronic obstructive pulmonary disease (COPD), broncho-constriction, gastroesophageal reflux disease (GERD), dysphagia, ulcer, urinary incontinence, bladder overactivity, irritable bowel syndrome (IBS), inflammatory bowel disease (IBD), colitis, Crohn's disease, cancer chemotherapy-induced emesis, or obesity, comprising administering a therapeutically effective amount of a compound of formula (I) according to any one of claim 1, 2, 3, 4, 5, 6, 7, 8, 9, 10, 11, 12, 13, 14, or 20, or a pharmaceutically acceptable salt thereof, to a subject in need thereof.

31. A method for treating inflammatory states, comprising burns, rheumatoid arthritis and osteoarthritis comprising administering a therapeutically effective amount of a compound of formula (I) according to any one of claim 1, 2, 3, 4, 5, 6, 7, 8, 9, 10, 11, 12, 13, 14, or 20, or a pharmaceutically acceptable salt thereof, to a subject in need thereof.

32. The method for treating pain according to claim 27, wherein the method comprises administering a therapeutically effective amount of N-[(4R)-7-chloro-2,2-bis(fluoromethyl)-3,4-dihydro-2H-chromen-4-yl]-N'-(3-methylisoquinolin-5-yl)urea, or a pharmaceutically acceptable salt thereof, to a subject in need thereof.

* * * * *